(12) United States Patent
Stangeland et al.

(10) Patent No.: US 8,242,164 B2
(45) Date of Patent: *Aug. 14, 2012

(54) 3-(PHENOXYPHENYLMETHYL) PYRROLIDINE COMPOUNDS

(75) Inventors: Eric L. Stangeland, Pacifica, CA (US); Priscilla Van Dyke, San Francisco, CA (US); Timothy J. Church, San Mateo, CA (US); Lori Jean Patterson, San Francisco, CA (US); Daisuke Roland Saito, Daly City, CA (US)

(73) Assignee: Theravance, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/984,076

(22) Filed: Jan. 4, 2011

(65) Prior Publication Data

US 2011/0275694 A1 Nov. 10, 2011

Related U.S. Application Data

(63) Continuation of application No. 12/507,965, filed on Jul. 23, 2009, now Pat. No. 7,888,386.

(60) Provisional application No. 61/135,828, filed on Jul. 24, 2008.

(51) Int. Cl.
*A61K 31/40* (2006.01)
*A61P 29/00* (2006.01)
*A61P 19/00* (2006.01)

(52) U.S. Cl. ..................................... 514/428
(58) Field of Classification Search .............. 514/428; 548/570

See application file for complete search history.

(56) References Cited

U.S. PATENT DOCUMENTS

| | | | |
|---|---|---|---|
| 3,634,437 A | 1/1972 | Todd | |
| 4,229,449 A | 10/1980 | Melloni et al. | |
| 4,243,807 A | 1/1981 | Friebe et al. | |
| 5,023,269 A | 6/1991 | Robertson et al. | |
| 5,037,841 A | 8/1991 | Schobe et al. | |
| 5,614,518 A | 3/1997 | Leeson et al. | |
| 6,518,284 B2 | 2/2003 | Venero et al. | |
| 7,294,637 B2 | 11/2007 | Aquila et al. | |
| 7,317,011 B2 | 1/2008 | Wong et al. | |
| 7,378,436 B2 | 5/2008 | Fish et al. | |
| 7,384,941 B2 | 6/2008 | Walter et al. | |
| 7,888,386 B2 * | 2/2011 | Stangeland et al. | 514/428 |
| 2002/0151712 A1 | 10/2002 | Lin et al. | |
| 2005/0245519 A1 | 11/2005 | Barta et al. | |
| 2005/0250775 A1 | 11/2005 | Fish et al. | |
| 2007/0015786 A1 | 1/2007 | Allen et al. | |
| 2007/0072859 A1 | 3/2007 | Boulet et al. | |
| 2007/0265306 A1 | 11/2007 | Venero et al. | |
| 2008/0153919 A1 | 6/2008 | Kranzler et al. | |
| 2010/0261762 A1 | 10/2010 | Dreyfus et al. | |
| 2010/0267743 A1 | 10/2010 | Stangeland et al. | |

FOREIGN PATENT DOCUMENTS

| | | |
|---|---|---|
| WO | WO 00/56318 A1 | 9/2000 |
| WO | WO 2006/099433 A1 | 9/2006 |
| WO | WO 2007/031828 A2 | 3/2007 |
| WO | WO 2008/023258 A1 | 2/2008 |

OTHER PUBLICATIONS

U.S. Appl. No. 12/834,128, Stangeland et al.
U.S. Appl. No. 12/835,944, Stangeland et al.
Fish et al., "Design and synthesis of morpholine derivatives. SAR for dual serotonin & noradrenaline reuptake inhibition", Bioorganic & Medicinal Chemistry Letters, 18, pp. 2562-2566, 2008.
Fish et al., "Derivatives of (3S)-N-(biphenyl-2-ylmethyl)pyrrolidin-3-amine as selective noradrenaline reuptake inhibitors: Reducing P-gp mediated efflux by modulation of H-bond acceptor capacity", Bioorganic & Medicinal Chemistry Letters, 18, pp. 4355-4359, 2008.
Fish et al., "4-Piperidines and 3-pyrrolidines as dual serotonin and noradrenaline reuptake inhibitors: Design, synthesis and structure-activity relationships", Bioorganic & Medicinal Chemistry Letters, 19, pp. 2829-2834, 2009.
Melloni et al., "Potential antidepressant agents. Alpha-aryloxy-benzyl derivatives of ethanolamine and morpholine", European Journal of Medicinal Chemistry, 19(3), pp. 235-242, 1984.
Murphy et al., "The Synthesis and Biological Evaluation of Novel Series of Nitrile-containing Fluoroquinolones as Antibacterial Agents", Bioorganic & Medicinal Chemistry Letters, 17, pp. 2150-2155 (2007).
Orjales et al., "Synthesis and binding studies of new [(aryl)(aryloxy)methyl]piperidine derivatives and related compounds as potential antidepressant drugs with high affinity for serotonin (5-HT) and norepinephrine (NE) transporters", Journal of Medicinal Chemistry, 46, pp. 5512-5532, 2003.

* cited by examiner

*Primary Examiner* — Yong Chu
(74) *Attorney, Agent, or Firm* — Jeffrey A. Hagenah; Shelley Eberle

(57) ABSTRACT

In one aspect, the invention relates to compounds of formula I:

(I)

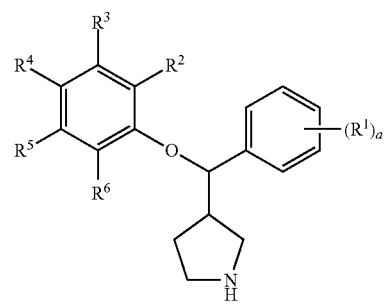

where a and $R^{1-6}$ are as defined in the specification, or a pharmaceutically acceptable salt thereof. The compounds of formula I are serotonin and norepinephrine reuptake inhibitors. In another aspect, the invention relates to pharmaceutical compositions comprising such compounds; methods of using such compounds; and process and intermediates for preparing such compounds.

9 Claims, 6 Drawing Sheets

3-(PHENOXYPHENYLMETHYL)PYRROLIDINE COMPOUNDS

CROSS-REFERENCE TO RELATED APPLICATIONS

This application is a continuation of U.S. Ser. No. 12/507,965, filed Jul. 23, 2009, now allowed, which claims the benefit of U.S. Provisional Application No. 61/135,828, filed on Jul. 24, 2008; the entire disclosures of which are incorporated herein by reference in their entirety.

BACKGROUND OF THE INVENTION

1. Field of the Invention

The present invention relates to 3-(phenoxyphenylmethyl) pyrrolidine compounds having activity as serotonin (5-HT) and norepinephrine (NE) reuptake inhibitors. The invention also relates to pharmaceutical compositions comprising such compounds, processes and intermediates for preparing such compounds and methods of using such compounds to treat a pain disorder, such as neuropathic pain, and other ailments.

2. State of the Art

Pain is an unpleasant sensory and emotional experience associated with actual or potential tissue damage, or described in terms of such damage (International Association for the Study of Pain, Pain Terminology). Chronic pain persists beyond acute pain or beyond the expected time for an injury to heal (American Pain Society. "Pain Control in the Primary Care Setting." 2006:15). Neuropathic pain is pain initiated or caused by a primary lesion or dysfunction in the nervous system. Peripheral neuropathic pain occurs when the lesion or dysfunction affects the peripheral nervous system and central neuropathic pain when the lesion or dysfunction affects the central nervous system (IASP).

Several types of therapeutic agents are currently used to treat neuropathic pain including, for example, tricyclic antidepressants (TCAs), serotonin and norepinephrine reuptake inhibitors (SNRIs), calcium channel ligands (e.g., gabapentin and pregabalin), topical lidocaine, and opioid agonists (e.g., morphine, oxycodone, methadone, levorphanol and tramadol). However, neuropathic pain can be very difficult to treat with no more than 40-60% of patients achieving, at best, partial relief of their pain (R. H. Dworkin et al. (2007) Pain 132:237-251 at 247). Moreover, all of the therapeutic agents currently used to treat neuropathic pain have various side effects (e.g., nausea, sedation, dizziness and somnolence) that can limit their effectiveness in some patients (Dworkin et al. supra. at 241).

SNRIs, such as duloxetine and venlafaxine, are often used as first line therapy for treating neuropathic pain. These agents inhibit the reuptake of both serotonin (5-hydroxytryptamine, 5-HT) and norepinephrine (NE) by binding to the serotonin and norepinephrine transporters (SERT and NET, respectively). However, both duloxetine and venlafaxine have higher affinity for SERT relative to NET (Vaishnavi et al. (2004) Biol. Psychiatry 55(3):320-322).

Preclinical studies suggest that inhibition of both SERT and NET may be necessary for maximally effective treatment of neuropathic and other chronic pain states (Jones et al. (2006) Neuropharmacology 51(7-8):1172-1180; Vickers et al. (2008) Bioorg. Med. Chem. Lett. 18:3230-3235; Fishbain et al. (2000) Pain Med. 1(4):310-316; and Mochizucki (2004) Human Psychopharmacology 19:S15-S19). However, in clinical studies, the inhibition of SERT has been reported to be related to nausea and other side effects (Greist et al. (2004) Clin. Ther. 26(9):1446-1455). Thus, therapeutic agents having more balanced SERT and NET affinity or slightly higher NET affinity are expected to be particularly useful for treating chronic pain while producing fewer side effects, such as nausea.

Thus, a need exists for novel compounds that are useful for treating chronic pain, such as neuropathic pain. In particular, a need exists for novel compounds that are useful for treating chronic pain and that have reduced side effects, such as nausea.

A need also exists for novel dual-acting compounds that inhibit both SERT and NET. In particular, a need exists for novel dual-acting compounds that have high affinity for NET (e.g., $pK_i \geq 8.0$ or $K_i \leq 10$ nM). Especially needed are novel dual-acting compounds that have high affinity for NET and which also have a relatively balanced affinity for SERT relative to NET (e.g., a SERT/NET binding $K_i$ ratio of 0.1 to 100), or which have higher affinity for NET relative to SERT.

SUMMARY OF THE INVENTION

The present invention provides novel compounds that have been found to possess serotonin reuptake inhibitory activity and norepinephrine reuptake inhibitory activity. Accordingly, compounds of the invention are expected to be useful and advantageous as therapeutic agents for those diseases and disorders that can be treated by inhibition of the serotonin and/or norepinephrine transporter, such as neuropathic pain.

One aspect of the invention relates to a compound of formula I:

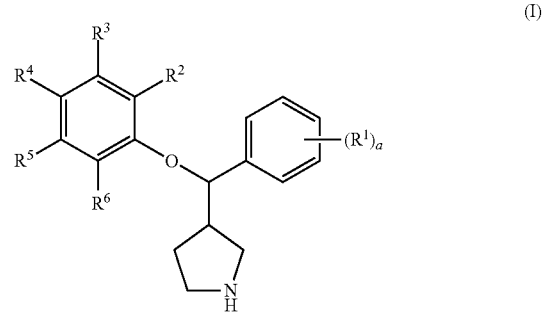

where:

a is 0 to 5;

each $R^1$ is independently selected from halo, —$C_{1-6}$alkyl, —$C_{2-6}$alkynyl, —O—$C_{1-6}$alkyl, —$C_{1-4}$alkylene-O—$C_{1-4}$alkyl, —$C_{0-1}$alkylene-phenyl, —O—$C_{0-3}$alkylene-phenyl, —$C_{0-6}$alkylene-OH, —CN, —$C_{0-2}$alkylene-COOH, —CHO, —C(O)—$C_{1-6}$alkyl, —C(O)O—$C_{1-4}$alkyl, —$CH_2SH$, —S—$C_{1-6}$alkyl, —$C_{1-4}$alkylene-S—$C_{1-4}$alkyl, —$SO_2$—$C_{1-6}$alkyl, —$SO_2NR^aR^b$, —$NHSO_2R^a$, —$C_{0-1}$alkylene-$NR^aR^b$, —NHC(O)—$C_{1-6}$alkyl, —C(O)$NR^aR^b$, and —$NO_2$;

$R^2$ through $R^6$ are independently selected from H, halo, —$C_{1-6}$alkyl, —$C_{2-6}$alkynyl, —O—$C_{1-6}$alkyl, —$C_{1-4}$alkylene-O—$C_{1-4}$alkyl, —$C_{0-1}$alkylene-phenyl, —O—$C_{0-3}$alkylene-phenyl, —$C_{0-6}$alkylene-OH, —CN, —$C_{0-2}$alkylene-COOH, —CHO, —C(O)—$C_{1-6}$alkyl, —C(O)O—$C_{1-4}$alkyl, —$CH_2SH$, —S—$C_{1-6}$alkyl, —$C_{1-4}$alkylene-S—$C_{1-4}$alkyl, —$SO_2$—$C_{1-6}$alkyl, —$SO_2NR^aR^b$, —$NHSO_2R^a$, —$C_{0-1}$alkylene-$NR^aR^b$, —NHC(O)—$C_{1-6}$alkyl, —C(O)$NR^aR^b$, and —$NO_2$;

$R^a$ and $R^b$ are independently H or —$C_{1-4}$alkyl;

each alkyl in $R^1$ through $R^6$ is optionally substituted with 1 to 5 fluoro atoms; and each phenyl in $R^1$ through $R^6$ is optionally substituted with 1 or 2 groups independently selected from halo, —$C_{1-6}$alkyl, and —O—$C_{1-6}$alkyl;

or a pharmaceutically acceptable salt thereof.

Another aspect of the invention relates to compounds of formula I having a configuration selected from:

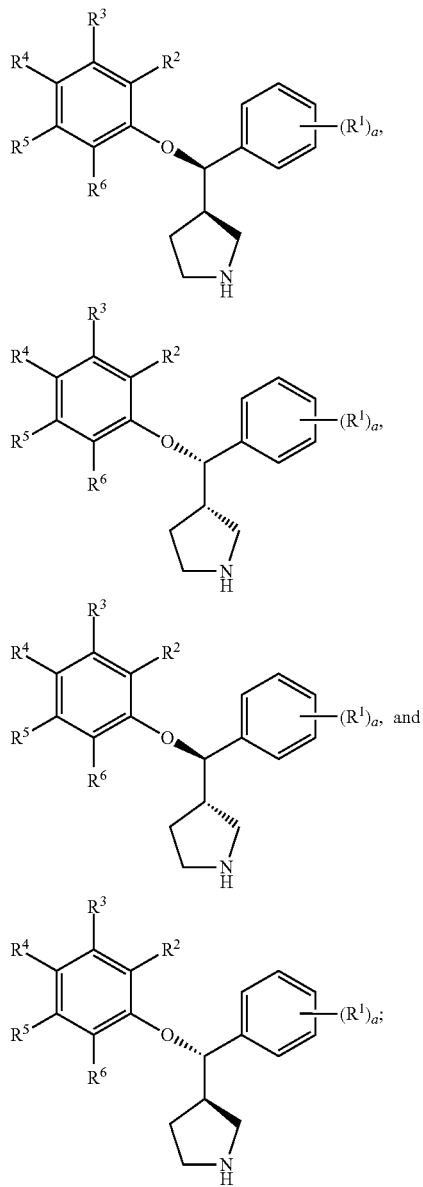

or enriched in a stereoisomeric form having such configuration.

Yet another aspect of the invention relates to pharmaceutical compositions comprising a pharmaceutically acceptable carrier and a compound of the invention. Such compositions may optionally contain other active agents such as anti-Alzheimer's agents, anticonvulsants, antidepressants, anti-Parkinson's agents, dual serotonin-norepinephrine reuptake inhibitors, non-steroidal anti-inflammatory agents, norepinephrine reuptake inhibitors, opioid agonists, selective serotonin reuptake inhibitors, sodium channel blockers, sympatholytics, and combinations thereof. Accordingly, in yet another aspect of the invention, a pharmaceutical composition comprises a compound of the invention, a second active agent, and a pharmaceutically acceptable carrier. Another aspect of the invention relates to a combination of active agents, comprising a compound of the invention and a second active agent. The compound of the invention can be formulated together or separately from the additional agent(s). When formulated separately, a pharmaceutically acceptable carrier may be included with the additional agent(s). Thus, yet another aspect of the invention relates to a combination of pharmaceutical compositions, the combination comprising: a first pharmaceutical composition comprising a compound of formula I or a pharmaceutically acceptable salt thereof and a first pharmaceutically acceptable carrier; and a second pharmaceutical composition comprising a second active agent and a second pharmaceutically acceptable carrier. The invention also relates to a kit containing such pharmaceutical compositions, for example where the first and second pharmaceutical compositions are separate pharmaceutical compositions.

Compounds of the invention possess serotonin reuptake inhibitory activity and norepinephrine reuptake inhibitory activity, and are therefore expected to be useful as therapeutic agents for treating patients suffering from a disease or disorder that is treated by the inhibition of the serotonin and/or the norepinephrine transporter. Thus, one aspect of the invention relates to a method of treating: a pain disorder such as neuropathic pain or fibromyalgia; a depressive disorder such as major depression; an affective disorder such as an anxiety disorder; attention deficit hyperactivity disorder; a cognitive disorder such as dementia; stress urinary incontinence; chronic fatigue syndrome; obesity; or vasomotor symptoms associated with menopause, comprising administering to a patient a therapeutically effective amount of a compound of the invention.

Still another aspect of the invention relates to a method for inhibiting serotonin reuptake in a mammal comprising administering to the mammal, a serotonin transporter-inhibiting amount of a compound of the invention. Yet another aspect of the invention relates to a method for inhibiting norepinephrine reuptake in a mammal comprising administering to the mammal, a norepinephrine transporter-inhibiting amount of a compound of the invention. And another aspect of the invention relates to a method for inhibiting serotonin reuptake and norepinephrine reuptake in a mammal comprising administering to the mammal, a serotonin transporter- and norepinephrine transporter-inhibiting amount of a compound of the invention.

Among the compounds of formula I, compounds of particular interest are those having an inhibitory constant ($pK_i$) at SERT greater than or equal to 7.5 and an inhibitory constant ($pK_i$) at NET greater than or equal to 7.0. In another embodiment, compounds of interest have balanced SERT and NET activity, i.e., have the same $pK_i$ value at both SERT and NET±0.5. Further compounds of particular interest are those having a serotonin reuptake inhibition $IC_{50}$ value of less than or equal to 100 nM and a norepinephrine reuptake inhibition $IC_{50}$ value of less than or equal to 100 nM.

Since compounds of the invention possess serotonin reuptake inhibitory activity and norepinephrine reuptake inhibitory activity, such compounds are also useful as research tools. Accordingly, one aspect of the invention relates to a method of using a compound of the invention as a research tool, comprising conducting a biological assay using a compound of the invention. Compounds of the invention can also be used to evaluate new chemical compounds. Thus another aspect of the invention relates to a method of evaluating a test compound in a biological assay, comprising: (a)

conducting a biological assay with a test compound to provide a first assay value; (b) conducting the biological assay with a compound of the invention to provide a second assay value; wherein step (a) is conducted either before, after or concurrently with step (b); and (c) comparing the first assay value from step (a) with the second assay value from step (b). Exemplary biological assays include a serotonin reuptake assay and a norepinephrine reuptake assay. Still another aspect of the invention relates to a method of studying a biological system or sample comprising serotonin transporters, norepinephrine transporters, or both, the method comprising: (a) contacting the biological system or sample with a compound of the invention; and (b) determining the effects caused by the compound on the biological system or sample.

The invention also relates to processes and intermediates useful for preparing compounds of the invention. Accordingly, one aspect of the invention relates to a process for preparing a compound of formula I, the process comprising deprotecting a compound of the formula:

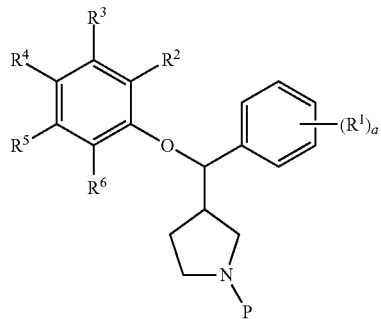

where P is an amino-protecting group to provide a compound of formula I, or a salt thereof. In other aspects, the invention relates to novel intermediates used in such processes. In one aspect of the invention, such novel intermediates have the formula of compound 8 or compound 8', as defined herein.

Another aspect of the invention relates to a process for preparing compound 2 or compound 2', which are intermediates useful for preparing compounds of the invention, comprising reacting compound 1 or compound 1' with sodium hypochlorite in the presence of 2,2,6,6-tetramethyl-1-piperidinyloxy, free radical (TEMPO) and potassium bromide in water; where compounds 1, 1', 2 and 2' are as defined herein.

Yet another aspect of the invention relates to the use of compounds of the invention for the manufacture of medicaments, especially for the manufacture of medicaments useful for treating pain disorders, depressive disorders, affective disorders, attention deficit hyperactivity disorder, cognitive disorders, stress urinary incontinence, for inhibiting serotonin reuptake in a mammal, or for inhibiting norepinephrine reuptake in a mammal. Still another aspect of the invention relates to the use of compounds of the invention as research tools. Other aspects and embodiments of the invention are disclosed herein.

BRIEF DESCRIPTION OF THE DRAWINGS

Various aspects of the present invention are illustrated by reference to the accompanying drawings.

DETAILED DESCRIPTION OF THE INVENTION

Definitions

Figure 1:
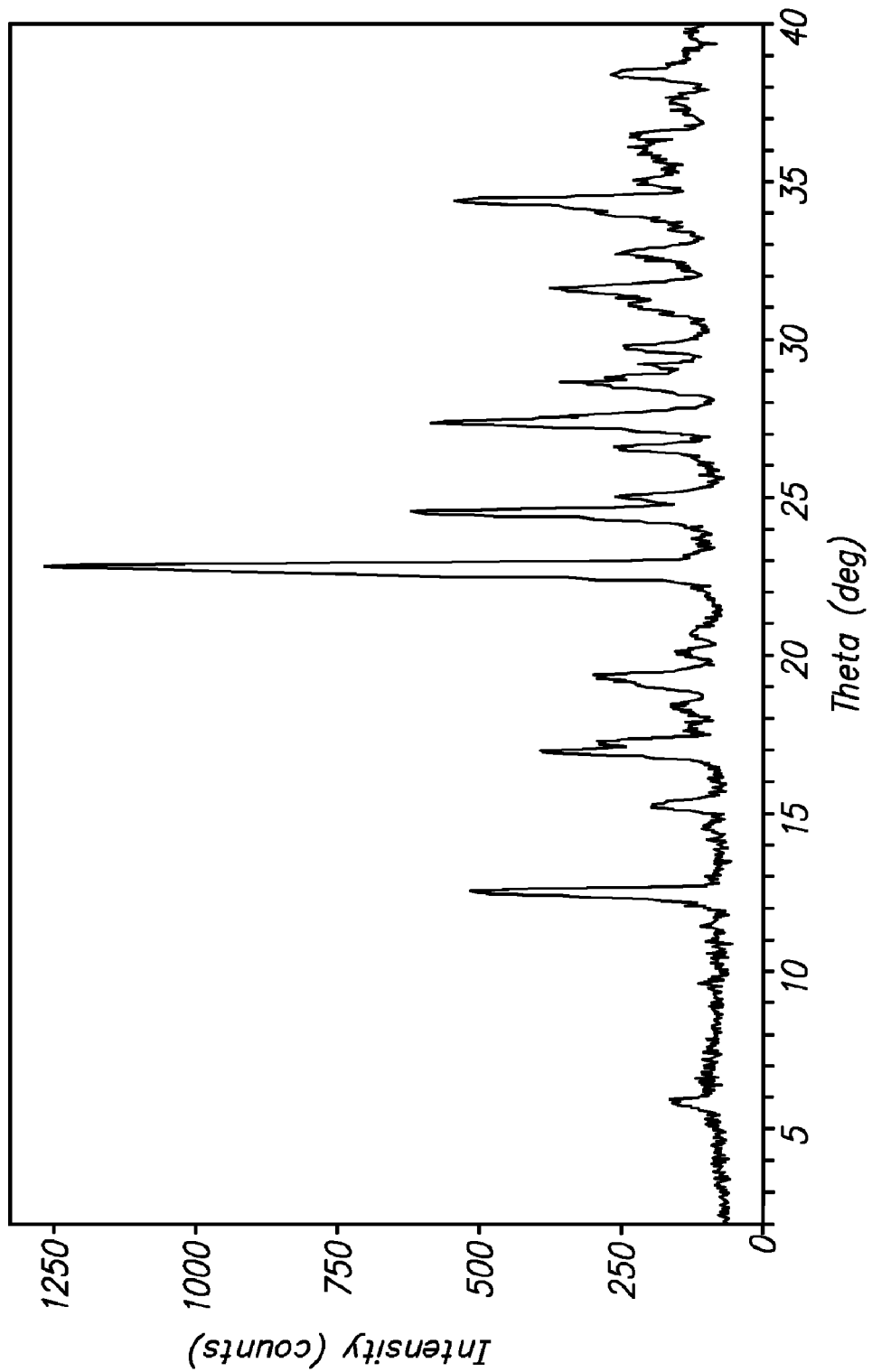
FIG. 1 shows a powder x-ray diffraction (PXRD) pattern of a crystalline monohydrochloride salt of the compound of Example 11, (S)-3-[(R)-(2,6-dichloro-3,5-difluorophenoxy)phenylmethyl]pyrrolidine.

When describing the compounds, compositions, methods and processes of the invention, the following terms have the following meanings unless otherwise indicated. Additionally, as used herein, the singular forms "a," "an" and "the" include the corresponding plural forms unless the context of use clearly dictates otherwise. The terms "comprising", "including," and "having" are intended to be inclusive and mean that there may be additional elements other than the listed elements. All numbers expressing quantities of ingredients, properties such as molecular weight, reaction conditions, and so forth used herein are to be understood as being modified in all instances by the term "about," unless otherwise indicated. Accordingly, the numbers set forth herein are approximations that may vary depending upon the desired properties sought to be obtained by the present invention. At least, and not as an attempt to limit the application of the doctrine of equivalents to the scope of the claims, each number should at least be construed in light of the reported significant digits and by applying ordinary rounding techniques.

The term "alkyl" means a monovalent saturated hydrocarbon group which may be linear or branched. Unless otherwise defined, such alkyl groups typically contain from 1 to 10 carbon atoms and include, for example, —$C_{1-2}$alkyl, —$C_{1-3}$alkyl, —$C_{1-4}$alkyl, —$C_{1-6}$alkyl, and —$C_{1-8}$alkyl. Representative alkyl groups include, by way of example, methyl, ethyl, n-propyl, isopropyl, n-butyl, sec-butyl, isobutyl, tent-butyl, n-pentyl, n-hexyl, n-heptyl, n-octyl, n-nonyl, n-decyl and the like.

When a specific number of carbon atoms is intended for a particular term used herein, the number of carbon atoms is shown preceding the term as subscript. For example, the term "—$C_{1-6}$alkyl" means an alkyl group having from 1 to 6 carbon atoms, and the term "—$C_{1-4}$alkylene" means an alkylene group having from 1 to 4 carbon atoms, where the carbon atoms are in any acceptable configuration.

The term "alkylene" means a divalent saturated hydrocarbon group that may be linear or branched. Unless otherwise defined, such alkylene groups typically contain from 0 to 10 carbon atoms and include, for example, —$C_{0-1}$alkylene, —$C_{0-2}$alkylene, —$C_{0-3}$alkylene, —$C_{0-6}$alkylene, —$C_{1-4}$alkylene, —$C_{2-4}$alkylene and —$C_{1-6}$alkylene. Representative alkylene groups include, by way of example, methylene, ethane-1,2-diyl ("ethylene"), propane-1,2-diyl, propane-1,3-diyl, butane-1,4-diyl, pentane-1,5-diyl and the like. It is understood that when the alkylene term includes zero carbons such as —$C_{0-1}$alkylene-, —$C_{0-3}$alkylene- or —$C_{0-6}$alkylene-, such terms are intended to include the absence of carbon atoms, i.e., the alkylene group is not present except for a covalent bond attaching the groups separated by the alkylene term.

The term "alkynyl" means a monovalent unsaturated hydrocarbon group which may be linear or branched and which has at least one, and typically 1, 2 or 3, carbon-carbon triple bonds. Unless otherwise defined, such alkynyl groups typically contain from 2 to 10 carbon atoms and include, for example, —$C_{2-4}$alkynyl, —$C_{2-6}$alkynyl and —$C_{3-10}$alkynyl. Representative alkynyl groups include, by way of example, ethynyl, n-propynyl, n-but-2-ynyl, n-hex-3-ynyl and the like.

The term "halo" means fluoro, chloro, bromo and iodo.

The term "pharmaceutically acceptable" refers to a material that is not biologically or otherwise unacceptable when used in the invention. For example, the term "pharmaceutically acceptable carrier" refers to a material that can be incorporated into a composition and administered to a patient without causing unacceptable biological effects or interacting in an unacceptable manner with other components of the composition. Such pharmaceutically acceptable materials typically have met the required standards of toxicological and manufacturing testing, and include those materials identified as suitable inactive ingredients by the U.S. Food and Drug Administration.

The term "pharmaceutically acceptable salt" means a salt prepared from a base or an acid which is acceptable for administration to a patient, such as a mammal (e.g., salts having acceptable mammalian safety for a given dosage regime). However, it is understood that the salts covered by the invention are not required to be pharmaceutically acceptable salts, such as salts of intermediate compounds that are not intended for administration to a patient. Pharmaceutically acceptable salts can be derived from pharmaceutically acceptable inorganic or organic bases and from pharmaceutically acceptable inorganic or organic acids. In addition, when a compound of formula I contains both a basic moiety, such as an amine, and an acidic moiety such as a carboxylic acid, zwitterions may be formed and are included within the term "salt" as used herein. Salts derived from pharmaceutically acceptable inorganic bases include ammonium, calcium, copper, ferric, ferrous, lithium, magnesium, manganic, manganous, potassium, sodium, and zinc salts, and the like. Salts derived from pharmaceutically acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable inorganic acids include salts of boric, carbonic, hydrohalic (hydrobromic, hydrochloric, hydrofluoric or hydroiodic), nitric, phosphoric, sulfamic and sulfuric acids. Salts derived from pharmaceutically acceptable organic acids include salts of aliphatic hydroxyl acids (e.g., citric, gluconic, glycolic, lactic, lactobionic, malic, and tartaric acids), aliphatic monocarboxylic acids (e.g., acetic, butyric, formic, propionic and trifluoroacetic acids), amino acids (e.g., aspartic and glutamic acids), aromatic carboxylic acids (e.g., benzoic, p-chlorobenzoic, diphenylacetic, gentisic, hippuric, and triphenylacetic acids), aromatic hydroxyl acids (e.g., o-hydroxybenzoic, p-hydroxybenzoic, 1-hydroxynaphthalene-2-carboxylic and 3-hydroxynaphthalene-2-carboxylic acids), ascorbic, dicarboxylic acids (e.g., fumaric, maleic, oxalic and succinic acids), glucoronic, mandelic, mucic, nicotinic, orotic, pamoic, pantothenic, sulfonic acids (e.g., benzenesulfonic, camphosulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, and the like.

The term "solvate" means a complex or aggregate formed by one or more molecules of a solute, e.g., a compound of formula I or a pharmaceutically acceptable salt thereof, and one or more molecules of a solvent. Such solvates are typically crystalline solids having a substantially fixed molar ratio of solute and solvent. Representative solvents include, by way of example, water, methanol, ethanol, isopropanol, acetic acid and the like. When the solvent is water, the solvate formed is a hydrate.

The term "therapeutically effective amount" means an amount sufficient to effect treatment when administered to a patient in need thereof, i.e., the amount of drug needed to obtain the desired therapeutic effect. For example, a therapeutically effective amount for treating neuropathic pain is an amount of compound needed to, for example, reduce, suppress, eliminate or prevent the symptoms of neuropathic pain or to treat the underlying cause of neuropathic pain. On the other hand, the term "effective amount" means an amount sufficient to obtain a desired result, which may not necessary be a therapeutic result. For example, when studying a system comprising a norepinephrine transporter, an "effective amount" may be the amount needed to inhibit norepinephrine reuptake.

The term "treating" or "treatment" as used herein means the treating or treatment of a disease or medical condition (such as neuropathic pain) in a patient, such as a mammal (particularly a human), that includes: (a) preventing the disease or medical condition from occurring, i.e., prophylactic treatment of a patient; (b) ameliorating the disease or medical condition, i.e., eliminating or causing regression of the disease or medical condition in a patient; (c) suppressing the disease or medical condition, i.e., slowing or arresting the development of the disease or medical condition in a patient; or (d) alleviating the symptoms of the disease or medical condition in a patient. For example, the term "treating neuropathic pain" would include preventing neuropathic pain from occurring, ameliorating neuropathic pain, suppressing neuropathic pain, and alleviating the symptoms of neuropathic pain. The term "patient" is intended to include those mammals, such as humans, that are in need of treatment or disease prevention, that are presently being treated for disease prevention or treatment of a specific disease or medical condition, as well as test subjects in which compounds of the invention are being evaluated or being used in a assay, for example an animal model.

All other terms used herein are intended to have their ordinary meaning as understood by those of ordinary skill in the art to which they pertain.

In one aspect, this invention relates to novel compounds of formula I:

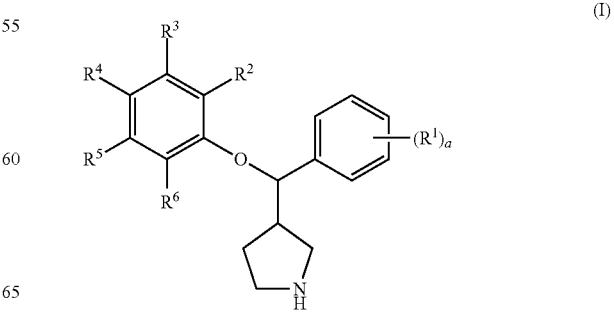

(I)

or a pharmaceutically acceptable salt thereof.

As used herein, the term "compound of the invention" includes all compounds encompassed by formula I such as the species embodied in formula Ia-Id, II-XXI, II'-XXI' and all other subspecies of such formulas. In addition, when the compound of the invention contain a basic or acidic group (e.g., amino or carboxyl groups), the compound can exist as a free base, free acid, or in various salt forms. All such salt forms are included within the scope of the invention. Accordingly, those skilled in the art will recognize that reference to a compound herein, for example, reference to a "compound of the invention" or a "compound of formula I" includes a compound of formula I as well as pharmaceutically acceptable salts of that compound unless otherwise indicated. Furthermore, solvates of compounds of formula I are included within the scope of this invention.

The compounds of formula I contain at least two chiral centers and therefore, these compounds may be prepared and used in various stereoisomeric forms. Accordingly, the invention also relates to racemic mixtures, pure stereoisomers (e.g., enantiomers and diastereoisomers), stereoisomer-enriched mixtures, and the like unless otherwise indicated. When a chemical structure is depicted herein without any stereochemistry, it is understood that all possible stereoisomers are encompassed by such structure. Thus, for example, the terms "compound of formula I," "compounds of formula II," and so forth, are intended to include all possible stereoisomers of the compound. Similarly, when a particular stereoisomer is shown or named herein, it will be understood by those skilled in the art that minor amounts of other stereoisomers may be present in the compositions of the invention unless otherwise indicated, provided that the utility of the composition as a whole is not eliminated by the presence of such other isomers. Individual enantiomers may be obtained by numerous methods that are well known in the art, including chiral chromatography using a suitable chiral stationary phase or support, or by chemically converting them into diastereoisomers, separating the diastereoisomers by conventional means such as chromatography or recrystallization, then regenerating the original enantiomers. Additionally, where applicable, all cis-trans or E/Z isomers (geometric isomers), tautomeric forms and topoisomeric forms of the compounds of the invention are included within the scope of the invention unless otherwise specified.

More specifically, compounds of formula I contain at least two chiral centers indicated by the symbols * and ** in the following formula:

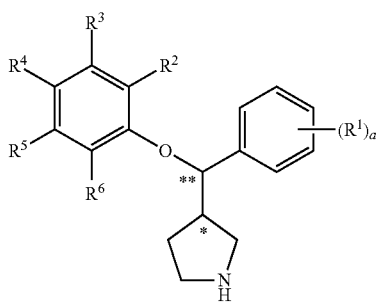

In one stereoisomer, both carbon atoms identified by the * and ** symbols have the (R) configuration. This embodiment of the invention is shown in formula Ia:

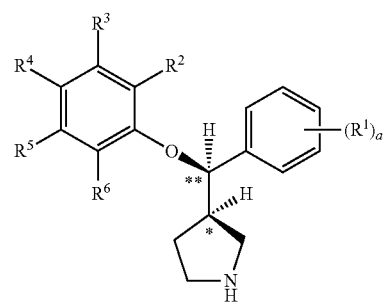

(Ia)

In this embodiment, compounds have the (R,R) configuration at the * and ** carbon atoms or are enriched in a stereoisomeric form having the (R,R) configuration at these carbon atoms.

In another stereoisomer, both carbon atoms identified by the * and ** symbols have the (S) configuration. This embodiment of the invention is shown in formula Ib:

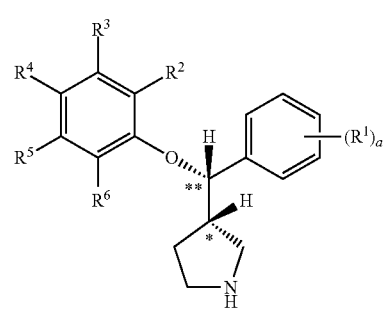

(Ib)

In this embodiment, compounds have the (S,S) configuration at the * and ** carbon atoms or are enriched in a stereoisomeric form having the (S,S) configuration at these carbon atoms.

In yet another stereoisomer, the carbon atom identified by the symbol * has the (S) configuration and the carbon atom identified by the symbol ** has the (R) configuration. This embodiment of the invention is shown in formula Ic:

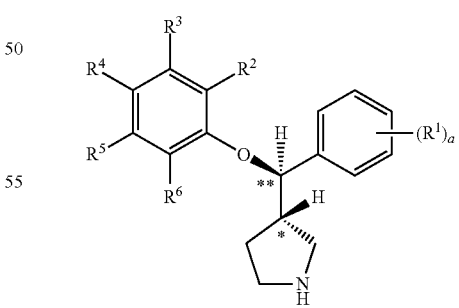

(Ic)

In this embodiment, compounds have the (S,R) configuration at the * and ** carbon atoms or are enriched in a stereoisomeric form having the (S,R) configuration at these carbon atoms.

In still another stereoisomer, the carbon atom identified by the symbol * has the (R) configuration and the carbon atom identified by the symbol ** has the (S) configuration. This embodiment of the invention is shown in formula Id:

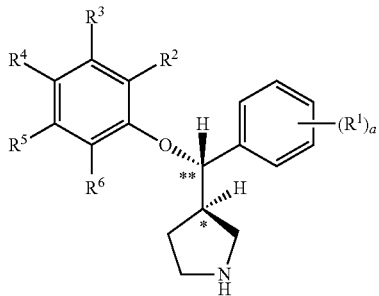

(Id)

In this embodiment, compounds have the (R,S) configuration at the * and ** carbon atoms or are enriched in a stereoisomeric form having the (R,S) configuration at these carbon atoms.

Compounds of formula Ia and Ib are enantiomers and therefore, in separate aspects, this invention relates to each individual enantiomer (i.e., Ia or Ib), a racemic mixture of Ia and Ib, or an enantiomer-enriched mixture of Ia and Ib comprising predominately Ia or predominately Ib. Similarly, compounds of formula Ic and Id are enantiomers and therefore, in separate aspects, this invention relates to each individual enantiomer (i.e., Ic or Id), a racemic mixture of Ic and Id, or a enantiomer-enriched mixture of Ic and Id comprising predominately Ic or predominately Id.

In some embodiments, in order to optimize the therapeutic activity of the compounds of the invention, e.g., to treat neuropathic pain, it may be desirable that the carbon atoms identified by the * and ** symbols have a particular (R,R), (S,S), (S,R), or (R,S) configuration or are enriched in a stereoisomeric form having such configuration. For example, in one embodiment, the compounds of the invention have the (S,R) configuration of formula Ic or are enriched in a stereoisomeric form having the (S,R) configuration, and in another embodiment, the compounds of the invention have the (R,S) configuration of formula Id, or are enriched in a stereoisomeric form having the (R,S) configuration. In other embodiments, the compounds of the invention are present as racemic mixtures, for example as a mixture of enantiomers of formula Ia and Ib, or as a mixture of enantiomers of formula Ic and Id.

The compounds of the invention, as well as those compounds used in their synthesis, may also include isotopically-labeled compounds, i.e., where one or more atoms have been enriched with atoms having an atomic mass different from the atomic mass predominately found in nature. Examples of isotopes that may be incorporated into the compounds of formula I, for example, include, but are not limited to, $^2$H, $^3$H, $^{13}$C, $^{14}$C, $^{15}$N, $^{18}$O, $^{17}$O, $^{35}$S, $^{36}$Cl, and $^{18}$F. Of particular interest are compounds of formula I enriched in tritium or carbon-14 which can be used, for example, in tissue distribution studies; compounds of formula I enriched in deuterium especially at a site of metabolism resulting, for example, in compounds having greater metabolic stability; and compounds of formula I enriched in a positron emitting isotope, such as $^{11}$C, $^{18}$F, $^{15}$O and $^{13}$N, which can be used, for example, in Positron Emission Topography (PET) studies.

The compounds of the invention have been found to possess serotonin reuptake inhibitory activity and norepinephrine reuptake inhibitory activity. Among other properties, such compounds are expected to be useful as therapeutic agents for treating chronic pain, such as neuropathic pain. By combining dual activity into a single compound, double therapy can be achieved, i.e., serotonin reuptake inhibitory activity and norepinephrine reuptake inhibitory activity, using a single active component. Since pharmaceutical compositions containing one active component are typically easier to formulate than compositions containing two active components, such single-component compositions provide a significant advantage over compositions containing two active components.

Many combined serotonin and norepinephrine reuptake inhibitors (SNRIs) are more selective for SERT than for NET. For example, milnacipran, duloxetine, and venlafaxine and exhibit 2.5-fold, 10-fold, and 100-fold selectivity (measured as $pK_i$) for SERT over NET, respectively. Some, however, are less selective, such as bicifadine, which has a $pK_i$ at SERT of 7.0 and a $pK_i$ at NET of 6.7. Since it may be desirable to avoid selective compounds, in one embodiment of the invention the compounds have a more balanced SERT and NET activity, i.e., have the same $pK_i$ value at both SERT and NET±0.5.

The nomenclature used herein to name the compounds of the invention is illustrated in the Examples herein. This nomenclature has been derived using the commercially-available AutoNom software (MDL, San Leandro, Calif.). Typically, compounds of formula I, have been named as 3-(phenoxyphenylmethyl)pyrrolidines.

Representative Embodiments

The following substituents and values are intended to provide representative examples of various aspects and embodiments of the invention. These representative values are intended to further define and illustrate such aspects and embodiments and are not intended to exclude other embodiments or to limit the scope of the invention. In this regard, the representation that a particular value or substituent is preferred is not intended in any way to exclude other values or substituents from the invention unless specifically indicated.

In one aspect, this invention relates to compounds of formula I:

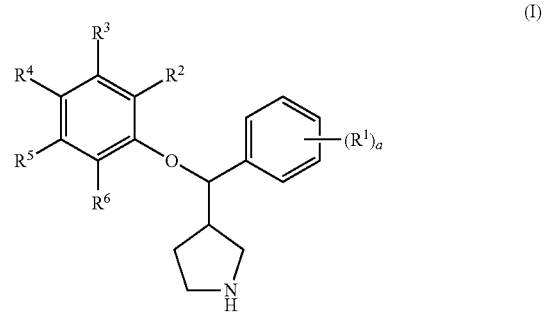

(I)

The integer a can be 0, 1, 2, 3, 4 or 5. In one particular embodiment, a is 0, 1 or 2.

Each $R^1$ is independently selected from halo, —$C_{1-6}$alkyl, —$C_{2-6}$alkynyl, —O—$C_{1-6}$alkyl, —$C_{1-4}$alkylene-O—$C_{1-4}$alkyl, —$C_{0-1}$alkylene-phenyl, —O—$C_{0-3}$alkylene-phenyl, —$C_{0-6}$alkylene-OH, —CN, —$C_{0-2}$alkylene-COOH, —CHO, —C(O)—$C_{1-6}$alkyl, —C(O)O—$C_{1-4}$alkyl, —$CH_2SH$, —S—$C_{1-6}$alkyl, —$C_{1-4}$alkylene-S—$C_{1-4}$alkyl, —$SO_2$—$C_{1-6}$alkyl, —$SO_2NR^aR^b$, —$NHSO_2R^a$, —$C_{0-1}$alkylene-$NR^aR^b$, —NHC(O)—$C_{1-6}$alkyl, —C(O)$NR^aR^b$, and —$NO_2$. Further, each alkyl group in $R^1$ is optionally substituted with 1 to 5 fluoro atoms. In addition, each phenyl group in $R^1$ may be substituted with 1 or 2 groups independently selected from halo, —$C_{1-6}$alkyl, and —O—$C_{1-6}$alkyl.

$R^2$ through $R^6$ are independently selected from H, halo, —$C_{1-6}$alkyl, —$C_{2-6}$alkynyl, —O—$C_{1-6}$alkyl, —$C_{1-4}$alkylene-O—$C_{1-4}$alkyl, —$C_{0-1}$alkylene-phenyl, —O—$C_{0-3}$alkylene-phenyl, —$C_{0-6}$alkylene-OH, —CN, —$C_{0-2}$alkylene-COOH, —CHO, —C(O)—$C_{1-6}$alkyl, —C(O)O—$C_{1-4}$alkyl, —$CH_2SH$, —S—$C_{1-6}$alkyl, —$C_{1-4}$alkylene-S—$C_{1-4}$alkyl, —$SO_2$—$C_{1-6}$alkyl, —$SO_2NR^aR^b$, —$NHSO_2R^a$, —$C_{0-1}$alkylene-$NR^aR^b$, —NHC(O)—$C_{1-6}$alkyl, —C(O)$NR^aR^b$, and —$NO_2$. Further, each alkyl group in $R^2$ through $R^6$ may be substituted with 1 to 5 fluoro atoms. In addition, each phenyl group in $R^2$ through $R^6$ may be substituted with 1 or 2 groups independently selected from halo, —$C_{1-6}$alkyl, and —O—$C_{1-6}$alkyl.

The $R^a$ and $R^b$ groups are independently H or —$C_{1-4}$alkyl. It is understood that when referring to "each alkyl" group in $R^1$ or in $R^{2-6}$, the term also includes any alkyl groups that might be present in the $R^a$ and $R^b$ moieties.

In some embodiments of the invention, one or more positions on the aryl ring are substituted with a non-hydrogen moiety. For example, one such embodiment may be described by stating that that "$R^2$ is a non-hydrogen moiety". It is understood that this means that $R^2$ can be any of the non-hydrogen moieties defined in formula I, i.e., halo, —$C_{1-6}$alkyl, —$C_{2-6}$alkynyl, —O—$C_{1-6}$alkyl, —$C_{1-4}$alkylene-O—$C_{1-4}$alkyl, —$C_{0-1}$alkylene-phenyl, —O—$C_{0-3}$alkylene-phenyl, —$C_{0-6}$alkylene-OH, —CN, —$C_{0-2}$alkylene-COOH, —CHO, —C(O)—$C_{1-6}$alkyl, —C(O)O—$C_{1-4}$alkyl, —$CH_2SH$, —S—$C_{1-6}$alkyl, —$C_{1-4}$alkylene-S—$C_{1-4}$alkyl, —$SO_2$—$C_{1-6}$alkyl, —$SO_2NR^aR^b$, —$NHSO_2R^a$, —$C_{0-1}$alkylene-$NR^aR^b$, —NHC(O)—$C_{1-6}$alkyl, —C(O)$NR^aR^b$, and —$NO_2$.

Exemplary halo groups include fluoro, chloro, bromo, and iodo. Exemplary —$C_{1-6}$alkyl groups include —$CH_3$, —$CH_2CH_3$, and —$CH(CH_3)_2$, as well as fluoro-substituted —$C_{1-6}$alkyl groups such as —$CF_3$. Exemplary —$C_{2-6}$alkynyl groups include —CH=$CH_2$. Exemplary —O—$C_{1-6}$alkyl groups include —$OCH_3$, —O—$CH_2CH_3$, and —OCH$(CH_3)_2$, as well as fluoro-substituted —O—$C_{1-6}$alkyl groups such as —$OCF_3$. Exemplary —$C_{1-4}$alkylene-O—$C_{1-4}$alkyl groups include —$CH_2$—$OCH_3$ and —$CH_2$—$OCH_2CH_3$. Exemplary —$C_{0-1}$alkylene-phenyl groups include phenyl and benzyl. Exemplary —O—$C_{0-3}$alkylene-phenyl groups include —O-phenyl and —O-benzyl. As noted above, each phenyl group in $R^1$ and $R^2$ through $R^6$ may be substituted with 1 or 2 groups independently selected from halo, —$C_{1-6}$alkyl, and —O—$C_{1-6}$alkyl. Examples of such substituted —O—$C_{0-3}$ alkylene-phenyl groups include —O-2,4-dichlorophenyl, —O-3-chlorophenyl, —O-3-ethylphenyl, —O-4-ethylphenyl, —O-2-ethoxyphenyl, and —O-4-ethoxyphenyl. Exemplary —$C_{0-6}$alkylene-OH groups include —OH and —$CH_2OH$. Exemplary —$C_{0-2}$alkylene-COOH groups include —COOH. Exemplary —C(O)—$C_{1-6}$alkyl groups include —C(O)$CH_3$ and —C(O)$CH_2CH_3$. Exemplary —C(O)O—$C_{1-4}$alkyl groups include —C(O)$OCH_3$, —C(O)$OCH_2CH_3$, and —C(O)$OCH(CH_3)_2$. Exemplary —S—$C_{1-6}$alkyl groups include —$SCH_3$. Exemplary —$C_{1-4}$alkylene-S—$C_{1-4}$alkyl groups include —$CH_2$—S—$CH_3$. Exemplary —$SO_2$—$C_{1-6}$alkyl groups include —$SO_2CH_3$. Exemplary —$SO_2NR^aR^b$ groups include —$SO_2NH_2$ and —$SO_2N(CH_3)_2$. Exemplary —$NHSO_2R^a$ groups include —$NHSO_2H$ and —$NHSO_2CH_3$. Exemplary —$C_{0-1}$alkylene-$NR^aR^b$ groups include —$NH_2$, —$N(CH_3)_2$, —$CH_2NH(CH_2CH_3)$, and —$CH_2N(CH_3)(CH_2CH_3)$. Exemplary —NHC(O)—$C_{1-6}$alkyl groups include —NHC(O)$CH_3$ and —NHC(O)$CH_2CH_3$. Exemplary —C(O)$NR^aR^b$ groups include —$CONH_2$, —CONH($CH_2CH_3$), and —C(O)N($CH_3$)$CH_2CH_3$.

In one embodiment, a is 1, and $R^1$ is halo, —$C_{1-6}$alkyl, —O—$C_{1-6}$alkyl optionally substituted with 1 to 5 fluoro atoms, —$C_{0-6}$alkylene-OH, —CN, —$C_{0-2}$alkylene-COOH, —CHO, —C(O)O—$C_{1-4}$alkyl or —C(O)$NR^aR^b$. In one particular embodiment, the $R^1$ group is at the 2 or 3 position. In another embodiment, a is 2, and each $R^1$ is independently halo, —$C_{1-6}$alkyl optionally substituted with 1 to 5 fluoro atoms, or —$SO_2$—$C_{1-6}$alkyl. In another embodiment, a is 2, one $R^1$ group is halo, and the other $R^1$ group is halo, —$C_{1-6}$ alkyl optionally substituted with 1 to 5 fluoro atoms, or —$SO_2$—$C_{1-6}$alkyl. In one particular embodiment, the $R^1$ groups are at the 3 and 5 positions.

In one embodiment, $R^2$ is: H; halo; —$C_{1-6}$alkyl optionally substituted with 1 to 3 fluoro atoms; —O—$C_{1-6}$alkyl optionally substituted with 1 to 3 fluoro atoms; —$C_{0-1}$alkylene-phenyl optionally substituted with 1 to 2 halo atoms; —O—$C_{0-3}$alkylene-phenyl; —$C_{0-6}$alkylene-OH; —CN; —C(O)—$C_{1-6}$alkyl; —C(O)O—$C_{1-4}$alkyl; —S—$C_{1-6}$alkyl; —$SO_2$—$C_{1-6}$alkyl; or —$NO_2$.

In one embodiment, $R^3$ is: H; halo; —$C_{1-6}$alkyl optionally substituted with 1 to 3 fluoro atoms; —O—$C_{1-6}$alkyl optionally substituted with 1 to 3 fluoro atoms; —O—$C_{0-3}$alkylene-phenyl optionally substituted with 1 halo, —$C_{1-6}$alkyl, or —O—$C_{1-6}$alkyl group; or —$NO_2$.

In one embodiment, $R^4$ is: H; halo; —$C_{1-6}$alkyl optionally substituted with 1 to 5 fluoro atoms; —O—$C_{1-6}$alkyl optionally substituted with 1 to 5 fluoro atoms; —$C_{0-1}$alkylene-phenyl; —O—$C_{0-3}$alkylene-phenyl; —$SO_2$—$C_{1-6}$alkyl; —C(O)$NH_2$; or —$NO_2$.

In one embodiment, $R^5$ is H, halo, or —$C_{1-6}$alkyl.

In one embodiment, $R^6$ is H, halo, —$C_{1-6}$alkyl, or —O—$C_{1-6}$alkyl.

In one embodiment, $R^2$ through $R^6$ are H. In one particular embodiment, a is 0, which can be depicted as formula II:

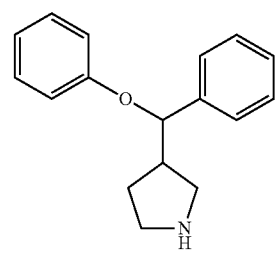

(II)

In another particular embodiment, a is 1 to 5, and $R^1$ is as defined for formula I, which can be depicted as formula II':

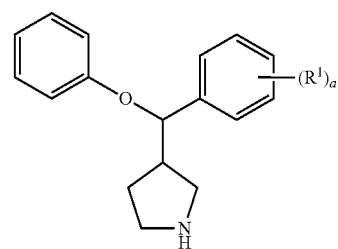

(II')

In one particular embodiment, a is 1 and $R^1$ is halo, —$C_{1-6}$alkyl, —O—$C_{1-6}$alkyl, —$C_{0-6}$alkylene-OH, or —CHO. In another embodiment, $R^1$ is 2-F, 3-Cl, 3-CH$_3$, 3-OCH$_3$, 3-OCF$_3$, 3-CH$_2$OH, or 3-CHO. In yet another embodiment, $R^1$ is 3-CHO.

In another embodiment, $R^2$ is a non-hydrogen moiety as defined for formula I, and $R^3$ through $R^6$ are H. In one particular embodiment, a is 0, which can be depicted as formula III:

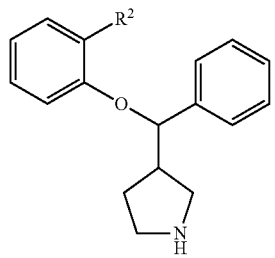

(III)

In one particular embodiment, $R^2$ is halo, —$C_{1-6}$alkyl, —O—$C_{1-6}$alkyl, —$C_{0-1}$alkylene-phenyl, —O—$C_{0-3}$alkylene-phenyl, —$C_{0-6}$alkylene-OH, —C(O)—$C_{1-6}$alkyl, —C(O)O—$C_{1-4}$alkyl, —S—$C_{1-6}$alkyl, —SO$_2$—$C_{1-6}$alkyl, or —NO$_2$; where each alkyl is optionally substituted with 1 to 5 fluoro atoms, and each phenyl is optionally substituted with 1 or 2 groups independently selected from halo. In yet another embodiment, $R^2$ is F, Cl, Br, I, —CH$_3$, —CH$_2$CH$_3$, —CH(CH$_3$)$_2$, —CF$_3$, —OCH$_3$, —O—CH$_2$CH$_3$, —OCH(CH$_3$)$_2$, —OCF$_3$, -phenyl, —CH$_2$-phenyl, —O-benzyl, —C(O)CH$_3$, —C(O)CH$_2$CH$_3$, or —NO$_2$. In still another embodiment, $R^2$ is F, Cl, Br, —CH$_2$CH$_3$, —CH(CH$_3$)$_2$, —CF$_3$, —OCH(CH$_3$)$_2$, —OCF$_3$, —CH$_2$-phenyl, or —O-benzyl. In another particular embodiment, a is 1 to 5, and $R^1$ is as defined for formula I, which can be depicted as formula III':

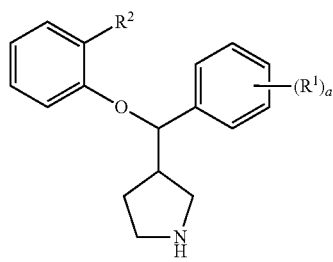

(III')

In one particular embodiment, a is 1 or 2; $R^1$ is halo, —$C_{1-6}$alkyl optionally substituted with 1 to 5 fluoro atoms, —O—$C_{1-6}$alkyl optionally substituted with 1 to 5 fluoro atoms, —$C_{0-6}$alkylene-OH, —CN, —SO$_2$—$C_{1-6}$alkyl, or —C(O)NR$^a$R$^b$; $R^2$ is halo, —$C_{1-6}$alkyl, —O—$C_{1-6}$alkyl, or —$C_{0-1}$alkylene-phenyl. In other embodiments: $R^2$ is halo, a is 1, and $R^1$ is halo, —$C_{1-6}$alkyl optionally substituted with 1 to 5 fluoro atoms, or —O—$C_{1-6}$alkyl optionally substituted with 1 to 5 fluoro atoms; or $R^2$ is —$C_{1-6}$alkyl, a is 1, and $R^1$ is halo or —O—$C_{1-6}$alkyl optionally substituted with 1 to 5 fluoro atoms; or $R^2$ is —O—$C_{1-6}$alkyl, a is 1 or 2, and each $R^1$ is independently halo, —$C_{1-6}$alkyl optionally substituted with 1 to 5 fluoro atoms, —O—$C_{1-6}$alkyl optionally substituted with 1 to 5 fluoro atoms, —$C_{0-6}$alkylene-OH, —CN, —SO$_2$—$C_{1-6}$alkyl, or —C(O)NR$^a$R$^b$; or $R^2$ is —$C_{0-1}$alkylene-phenyl, a is 2, and each $R^1$ is independently halo. In other embodiments: $R^2$ is halo, a is 1, and $R^1$ is halo, —$C_{1-6}$alkyl, or —O—$C_{1-6}$alkyl; or $R^2$ is —$C_{1-6}$alkyl, a is 1, and $R^1$ is halo or —O—$C_{1-6}$alkyl; or $R^2$ is —O—$C_{1-6}$alkyl, a is 1 or 2, and each $R^1$ is independently halo, —$C_{1-6}$alkyl, —O—$C_{1-6}$alkyl optionally substituted with 1 to 5 fluoro atoms, —$C_{0-6}$alkylene-OH, —CN, or —CONH$_2$. In additional embodiments: $R^2$ is Cl, a is 1, and $R^1$ is 2-Cl, 3-Cl, 3-F, 3-CH$_3$, or 3-OCH$_3$; or $R^2$ is —CH(CH$_3$)$_2$, a is 1, and $R^1$ is 3-Cl, 3-F, or 3-OCH$_3$; or $R^2$ is —OCH$_3$, a is 1, and $R^1$ is 2-Cl, 3-Cl, 3-F, 4-Cl, 2-OCF$_3$, 3-CH$_2$OH, 3-CN, 3-CONH$_2$, or 4-CN; or $R^2$ is —OCH$_3$, a is 2, one $R^1$ is 3-F and the other $R^1$ is 5-F, 5-Cl, or 5-CH$_3$.

In another embodiment, $R^3$ is a non-hydrogen moiety as defined for formula I, and $R^2$ and $R^4$ through $R^6$ are H. In one particular embodiment, a is 0, which can be depicted as formula IV:

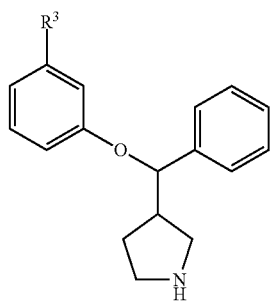

(IV)

In one particular embodiment, $R^3$ is: halo; —$C_{1-6}$alkyl optionally substituted with 1 to 5 fluoro atoms; —O—$C_{1-6}$alkyl optionally substituted with 1 to 5 fluoro atoms; —O—$C_{0-3}$alkylene-phenyl optionally substituted with a halo, —$C_{1-6}$alkyl, or —O—$C_{1-6}$alkyl group; or —NO$_2$. In another embodiment, the —O—$C_{0-3}$alkylene-phenyl group is optionally substituted with 3-Cl, 3-ethyl, 4-ethyl, 2-ethoxy, or 4-ethoxy. In yet another embodiment, $R^3$ is: halo; —$C_{1-6}$alkyl; or —O-phenyl optionally substituted with a halo group. In another embodiment, $R^3$ is: F; Cl; Br; I; —CH$_3$; or —O-phenyl optionally substituted with 3-Cl, 4-F, or 4-Cl. In yet another embodiment, $R^3$ is F. In another embodiment, a is 1 to 5, and $R^1$ is as defined for formula I, which can be depicted as formula IV':

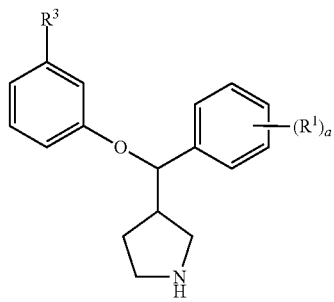

(IV')

In one particular embodiment, $R^3$ is halo; a is 1 and is halo, —$C_{1-6}$alkyl, or —O—$C_{1-6}$alkyl optionally substituted with 1 to 5 fluoro atoms; or a is 2 and $R^1$ is independently halo or —SO$_2$—$C_{1-6}$alkyl. In other embodiments: $R^3$ is Cl, a is 1, and $R^1$ is 3-Cl, 2-F, 3-F, 2-CH$_3$, 3-CH$_3$, 3-OCH$_3$, or 3-OCF$_3$; or $R^3$ is F, a is 2, one $R^1$ is 3-$SO_2CH_3$ and the other $R^1$ is 5-F. In yet another embodiment, $R^3$ is Cl and $R^1$ is 3-Cl or 3-F.

In another embodiment, $R^4$ is a non-hydrogen moiety as defined for formula I, and $R^2$, $R^3$, $R^5$, and $R^6$ are H. In one particular embodiment, a is 0, which can be depicted as formula V:

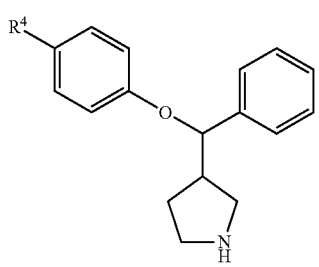

(V)

In one particular embodiment, $R^4$ is: halo; —$C_{1-6}$alkyl optionally substituted with 1 to 5 fluoro atoms; —O—$C_{1-6}$alkyl optionally substituted with 1 to 5 fluoro atoms; —$C_{0-1}$alkylene-phenyl; —O—$C_{0-3}$alkylene-phenyl; —$SO_2$—$C_{1-6}$lkyl; or —C(O)$NR^aR^b$. In yet another embodiment, $R^4$ is —Cl, —$CH_3$, or —O-benzyl. In another embodiment, a is 1 to 5, and $R^1$ is as defined for formula I, which can be depicted as formula V':

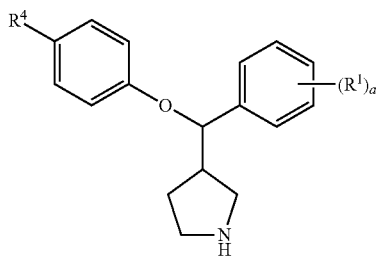

(V')

In one particular embodiment, $R^4$ is halo; a is 1; and $R^1$ is halo, —$C_{1-6}$alkyl, or —O—$C_{1-6}$alkyl optionally substituted with 1 to 5 fluoro atoms.

In another embodiment, $R^2$ and $R^3$ are non-hydrogen moieties as defined for formula I, and $R^4$ through $R^6$ are H. In one particular embodiment, a is 0, which can be depicted as formula VI:

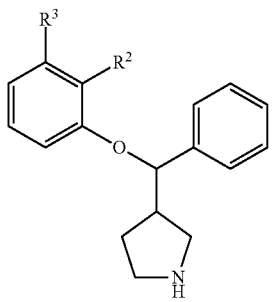

(VI)

In one particular embodiment, $R^2$ is halo, —$C_{1-6}$alkyl, —O—$C_{1-6}$alkyl, —CN, —C(O)—$C_{1-6}$alkyl, or —C(O)O—$C_{1-4}$alkyl; and $R^3$ is halo, —$C_{1-6}$alkyl optionally substituted with 1 to 5 fluoro atoms, —O—$C_{1-6}$alkyl, or —O—$C_{0-3}$alkylene-phenyl. In other embodiments: $R^2$ is halo, and $R^3$ is halo, —$C_{1-6}$alkyl optionally substituted with 1 to 5 fluoro atoms, or —O—$C_{0-3}$alkylene-phenyl; or $R^2$ is —$C_{1-6}$alkyl and $R^3$ is halo or —$C_{1-6}$alkyl; or $R^2$ is —O—$C_{1-6}$alkyl and $R^3$ is halo, —O—$C_{1-6}$alkyl, or —$C_{1-6}$alkyl optionally substituted with 1 to 5 fluoro atoms; or $R^2$ is —CN, —C(O)—$C_{1-6}$alkyl, or —C(O)O—$C_{1-4}$alkyl, and $R^3$ is halo. In yet other embodiments: $R^2$ is halo and $R^3$ is halo or —O—$C_{0-3}$alkylene-phenyl; or $R^2$ is —$C_{1-6}$alkyl and $R^3$ is halo or —$C_{1-6}$alkyl; or $R^2$ is —O—$C_{1-6}$alkyl and $R^3$ is halo; or $R^2$ is —C(O)—$C_{1-6}$alkyl and $R^3$ is F; or $R^2$ is —C(O)O—$C_{1-4}$alkyl, and $R^3$ is halo. In other embodiments: $R^2$ is Cl and $R^3$ is F, Cl or —O-phenyl; or $R^2$ is F and $R^3$ is F, Cl or —O-phenyl; or $R^2$ is —$CH_3$, and $R^3$ is F, Cl, or —$CH_3$; or $R^2$ is —$OCH_3$ and $R^3$ is F; or $R^2$ is —C(O)$CH_3$ and $R^3$ is F; or $R^2$ is —C(O)$OCH_3$ and $R^3$ is F. In yet another embodiment, $R^2$ is —$OCH_3$ and $R^3$ is F. In another embodiment, a is 1 to 5, and $R^1$ is as defined for formula I, which can be depicted as formula VI':

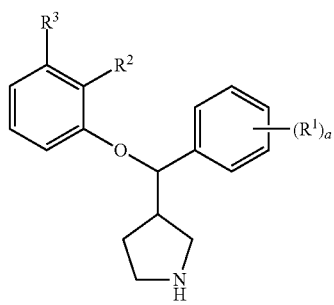

(VI')

In another particular embodiment, $R^2$ and $R^3$ are independently halo; a is 1 and $R^1$ is halo, —$C_{1-6}$alkyl, or —O—$C_{1-6}$alkyl optionally substituted with 1 to 5 fluoro atoms; or a is 2, and each $R^1$ is independently halo or —$SO_2$—$C_{1-6}$alkyl. In other embodiments: $R^2$ and $R^3$ are Cl, a is 1, and $R^1$ is 2-F, 3-F, 3-Cl, 2-$CH_3$, 3-$CH_3$, 3-$OCH_3$, or 3-$OCF_3$; or $R^2$ is Cl, $R^3$ is F, a is 2, one $R^1$ is 3-$SO_2CH_3$ and the other $R^1$ is 5-F. In another embodiment, $R^2$ and $R^3$ are Cl, a is 1, and $R^1$ is 2-F, 3-Cl, or 3-$OCH_3$.

In another embodiment, $R^2$ and $R^4$ are non-hydrogen moieties as defined for formula I, and $R^3$, $R^5$ and $R^6$ are H. In one particular embodiment, a is 0, which can be depicted as formula VII:

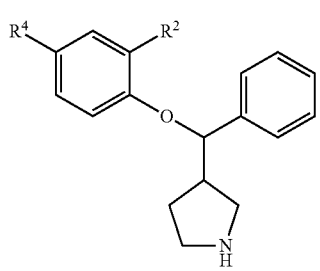

(VII)

In one particular embodiment, $R^2$ is halo, —$C_{1-6}$alkyl optionally substituted with 1 to 5 fluoro atoms, —O—$C_{1-6}$alkyl, —C(O)—$C_{1-6}$alkyl, or —$NO_2$; and $R^4$ is halo, —$C_{1-6}$alkyl, or —$NO_2$. In other embodiments: $R^2$ and $R^4$ are independently halo; or $R^2$ is halo and $R^4$ is halo, —$C_{1-6}$alkyl, or —NO$_2$; or R$^2$ is —C$_{1-6}$alkyl optionally substituted with 1 to 5 fluoro atoms and R$^4$ is halo; or R$^2$ is —C$_{1-6}$alkyl and R$^4$ is —NO$_2$; or R$^2$ is —O—C$_{1-6}$alkyl and R$^4$ is halo or —NO$_2$; or R$^2$ is —C(O)—C$_{1-6}$alkyl and R$^4$ is halo; or R$^2$ is —C(O)O—C$_{1-4}$alkyl and R$^4$ is halo; or R$^2$ is —NO$_2$ and R$^4$ is —C$_{1-6}$alkyl. In yet other embodiments: R$^2$ is halo and R$^4$ is halo or —C$_{1-6}$alkyl; or R$^2$ is —C$_{1-6}$alkyl or —O—C$_{1-6}$alkyl and R$^4$ is halo; or R$^2$ is —C$_{1-6}$alkyl substituted with 1 to 5 fluoro atoms and R$^4$ is Cl; or R$^2$ is —C(O)O—C$_{1-4}$alkyl and R$^4$ is halo; or R$^2$ is —NO$_2$ and R$^4$ is —C$_{1-6}$alkyl. In still other embodiments: R$^2$ is Cl and R$^4$ is Cl, F, or —CH$_3$; or R$^2$ is F and R$^4$ is F or Cl; or R$^2$ is —CH$_3$ and R$^4$ is F or Cl; R$^2$ is —CH$_2$CH$_3$ and R$^4$ is F; or R$^2$ is —O—CH$_3$ and R$^4$ is Cl or F; or R$^2$ is —CF$_3$ and R$^4$ is Cl; or R$^2$ is —C(O)OCH$_3$ or —C(O)OCH$_2$CH$_3$, and R$^4$ is Cl; or R$^2$ is —NO$_2$ and R$^4$ is —CH$_3$. In additional embodiments: R$^2$ is Cl and R$^4$ is F; or R$^2$ is —CH$_2$CH$_3$ and R$^4$ is F. In another embodiment, a is 1 to 5, and R$^1$ is as defined for formula I, which can be depicted as formula VII':

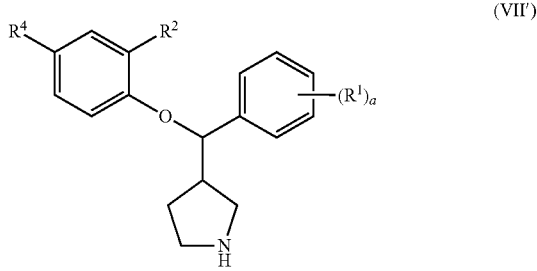

(VII')

In one particular embodiment, a is 1 or 2; each R$^1$ is independently halo, —C$_{1-6}$alkyl, —CN, or —SO$_2$—C$_{1-6}$alkyl; and R$^2$ and R$^4$ are independently halo, —C$_{1-6}$alkyl, —O—C$_{1-6}$alkyl, or —NO$_2$. In other embodiments: R$^2$ and R$^4$ are halo, a is 1, and R$^1$ is halo, —CN, or —SO$_2$—C$_{1-6}$alkyl; or R$^2$ and R$^4$ are halo, a is 2, and each R$^1$ is independently halo or —C$_{1-6}$alkyl; or R$^2$ is —O—C$_{1-6}$alkyl, R$^4$ is halo, a is 1, and R$^1$ is halo; or R$^2$ is —CH$_2$CH$_3$ or —OCH$_3$, R$^4$ is halo, a is 2, and each R$^1$ is independently halo; or R$^2$ is —O—C$_{1-6}$alkyl, R$^4$ is —NO$_2$, a is 1, and R$^1$ is halo or —C$_{1-6}$alkyl. In other embodiments: R$^2$ and R$^4$ are F, a is 1, and R$^1$ is 2-SO$_2$CH$_3$ or 4-SO$_2$CH$_3$; R$^2$ is F, R$^4$ is Cl, a is 1, and R$^1$ is 2-Cl, 4-F, 4-Cl, 3-CN, or 4-CN; or R$^2$ is F, R$^4$ is Cl, a is 2, one R$^1$ is 3-F and the other R$^1$ is 5-F, 5-Cl, or 5-CH$_3$; or R$^2$ is F, R$^4$ is Cl, a is 2, one R$^1$ is 3-CH$_3$ and the other R$^1$ is 5-CH$_3$; or R$^2$ is —OCH$_3$, R$^4$ is F, a is 1, and R$^1$ is 2-Cl; or R$^2$ is —CH$_2$CH$_3$, R$^4$ is F, a is 2, one R$^1$ is 3-F and the other R$^1$ is 5-F; or R$^2$ is —OCH$_3$, R$^4$ is F or Cl, a is 2, one R$^1$ is 3-F and the other R$^1$ is 5-F; or R$^2$ is —OCH$_3$, R$^4$ is —NO$_2$, a is 1, and R$^1$ is 3-Cl or 3-CH$_3$. In yet other embodiments: R$^2$ and R$^4$ are halo, a is 1, and R$^1$ is —CN; or R$^2$ and R$^4$ are halo, a is 2, and each R$^1$ is independently halo or —C$_{1-6}$alkyl; or R$^2$ is —C$_{1-6}$alkyl or —O—C$_{1-6}$alkyl, R$^4$ is halo, a is 2, each R$^1$ is independently halo. In other embodiments: R$^2$ is F, R$^4$ is Cl, a is 1, and R$^1$ is 3-CN; or R$^2$ is F, R$^4$ is Cl, a is 2, one R$^1$ is 3-F and the other R$^1$ is 5-F, 5-Cl, or 5-CH$_3$; or R$^2$ is —CH$_2$CH$_3$, R$^4$ is F, a is 2, one R$^1$ is 3-F and the other R$^1$ is 5-F; or R$^2$ is —OCH$_3$, R$^4$ is F or Cl, a is 2, one R$^1$ is 3-F and the other R$^1$ is 5-F.

In another embodiment, R$^2$ and R$^5$ are non-hydrogen moieties as defined for formula I, and R$^3$, R$^4$ and R$^6$ are H. In one particular embodiment, a is 0, which can be depicted as formula VIII:

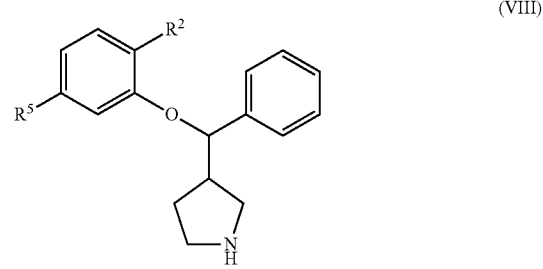

(VIII)

In one particular embodiment, R$^2$ is halo, —C$_{1-6}$alkyl, —O—C$_{1-6}$alkyl, —CN, —C(O)—C$_{1-6}$alkyl, or —C(O)O—C$_{1-4}$alkyl; and R$^5$ is halo, —C$_{1-6}$alkyl, or —O—C$_{1-6}$alkyl. In other embodiments: R$^2$ is halo and R$^5$ is halo or —C$_{1-6}$alkyl; or R$^2$ is —C$_{1-6}$alkyl and R$^5$ is halo; or R$^2$ is —O—C$_{1-6}$alkyl or —CN, and R$^5$ is halo; or R$^2$ is —O—C$_{1-6}$alkyl and R$^5$ is —C$_{1-6}$alkyl; or R$^2$ is —C(O)—C$_{1-6}$alkyl and R$^5$ is halo or —O—C$_{1-6}$alkyl; or R$^2$ is —C(O)O—C$_{1-4}$alkyl and R$^5$ is halo. In yet other embodiments: R$^2$ is halo and R$^5$ is halo or —C$_{1-6}$alkyl; or R$^2$ is —C$_{1-6}$alkyl or —O—C$_{1-6}$alkyl and R$^5$ is halo; or R$^2$ is —O—C$_{1-6}$alkyl and R$^5$ is —C$_{1-6}$alkyl. In other embodiments: R$^2$ is F and R$^5$ is F, Cl, Br, or —CH$_3$; or R$^2$ is Cl and R$^5$ is F or Cl; or R$^2$ is —CH$_3$ and R$^5$ is F or Cl; or R$^2$ is —O—CH$_3$ and R$^5$ is F, Cl, or —CH$_3$. In additional embodiments: R$^2$ is F and R$^5$ is F; R$^2$ is Cl and R$^5$ is F or Cl; or R$^2$ is —O—CH$_3$ and R$^5$ is F. In another embodiment, a is 1 to 5, and R$^1$ is as defined for formula I, which can be depicted as formula VIII':

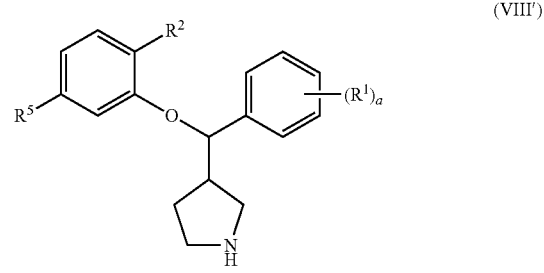

(VIII')

In one particular embodiment, a is 1 or 2; each R$^1$ is independently halo —C$_{1-6}$alkyl, or —O—C$_{1-6}$alkyl, where —O—C$_{1-6}$alkyl is optionally substituted with 1 to 5 fluoro atoms; R$^2$ is halo or —O—C$_{1-6}$alkyl; and R$^5$ is halo. In other embodiments: R$^2$ is F or Cl, R$^5$ is Cl, a is 2 and each R$^1$ is F; or R$^2$ is —O—CH$_3$, R$^5$ is Cl; a is 1, and R$^1$ is Cl, 2-F, 3-F, 3-CH$_3$, 3-OCH$_3$ or 3-OCF$_3$; or R$^2$ is —O—CH$_3$, R$^5$ is F, a is 2, and each R$^1$ is F. In yet another embodiment, R$^2$ is F or Cl, R$^5$ is Cl, a is 2, and each R$^1$ is F; or R$^2$ is —O—CH$_3$, R$^5$ is Cl, a is 1, and R$^1$ is Cl; or R$^2$ is —O—CH$_3$, R$^5$ is F, a is 2, and each R$^1$ is F. In another embodiment, R$^2$ is F or Cl, R$^5$ is Cl, a is 2, one R$^1$ is 3-F and one R$^1$ is 5-F; or R$^2$ is —O—CH$_3$, R$^5$ is Cl, a is 1 and R$^1$ is 3-Cl; or R$^2$ is —O—CH$_3$, R$^5$ is F, a is 2, one R$^1$ is 3-F and the other R$^1$ is 5-F.

In another embodiment, R$^2$ and R$^6$ are non-hydrogen moieties as defined for formula I, and R$^3$, R$^4$ and R$^5$ are H. In one particular embodiment, a is 0, which can be depicted as formula IX:

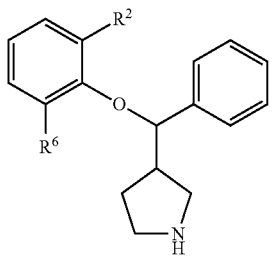

(IX)

In one particular embodiment, $R^2$ is halo, —$C_{1-6}$alkyl, —O—$C_{1-6}$alkyl, or —C(O)O—$C_{1-4}$alkyl; and $R^6$ is halo or —$C_{1-6}$alkyl. In other embodiments: $R^2$ is F and $R^6$ is F, Cl, or —CH$_3$; $R^2$ is Cl and $R^6$ is F or Cl; or $R^2$ is —CH$_3$ and $R^6$ is Cl or —CH$_2$CH$_3$; or $R^2$ is —OCH$_3$ and $R^6$ is F; or $R^2$ is —C(O)OCH$_3$ and $R^6$ is Cl. In yet other embodiments: $R^2$ is halo, —$C_{1-6}$alkyl, or —O—$C_{1-6}$alkyl, and $R^6$ is halo; or $R^2$ is halo and $R^6$ is —$C_{1-6}$alkyl; or $R^2$ is —C(O)O—$C_{1-4}$alkyl and $R^6$ is halo. In other embodiments: $R^2$ is F or Cl and $R^6$ is F or Cl; or $R^2$ is F and $R^6$ is —CH$_3$; or $R^2$ is —CH$_3$ and $R^6$ is Cl; or $R^2$ is —OCH$_3$ and $R^6$ is F; or $R^2$ is —C(O)OCH$_3$ and $R^6$ is Cl. In additional embodiments: $R^2$ is F or Cl and $R^6$ is F or Cl. In another embodiment, a is 1 to 5, and each $R^1$ is as defined for formula I, which can be depicted as formula IX':

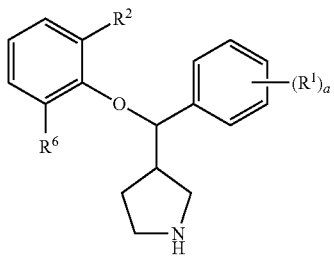

(IX')

In one particular embodiment, a is 1 or 2; each $R^1$ is independently halo, —$C_{1-6}$alkyl, —O—$C_{1-6}$alkyl optionally substituted with 1 to 5 fluoro atoms, —CN, —SO$_2$—$C_{1-6}$alkyl, or —C(O)NH$_2$; $R^2$ is halo; and $R^6$ is halo or —O—$C_{1-6}$alkyl. In other embodiments: $R^2$ and $R^6$ are halo, a is 1, and $R^1$ is halo, —$C_{1-6}$alkyl, —O—$C_{1-6}$alkyl optionally substituted with 1 to 5 fluoro atoms, —CN, —SO$_2$—$C_{1-6}$alkyl, or —C(O)NH$_2$; or $R^2$ and $R^6$ are halo, a is 2, one $R^1$ is halo, and the other $R^1$ is halo or —$C_{1-6}$alkyl; or $R^2$ is halo and $R^6$ is —O—$C_{1-6}$alkyl, a is 1 or 2, and each $R^1$ is independently halo. In yet other embodiments: $R^2$ and $R^6$ are Cl, a is 1 and $R^1$ is halo, —$C_{1-6}$alkyl, —O—$C_{1-6}$alkyl, —CN, or —C(O)NR$^a$R$^b$, where R$^a$ and R$^b$ are H; or $R^2$ and $R^6$ are Cl, a is 2, one $R^1$ is halo and the other $R^1$ is halo or —$C_{1-6}$alkyl; or $R^2$ is F, $R^6$ is Cl, a is 2, and $R^1$ is independently halo; or $R^2$ is F and $R^6$ is —OCH$_3$, a is 1 or 2, and each $R^1$ is independently halo. In other embodiments: $R^2$ and $R^6$ are Cl, a is 1 and $R^1$ is 2-Cl, 3-Cl, 4-Cl, 4-F, 3-CH$_3$, 3-OCH$_3$, 3-CN, 4-CN, 3-C(O)NH$_2$, or 4-C(O)NH$_2$; or $R^2$ and $R^6$ are Cl, a is 2, one $R^1$ is 3-F, and the other $R^1$ is 5-F, 5-Cl, or 5-CH$_3$; or $R^2$ is F, $R^6$ is Cl, a is 2, one $R^1$ is 3-F and the other $R^1$ is 5-F; or $R^2$ is F, $R^6$ is —OCH$_3$, a is 1, and $R^1$ is 2-Cl; or $R^2$ is F, $R^6$ is —OCH$_3$, a is 1, and $R^1$ is 2-Cl; or $R^2$ is F, $R^6$ is —OCH$_3$, a is 2, one $R^1$ is 3-F and the other $R^1$ is 5-F.

In another embodiment, $R^3$ and $R^4$ are non-hydrogen moieties as defined for formula I, and $R^2$, $R^5$ and $R^6$ are H. In one particular embodiment, a is 0, which can be depicted as formula X:

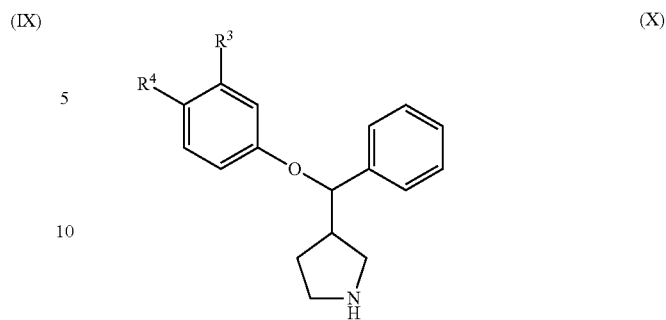

(X)

In one particular embodiment, $R^3$ is halo, —$C_{1-6}$alkyl optionally substituted with 1 to 5 fluoro atoms, or —O—$C_{1-6}$alkyl; and $R^4$ is halo, —$C_{1-6}$alkyl, or —O—$C_{1-6}$alkyl. In other embodiments: $R^3$ is halo and $R^4$ is halo or —$C_{1-6}$alkyl; or $R^3$ is —$C_{1-6}$alkyl optionally substituted with 1 to 5 fluoro atoms and $R^4$ is halo; or $R^3$ is —O—$C_{1-6}$alkyl and $R^4$ is halo or —O—$C_{1-6}$alkyl. In yet other embodiments, $R^3$ is halo and $R^4$ is —$C_{1-6}$alkyl. In other embodiments: $R^3$ is F and $R^4$ is —CH$_3$. In another embodiment, a is 1 to 5, and each $R^1$ is as defined for formula I, which can be depicted as formula X':

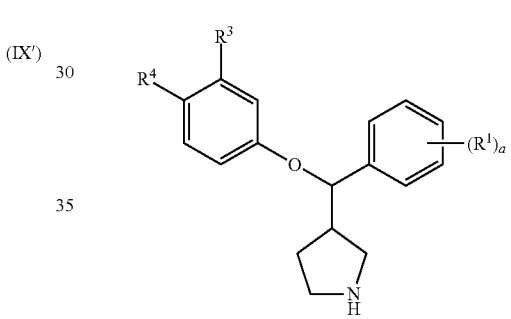

(X')

In another embodiment, $R^3$ and $R^5$ are non-hydrogen moieties as defined for formula I, and $R^2$, $R^4$ and $R^6$ are H. In one embodiment, a is 0, which can be depicted as formula XI:

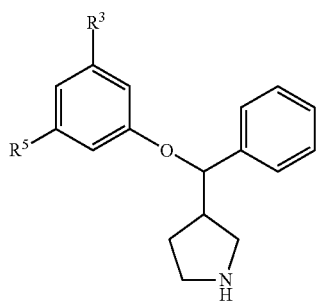

(XI)

In one particular embodiment, $R^3$ and $R^5$ are independently halo or —$C_{1-6}$alkyl. In other embodiments: $R^3$ is F and $R^5$ is F, Cl or —CH$_3$; or $R^3$ is Cl and $R^5$ is Cl or Br; or $R^3$ and $R^5$ are —CH$_3$. In yet another embodiment, $R^3$ and $R^5$ are independently halo. In other embodiments: $R^3$ and $R^5$ are independently F or Cl. In another embodiment, $R^3$ and $R^5$ are F. In another embodiment, a is 1 to 5 and each $R^1$ is as defined for formula I, which can be depicted as formula XI':

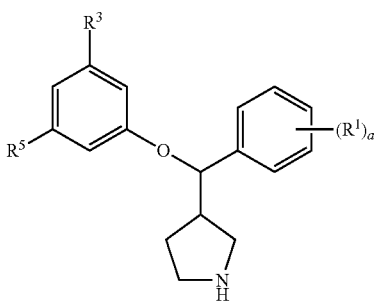

(XI′)

In one particular embodiment, $R^3$ and $R^5$ are independently halo; a is 1 or 2; each $R^1$ is independently halo, —$C_{1-6}$alkyl, or —O—$C_{1-6}$alkyl. In other embodiments: $R^3$ and $R^5$ are Cl, a is 1 and $R^1$ is 2-Cl, 3-Cl, 4-Cl, 2-F, 3-F, 4-F, 2-$CH_3$, 3-$CH_3$, 4-$CH_3$, or 3-$OCH_3$, or a is 2, one $R^1$ is 3-F and the other $R^1$ is 5-F, 5-Cl or 5-$CH_3$; or $R^3$ and $R^5$ are F, a is 1, and $R^1$ is 2-Cl. In another embodiment, $R^3$ and $R^5$ are Cl, a is 1, and $R^1$ is 2-Cl, 4-F, or 4-$CH_3$; or a is 2; one $R^1$ is 3-F and the other $R^1$ is 5-F, 5-Cl or 5-$CH_3$.

In another embodiment, $R^2$, $R^3$, and $R^4$ are non-hydrogen moieties as defined for formula I, and $R^5$ and $R^6$ are H. In one particular embodiment, a is 0, which can be depicted as formula XII:

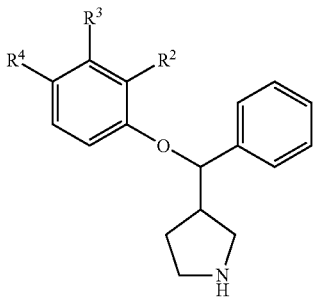

(XII)

In one particular embodiment, $R^2$ is halo or —C(O)—$C_{1-6}$alkyl; $R^3$ is halo, —$C_{1-6}$alkyl, or —O—$C_{1-6}$alkyl; and $R^4$ is halo or —$C_{1-6}$alkyl. In other embodiments: $R^2$, $R^3$ and $R^4$ are independently halo; or $R^2$ and $R^3$ are independently halo, and $R^4$ is —$C_{1-6}$alkyl; or $R^2$ and $R^4$ are independently halo, and $R^3$ is —$C_{1-6}$alkyl. In another embodiment, $R^2$, $R^3$ and $R^4$ are F; or $R^2$ is F, $R^3$ is F, and $R^4$ is Cl or —$CH_3$; or $R^2$ is F, $R^3$ is —$CH_3$, and $R^4$ is F; or $R^2$ and $R^4$ are Cl and $R^3$ is F. In another embodiment, a is 1 to 5 and each $R^1$ is as defined for formula I, which can be depicted as formula XII′:

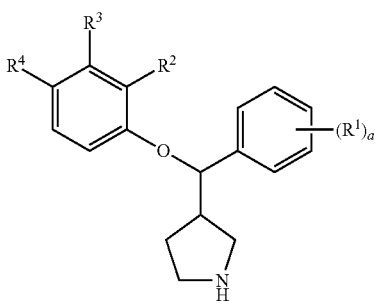

(XII′)

In one particular embodiment, a is 1 or 2; and $R^1$, $R^2$, $R^3$, and $R^4$ are independently halo. In other embodiments: $R^2$, $R^3$, and $R^4$ are F, a is 1 and $R^1$ is 2-halo, or a is 2, one $R^1$ is 3-halo and the other $R^1$ is 5-halo. In yet another embodiment, $R^2$, $R^3$, and $R^4$ are F, a is 2, one $R^1$ is 3-halo and the other $R^1$ is 5-halo. In another embodiment, $R^2$, $R^3$, and $R^4$ are F, a is 2, one $R^1$ is 3-F and the other $R^1$ is 5-F.

In another embodiment, $R^2$, $R^3$, and $R^5$ are non-hydrogen moieties as defined for formula I, and $R^4$ and $R^6$ are H. In one particular embodiment, a is 0, which can be depicted as formula XIII:

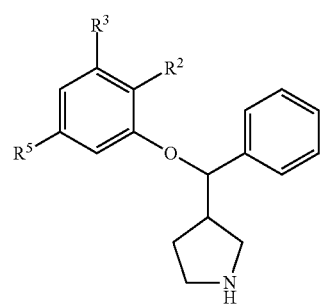

(XIII)

In one particular embodiment, $R^2$ is halo, —O—$C_{1-6}$alkyl, or —C(O)—$C_{1-6}$alkyl; $R^3$ is halo; and $R^5$ is halo or —$C_{1-6}$alkyl optionally substituted with 1 to 5 fluoro atoms. In other embodiments: $R^2$, $R^3$, and $R^5$ are independently halo; or $R^2$ is —O—$C_{1-6}$alkyl or —C(O)—$C_{1-6}$alkyl, and $R^3$ and $R^4$ are independently halo; or $R^2$ and $R^3$ are independently halo, and $R^5$ is —$C_{1-6}$alkyl optionally substituted with 1 to 5 fluoro atoms. In other embodiments: $R^2$, $R^3$, and $R^5$ are F; or $R^2$, $R^3$, and $R^5$ are Cl; or $R^2$ is Cl, $R^3$ is F, and $R^4$ is Cl; or $R^2$ is —O—$CH_3$, $R^3$ is F, and $R^4$ is F. In another embodiment, a is 1 to 5 and each $R^1$ is as defined for formula I, which can be depicted as formula XIII′:

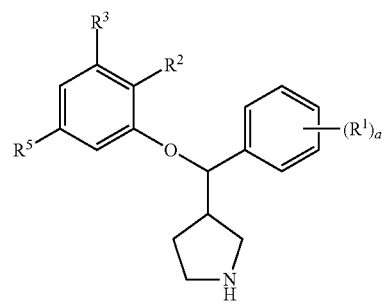

(XIII′)

In one particular embodiment, a is 1 or 2; and each $R^1$, $R^2$, $R^3$, and $R^5$ are independently halo. In other embodiments: $R^2$, $R^3$, and $R^5$ are F, a is 1, and $R^1$ is 2-Cl; or $R^2$, $R^3$, and $R^5$ are F, a is 2, one $R^1$ is 3-F and the other $R^1$ is 5-F; or $R^2$, $R^3$, and $R^5$ are Cl, a is 1, and $R^1$ is 2-Cl or 4-Cl; or $R^2$, $R^3$, and $R^5$ are Cl, a is 2, one $R^1$ is 3-F and the other $R^1$ is 5-F. In yet other embodiments: $R^2$, $R^3$, and $R^5$ are F, a is 1, and $R^1$ is 2-Cl; or $R^2$, $R^3$, and $R^5$ are F, a is 2, one $R^1$ is 3-F and the other $R^1$ is 5-F; or $R^2$, $R^3$, and $R^5$ are Cl, a is 1, and $R^1$ is 2-Cl; or $R^2$, $R^3$, and $R^5$ are Cl, a is 2, one $R^1$ is 3-F and the other $R^1$ is 5-F.

In another embodiment, $R^2$, $R^3$, and $R^6$ are non-hydrogen moieties as defined for formula I, and $R^4$ and $R^5$ are H. In one particular embodiment, a is 0, which can be depicted as formula XIV:

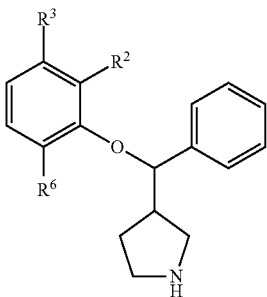

(XIV)

In one particular embodiment, $R^2$ is halo, —C(O)—$C_{1-6}$alkyl, or —C(O)O—$C_{1-4}$alkyl; $R^3$ is halo, —$C_{1-6}$alkyl, or —O—$C_{1-6}$alkyl; and $R^6$ is halo, —$C_{1-6}$alkyl, or —O—$C_{1-6}$alkyl. In yet another embodiment, $R^2$ is halo, $R^3$ is halo, and $R^6$ is halo or —O—$C_{1-6}$alkyl; or $R^2$ is halo, $R^3$ is —$C_{1-6}$alkyl or —O—$C_{1-6}$alkyl, and $R^6$ is halo; or $R^2$ is —C(O)—$C_{1-6}$alkyl, $R^3$ is halo, and $R^6$ is —$C_{1-6}$alkyl; or $R^2$ is —C(O)O—$C_{1-4}$alkyl and $R^3$ and $R^6$ are halo. In still another embodiment, $R^2$ is halo, $R^3$ is halo and $R^6$ is halo or —O—$C_{1-6}$alkyl; or $R^2$ is halo, $R^3$ is —$C_{1-6}$alkyl or —O—$C_{1-6}$alkyl, and $R^6$ is halo. In other embodiments: $R^2$ is F, $R^3$ is F, and $R^6$ is F or —OCH$_3$; or $R^2$ is F, $R^3$ is Cl or —OCH$_3$, and $R^6$ is F; or $R^2$ is F, $R^3$ is —CH$_3$, and $R^6$ is F or Cl; or $R^2$ is Cl, $R^3$ is Cl, and $R^6$ is Cl or F; or $R^2$ is Cl, $R^3$ is F, and $R^6$ is F or —OCH$_3$; or $R^2$ is Cl, $R^3$ is —CH$_3$, and $R^6$ is F or Cl; or $R^2$ is F, $R^6$ is Cl and $R^3$ is Cl or —OCH$_3$; or $R^2$ is Cl, $R^6$ is F and $R^3$ is —OCH$_3$. In another embodiment, a is 1 to 5 and each $R^1$ is as defined for formula I, which can be depicted as formula XIV':

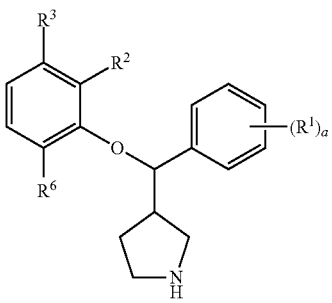

(XIV')

In one particular embodiment, a is 1 or 2; each $R^1$ is independently halo, —$C_{1-6}$alkyl, —$C_{0-6}$alkylene-OH, —CN, —SO$_2$—$C_{1-6}$alkyl, or —C(O)NH$_2$; $R^2$ is halo; $R^3$ is halo or —$C_{1-6}$alkyl; and $R^6$ is halo or —O—$C_{1-6}$alkyl. In other embodiments: $R^2$ is halo, $R^3$ is halo, $R^6$ is halo, a is 1, and $R^1$ is halo, —CN, or —C(O)NR$^a$R$^b$, where R$^a$ and R$^b$ are H; $R^2$ is halo, $R^3$ is —$C_{1-6}$alkyl, $R^6$ is halo, a is 1, and $R^1$ is halo, —$C_{0-6}$alkylene-OH, —CN, or —SO$_2$—$C_{1-6}$alkyl; or $R^2$ is halo, $R^3$ is halo, $R^6$ is halo or —O—$C_{1-6}$alkyl, a is 2, and each $R^1$ is independently halo; or $R^2$ is halo, $R^3$ is —$C_{1-6}$alkyl, $R^6$ is halo, a is 2, one $R^1$ is halo and the other $R^1$ is halo or —$C_{1-6}$alkyl. In yet other embodiments: $R^2$ is halo, $R^3$ is halo, $R^6$ is halo, a is 1, and $R^1$ is halo, —CN, or —C(O)NR$^a$R$^b$, where R$^a$ and R$^b$ are H; $R^2$ is halo, $R^3$ is —$C_{1-6}$alkyl, $R^6$ is halo, a is 1, and $R^1$ is halo, —$C_{0-6}$alkylene-OH, or —CN; or $R^2$ is halo, $R^3$ is halo, $R^6$ is halo or —O—$C_{1-6}$alkyl, a is 2, and each $R^1$ is independently halo; or $R^2$ is halo, $R^3$ is —$C_{1-6}$alkyl, $R^6$ is halo, a is 2, one $R^1$ is halo and the other $R^1$ is halo or —$C_{1-6}$alkyl. In other embodiments: $R^2$ is Cl, $R^3$ is Cl, $R^6$ is Cl, a is 1, and $R^1$ is 2-Cl; or $R^2$ is Cl, $R^3$ is —CH$_3$, $R^6$ is Cl, a is 1, and $R^1$ is 4-Cl, 3-CN, 4-CN, or 3-CH$_2$OH; or $R^2$ is Cl, $R^3$ is Cl, $R^6$ is F, a is 1, and $R^1$ is 3-CN or 3-C(O)NH$_2$; or $R^2$ is F, $R^3$ is F or Cl, $R^6$ is F, a is 2, one $R^1$ is 3-F and the other $R^1$ is 5-F; or $R^2$ is Cl, $R^3$ is Cl, $R^6$ is Cl, a is 2, one $R^1$ is 3-F and the other $R^1$ is 5-F; or $R^2$ is Cl, $R^3$ is F, $R^6$ is F, a is 2, one $R^1$ is 3-F and the other $R^1$ is 5-F; or $R^2$ is F, $R^3$ is F, $R^6$ is F or —OCH$_3$, a is 2, one $R^1$ is 3-F and the other $R^1$ is 5-F; or $R^2$ is F, $R^3$ is —CH$_3$, $R^6$ is F or Cl, one $R^1$ is 3-F and the other $R^1$ is 5-F; or $R^2$ is Cl, $R^3$ is —CH$_3$, $R^6$ is Cl, a is 2, one $R^1$ is 3-F and the other $R^1$ is 5-Cl, 5-F, or 5-CH$_3$; or $R^2$ is Cl, $R^3$ is —CH$_3$, $R^6$ is F, a is 2, one $R^1$ is 3-F and the other $R^1$ is 5-F.

In another embodiment, $R^2$, $R^4$, and $R^5$ are non-hydrogen moieties as defined for formula I, and $R^3$ and $R^6$ are H. In one particular embodiment, a is 0, which can be depicted as formula XV:

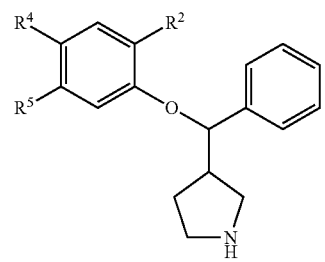

(XV)

In one particular embodiment, $R^2$ is halo, —O—$C_{1-6}$alkyl, or —C(O)—$C_{1-6}$alkyl; $R^4$ is halo or —$C_{1-6}$alkyl; and $R^5$ is halo or —$C_{1-6}$alkyl. In yet another embodiment, $R^2$ is halo or —O—$C_{1-6}$alkyl; and $R^4$ and $R^5$ are independently halo; or $R^2$ is halo and $R^4$ and $R^5$ are independently —$C_{1-6}$alkyl; or $R^2$ is —C(O)—$C_{1-6}$alkyl, $R^4$ is —$C_{1-6}$alkyl, and $R^5$ is halo; or $R^2$ and $R^5$ are independently halo, and $R^4$ is —$C_{1-6}$alkyl. In other embodiments: $R^2$, $R^4$, and $R^5$ are F; or $R^2$ is —OCH$_3$, $R^4$ is Cl, and $R^5$ is F; or $R^2$ is Cl, $R^4$ is —CH$_3$, and $R^5$ is F. In another embodiment, a is 1 to 5 and each $R^1$ is as defined for formula I, which can be depicted as formula XV':

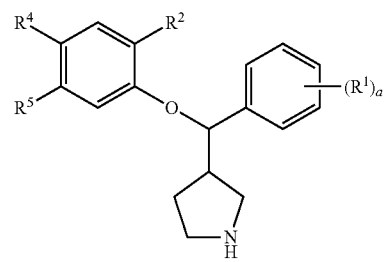

(XV')

In one particular embodiment, a is 2; each $R^1$ is independently halo; and $R^2$, $R^4$, and $R^5$ are independently halo or —O—$C_{1-6}$alkyl. In yet another embodiment, a is 2; each $R^1$ is independently halo; $R^2$ is halo or —O—$C_{1-6}$alkyl; and $R^4$ and $R^5$ are independently halo. In another embodiment, one $R^1$ is 3-F and the other $R^1$ is 5-F; $R^2$, $R^4$, and $R^5$ are F; or $R^2$ is —OCH$_3$, $R^4$ is Cl, and $R^5$ is F.

In another embodiment, $R^2$, $R^4$, and $R^6$ are non-hydrogen moieties as defined for formula I, and $R^3$ and $R^5$ are H. In one particular embodiment, a is 0, which can be depicted as formula XVI:

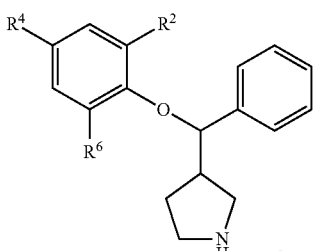
(XVI)

In one particular embodiment, $R^2$, $R^4$, and $R^6$ are independently halo, —$C_{1-6}$alkyl, —O—$C_{1-6}$alkyl, —C(O)—$C_{1-6}$alkyl, or —C(O)O—$C_{1-4}$alkyl. In other embodiments: $R^2$ is F, —$CH_2CH_3$, or —C(O)$CH_3$, $R^4$ is F, and $R^6$ is F; or $R^2$ is F, $R^4$ is —$OCH_3$, and $R^6$ is F; or $R^2$ is F, $R^4$ is Cl, and $R^6$ is F, Cl, or Br; or $R^2$ is Cl, $R^4$ is F or Cl, and $R^6$ is Cl; or $R^2$ is Cl, $R^4$ is Cl, and $R^6$ is —$CH_3$; or $R^2$ is Cl, $R^4$ is —$CH_3$, and $R^6$ is Cl; or $R^2$ is Br, $R^4$ is F, and $R^6$ is Br; or $R^2$ is —$CH_3$, $R^4$ is Cl, and $R^6$ is Cl; or $R^2$ is —$CH_3$, $R^4$ is —$CH_3$, and $R^6$ is —$CH_3$; or $R^2$ is —C(O)$OCH_3$ and $R^4$ and $R^6$ are F. In yet other embodiments: $R^2$ is F, —$CH_2CH_3$, or —C(O)$CH_3$, $R^4$ is F, and $R^6$ is F; or $R^2$ is F, $R^4$ is Cl, and $R^6$ is F or Cl; or $R^2$ is Cl, $R^4$ is F, and $R^6$ is Cl; or $R^2$ is —C(O)$OCH_3$ and $R^4$ and $R^6$ are F. In another embodiment, $R^2$ is F, $R^4$ is F, and $R^6$ is F. In another embodiment, a is 1 to 5 and each $R^1$ is as defined for formula I, which can be depicted as formula XVI':

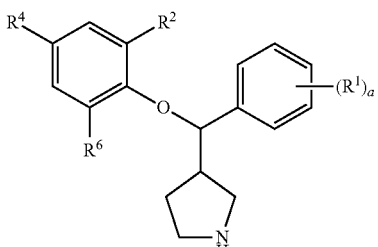
(XVI')

In one particular embodiment, a is 1 or 2; each $R^1$ is independently halo, —CN, —$SO_2$—$C_{1-6}$alkyl, or —C(O)$NR^aR^b$, where $R^a$ and $R^b$ are H; and $R^2$, $R^4$, and $R^6$ are independently halo or —$C_{1-6}$alkyl. In other embodiments: $R^2$ is F, $R^4$ is Cl, $R^6$ is F, a is 1, and $R^1$ is 2-Cl; or $R^2$ is Cl, $R^4$ is F, $R^6$ is Cl, a is 1, and $R^1$ is 2-Cl; or $R^2$ is F, $R^4$ is F, $R^6$ is F, a is 1 and $R^1$ is 3-CN, 4-CN, 3-C(O)$NH_2$, 4-C(O)$NH_2$, or 4-$SO_2CH_3$; or $R^2$ is F, $R^4$ is F, $R^6$ is F, a is 2, one $R^1$ is 3-F and the other $R^1$ is 5-F; or $R^2$ is Cl, $R^4$ is —$CH_3$; $R^6$ is Cl, a is 2, and one $R^1$ is 3-F and the other $R^1$ is 5-F. In yet other embodiments: $R^2$ is F, $R^4$ is F, $R^6$ is F, a is 1 and $R^1$ is 3-CN or 3-C(O)$NH_2$; or $R^2$ is F, $R^4$ is F, $R^6$ is F, a is 2, one $R^1$ is 3-F and the other $R^1$ is 5-F.

In another embodiment, $R^3$, $R^4$, and $R^5$ are non-hydrogen moieties as defined for formula I, and $R^2$ and $R^6$ are H. In one particular embodiment, a is 0, which can be depicted as formula XVII:

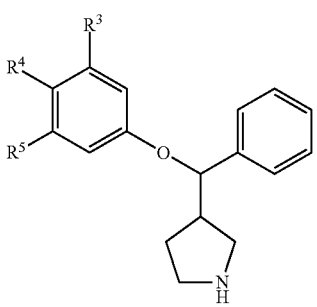
(XVII)

In another embodiment, $R^3$ is halo or —$C_{1-6}$alkyl; $R^5$ is halo or —$C_{1-6}$alkyl; and $R^4$ is halo or —O—$C_{1-6}$alkyl. In other embodiments: $R^3$ and $R^5$ are halo, and $R^4$ is halo or —O—$C_{1-6}$ alkyl; or $R^3$ and $R^5$ are $C_{1-6}$alkyl, and $R^4$ is halo. In another embodiment, a is 1 to 5 and each $R^1$ is as defined for formula I, which can be depicted as formula XVII':

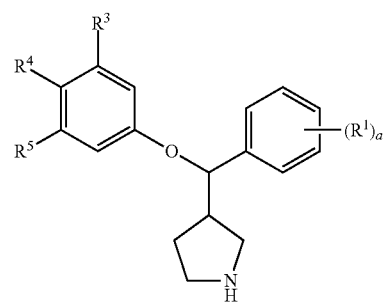
(XVII')

In another embodiment, $R^2$, $R^3$, $R^4$, and $R^5$ are non-hydrogen moieties as defined for formula I, and $R^6$ is H. In one particular embodiment, a is 0, which can be depicted as formula XVIII:

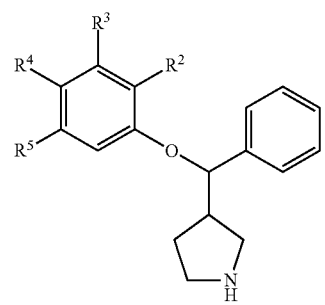
(XVIII)

In another embodiment, a is 1 to 5 and each $R^1$ is as defined for formula I, which can be depicted as formula XVIII':

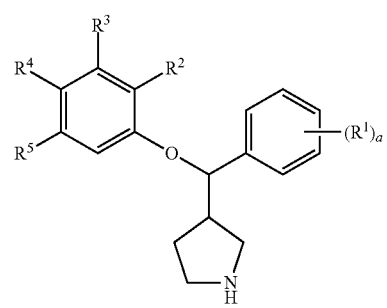
(XVIII')

In another embodiment, $R^2$, $R^3$, $R^4$, and $R^6$ are non-hydrogen moieties as defined for formula I, and $R^5$ is H. In one particular embodiment, a is 0, which can be depicted as formula XIX:

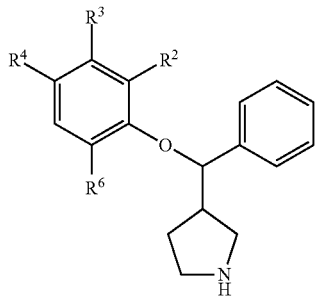
(XIX)

In another embodiment, a is 1 to 5 and each $R^1$ is as defined for formula I, which can be depicted as formula XIX':

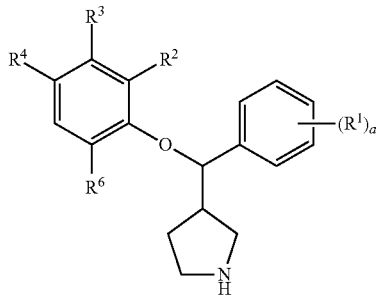
(XIX')

In another embodiment, $R^2$, $R^3$, $R^5$, and $R^6$ are non-hydrogen moieties as defined for formula I, and $R^4$ is H. In one particular embodiment, a is 0, which can be depicted as formula XX:

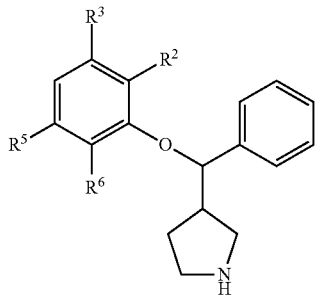
(XX)

In one particular embodiment, $R^2$, $R^3$, $R^5$, and $R^6$ are independently halo or —$C_{1-6}$alkyl. In other embodiments: $R^2$, $R^3$, $R^5$, and $R^6$ are F; or $R^2$, $R^3$, $R^5$, and $R^6$ are Cl; or $R^2$ and $R^6$ are Cl, and $R^3$ and $R^5$ are F; or $R^2$, $R^3$, $R^5$, and $R^6$ are —$CH_3$; or $R^2$, $R^3$, and $R^5$ are F, and $R^6$ is Cl. In yet another embodiment, $R^2$, $R^3$, $R^5$, and $R^6$ are independently halo. In another embodiment, $R^2$, $R^3$, $R^5$, and $R^6$ are F; or $R^2$, $R^3$, $R^5$, and $R^6$ are Cl; or $R^2$ and $R^6$ are Cl, and $R^3$ and $R^5$ are F; or $R^2$, $R^3$, and $R^5$ are F, and $R^6$ is Cl. In another embodiment, a is 1 to 5 and each $R^1$ is as defined for formula I, which can be depicted as formula XX':

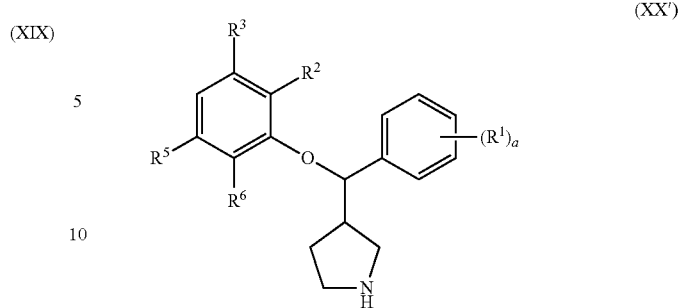
(XX')

In one particular embodiment, $R^1$ is halo, —$C_{0-2}$alkylene-COOH, —CHO, —C(O)O—$C_{1-4}$alkyl, —$C_{0-1}$alkylene-$NR^aR^b$, or —C(O)$NR^aR^b$; and $R^2$, $R^3$, $R^5$, and $R^6$ are independently halo. In other embodiments: $R^2$ and $R^6$ are Cl, $R^3$ and $R^5$ are F; a is 1 and $R^1$ is 2-Cl, 3-COOH, 3-CHO, 3-C(O)OCH$_3$, 3-C(O)OCH$_2$CH$_3$, 3-CH$_2$NH(CH$_2$CH$_3$), 3-CH$_2$N(CH$_3$)(CH$_2$CH$_3$), 3-C(O)—NHCH$_2$CH$_3$, or 3-C(O)—N(CH$_3$)CH$_2$CH; or a is 2, one $R^1$ is 3-F and the other $R^1$ is F. In yet another embodiment, $R^1$, $R^2$, $R^3$, $R^5$, and $R^6$ are independently halo. In other embodiments: $R^2$ and $R^6$ are Cl, $R^3$ and $R^5$ are F; a is 1 and $R^1$ is 2-Cl or a is 2, one $R^1$ is 3-F and the other $R^1$ is F.

In another embodiment, $R^2$, $R^3$, $R^4$, $R^5$, and $R^6$ are non-hydrogen moieties as defined for formula I. In one particular embodiment, a is 0, which can be depicted as formula XXI:

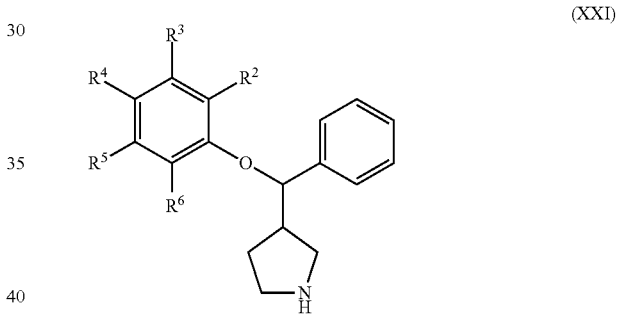
(XXI)

In one particular embodiment, $R^2$ is halo, —C(O)—$C_{1-6}$alkyl, or —C(O)O—$C_{1-4}$alkyl; $R^3$, $R^5$, and $R^6$ are independently halo; and $R^4$ is halo or —$C_{1-6}$alkyl optionally substituted with 1 to 5 fluoro atoms. In yet other embodiments: $R^2$, $R^3$, $R^4$, $R^5$, and $R^6$ are F; or $R^2$, $R^3$, $R^5$, and $R^6$ are F, and $R^4$ is F, Cl, or —$CF_3$; or $R^2$, $R^4$, and $R^6$ are Cl and $R^3$ and $R^5$ are F; or $R^2$ is —C(O)—$C_{1-6}$alkyl or —C(O)O—$C_{1-4}$alkyl, and $R^3$, $R^4$, $R^5$, and $R^6$ are F. In still another embodiment, $R^2$, $R^3$, $R^4$, $R^5$, and $R^6$ are F; or $R^2$ is —C(O)O—$C_{1-4}$alkyl, and $R^3$, $R^4$, $R^5$, and $R^6$ are F. In yet another embodiment, $R^2$, $R^3$, $R^4$, $R^5$, and $R^6$ are F. In another embodiment, a is 1 to 5 and each $R^1$ is as defined for formula I, which can be depicted as formula XXI':

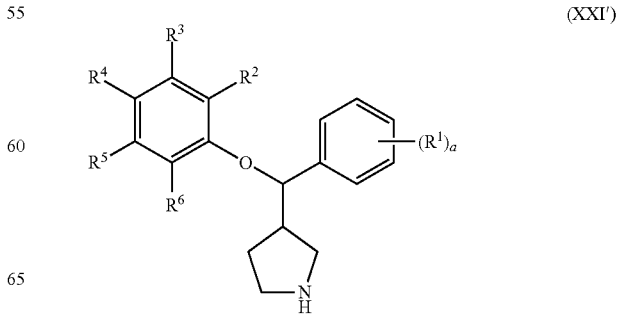
(XXI')

In one embodiment, the compounds of the invention exhibit a NET $pK_i \geq 8$ and a SERT $K_i$/NET $K_i$ in the range of 0.1-100. In reporting such ratios herein, all ratios have been rounded off to the nearest tenth. In one particular embodiment, such compounds have formula (II)-(XXI) or (II')-(XXI').

In addition, particular compounds of formula I that are of interest include those set forth in the Examples below, as well a pharmaceutically acceptable salt thereof.

General Synthetic Procedures

Compounds of the invention can be prepared from readily available starting materials using the following general methods, the procedures set forth in the Examples, or by using other methods, reagents, and starting materials that are known to those skilled in the art. Although the following procedures may illustrate a particular embodiment of the invention, it is understood that other embodiments of the invention can be similarly prepared using the same or similar methods or by using other methods, reagents and starting materials known to those of ordinary skill in the art. It will also be appreciated that where typical or preferred process conditions (i.e., reaction temperatures, times, mole ratios of reactants, solvents, pressures, etc.) are given, other process conditions can also be used unless otherwise stated. While optimum reaction conditions will typically vary depending on various reaction parameters such as the particular reactants, solvents and quantities used, those of ordinary skill in the art can readily determine suitable reaction conditions using routine optimization procedures.

Additionally, as will be apparent to those skilled in the art, conventional protecting groups may be necessary or desired to prevent certain functional groups from undergoing undesired reactions. The choice of a suitable protecting group for a particular functional group as well as suitable conditions and reagents for protection and deprotection of such functional groups are well-known in the art. Protecting groups other than those illustrated in the procedures described herein may be used, if desired. For example, numerous protecting groups, and their introduction and removal, are described in Greene and Wuts, *Protecting Groups in Organic Synthesis*, Third Edition, Wiley, New York, 1999, and references cited therein.

More particularly, in the schemes below, P represents an "amino-protecting group," a term used herein to mean a protecting group suitable for preventing undesired reactions at an amino group. Representative amino-protecting groups include, but are not limited to, t-butoxycarbonyl (BOC), trityl (Tr), benzyloxycarbonyl (Cbz), 9-fluorenylmethoxycarbonyl (Fmoc), formyl, benzyl, and the like. Standard deprotection techniques and reagents such as TFA in DCM or HCl in 1,4-dioxane, methanol, or ethanol, are used to remove protecting groups, when present. For example, a BOC group can be removed using an acidic reagent such as hydrochloric acid, trifluoroacetic acid and the like; while a Cbz group can be removed by employing catalytic hydrogenation conditions such as $H_2$ (1 atm), 10% Pd/C in an alcoholic solvent.

Suitable inert diluents or solvents for use in these schemes include, by way of illustration and not limitation, tetrahydrofuran (THF), acetonitrile, N,N-dimethylformamide (DMF), dimethylsulfoxide (DMSO), toluene, dichloromethane (DCM), chloroform ($CHCl_3$), and the like.

All reactions are typically conducted at a temperature within the range of about −78° C. to 110° C., for example at room temperature. Reactions may be monitored by use of thin layer chromatography (TLC), high performance liquid chromatography (HPLC), and/or LCMS until completion. Reactions may be complete in minutes, may take hours, typically from 1-2 hours and up to 48 hours, or days, such as up to 3-4 days. Upon completion, the resulting mixture or reaction product may be further treated in order to obtain the desired product. For example, the resulting mixture or reaction product may be subjected to one or more of the following procedures: dilution (for example with saturated $NaHCO_3$); extraction (for example, with ethyl acetate, $CHCl_3$, DCM, aqueous HCl); washing (for example, with DCM, saturated aqueous NaCl, or saturated aqueous $NaHCO_3$); drying (for example, over $MgSO_4$ or $Na_2SO_4$, or in vacuo); filtration; being concentrated (for example, in vacuo); being redissolved (for example in a 1:1 acetic acid:$H_2O$ solution); and/or purification (for example by preparative HPLC or reverse phase preparative HPLC).

By way of illustration, compounds of formula I, as well as their salts, can be prepared by one or more of the following schemes.

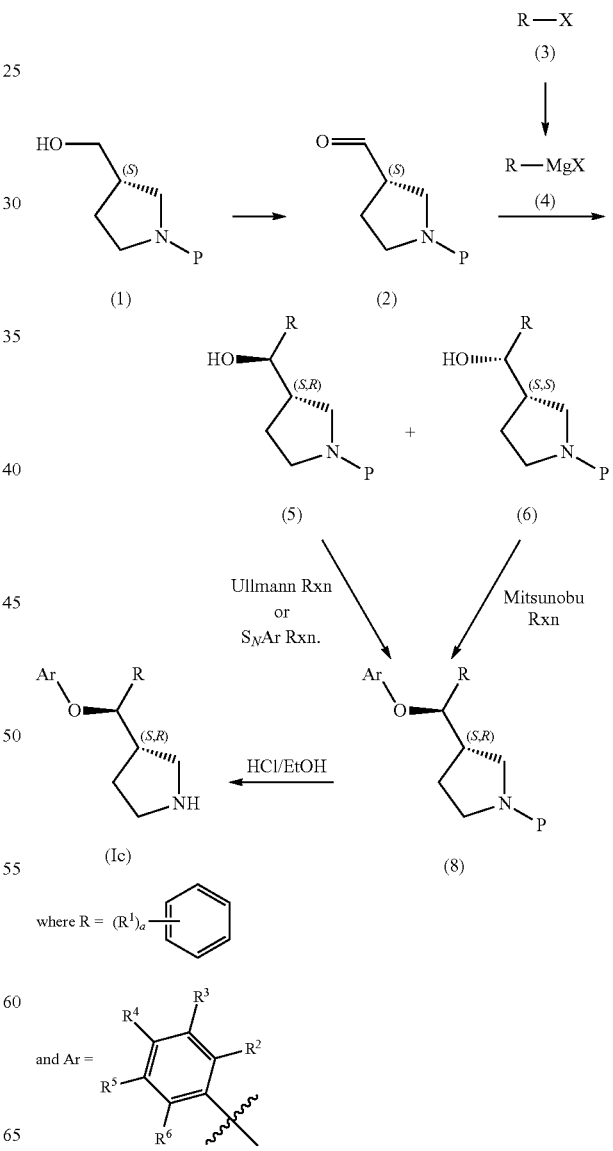

While Scheme I illustrates formation of the (S,R) enantiomer of the compound of formula I, the (R,S) enantiomer of the compound of formula I can be made in a similar manner, using the (R) stereoisomer compound 1' as the starting material, which forms the (R,S) and (R,R) alcohol compounds 5' and 6', respectively:

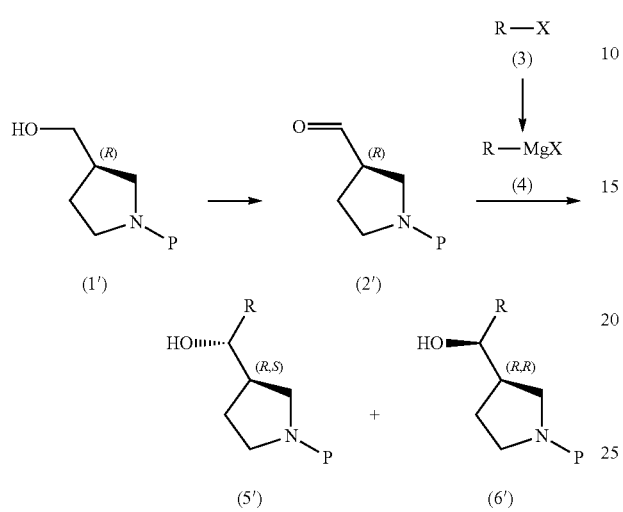

Preparation of Compound 2 or 2'

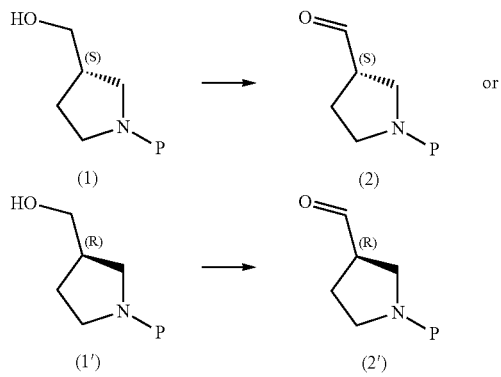

Compound 2 can be prepared by the 2,2,6,6-tetramethyl-1-piperidinyloxy, free radical (TEMPO) mediated oxidation of compound 1. Compound 1, where P is Boc or benzyl, is commercially available. Alternately, Compound 2 can be prepared by oxidizing compound 1 using any oxidizing agent suitable for converting a primary alcohol into an aldehyde. Representative oxidizing agents include, for example, dimethyl sulfoxide, Collin's reagent, Corey's reagent, pyridinium dichromate and the like.

Compound 2' can be prepared in a similar manner, using R-Boc-3-pyrrolidinemethanol, also known as (R)-3-hydroxymethylpyrrolidine-1-carboxylic acid t-butyl ester, as starting material compound 1'. Thus, one embodiment of the invention relates to the preparation of compound 2 or compound 2', by reacting compound 1 or compound 1', respectively, with sodium hypochlorite in the presence of TEMPO and potassium bromide in water. This method is particularly useful by minimizing the amount of racemization that can occur when the alcohol 1 or 1' is oxidized.

Preparation of Compound 4

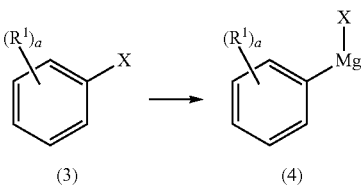

Compound 4 is a Grignard reagent, and serves to introduce the unsubstituted (a=0) or substituted phenyl group into compound 2. Compound 4 can be readily prepared by treating a compound 3 (for example, where X is bromo or iodo) with magnesium metal. See for example, Knochel et al. (2003) *Angew. Chem., Int. Ed.* 42(36):4302-4320. Compound 4 may also be commercially available, examples of which include phenylmagnesium bromide.

Alternately, other reagents can be used to introduce the phenyl group into compound 2 or 2'. For example, compound 4 can be replaced with:

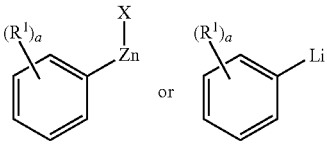

in Scheme I. Both compounds are commercially available or can be prepared by techniques that are known in the art.

Preparation and Separation of Compounds 5 and 6

The Grignard reaction between compound 2 and compound 4 is typically conducted using standard Grignard reaction conditions. For example, compound 2, in a suitable solvent such as THF, is cooled under nitrogen to about −78° C. Compound 4 in a suitable solvent such as THF is added dropwise and the solution is allowed to warm to room temperature, typically overnight. The reaction is then quenched, for example using saturated NH$_4$Cl. Purification and separation by preparative HPLC or crystallization will then yield compounds 5 and 6. Examples of compounds 5 and 6 include (S)-3-((R)-hydroxyphenylmethyl)pyrrolidine-1-carboxylic acid t-butyl ester and (S)-3-((S)-hydroxyphenylmethyl)pyrrolidine-1-carboxylic acid t-butyl ester, respectively.

Compounds 5 and/or 6 can also be prepared by reduction of the corresponding ketone (compound 11) as shown in Scheme II.

Similarly, compound 2' as the starting material will yield compounds 5' and 6'. Examples compounds 5' and 6' include (R)-3-((S)-hydroxyphenylmethyl)pyrrolidine-1-carboxylic acid t-butyl ester and (R)-3-((R)-hydroxyphenylmethyl)pyrrolidine-1-carboxylic acid t-butyl ester, respectively.

Ullmann Preparation of Compounds of Formula I

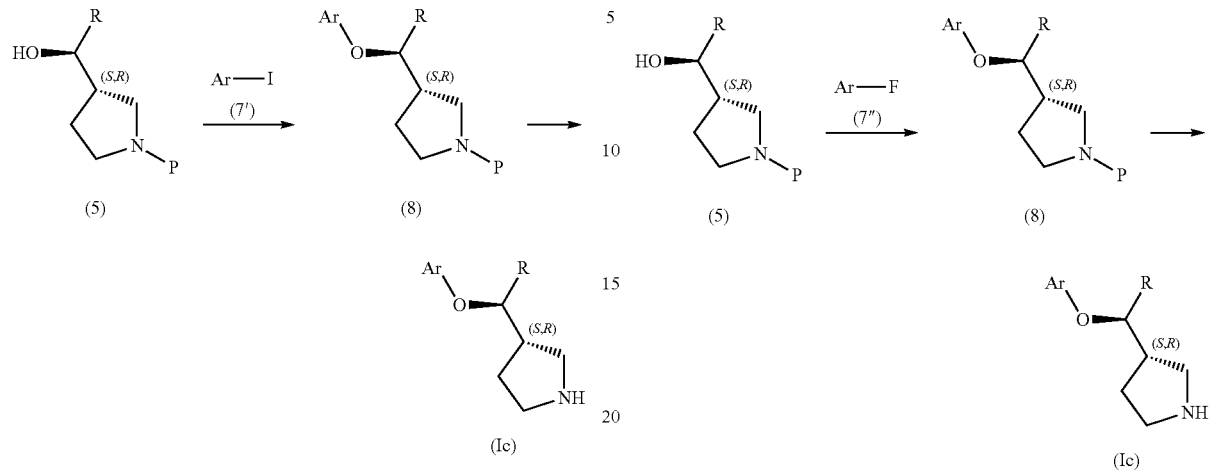

Compound 5 can then be coupled to an appropriate aryl iodide (compound 7') under Ullmann reaction conditions to provide compound 8. The Ullmann reaction is typically conducted in the presence of a copper(I) iodide/1,10-phenanthroline catalyst and a base such as cesium carbonate, in an appropriate solvent such as toluene or DMF. The reaction vessel is sealed and the mixture is heated at about 100-110° C. until the reaction is complete, typically about 3 days, yielding compound 8, which is then deprotected to yield the compound of formula (I). This final step is conducted under standard deprotection conditions, which will vary depending upon the protecting group used. For example, removal of the BOC group can be done using HCl and ethanol.

In a similar manner, the (R,S) compound 8' can be formed by using compound 5':

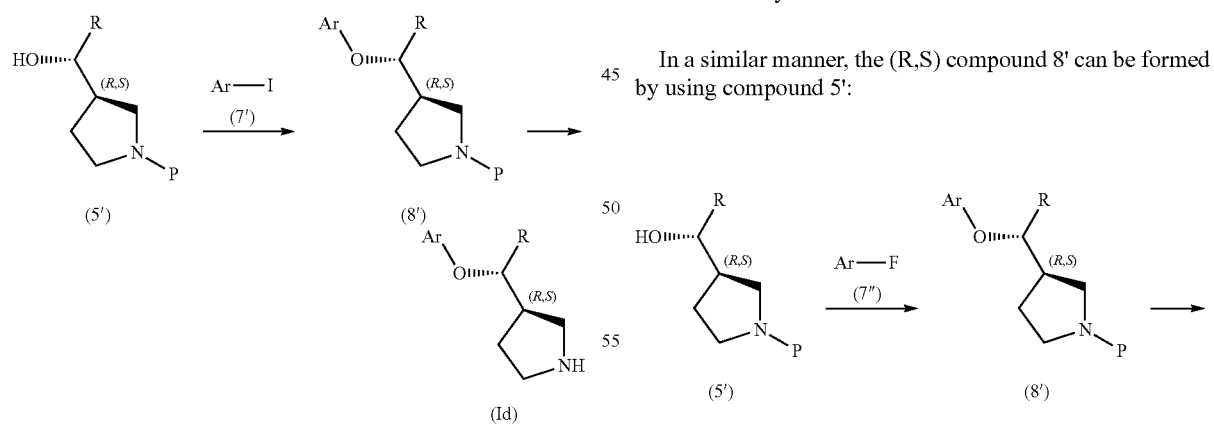

Examples of compound 5 include (S)-3-((R)-hydroxyphenylmethyl)pyrrolidine-1-carboxylic acid t-butyl ester. Examples of compound 5' include (R)-3-(S)-hydroxyphenylmethyl)pyrrolidine-1-carboxylic acid t-butyl ester. Examples of compound 7' include 2,4-difluoro-1-iodobenzene, 4-chloro-2-fluoro-1-iodobenzene, and 1,3-dichloro-5-iodobenzene.

$S_NAr$ Preparation of Compounds of Formula I

Alternatively, compound 8 can be prepared by reacting compound 5 with an appropriate aryl fluoride (compound 7") using a nucleophilic aromatic substitution reaction ($S_NAr$). For example, sodium hydride is slowly added to compound 5 that has been dissolved in an appropriate solvent such as DMF. An appropriate aryl fluoride (compound 7") is then added and the mixture is stirred at about 70° C. until the reaction is complete, about 3 hours, yielding compound 8, which is then deprotected to yield the compound of formula (I). Examples of compound 5 include (S)-3-((R)-hydroxyphenylmethyl)pyrrolidine-1-carboxylic acid t-butyl ester. Examples of compound 7" include 1-fluoro-2-methanesulfonyl-benzene, 1-fluoro-3-nitrobenzene, 1-(2-fluorophenyl)ethanone, 2-chloro-1,3-difluorobenzene, and 2-fluorobenzoic acid methyl ester.

In a similar manner, the (R,S) compound 8' can be formed by using compound 5':

Mitsunobu Preparation of Compounds of Formula I

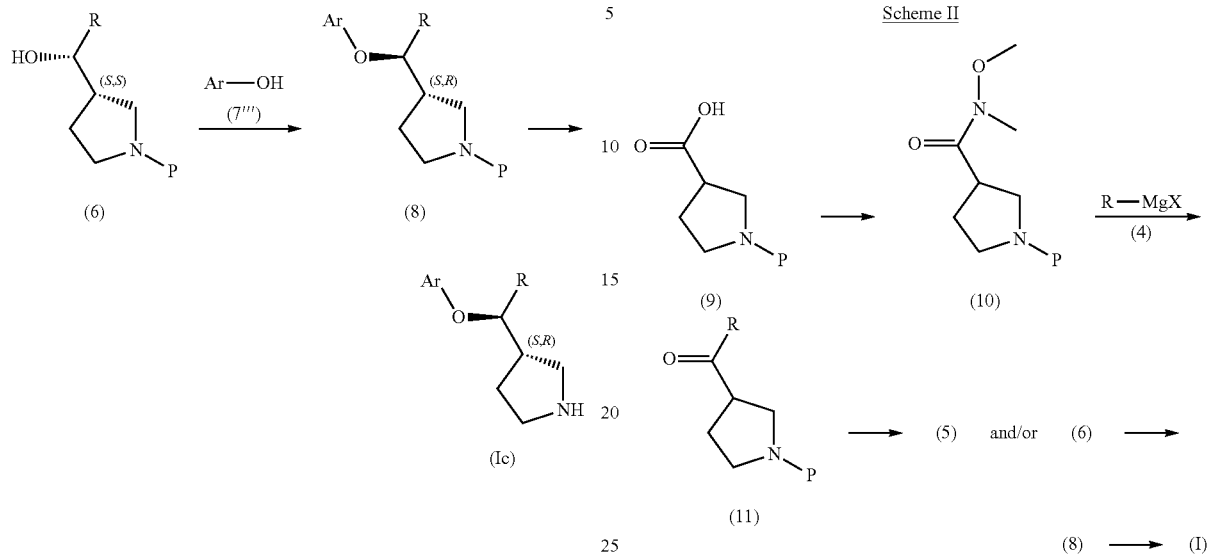

Compound 6 can also be converted into compound 8 using the Mitsunobu coupling reaction (Mitsunobu and Yamada (1967) *M. Bull. Chem. Soc. JPN.* 40:2380-2382). This reaction is typically conducted using standard Mitsunobu coupling conditions, using a redox system containing an azodicarboxylate such as diethyl azodicarboxylate or diisopropyl azodicarboxylate (DIAD) and a phosphine catalyst such as triphenylphosphine (PPh₃). For example, compound 6 is combined with an appropriate phenol (compound 7'''), and PPh₃ in an appropriate solvent such as THF. While the mixture is sonicated, DIAD is added, yielding compound 8, which is then deprotected to yield the compound of formula (I). Typically, approximately equimolar amounts of PPh₃ and DIAD are used. Examples of compound 6 include (S)-3-((S)-hydroxyphenylmethyl)pyrrolidine-1-carboxylic acid t-butyl ester. Examples of compound 7''' include 2-chloro-6-fluoro-3-methylphenol, 2-chloro-3,5-difluorophenol, 2-chloro-3,6-difluorophenol, 2,6-dichloro-3,5-difluorophenol, and 2,4,6-trifluorophenol, of which are commercially available.

In a similar manner, the (R,S) compound 8' can be formed by using the compound 6'.

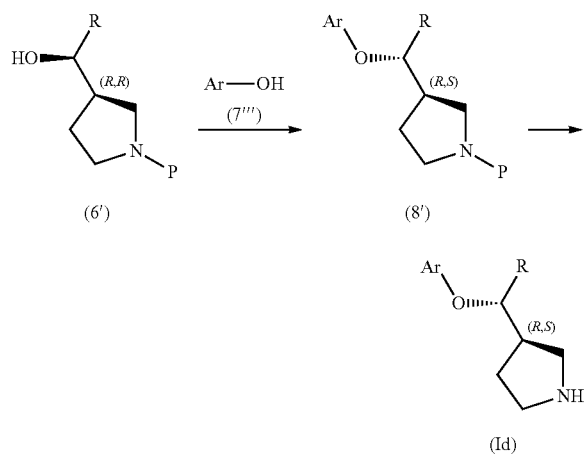

Examples of compound 6' include (R)-3-((R)-hydroxyphenylmethyl)pyrrolidine-1-carboxylic acid t-butyl ester.

Scheme II

As shown in Scheme II, compound 9 is first converted to the corresponding Weinreb amide which is then reacted with a Grignard reagent to form compound 11. The first reaction can be conducted using either racemic or chiral starting material 9. Since the subsequent reactions do not typically affect the stereochemistry of this starting chiral center, the stereochemistry desired at this chiral center for later intermediates and products can selected by proper choice of starting material 9.

Preparation of Compound 11

The Weinreb amide 10 is typically synthesized using standard reaction conditions from the corresponding carboxylic acid, compound 9. For example, compound 9 (mixture of (R) and (S) enantiomers), appropriate coupling reagents (for example HOBt and HCTU), and N,O-dimethylhydroxylamine HCl are combined with an appropriate solvent such as DMF. The mixture is cooled, typically at 0° C. using an ice bath, followed by the slow addition of a base such as DIPEA. The mixture is allowed to warm to room temperature and stirred until the reaction is complete (typically about 15 hours) to yield a mixture of the (R) and (S) enantiomers of compound 10.

Compound 10 is then reacted with a Grignard reagent 4 to provide compound 11. For example, compound 10, in a suitable solvent such as THF, is cooled under nitrogen to about −100° C. Compound 4 in a suitable solvent such as THF is added dropwise and the solution is allowed to warm to room temperature, typically for about 30 minutes to 2 hours. After cooling in an ice bath, the reaction is quenched, for example by the slow addition of water. Purification by flash chromatography will then yield compound 11, which is a mixture of the (R) and (S) enantiomers. Examples of starting material compound 9 include pyrrolidine-1,3-dicarboxylic acid 1-t-butyl ester.

The (S) compound 11' can be prepared in a similar manner as the mixture, but using (3S)-Boc-β-Proline-OH, also known as (S)-pyrrolidine-1,3-dicarboxylic acid 1-t-butyl ester, as the compound 9' starting material:

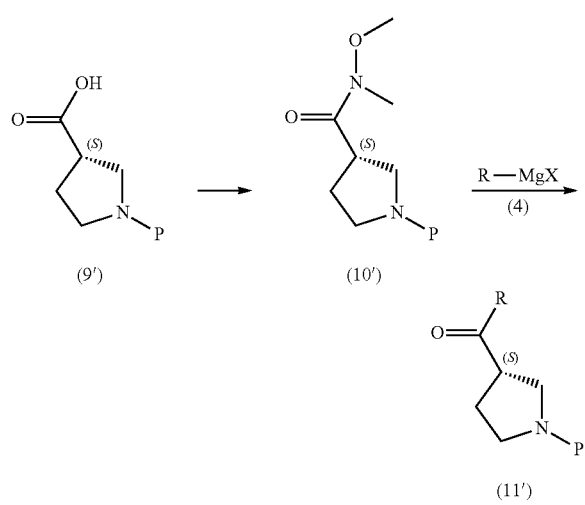

The (R) compound 11" can be prepared in a similar manner, but using (R)-1-N-Boc-β-Proline, also known as (R)-pyrrolidine-1,3-dicarboxylic acid 1-t-butyl ester, as the compound 9" starting material:

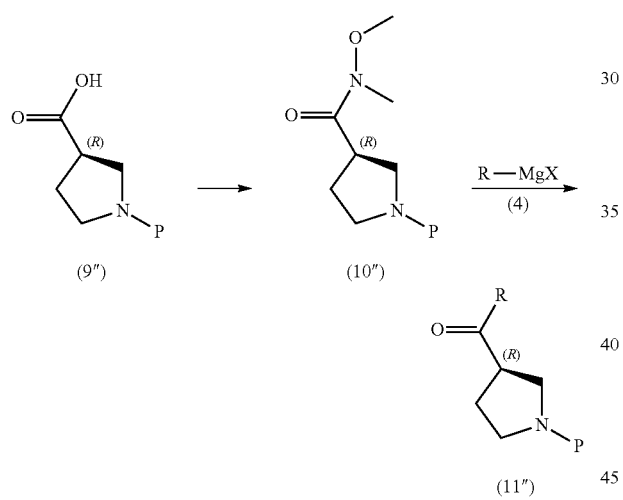

Preparation of Compound 5 and Compound 6

A mixture of compound 5 (S,R) and compound 6 (S,S) can be prepared from (S) compound 11'. Compound 11' in an appropriate solvent such as methanol (typically at 0° C.) is combined with a reducing agent such as sodium borohydride. The mixture is allowed to warm to room temperature and stirred until the reaction is complete (typically about 1 hour). The resulting mixture of compounds 5 (S,R) and 6 (S,S) may be purified by flash chromatography. In a similar manner, a mixture of enantiomer compounds 5' (R,S) and 6' (R,R) can be prepared from (R) compound 11".

Alternately, compound 11 can be reduced using asymmetric conditions to prepare a mixture of compounds 5 (S,R) and 6 (R,R) which can be separated by silica or reverse phase chromatography to yield enantiomerically pure compounds 5 and 6. The asymmetric reduction of the ketone may be carried out using the appropriate chiral reagents such as Corey-Bakshi-Shibata (CBS) catalyst, asymmetric hydrogenation or asymmetric transfer hydrogenation with the appropriate chiral ligand. See, for example, Corey et al. (1988) *J. Org. Chem.* 53:2861-2863.

Similarly, the single compound 5 (S,R) or the single compound 6 (S,S) may be synthesized from the (S) compound 11' and a chiral asymmetric reduction using the appropriate chiral reagents. Likewise, the single compound 5' (R,S) or the single compound 6' (R,R) may be synthesized from the (R) compound 11" and a chiral asymmetric reduction using the appropriate chiral reagents.

If desired, pharmaceutically acceptable salts of the compounds of formula I can be prepared by contacting the free acid or base form of a compound of formula I with a pharmaceutically acceptable base or acid.

Certain of the intermediates described herein are believed to be novel and accordingly, such compounds are provided as further aspects of the invention including, for example, compounds 8 and 8':

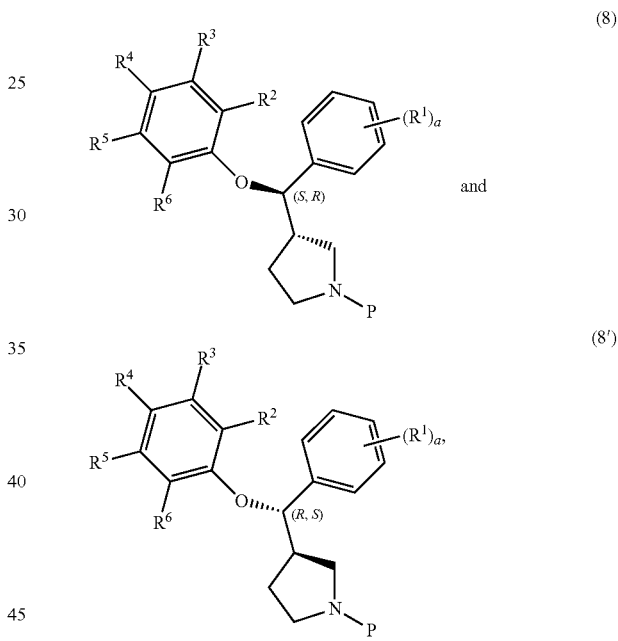

where P represents an amino-protecting group, particularly t-butoxycarbonyl (BOC). In one embodiment of the invention, compounds of the invention can be prepared by deprotecting a compound of the formula:

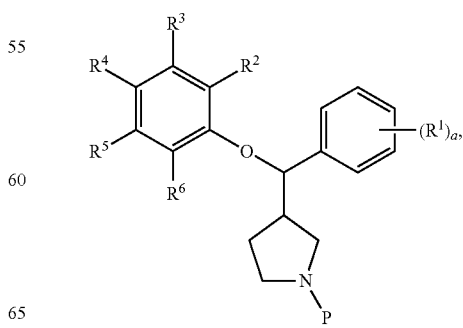

where P represents an amino-protecting group, to provide a compound of formula I, or a salt thereof. In one particular embodiment, such unprotected compounds have the formula of compounds 8 or 8'.

Further details regarding specific reaction conditions and other procedures for preparing representative compounds of the invention or intermediates thereof are described in the Examples set forth herein.

Utility

Compounds of the invention possess serotonin and norepinephrine reuptake inhibitory activity, and in one embodiment, at nanomolar potencies. Thus, these compounds have therapeutic utility as combined serotonin and norepinephrine reuptake inhibitors (SNRIs). In one embodiment, compounds of the invention are equipotent at both targets, i.e., possess approximately equal serotonin reuptake inhibitory activity and norepinephrine reuptake inhibitory activity.

The inhibition constant ($K_i$) of a compound is the concentration of competing ligand in a competition assay that would occupy 50% of the transporters if no radioligand were present. $K_i$ values can be determined from radioligand competition binding studies with $^3$H-nisoxetine (for the norepinephrine transporter, NET) and $^3$H-citalopram (for the serotonin transporter, SERT), as described in Assay 1. These $K_i$ values are derived from $IC_{50}$ values in the binding assay using the Cheng-Prusoff equation and the $K_d$ of the radioligand (Cheng & Prusoff (1973) *Biochem. Pharmacol.* 22(23):3099-3108). Functional $IC_{50}$ values can be determined in the functional inhibition of uptake assays described in Assay 2. These $IC_{50}$ values can be converted to $K_i$ values using the Cheng-Prusoff equation and the $K_m$ of the transmitter for the transporter. It is noted however, that the uptake assay conditions described in Assay 2 are such that the $IC_{50}$ values are very close to the $K_i$ values, should a mathematical conversion be desired, since the neurotransmitter concentration (5-HT or NE) used in the assay is well below its $K_m$ for the respective transporter.

One measure of the affinity of a compound for SERT or NET is the inhibitory constant ($pK_i$) for binding to the transporter. The $pK_i$ value is the negative logarithm to base 10 of the $K_i$. Compounds of the invention of particular interest are those having a $pK_i$ at SERT greater than or equal to 7.5. Compounds of the invention of particular interest also include those having a $pK_i$ at NET greater than or equal to 7.0. In another embodiment, compounds of interest have a $pK_i$ at NET greater than or equal to 8.0, and in yet another embodiment, compounds of interest have a $pK_i$ at NET within the range of 8.0 to 9.0. In one embodiment, compounds of interest have a $pK_i$ at SERT and at NET of greater than or equal to 7.5. In another embodiment, compounds of interest have a $pK_i$ at SERT and at NET greater than or equal to 8.0. Such values can be determined by techniques that are well know in the art, as well as in the assays described herein.

In one embodiment, compounds of the invention exhibit a NET $pK_i \geq 8$ and a SERT $K_i$/NET $K_i$ in the range of 0.1 to 100; and in other embodiments, exhibit a SERT $K_i$/NET $K_i$ in the range of 0.3 to 100, 0.3 to 10, or 0.1 to 30. In another embodiment, compounds of the invention exhibit a NET $pK_i \geq 9$ and a SERT $K_i$/NET $K_i$ in the range of 0.1 to 100; and in others embodiments, exhibit a SERT $K_i$/NET $K_i$ in the range of 0.3 to 100, 0.3 to 10, or 0.1 to 30.

Another measure of serotonin and norepinephrine reuptake inhibition is the $pIC_{50}$ value. In one embodiment, compounds of interest are those having a serotonin reuptake inhibition $pIC_{50}$ value greater than or equal to 7.5. Compounds of the invention of particular interest also include those having a norepinephrine reuptake inhibition $pIC_{50}$ value greater than or equal to 7.0. In another embodiment, compounds of interest have a norepinephrine reuptake inhibition $pIC_{50}$ value greater than or equal to 8.0, and in yet another embodiment, compounds of interest have a norepinephrine reuptake inhibition $pIC_{50}$ value within the range of 8.0 to 9.0. In one embodiment, compounds of interest have a serotonin reuptake inhibition $pIC_{50}$ value and a norepinephrine reuptake inhibition $pIC_{50}$ value of greater than or equal to 7.5. In another embodiment, compounds of interest have a serotonin reuptake inhibition $pIC_{50}$ value and a norepinephrine reuptake inhibition $pIC_{50}$ value greater than or equal to 8.0. In one particular embodiment, the compounds of the invention have balanced $pIC_{50}$ values.

In another embodiment, compounds of the invention are selective for inhibition of SERT and NET over the dopamine transporter (DAT). For example in this embodiment, compounds of particular interest are those that exhibit a binding affinity for SERT and NET that is at least 5 times higher than the binding affinity for DAT, or that is at least 10 times higher than for DAT, or at least 20 or 30 times higher than for DAT. In another embodiment, the compounds do not exhibit significant DAT inhibition. In still another embodiment, the compounds exhibit less than 50% inhibition of DAT activity when measured at a concentration of 794 nM. Under the assay conditions used, a compound which exhibits $\leq 50\%$ inhibition would have an estimated $pK_i$ value at DAT of $\leq 6.1$.

In still another embodiment, compounds of the invention possess dopamine reuptake inhibitory activity as well as serotonin and norepinephrine reuptake inhibitory activity. For example in this embodiment, compounds of particular interest are those that exhibit a $pK_i$ at SERT and NET greater than or equal to 8.0, and a $pK_i$ at DAT greater than or equal to 7.0.

It is noted that in some cases, compounds of the invention may possess either weak serotonin reuptake inhibitory activity or weak norepinephrine reuptake inhibitory activity. In these cases, those of ordinary skill in the art will recognize that such compounds still have utility as primarily either a NET inhibitor or a SERT inhibitor, respectively, or will have utility as research tools.

Exemplary assays to determine the serotonin and/or norepinephrine reuptake inhibiting activity of compounds of the invention include by way of illustration and not limitation, assays that measure SERT and NET binding, for example, as described in Assay 1. In addition, it is useful to understand the level of DAT binding and uptake in an assay such as that described in Assay 1. Useful secondary assays include neurotransmitter uptake assays to measure competitive inhibition of serotonin and norepinephrine uptake into cells expressing the respective human or rat recombinant transporter (hSERT, hNET, or hDAT) as described in Assay 2, and ex vivo radioligand binding and neurotransmitter uptake assays that are used to determine the in vivo occupancy of SERT, NET and DAT in tissue as described in Assay 3. Other assays that are useful to evaluate pharmacological properties of test compounds include those listed in Assay 4. Exemplary in vivo assays include the formalin paw test described in Assay 5, which is a reliable predictor of clinical efficacy for the treatment of neuropathic pain, and the spinal nerve ligation model described in Assay 6. The aforementioned assays are useful in determining the therapeutic utility, for example, the neuropathic pain relieving activity, of compounds of the invention. Other properties and utilities of compounds of the invention can be demonstrated using various in vitro and in vivo assays well-known to those skilled in the art.

Compounds of the invention are expected to be useful for the treatment and/or prevention of medical conditions in which the regulation of monoamine transporter function is implicated, in particular those conditions mediated by or responsive to the inhibition of serotonin and norepinephrine reuptake. Thus it is expected that patients suffering from a disease or disorder that is treated by the inhibition of the serotonin and/or the norepinephrine transporter can be treated by administering a therapeutically effective amount of a serotonin and norepinephrine reuptake inhibitor of the invention. Such medical conditions include, by way of example, pain disorders such as neuropathic pain and chronic pain, depressive disorders such as major depression, affective disorders such as an anxiety disorder, attention deficit hyperactivity disorder, cognitive disorders such as dementia, and stress urinary incontinence.

The amount of active agent administered per dose or the total amount administered per day may be predetermined or it may be determined on an individual patient basis by taking into consideration numerous factors, including the nature and severity of the patient's condition, the condition being treated, the age, weight, and general health of the patient, the tolerance of the patient to the active agent, the route of administration, pharmacological considerations such as the activity, efficacy, pharmacokinetics and toxicology profiles of the active agent and any secondary agents being administered, and the like. Treatment of a patient suffering from a disease or medical condition (such as neuropathic pain) can begin with a predetermined dosage or a dosage determined by the treating physician, and will continue for a period of time necessary to prevent, ameliorate, suppress, or alleviate the symptoms of the disease or medical condition. Patients undergoing such treatment will typically be monitored on a routine basis to determine the effectiveness of therapy. For example, in treating neuropathic pain, a measure of the effectiveness of treatment may involve assessment of the patient's quality of life, e.g., improvements in the patient's sleeping patterns, work attendance, ability to exercise and be ambulatory, etc. Pain scales, operating on a point basis, may also be used to help evaluate a patient's pain level. Indicators for the other diseases and conditions described herein, are well-known to those skilled in the art, and are readily available to the treating physician. Continuous monitoring by the physician will ensure that the optimal amount of active agent will be administered at any given time, as well as facilitating the determination of the duration of treatment. This is of particular value when secondary agents are also being administered, as their selection, dosage, and duration of therapy may also require adjustment. In this way, the treatment regimen and dosing schedule can be adjusted over the course of therapy so that the lowest amount of active agent that exhibits the desired effectiveness is administered and, further, that administration is continued only so long as is necessary to successfully treat the disease or medical condition.

Pain Disorders

SNRIs have been shown to have a beneficial effect on pain such as painful diabetic neuropathy (duloxetine, Goldstein et al. (2005) *Pain* 116:109-118; venlafaxine, Rowbotham et al. (2004) *Pain* 110:697-706), fibromyalgia (duloxetine, Russell et al (2008) *Pain* 136(3):432-444; milnacipran, Vitton et al. (2004) *Human Psychopharmacology* 19:S27-S35), and migraine (venlafaxine, Ozyalcin et al. (2005) *Headache* 45(2):144-152). Thus, one embodiment of the invention relates to a method for treating a pain disorder, comprising administering to a patient a therapeutically effective amount of a compound of the invention. Typically, the therapeutically effective amount will be the amount that is sufficient to relieve the pain. Exemplary pain disorders include, by way of illustration, acute pain, persistent pain, chronic pain, inflammatory pain, and neuropathic pain. More specifically, these include pain associated with or caused by: arthritis; back pain including chronic low back pain; cancer, including tumor related pain (e.g. bone pain, headache, facial pain or visceral pain) and pain associated with cancer therapy (e.g. post-chemotherapy syndrome, chronic post-surgical pain syndrome and post-radiation syndrome); carpal tunnel syndrome; fibromyalgia; headaches including chronic tension headaches; inflammation associated with polymyalgia, rheumatoid arthritis and osteoarthritis; migraine; neuropathic pain including complex regional pain syndrome; overall pain; post-operative pain; shoulder pain; central pain syndromes, including post-stroke pain, and pain associated with spinal cord injuries and multiple sclerosis; phantom limb pain; pain associated with Parkinson's disease; and visceral pain (e.g., irritable bowel syndrome). Of particular interest is the treatment of neuropathic pain, which includes diabetic peripheral neuropathy (DPN), HIV-related neuropathy, post-herpetic neuralgia (PHN), and chemotherapy-induced peripheral neuropathy. When used to treat pain disorders such as neuropathic pain, compounds of the invention may be administered in combination with other therapeutic agents, including anti-convulsants, antidepressants, muscle relaxants, NSAIDs, opioid agonists, selective serotonin reuptake inhibitors, sodium channel blockers, and sympatholytics. Exemplary compounds within these classes are described herein.

Depressive Disorders

Another embodiment of the invention relates to a method of treating a depressive disorder, comprising administering to a patient a therapeutically effective amount of a compound of the invention. Typically, the therapeutically effective amount will be the amount that is sufficient to alleviate depression and provide a sense of general well-being. Exemplary depressive disorders include, by way of illustration and not limitation: depression associated with Alzheimer's disease, bipolar disorder, cancer, child abuse, infertility, Parkinson's disease, postmyocardial infarction, and psychosis; dysthymia; grumpy or irritable old man syndrome; induced depression; major depression; pediatric depression; postmenopausal depression; post partum depression; recurrent depression; single episode depression; and subsyndromal symptomatic depression. Of particular interest is the treatment of major depression. When used to treat depressive disorders, compounds of the invention may be administered in combination with other therapeutic agents, including antidepressants and dual serotonin-norepinephrine reuptake inhibitors. Exemplary compounds within these classes are described herein.

Affective Disorders

Another embodiment of the invention relates to a method of treating an affective disorder, comprising administering to a patient a therapeutically effective amount of a compound of the invention. Exemplary affective disorders include, by way of illustration and not limitation: anxiety disorders such as general anxiety disorder; avoidant personality disorder; eating disorders such as anorexia nervosa, bulimia nervosa and obesity; obsessive compulsive disorder; panic disorder; personality disorders such as avoidant personality disorder and attention deficit hyperactivity disorder (ADHD); post-traumatic stress syndrome; phobias such as agoraphobia, as well as simple and other specific phobias, and social phobia; premenstrual syndrome; psychotic disorders, such as schizophrenia and mania; seasonal affective disorder; sexual dysfunction, including premature ejaculation, male impotence, and female sexual dysfunction such as female sexual arousal disorder; social anxiety disorder; and substance abuse disorders, including chemical dependencies such as addictions to alcohol, benzodiazepines, cocaine, heroin, nicotine and phenobarbital, as well as withdrawal syndromes that may arise from these dependencies. When used to treat affective disorders, compounds of the invention may be administered in combination with other therapeutic agents, including antidepressants. Exemplary compounds within these classes are described herein.

Atomoxetine, which is 10-fold NET selective, is approved for attention deficit hyperactivity disorder (ADHD) therapy, and clinical studies have shown that the SNRI, venlafaxine, can also have a beneficial effect in treating ADHD (Mukaddes et al. (2002) *Eur. Neuropsychopharm.* 12(Supp 3):421). Thus, the compounds of the invention are also expected to be useful in methods for treating attention deficit hyperactivity disorder by administering to a patient a therapeutically effective amount of a compound of the invention. When used to treat depression, compounds of the invention may be administered in combination with other therapeutic agents, including antidepressants. Exemplary compounds within these classes are described herein.

Cognitive Disorders

Another embodiment of the invention relates to a method of treating a cognitive disorder, comprising administering to a patient a therapeutically effective amount of a compound of the invention. Exemplary cognitive disorders include, by way of illustration and not limitation: dementia, which includes degenerative dementia (e.g., Alzheimer's disease, Creutzfeldt-Jakob disease, Huntingdon's chorea, Parkinson's disease, Pick's disease, and senile dementia), vascular dementia (e.g., multi-infarct dementia), and dementia associated with intracranial space occupying lesions, trauma, infections and related conditions (including HIV infection), metabolism, toxins, anoxia and vitamin deficiency; and mild cognitive impairment associated with ageing, such as age associated memory impairment, amnesiac disorder and age-related cognitive decline. When used to treat cognitive disorders, compounds of the invention may be administered in combination with other therapeutic agents, including anti-Alzheimer's agents and anti-Parkinson's agents. Exemplary compounds within these classes are described herein.

Other Disorders

SNRIs have also been shown to be effective for the treatment of stress urinary incontinence (Dmochowski (2003) *Journal of Urology* 170(4): 1259-1263). Thus, another embodiment of the invention relates to a method for treating stress urinary incontinence, comprising administering to a patient a therapeutically effective amount of a compound of the invention. When used to treat stress urinary incontinence, compounds of the invention may be administered in combination with other therapeutic agents, including anticonvulsants. Exemplary compounds within these classes are described herein.

Duloxetine, an SNRI, is undergoing clinical trials for evaluating its efficacy in treating chronic fatigue syndrome, and has recently been shown to be effective in treating fibromyalgia (Russell et al (2008) *Pain* 136(3):432-444). The compounds of the invention, due to their ability to inhibit SERT and NET, are also expected to have this utility, and another embodiment of the invention relates to a method for treating chronic fatigue syndrome, comprising administering to a patient a therapeutically effective amount of a compound of the invention.

Sibutramine, a norepinephrine and dopamine reuptake inhibitor, has been shown to be useful in treating obesity (Wirth et al. (2001) *JAMA* 286(11):1331-1339). The compounds of the invention, due to their ability to inhibit NET, are also expected to have this utility, and another embodiment of the invention relates to a method for treating obesity, comprising administering to a patient a therapeutically effective amount of a compound of the invention.

Desvenlafaxine, an SNRI, has been shown to relieve vasomotor symptoms associated with menopause (Deecher et al. (2007) *Endocrinology* 148(3):1376-1383). The compounds of the invention, due to their ability to inhibit SERT and NET, are also expected to have this utility, and another embodiment of the invention relates to a method for treating vasomotor symptoms associated with menopause, comprising administering to a patient a therapeutically effective amount of a compound of the invention.

Research Tools

Since compounds of the invention possess both serotonin reuptake inhibition activity and norepinephrine reuptake inhibition activity, such compounds are also useful as research tools for investigating or studying biological systems or samples having serotonin or norepinephrine transporters. Any suitable biological system or sample having serotonin and/or norepinephrine transporters may be employed in such studies which may be conducted either in vitro or in vivo. Representative biological systems or samples suitable for such studies include, but are not limited to, cells, cellular extracts, plasma membranes, tissue samples, isolated organs, mammals (such as mice, rats, guinea pigs, rabbits, dogs, pigs, humans, and so forth), and the like, with mammals being of particular interest. In one particular embodiment of the invention, serotonin reuptake in a mammal is inhibited by administering a serotonin reuptake-inhibiting amount of a compound of the invention. In another particular embodiment, norepinephrine reuptake in a mammal is inhibited by administering a norepinephrine reuptake-inhibiting amount of a compound of the invention. Compounds of the invention can also be used as research tools by conducting biological assays using such compounds.

When used as a research tool, a biological system or sample comprising a serotonin transporter and/or a norepinephrine transporter is typically contacted with a serotonin reuptake-inhibiting or norepinephrine reuptake-inhibiting amount of a compound of the invention. After the biological system or sample is exposed to the compound, the effects of inhibiting serotonin reuptake and/or norepinephrine reuptake are determined using conventional procedures and equipment. Exposure encompasses contacting cells or tissue with the compound, administering the compound to a mammal, for example by i.p. or i.v. administration, and so forth. This determining step may comprise measuring a response, i.e., a quantitative analysis or may comprise an observation, i.e., a qualitative analysis. Measuring a response involves, for example, determining the effects of the compound on the biological system or sample using conventional procedures and equipment, such as serotonin and norepinephrine reuptake assays. The assay results can be used to determine the activity level as well as the amount of compound necessary to achieve the desired result, i.e., a serotonin reuptake-inhibiting and a norepinephrine reuptake-inhibiting amount.

Additionally, compounds of the invention can be used as research tools for evaluating other chemical compounds, and thus are also useful in screening assays to discover, for example, new compounds having both serotonin reuptake-inhibiting activity and norepinephrine reuptake-inhibiting activity. In this manner, a compound of the invention is used as a standard in an assay to allow comparison of the results obtained with a test compound and with compounds of the invention to identify those test compounds that have about equal or superior reuptake-inhibiting activity, if any. For example, reuptake data for a test compound or a group of test compounds is compared to the reuptake data for a compound of the invention to identify those test compounds that have the desired properties, e.g., test compounds having reuptake-inhibiting activity about equal or superior to a compound of the invention, if any. This aspect of the invention includes, as separate embodiments, both the generation of comparison data (using the appropriate assays) and the analysis of the test data to identify test compounds of interest. Thus, a test compound can be evaluated in a biological assay, by a method comprising the steps of: (a) conducting a biological assay with a test compound to provide a first assay value; (b) conducting the biological assay with a compound of the invention to provide a second assay value; wherein step (a) is conducted either before, after or concurrently with step (b); and (c) comparing the first assay value from step (a) with the second assay value from step (b). Exemplary biological assays include serotonin and norepinephrine reuptake assays.

Pharmaceutical Compositions and Formulations

Compounds of the invention are typically administered to a patient in the form of a pharmaceutical composition or formulation. Such pharmaceutical compositions may be administered to the patient by any acceptable route of administration including, but not limited to, oral, rectal, vaginal, nasal, inhaled, topical (including transdermal) and parenteral modes of administration. Further, the compounds of the invention may be administered, for example orally, in multiple doses per day (e.g. twice, three times or four times daily), in a single daily dose, in a twice-daily dose, in a single weekly dose, and so forth. It will be understood that any form of the compounds of the invention, (i.e., free base, pharmaceutically acceptable salt, solvate, etc.) that is suitable for the particular mode of administration can be used in the pharmaceutical compositions discussed herein.

Accordingly, in one embodiment, the invention relates to a pharmaceutical composition comprising a pharmaceutically acceptable carrier and a compound of the invention. The compositions may contain other therapeutic and/or formulating agents if desired. When discussing compositions, the "compound of the invention" may also be referred to herein as the "active agent," to distinguish it from other components of the formulation, such as the carrier. Thus, it is understood that the term "active agent" includes compounds of formula I as well as pharmaceutically acceptable salts and solvates of that compound.

The pharmaceutical compositions of the invention typically contain a therapeutically effective amount of a compound of the invention. Those skilled in the art will recognize, however, that a pharmaceutical composition may contain more than a therapeutically effective amount, i.e., bulk compositions, or less than a therapeutically effective amount, i.e., individual unit doses designed for multiple administration to achieve a therapeutically effective amount. Typically, the composition will contain from about 0.01-95 wt % of active agent, including, from about 0.01-30 wt %, such as from about 0.01-10 wt %, with the actual amount depending upon the formulation itself, the route of administration, the frequency of dosing, and so forth. In one embodiment, a composition suitable for an oral dosage form, for example, may contain about 5-70 wt %, or from about 10-60 wt % of active agent.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable composition for a particular mode of administration is well within the scope of those skilled in the pharmaceutical arts. Additionally, carriers or excipients used in such compositions are commercially available. By way of further illustration, conventional formulation techniques are described in *Remington: The Science and Practice of Pharmacy*, 20$^{th}$ Edition, Lippincott Williams & White, Baltimore, Md. (2000); and H. C. Ansel et al., *Pharmaceutical Dosage Forms and Drug Delivery Systems*, 7$^{th}$ Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; compressed propellant gases, such as chlorofluorocarbons and hydrofluorocarbons; and other non-toxic compatible substances employed in pharmaceutical compositions.

Pharmaceutical compositions are typically prepared by thoroughly and intimately mixing or blending the active agent with a pharmaceutically acceptable carrier and one or more optional ingredients. The resulting uniformly blended mixture may then be shaped or loaded into tablets, capsules, pills, canisters, cartridges, dispensers, and the like, using conventional procedures and equipment.

In one embodiment, the pharmaceutical compositions are suitable for oral administration. One exemplary dosing regimen would be an oral dosage form administered once or twice daily. Suitable compositions for oral administration may be in the form of capsules, tablets, pills, lozenges, cachets, dragees, powders, granules; solutions or suspensions in an aqueous or non-aqueous liquid; oil-in-water or water-in-oil liquid emulsions; elixirs or syrups; and the like; each containing a predetermined amount of the active agent.

When intended for oral administration in a solid dosage form (i.e., as capsules, tablets, pills, and the like), the composition will typically comprise the active agent and one or more pharmaceutically acceptable carriers, such as sodium citrate or dicalcium phosphate. Solid dosage forms may also comprise: fillers or extenders, such as starches, microcrystalline cellulose, lactose, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof; coloring agents; and buffering agents.

Release agents, wetting agents, coating agents, sweetening, flavoring and perfuming agents, preservatives and antioxidants may also be present in the pharmaceutical compositions. Exemplary coating agents for tablets, capsules, pills and like, include those used for enteric coatings, such as cellulose acetate phthalate, polyvinyl acetate phthalate, hydroxypropyl methylcellulose phthalate, methacrylic acid-methacrylic acid ester copolymers, cellulose acetate trimellitate, carboxymethyl ethyl cellulose, hydroxypropyl methyl cellulose acetate succinate, and the like. Examples of pharmaceutically acceptable antioxidants include: water-soluble antioxidants, such as ascorbic acid, cysteine hydrochloride, sodium bisulfate, sodium metabisulfate, sodium sulfite and the like; oil-soluble antioxidants, such as ascorbyl palmitate, butylated hydroxyanisole, butylated hydroxytoluene, lecithin, propyl gallate, alpha-tocopherol, and the like; and metal-chelating agents, such as citric acid, ethylenediamine tetraacetic acid, sorbitol, tartaric acid, phosphoric acid, and the like.

Compositions may also be formulated to provide slow or controlled release of the active agent using, by way of example, hydroxypropyl methyl cellulose in varying proportions or other polymer matrices, liposomes and/or microspheres. In addition, the pharmaceutical compositions of the invention may contain opacifying agents and may be formulated so that they release the active agent only, or preferentially, in a certain portion of the gastrointestinal tract, optionally, in a delayed manner. Examples of embedding compositions which can be used include polymeric substances and waxes. The active agent can also be in microencapsulated form, if appropriate, with one or more of the above-described excipients.

Suitable liquid dosage forms for oral administration include, by way of illustration, pharmaceutically acceptable emulsions, microemulsions, solutions, suspensions, syrups and elixirs. Liquid dosage forms typically comprise the active agent and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (e.g., cottonseed, groundnut, corn, germ, olive, castor and sesame oils), glycerol, tetrahydrofuryl alcohol, polyethylene glycols and fatty acid esters of sorbitan, and mixtures thereof. Suspensions may contain suspending agents such as, for example, ethoxylated isostearyl alcohols, polyoxyethylene sorbitol and sorbitan esters, microcrystalline cellulose, aluminium metahydroxide, bentonite, agar-agar and tragacanth, and mixtures thereof.

When intended for oral administration, the pharmaceutical compositions of the invention may be packaged in a unit dosage form. The term "unit dosage form" refers to a physically discrete unit suitable for dosing a patient, i.e., each unit containing a predetermined quantity of the active agent calculated to produce the desired therapeutic effect either alone or in combination with one or more additional units. For example, such unit dosage forms may be capsules, tablets, pills, and the like.

In another embodiment, the compositions of the invention are suitable for inhaled administration, and will typically be in the form of an aerosol or a powder. Such compositions are generally administered using well-known delivery devices, such as a nebulizer, dry powder, or metered-dose inhaler. Nebulizer devices produce a stream of high velocity air that causes the composition to spray as a mist that is carried into a patient's respiratory tract. An exemplary nebulizer formulation comprises the active agent dissolved in a carrier to form a solution, or micronized and combined with a carrier to form a suspension of micronized particles of respirable size. Dry powder inhalers administer the active agent as a free-flowing powder that is dispersed in a patient's air-stream during inspiration. An exemplary dry powder formulation comprises the active agent dry-blended with an excipient such as lactose, starch, mannitol, dextrose, polylactic acid, polylactide-co-glycolide, and combinations thereof. Metered-dose inhalers discharge a measured amount of the active agent using compressed propellant gas. An exemplary metered-dose formulation comprises a solution or suspension of the active agent in a liquefied propellant, such as a chlorofluorocarbon or hydrofluoroalkane. Optional components of such formulations include co-solvents, such as ethanol or pentane, and surfactants, such as sorbitan trioleate, oleic acid, lecithin, and glycerin. Such compositions are typically prepared by adding chilled or pressurized hydrofluoroalkane to a suitable container containing the active agent, ethanol (if present) and the surfactant (if present). To prepare a suspension, the active agent is micronized and then combined with the propellant. Alternatively, a suspension formulation can be prepared by spray drying a coating of surfactant on micronized particles of the active agent. The formulation is then loaded into an aerosol canister, which forms a portion of the inhaler.

Compounds of the invention can also be administered parenterally (e.g., by subcutaneous, intravenous, intramuscular, or intraperitoneal injection). For such administration, the active agent is provided in a sterile solution, suspension, or emulsion. Exemplary solvents for preparing such formulations include water, saline, low molecular weight alcohols such as propylene glycol, polyethylene glycol, oils, gelatin, fatty acid esters such as ethyl oleate, and the like. A typical parenteral formulation is a sterile pH 4-7 aqueous solution of the active agent. Parenteral formulations may also contain one or more solubilizers, stabilizers, preservatives, wetting agents, emulsifiers, and dispersing agents. These formulations may be rendered sterile by use of a sterile injectable medium, a sterilizing agent, filtration, irradiation, or heat.

Compounds of the invention can also be administered transdermally using known transdermal delivery systems and excipients. For example, the compound can be admixed with permeation enhancers, such as propylene glycol, polyethylene glycol monolaurate, azacycloalkan-2-ones and the like, and incorporated into a patch or similar delivery system. Additional excipients including gelling agents, emulsifiers and buffers, may be used in such transdermal compositions if desired.

If desired, compounds of the invention may be administered in combination with one or more other therapeutic agents. Thus, in one embodiment, compositions of the invention may optionally contain other drugs that are co-administered with a compound of the invention. For example, the composition may further comprise one or more drugs (also referred to as "secondary agents(s)") selected from the group of anti-Alzheimer's agents, anticonvulsants (antiepileptics), antidepressants, anti-Parkinson's agents, dual serotonin-norepinephrine reuptake inhibitors (SNRTs), non-steroidal anti-inflammatory agents (NSAIDs), norepinephrine reuptake inhibitors, opioid agonists (opioid analgesics), selective serotonin reuptake inhibitors, sodium channel blockers, sympatholytics, and combinations thereof. Numerous examples of such therapeutic agents are well known in the art, and examples are described herein. By combining a compound of the invention with a secondary agent, triple therapy can be achieved, i.e., serotonin reuptake inhibitory activity, norepinephrine reuptake inhibitory activity, and activity associated with the secondary agent (e.g., antidepressant activity), using only two active components. Since pharmaceutical compositions containing two active components are typically easier to formulate than compositions containing three active components, such two-component compositions provide a significant advantage over compositions containing three active components. Accordingly, in yet another aspect of the invention, a pharmaceutical composition comprises a compound of the invention, a second active agent, and a pharmaceutically acceptable carrier. Third, fourth etc. active agents may also be included in the composition. In combination therapy, the amount of compound of the invention that is administered, as well as the amount of secondary agents, may be less than the amount typically administered in monotherapy.

A compound of the invention may be either physically mixed with the second active agent to form a composition containing both agents; or each agent may be present in separate and distinct compositions which are administered to the patient simultaneously or sequentially. For example, a compound of the invention can be combined with a second active agent using conventional procedures and equipment to form a combination of active agents comprising a compound of the invention and a second active agent. Additionally, the active agents may be combined with a pharmaceutically acceptable carrier to form a pharmaceutical composition comprising a compound of the invention, a second active agent and a pharmaceutically acceptable carrier. In this embodiment, the components of the composition are typically mixed or blended to create a physical mixture. The physical mixture is then administered in a therapeutically effective amount using any of the routes described herein.

Alternatively, the active agents may remain separate and distinct before administration to the patient. In this embodiment, the agents are not physically mixed together before administration but are administered simultaneously or at separate times as separate compositions. Such compositions can be packaged separately or may be packaged together in a kit. When administered at separate times, the secondary agent will typically be administered less than 24 hours after administration of the compound of the invention, ranging anywhere from concurrent with administration of the compound of the invention to about 24 hours post-dose. This is also referred to as sequential administration. Thus, a compound of the invention can be orally administered simultaneously or sequentially with another active agent using two tablets, with one tablet for each active agent, where sequential may mean being administered immediately after administration of the compound of the invention or at some predetermined time later (e.g., one hour later or three hours later). Alternatively, the combination may be administered by different routes of administration, i.e., one orally and the other by inhalation.

In one embodiment, the kit comprises a first dosage form comprising a compound of the invention and at least one additional dosage form comprising one or more of the secondary agents set forth herein, in quantities sufficient to carry out the methods of the invention. The first dosage form and the second (or third, etc.) dosage form together comprise a therapeutically effective amount of active agents for the treatment or prevention of a disease or medical condition in a patient.

Secondary agent(s), when included, are present in a therapeutically effective amount. i.e., are typically administered in an amount that produces a therapeutically beneficial effect when co-administered with a compound of the invention. The secondary agent can be in the form of a pharmaceutically acceptable salt, solvate, optically pure stereoisomer, and so forth. Thus, secondary agents listed below are intended to include all such forms, and are commercially available or can be prepared using conventional procedures and reagents.

Representative anti-Alzheimer's agents include, but are not limited to: donepezil, galantamine, memantine, rivastigmine, selegiline, tacrine, and combinations thereof.

Representative anticonvulsants (antiepileptics) include, but are not limited to: acetazolamide, albutoin, 4-amino-3-hydroxybutyric acid, beclamide, carbamazepine, cinromide, clomethiazole, clonazepam, diazepam, dimethadione, eterobarb, ethadione, ethosuximide, ethotoin, felbamate, fosphenytoin, gabapentin, lacosamide, lamotrigine, lorazepam, magnesium bromide, magnesium sulfate, mephenytoin, mephobarbital, methsuximide, midazolam, nitrazepam, oxazepam, oxcarbazepine, paramethadione, phenacemide, pheneturide, phenobarbital, phensuximide, phenytoin, potassium bromide, pregabalin, primidone, progabide, sodium bromide, sodium valproate, sulthiame, tiagabine, topiramate, trimethadione, valproic acid, valpromide, vigabatrin, zonisamide, and combinations thereof. In a particular embodiment, the anticonvulsant is selected from carbamazepine, gabapentin, pregabalin, and combinations thereof.

Representative antidepressants include, but are not limited to: adinazolam, amitriptyline, clomipramine, desipramine, dothiepin (e.g., dothiepin hydrochloride), doxepin, imipramine, lofepramine, mirtazapine, nortriptyline, protriptyline, trimipramine, venlafaxine, zimelidine, and combinations thereof.

Representative anti-Parkinson's agents include, but are not limited to: amantadine, apomorphine, benztropine, bromocriptine, carbidopa, diphenhydramine, entacapone, levodopa, pergolide, pramipexole, ropinirole, selegiline, tolcapone, trihexyphenidyl, and combinations thereof.

Representative dual serotonin-norepinephrine reuptake inhibitors (SNRIs) include, but are not limited to: bicifadine, desvenlafaxine, duloxetine, milnacipran, nefazodone, venlafaxine, and combinations thereof Representative non-steroidal anti-inflammatory agents (NSAIDs) include, but are not limited to: acemetacin, acetaminophen, acetyl salicylic acid, alclofenac, alminoprofen, amfenac, amiprilose, amoxiprin, anirolac, apazone, azapropazone, benorilate, benoxaprofen, bezpiperylon, broperamole, bucloxic acid, carprofen, clidanac, diclofenac, diflunisal, diftalone, enolicam, etodolac, etoricoxib, fenbufen, fenclofenac, fenclozic acid, fenoprofen, fentiazac, feprazone, flufenamic acid, flufenisal, fluprofen, flurbiprofen, furofenac, ibufenac, ibuprofen, indomethacin, indoprofen, isoxepac, isoxicam, ketoprofen, ketorolac, lofemizole, lornoxicam, meclofenamate, meclofenamic acid, mefenamic acid, meloxicam, mesalamine, miroprofen, mofebutazone, nabumetone, naproxen, niflumic acid, nimesulide, nitroflurbiprofen, olsalazine, oxaprozin, oxpinac, oxyphenbutazone, phenylbutazone, piroxicam, pirprofen, pranoprofen, salsalate, sudoxicam, sulfasalazine, sulindac, suprofen, tenoxicam, tiopinac, tiaprofenic acid, tioxaprofen, tolfenamic acid, tolmetin, triflumidate, zidometacin, zomepirac, and combinations thereof. In a particular embodiment, the NSAID is selected from etodolac, flurbiprofen, ibuprofen, indomethacin, ketoprofen, ketorolac, meloxicam, naproxen, oxaprozin, piroxicam, and combinations thereof. In a particular embodiment, the NSAID is selected from ibuprofen, indomethacin, nabumetone, naproxen (for example, naproxen sodium), and combinations thereof Representative muscle relaxants include, but are not limited to: carisoprodol, chlorzoxazone, cyclobenzaprine, diflunisal, metaxalone, methocarbamol, and combinations thereof.

Representative norepinephrine reuptake inhibitors include, but are not limited to: atomoxetine, buprorion and the buprorion metabolite hydroxybuproprion, maprotiline, reboxetine (for example, (S,S)-reboxetine), viloxazine, and combinations thereof In a particular embodiment, the norepinephrine reuptake inhibitor is selected from atomoxetine, reboxetine, and combinations thereof Representative opioid agonists (opioid analgesics) include, but are not limited to: buprenorphine, butorphanol, codeine, dihydrocodeine, fentanyl, hydrocodone, hydromorphone, levallorphan, levorphanol, meperidine, methadone, morphine, nalbuphine, nalmefene, nalorphine, naloxone, naltrexone, nalorphine, oxycodone, oxymorphone, pentazocine, propoxyphene, tramadol, and combinations thereof. In certain embodiments, the opioid agonist is selected from codeine, dihydrocodeine, hydrocodone, hydromorphone, morphine, oxycodone, oxymorphone, tramadol, and combinations thereof.

Representative selective serotonin reuptake inhibitors (SSRIs) include, but are not limited to: citalopram and the citalopram metabolite desmethylcitalopram, dapoxetine, escitalopram (e.g., escitalopram oxalate), fluoxetine and the fluoxetine desmethyl metabolite norfluoxetine, fluvoxamine (e.g., fluvoxamine maleate), paroxetine, sertraline and the sertraline metabolite demethylsertraline, and combinations thereof. In certain embodiments, the SSRI is selected from citalopram, paroxetine, sertraline, and combinations thereof.

Representative sodium channel blockers include, but are not limited to: carbamazepine, fosphenytoin, lamotrignine, lidocaine, mexiletine, oxcarbazepine, phenytoin, and combinations thereof.

Representative sympatholytics include, but are not limited to: atenolol, clonidine, doxazosin, guanethidine, guanfacine, modafinil, phentolamine, prazosin, reserpine, tolazoline (e.g., tolazoline hydrochloride), tamsulosin, and combinations thereof.

The following formulations illustrate representative pharmaceutical compositions of the present invention:

Exemplary Hard Gelatin Capsules for Oral Administration

A compound of the invention (50 g), spray-dried lactose (440 g) and magnesium stearate (10 g) are thoroughly blended. The resulting composition is then loaded into hard gelatin capsules (500 mg of composition per capsule).

Alternately, a compound of the invention (20 mg) is thoroughly blended with starch (89 mg), microcrystalline cellulose (89 mg) and magnesium stearate (2 mg). The mixture is then passed through a No. 45 mesh U.S. sieve and loaded into a hard gelatin capsule (200 mg of composition per capsule).

Exemplary Gelatin Capsule Formulation for Oral Administration

A compound of the invention (100 mg) is thoroughly blended with polyoxyethylene sorbitan monooleate (50 mg) and starch powder (250 mg). The mixture is then loaded into a gelatin capsule (400 mg of composition per capsule).

Alternately, a compound of the invention (40 mg) is thoroughly blended with microcrystalline cellulose (Avicel PH 103; 259.2 mg) and magnesium stearate (0.8 mg). The mixture is then loaded into a gelatin capsule (Size #1, White, Opaque) (300 mg of composition per capsule).

Exemplary Tablet Formulation for Oral Administration

A compound of the invention (10 mg), starch (45 mg) and microcrystalline cellulose (35 mg) are passed through a No. 20 mesh U.S. sieve and mixed thoroughly. The granules so produced are dried at 50-60° C. and passed through a No. 16 mesh U.S. sieve. A solution of polyvinylpyrrolidone (4 mg as a 10% solution in sterile water) is mixed with sodium carboxymethyl starch (4.5 mg), magnesium stearate (0.5 mg), and talc (1 mg), and this mixture is then passed through a No. 16 mesh U.S. sieve. The sodium carboxymethyl starch, magnesium stearate and talc are then added to the granules. After mixing, the mixture is compressed on a tablet machine to afford a tablet weighing 100 mg.

Alternately, a compound of the invention (250 mg) is thoroughly blended with microcrystalline cellulose (400 mg), silicon dioxide fumed (10 mg), and stearic acid (5 mg). The mixture is then compressed to form tablets (665 mg of composition per tablet).

Alternately, a compound of the invention (400 mg) is thoroughly blended with cornstarch (50 mg), croscarmellose sodium (25 mg), lactose (120 mg), and magnesium stearate (5 mg). The mixture is then compressed to form a single-scored tablet (600 mg of compositions per tablet).

Exemplary Suspension Formulation for Oral Administration

The following ingredients are mixed to form a suspension containing 100 mg of active agent per 10 mL of suspension:

| Ingredients | Amount |
| --- | --- |
| Compound of the invention | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum ® K (magnesium aluminum silicate) | 1.0 g |
| Flavoring | 0.035 mL |
| Colorings | 0.5 mg |
| Distilled water | q.s. to 100 mL |

Exemplary Injectable Formulation for Administration by Injection

A compound of the invention (0.2 g) is blended with 0.4 M sodium acetate buffer solution (2.0 mL). The pH of the resulting solution is adjusted to pH 4 using 0.5 N aqueous hydrochloric acid or 0.5 N aqueous sodium hydroxide, as necessary, and then sufficient water for injection is added to provide a total volume of 20 mL. The mixture is then filtered through a sterile filter (0.22 micron) to provide a sterile solution suitable for administration by injection.

Exemplary Compositions for Administration by Inhalation

A compound of the invention (0.2 mg) is micronized and then blended with lactose (25 mg). This blended mixture is then loaded into a gelatin inhalation cartridge. The contents of the cartridge are administered using a dry powder inhaler, for example.

Alternately, a micronized compound of the invention (10 g) is dispersed in a solution prepared by dissolving lecithin (0.2 g) in demineralized water (200 mL). The resulting suspension is spray dried and then micronized to form a micronized composition comprising particles having a mean diameter less than about 1.5 μm. The micronized composition is then loaded into metered-dose inhaler cartridges containing pressurized 1,1,1,2-tetrafluoroethane in an amount sufficient to provide about 10 μg to about 500 μg of the compound of the invention per dose when administered by the inhaler.

Alternately, a compound of the invention (25 mg) is dissolved in citrate buffered (pH 5) isotonic saline (125 mL). The mixture is stirred and sonicated until the compound is dissolved. The pH of the solution is checked and adjusted, if necessary, to pH 5 by slowly adding aqueous 1N sodium hydroxide. The solution is administered using a nebulizer device that provides about 10 μg to about 500 μg of the compound of the invention per dose.

EXAMPLES

The following Preparations and Examples are provided to illustrate specific embodiments of the invention. These specific embodiments, however, are not intended to limit the scope of the invention in any way unless specifically indicated.

The following abbreviations have the following meanings unless otherwise indicated and any other abbreviations used herein and not defined have their standard meaning.

AcOH acetic acid
$BH_3.Me_2S$ borane dimethylsulphide complex
BOC t-butoxycarbonyl
BSA bovine serum albumin
DCM dichloromethane (i.e., methylene chloride)
DIAD diisopropyl azodicarboxylate
DIPEA N,N-diisopropylethylamine
DMEM Dulbecco's Modified Eagle's Medium
DMF N,N-dimethylformamide
DMSO dimethylsulfoxide
EDTA ethylenediaminetetraacetic acid
EtOAc ethyl acetate
EtOH ethanol
FBS fetal bovine serum
HCTU 5-chloro-1-[bis(dimethylamino)methylene]-1H-benzotriazolium 3-oxide hexafluorophosphate
hDAT human dopamine transporter
HEPES 4-(2-hydroxyethyl)-1-piperazineethanesulfonic acid
hNET human norepinephrine transporter
HOBt 1-hydroxybenzotriazole, hydrate
hSERT human serotonin transporter
5-HT 5-hydroxytryptamine
IPA isopropanol
LiHMDS lithium hexamethyl disilazide
MeOH methanol
NA noradrenaline
PBS phosphate buffered saline
$PPh_3$ triphenylphosphine
TEMPO 2,2,6,6-tetramethyl-1-piperidinyloxy, free radical
TFA trifluoroacetic acid
THF tetrahydrofuran Any other abbreviations used herein but not defined have their standard, generally accepted meaning. Unless noted otherwise, all materials, such as reagents, starting materials and solvents, were purchased from commercial suppliers (such as Sigma-Aldrich, Fluka Riedel-de Haën, and the like) and were used without further purification.

Assay 1 hSERT, hNET, and hDAT Binding Assays

Membrane radioligand binding assays were used to measure competitive inhibition of labeled ligand ($^3$H-citalopram or $^3$H-nisoxetine or $^3$H-WIN35428) binding to membranes prepared from cells expressing the respective human recombinant transporter (hSERT or hNET or hDAT) in order to determine the $pK_i$ values of test compounds at the transporters.

Membrane Preparation from Cells Expressing hSERT, hNET, or hDAT

Recombinant human embryonic kidney (HEK-293) derived cell lines stably transfected with hSERT or hNET, respectively, were grown in DMEM medium supplemented with 10% dialyzed FBS (for hSERT) or FBS (for hNET), 100 μg/ml penicillin, 100 μg/ml streptomycin, 2 mM L-glutamine and 250 μg/ml of the aminoglycoside antibiotic G418, in a 5% $CO_2$ humidified incubator at 37° C. When cultures reached 80% confluence, the cells were washed thoroughly in PBS (without $Ca^{2+}$ and $Mg^{2+}$) and lifted with 5 mM EDTA in PBS. Cells were pelleted by centrifugation, resuspended in lysis buffer (10 mM Tris-HCl, pH7.5 containing 1 mM EDTA), homogenized, pelleted by centrifugation, then resuspended in 50 mM Tris-HCl, pH 7.5 and 10% sucrose at 4° C. Protein concentration of the membrane suspension was determined using a Bio-Rad Bradford Protein Assay kit. Membranes were snap frozen and stored at −80° C. Chinese hamster ovary membranes expressing hDAT (CHO-DAT) were purchased from PerkinElmer and stored at −80° C.

Binding Assays

Binding assays were performed in a 96-well assay plate in a total volume of 200 μl assay buffer (50 mM Tris-HCl, 120 mM NaCl, 5 mM KCl, pH 7.4) with 0.5, 1, and 3 μg membrane protein, for SERT, NET and DAT, respectively. Saturation binding studies, to determine radioligand $K_d$ values for $^3$H-citalopram, $^3$H-nisoxetine, or $^3$H-WIN35428, respectively were conducted using 12 different radioligand concentrations ranging from 0.005-10 nM ($^3$H-citalopram); 0.01-20 nM ($^3$H-nisoxetine) and 0.2-50 nM ($^3$H-WIN35428). Displacement assays for determination of $pK_i$ values of test compounds were conducted with 1.0 nM $^3$H-citalopram, 1.0 nM $^3$H-nisoxetine or 3.0 nM $^3$H-WIN35428, at 11 different concentrations of test compound ranging from 10 pM to 100 μM.

Stock solutions (10 mM in DMSO) of test compound were prepared and serial dilutions made using Dilution Buffer (50 mM Tris-HCl, 120 mM NaCl, 5 mM KCl, pH 7.4, 0.1% BSA, 400 μM ascorbic acid). Non-specific radioligand binding was determined in the presence of 1 μM duloxetine, 1 μM desipramine or 10 μM GBR12909 (each in Dilution Buffer) for the hSERT, hNET or hDAT assays, respectively.

Following a 60 minute incubation at 22° C. (or a period sufficient to reach equilibrium), the membranes were harvested by rapid filtration over a 96-well UniFilter GF/B plate, pretreated with 0.3% polyethyleneimine, and washed 6 times with 300 μl wash buffer (50 mM Tris-HCl, 0.9% NaCl, pH 7.5 at 4° C.). Plates were dried overnight at room temperature, ~45 μl of MicroScint™-20 (Perkin Elmer) added and bound radioactivity quantitated via liquid scintillation spectroscopy. Competitive inhibition curves and saturation isotherms were analyzed using GraphPad Prism Software package (GraphPad Software, Inc., San Diego, Calif.). $IC_{50}$ values were generated from concentration response curves using the Sigmoidal Dose Response (variable slope) algorithm in Prism GraphPad. $K_d$ and $B_{max}$ values for the radioligand were generated from saturation isotherms using the Saturation Binding Global Fit algorithm in Prism GraphPad. $pK_i$ (negative decadic logarithm of $K_i$) values for test compounds were calculated from the best-fit $IC_{50}$ values, and the $K_d$ value of the radioligand, using the Cheng-Prusoff equation (Cheng & Prusoff (1973) *Biochem. Pharmacol.* 22(23):3099-3108): $K_i = IC_{50}/(1+[L]/K_d)$, where [L]=concentration radioligand.

All the aforementioned compounds were tested in this assay and found to exhibit a SERT $pK_i \geq 5.0$ and a NET $pK_i \geq 5.0$, with numerous compounds exhibiting a SERT $pK_i \geq 7.0$ and/or NET $pK_i \geq 7.0$ and several exhibiting a SERT $pK_i \geq 8.0$ and/or NET $pK_i \geq 8.0$.

Assay 2 hSERT, hNET, and hDAT Neurotransmitter Uptake Assays

Neurotransmitter uptake assays were used to measure competitive inhibition of $^3$H-serotonin ($^3$H-5-HT), $^3$H-norepinephrine ($^3$H-NE), and $^3$H-dopamine ($^3$H-DA) uptake into cells expressing the respective transporter (hSERT, hNET or hDAT) in order to determine the $pIC_{50}$ values of test compounds at the transporters.

$^3$H-5-HT, $^3$H-NE, and $^3$H-DA Uptake Assays

HEK-293 derived cell lines stably-transfected with hSERT, hNET, or hDAT, respectively, were grown in DMEM medium supplemented with 10% dialyzed FBS (for hSERT) or FBS (for hNET and hDAT), 100 μg/ml penicillin, 100 μg/ml streptomycin, 2 mM L-glutamine and 250 μg/ml of the aminoglycoside antibiotic G418 (for hSERT and hNET) or 800 ug/ml (for hDAT), in a 5% $CO_2$ humidified incubator at 37° C. When cultures reached 80% confluence, the cells were washed thoroughly in PBS (without $Ca^{2+}$ and $Mg^{2+}$) and lifted with 5 mM EDTA in PBS. Cells were harvested by centrifugation at 1100 rpm for 5 minutes, washed once by resuspension in PBS, then centrifuged. The supernatant was discarded and the cell pellet resuspended, by gentle trituration, in room temperature Krebs-Ringer bicarbonate buffer containing HEPES (10 mM), $CaCl_2$ (2.2 mM), ascorbic acid (200 μM) and pargyline (200 μM), pH 7.4. The final concentration of cells in the cell suspension was $7.5 \times 10^4$ cells/ml, $1.25 \times 10^5$ cells/ml, and $5.0 \times 10^4$ cells/ml for SERT, NET, and DAT cell lines, respectively.

Neurotransmitter uptake assays were performed in a 96-well assay plate in a total volume of 400 μl assay buffer (Krebs-Ringer bicarbonate buffer containing HEPES (10 mM), $CaCl_2$ (2.2 mM), ascorbic acid (200 μM) and pargyline (200 μM), pH 7.4) with $1.5 \times 10^4$ and $2.5 \times 10^4$ cells, for SERT and NET, respectively. Competition assays for determination of $pIC_{50}$ values of test compounds were conducted with 11 different concentrations, ranging from 10 pM to 100 μM. Stock solutions (10 mM in DMSO) of test compound were prepared and serial dilutions prepared using 50 mM Tris-HCl, 120 mM NaCl, 5 mM KCl, pH 7.4, 0.1% BSA, 400 μM ascorbic acid. Test compounds were incubated for 30 minutes at 37° C. with the respective cells, prior to addition of radiolabeled neurotransmitter, $^3$H-5-HT (20 nM final concentration), $^3$H-NE (50 nM final concentration), or $^3$H-DA (100 nM final concentration). Non-specific neurotransmitter uptake was determined in the presence of 2.5 μM duloxetine or 2.5 μM desipramine (each in Dilution Buffer) for the hSERT, hNET, or hDAT assays, respectively.

Following a 10 minute incubation, at 37° C., with radioligand, the cells were harvested by rapid filtration over a 96-well UniFilter GF/B plate, pretreated with 1% BSA, and washed 6 times with 650 μl wash buffer (ice cold PBS). Plates were dried overnight at 37° C., ~45 μl of MicroScint™-20 (Perkin Elmer) added and incorporated radioactivity quantitated via liquid scintillation spectroscopy. Competitive inhibition curves were analyzed using GraphPad Prism Software package (GraphPad Software, Inc., San Diego, Calif.). $IC_{50}$ values were generated from concentration response curves using the Sigmoidal Dose Response (variable slope) algorithm in Prism GraphPad.

Assay 3

Ex Vivo SERT and NET Transporter Occupancy Studies

Ex vivo radioligand binding and neurotransmitter uptake assays were used to determine the in vivo occupancy of SERT and NET, in selected brain regions, following in vivo administration (acute or chronic) of test compounds. Following administration of test compound (by intravenous, intraperitoneal, oral, subcutaneous or other route) at the appropriate dose (0.0001 to 100 mg/kg), rats ($\geq$n=4 per group) were euthanized at specific time points (10 minutes to 48 hours) by decapitation and the brain dissected on ice. Relevant brain regions were dissected, frozen and stored at −80° C. until use.

Ex Vivo SERT and NET Radioligand Binding Assays

For ex vivo radioligand binding assays, the initial rates of association of SERT ($^3$H-citalopram), and NET-($^3$H-nisoxetine) selective radioligands with rat brain crude homogenates, prepared from vehicle and test compound-treated animals, were monitored (see Hess et al. (2004) *J. Pharmacol. Exp. Ther.* 310(2):488-497). Crude brain tissue homogenates were prepared by homogenizing frozen tissue pieces in 0.15 ml (per mg wet weight) of 50 mM Tris-HCl, 120 mM NaCl, 5 mM KCl, pH 7.4 buffer. Radioligand association assays were performed in a 96-well assay plate in a total volume of 200 μl assay buffer (50 mM Tris-HCl, 120 mM NaCl, 5 mM KCl, 0.025% BSA, pH 7.4) with 650 μg wet weight tissue (equivalent to 25 μg protein). Homogenates were incubated for up to 5 minutes with $^3$H-citalopram (3 nM) and $^3$H-nisoxetine (5 nM), respectively, prior to termination of the assay by rapid filtration over a 96-well UniFilter GF/B plate, pretreated with 0.3% polyethyleneimine. Filters then were washed 6 times with 300 μl wash buffer (50 mM Tris-HCl, 0.9% NaCl, pH 7.4 at 4° C.). Non-specific radioligand binding was determined in the presence of 1 μM duloxetine, or 1 μM despiramine, for $^3$H-citalopram or $^3$H-nisoxetine, respectively. The plates were dried overnight at room temperature, ~45 μl of MicroScint™-20 (Perkin Elmer) added and bound radioactivity quantitated via liquid scintillation spectroscopy. The initial rates of association of $^3$H-citalopram and $^3$H-nisoxetine were determined by linear regression using GraphPad Prism Software package (GraphPad Software, Inc., San Diego, Calif.). The average rate of radioligand association to brain tissue homogenates from vehicle-treated animals was determined. The % occupancy of test compounds then was determined using the following equation:

% occupancy=100×(1−(initial rate association for test compound-treated tissue/mean rate association for vehicle-treated tissue))

$ED_{50}$ values were determined by plotting the log 10 of the dose of the test compound against the % occupancy. $ED_{50}$ values were generated from concentration response curves using the Sigmoidal Dose Response (variable slope) algorithm in GraphPad Prism.

Ex Vivo SERT and NET Uptake Assays

Ex vivo neurotransmitter uptake assays, in which the uptake of $^3$H-5-HT or $^3$H-NE into rat brain crude homogenates, prepared from vehicle and test compound-treated animals, were used to measure in vivo SERT and NET transporter occupancy (see Wong et al. (1993) *Neuropsychopharmacology* 8(1):23-33). Crude brain tissue homogenates were prepared by homogenizing frozen tissue pieces in 0.5 ml (per mg wet weight) of 10 mM HEPES buffer pH 7.4, containing 0.32 M sucrose, 200 µM ascorbic acid and 200 µM pargyline, at 22° C. Neurotransmitter uptake assays were performed in a 96-well Axygen plate in a total volume of 350 µl assay buffer (Krebs-Ringer bicarbonate buffer with 10 mM HEPES, 2.2 mM $CaCl_2$, 200 µM ascorbic acid and 200 µM pargyline, pH 7.4) with 50 µg protein. Homogenates were incubated for 5 minutes at 37° C. with $^3$H-5-HT (20 nM) and $^3$H-NE (50 nM), respectively, prior to termination of the assay by rapid filtration over a 96-well UniFilter GF/B plate, pretreated with 1% BSA. Plates were washed 6 times with 650 µl wash buffer (ice cold PBS) and dried overnight at 37° C., prior to addition of ~45 µl of MicroScint™-20 (Perkin Elmer) added. Incorporated radioactivity was quantitated via liquid scintillation spectroscopy. Non-specific neurotransmitter uptake was determined in parallel assays in which tissue homogenates were incubated with $^3$H-5-HT (20 nM) or $^3$H-NE (50 nM) for 5 minutes at 4° C.

Assay 4

Other Assays

Other assays that were used to evaluate the pharmacological properties of test compounds include, but are not limited to, cold ligand binding kinetics assays (Motulsky and Mahan (1984) *Molecular Pharmacol.* 25(1):1-9) with membranes prepared from cells expressing hSERT or hNET; conventional membrane radioligand binding assays using radiolabeled, for example, tritiated, test compound; radioligand binding assays using native tissue from, for example rodent or human brain; neurotransmitter uptake assays using human or rodent platelets; neurotransmitter uptake assays using crude, or pure, synaptosome preparations from rodent brain.

Assay 5

Formalin Paw Test

Compounds are assessed for their ability to inhibit the behavioral response evoked by a 50 µl injection of formalin (5%). A metal band is affixed to the left hind paw of male Sprague-Dawley rats (200-250 g) and each rat is conditioned to the band for 60 minutes within a plastic cylinder (15 cm diameter). Compounds are prepared in pharmaceutically acceptable vehicles and administered systemically (i.p., p.o.) at pre-designated times before formalin challenge. Spontaneous nociceptive behaviors consisting of flinching of the injected (banded) hind paw are counted continuously for 60 minutes using an automated nociception analyzer (UCSD Anesthesiology Research, San Diego, Calif.). Antinociceptive properties of test articles are determined by comparing the number of flinches in the vehicle and compound-treated rats (Yaksh T L, et al., "An automated flinch detecting system for use in the formalin nociceptive bioassay" (2001) *J. Appl. Physiol.* 90(6):2386-2402).

Assay 6

Spinal Nerve Ligation Model

Compounds are assessed for their ability to reverse tactile allodynia (increased sensitivity to an innocuous mechanical stimulus) induced by nerve injury. Male Sprague-Dawley rats are surgically prepared as described in Kim and Chung "An experimental model for peripheral neuropathy produced by segmental spinal nerve ligation in the rat" (1992) *Pain* 50(3): 355-363. Mechanical sensitivity is determined as the 50% withdrawal response to innocuous mechanical stimuli (Chaplan et al., "Quantitative assessment of tactile allodynia in the rat paw" (1994) *J. Neurosci. Methods* 53(1):55-63) before and after nerve injury. One to four weeks post-surgery, compounds are prepared in pharmaceutically acceptable vehicles and administered systemically (i.p., p.o.). The degree of nerve injury-induced mechanical sensitivity before and after treatment serves as an index of the compounds' antinociceptive properties.

Powder X-Ray Diffraction

Powder X-ray diffraction patterns were obtained with a Rigaku Miniflex PXRD diffractometer using Cu Kα (30.0 kV, 15.0 mA) radiation. Analyses were performed with the goniometer running in continuous-scan mode of 2° (2θ) per min with a step size of 0.03° over a range of 2 to 40° in two-theta angle. Samples were prepared on quartz specimen holders as a thin layer of powdered material. The instrument was calibrated with a silicon metal standard, within ±0.02° two-theta angle.

Thermal Analysis

Differential scanning calorimetry (DSC) was performed using a TA Instruments Model Q-100 module with a Thermal Analyst controller. Data were collected and analyzed using TA Instruments Thermal Solutions software. A 1.64 mg sample of the crystalline form of Example 2 was accurately weighed into a covered aluminum pan. After a 5 minute isothermal equilibration period at 22° C., the sample was heated using a linear heating ramp of 10° C./min from 22° C. to 250° C.

Thermogravimetric analysis (TGA) was performed using a TA Instruments Model Q-50 module equipped with high resolution capability. Data were collected and analyzed using TA Instruments Thermal Solutions software. A sample weighing about 2 mg was placed onto a platinum pan and scanned with a high resolution-heating rate from ambient temperature to 300° C. The balance and furnace chambers were purged with nitrogen flows during use.

Preparation 1

3-Benzoyl-2-oxopyrrolidine-1-carboxylic Acid t-Butyl Ester

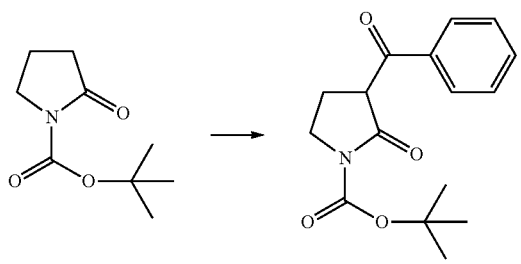

To a stirred solution of 1-(t-butoxycarbonyl)-2-pyrrolidinone (11.9 g, 64.3 mmol) in dry THF (190 mL) at −78° C. was added a solution of LiHMDS (1.0M in toluene, 135 mL, 135 mmol). After stirring at −78° C. for 2 hours, benzoyl chloride (7.5 mL, 64.3 mmol) was added dropwise over 5 minutes while keeping the temperature below −50° C. The mixture was stirred at −78° C. for 4 hours, and the reaction was then quenched with a saturated aqueous $NH_4Cl$ solution (200 mL). The mixture was diluted with EtOAc (300 mL) and the organic layer was washed with saturated $NaHCO_3$ (200 mL×2) and saturated aqueous NaCl (200 mL). The organic layer was dried over $MgSO_4$, filtered and concentrated, and the crude product was purified by flash column chromatography (20-60% EtOAc in hexanes) to afford the title compound (14.5 g) as a yellow oil.

MS m/z: $[M+H]^+$ calcd for $C_{16}H_{19}NO_4$, 290.13. $^1$H-NMR (400 MHz, $CD_3OD$): δ(ppm)=8.09-8.07 (m, 2H), 7.67-7.63 (m, 1H), 7.56-7.52 (m, 2H), 4.86 (obscure, 1H, overlap with water solvent), 3.89-3.78 (m, 2H), 2.47-2.42 (m, 1H), 2.34-2.29 (m, 1H), 1.55 (s, 9H).

Preparation 2

3-(Hydroxyphenylmethyl)pyrrolidine-1-carboxylic Acid t-Butyl Ester

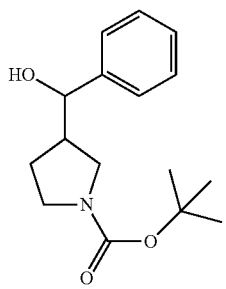

Under nitrogen, $BH_3·Me_2S$ (13.1 mL, 138 mmol) was added dropwise over 10 minutes to a mixture of 3-benzoyl-2-oxopyrrolidine-1-carboxylic acid t-butyl ester (8.0 g, 28 mmol) dissolved in dry THF (90 mL). The mixture was stirred at room temperature for 1 hour, heated at 65° C. for 1 hour and cooled to room temperature. The mixture was slowly quenched with pre-cooled MeOH (25 mL). After completion of the addition, the mixture was diluted with EtOAc (75 mL) and washed with saturated aqueous $NaHCO_3$ solution (2×50 mL). The organic layer was dried over $MgSO_4$, filtered and concentrated in vacuo to obtain a crude mixture containing a 3:1 RS/SR:SS/RR mixture of stereoisomers. The crude product was purified by reverse phase preparative HPLC to obtain the RS/SR mixture of enantiomers (white solid, 2.4 g) and the SS/RR mixture of enantiomers (clear oil, 1.0 g) of the title compound.

RS/SR mixture of enantiomers: MS m/z: $[M+H]^+$ calcd for $C_{16}H_{23}NO_3$, 278.36. Found 278.3. $^1$H-NMR (400 MHz, DMSO-$d_6$): δ(ppm)=7.32 (m, 4H), 7.27-7.22 (m, 1H), 4.40 (d, J=7.2, 1H), 3.32 (m, 1H), 3.15-3.10 (m, 1H), 3.00-2.88 (m, 2H), 2.45-2.35 (m, 1H), 1.88-1.75 (m, 2H), 1.35 (s, 9H).

SS/RR mixture of enantiomers: MS m/z: $[M+H]^+$ calcd for $C_{16}H_{23}NO_3$, 278.36. Found 278.3. $^1$H-NMR (400 MHz, DMSO-$d_6$): δ(ppm)=7.33 (m, 4H), 7.25-7.23 (m, 1H), 4.36 (t, J=6.8, 1H), 3.36-3.27 (m, 2H), 3.17-3.09 (m, 2H), 2.45-2.33 (m, 2H), 1.55-1.40 (m, 1H), 1.38 (s, 9H).

Preparation 3

3-(Phenyl-o-tolyloxymethyl)pyrrolidine-1-carboxylic Acid t-Butyl Ester (3a; $R^2$=—$CH_3$), 3-(Phenoxyphenylmethyl)pyrrolidine-1-carboxylic Acid t-Butyl Ester (3b; $R^2$=—H), and 3-[(2-Methoxyphenoxy)phenylmethyl]pyrrolidine-1-carboxylic Acid t-Butyl Ester (3c; $R^2$=—$OCH_3$)

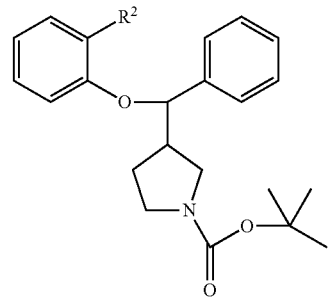

3-(Phenyl-o-tolyloxymethyl)pyrrolidine-1-carboxylic acid t-butyl ester (3a): Under air, the RS/SR mixture of enantiomers of 3-(hydroxyphenylmethyl)pyrrolidine-1-carboxylic acid t-butyl ester (156 mg, 0.56 mmol), 2-iodotoluene (144 μl, 1.1 mmol), CuI (22 mg, 112 μmol), 1,10-phenanthroline (41 mg, 224 μmol) and $Cs_2CO_3$ (365 mg, 1.1 mmol) in dry toluene (0.5 mL) were combined in a sealed tube and heated at 120° C. for 48 hours. The mixture was cooled to room temperature and diluted with DCM, passed through a pad of Celite. The filtrate was purified by flash chromatography on silica gel (hexane/EtOAc:10/1) to yield title compound 3a (149 mg) as a yellow oil. $^1$H-NMR (300 MHz, DMSO-$d_6$): δ (ppm)=7.41-7.32 (m, 4H), 7.31-7.24 (m, 1H), 7.10 (m, 1H), 6.95 (m, 1H), 6.71 (m, 2H), 5.29 (d, J=7.2, 1H), 3.44-3.35 (m, 1H), 3.26-3.18 (m, 1H), 3.16-3.04 (m, 2H), 2.73-2.68 (m, 1H), 2.24 (s, 3H), 2.10-1.96 (m, 1H), 1.94-1.81 (m, 1H), 1.37 (m, 9H).

Title compound 3b was synthesized in a similar manner using iodobenzene as the aryl halide (47% yield).

Under air, the RS/SR mixture of enantiomers of 3-(hydroxyphenylmethyl)pyrrolidine-1-carboxylic acid t-butyl ester (382 mg, 1.4 mmol), was dissolved in dry toluene (2.2 mL).

To this was added 2-iodoanisole (360 μl, 2.8 mmol), CuI (80 mg, 0.4 mmol), 1,10-phenanthroline (100 mg, 0.8 mmol) and Cs$_2$CO$_3$ (897 mg, 2.8 mmol). Air was bubbled through the reaction mixture, sealed tightly, and heated at 105° C. over 48 hours. The mixture was cooled to room temperature, rinsed with DCM, filtered, and concentrated to afford title compound 3c as an oily residue, which was used without further purification.

Compounds 3a, 3b, and 3c were obtained as a RS/SR mixtures of enantiomer.

Example 1

3-(Phenyl-o-tolyloxymethyl)pyrrolidine

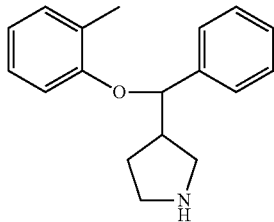

3-(Phenyl-o-tolyloxymethyl)pyrrolidine-1-carboxylic acid t-butyl ester (149 mg, 405 μmol) was dissolved in a solution of HCl in EtOH (1.25M, 3 mL) and stirred at room temperature for 3 hours, and then evaporated to dryness. The residue was purified by flash chromatography on silica gel (CH$_2$Cl$_2$/MeOH:9/1) to afford the RS/SR mixture of enantiomers of the hydrochloride salt of the title compound as a yellow foam (112 mg, 98% purity).

MS m/z: [M+H]$^+$ calcd for C$_{18}$H$_{21}$NO, 268.16. Found 267.36. Found for C$_{18}$H$_{21}$NO.HCl, 303.84. $^1$H-NMR (300 MHz, DMSO-d$_6$): MS-APCI: 268 ([M+H]$^+$, 100). Analytical HPLC (gradient: 5 min, 5%→100% acetonitrile): R$^t$ in min (integration): 5.05 (98%). δ (ppm)=9.18 (bs, 2H), 7.44-7.32 (m, 4H), 7.30-7.26 (m, 1H), 7.10 (m, 1H), 6.99-6.93 (m, 1H), 6.77-6.66 (m, 2H), 5.45 (d, J=6.8, 1H), 3.41-3.35 (m, 1H), 3.26-3.10 (m, 2H), 3.01-2.92 (m, 1H), 2.82-2.77 (m, 1H), 2.27 (s, 3H), 2.12-1.97 (m, 2H).

Example 2

3-[(2-Methoxyphenoxy)phenylmethyl]pyrrolidine

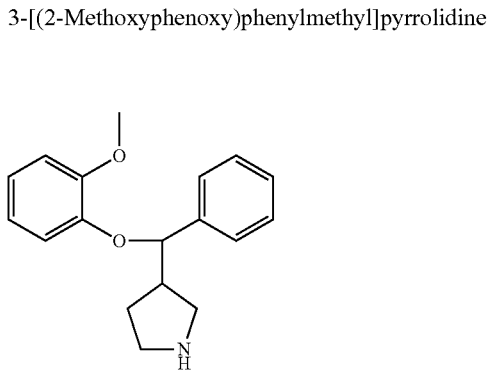

3-[(2-Methoxyphenoxy)phenylmethyl]pyrrolidine-1-carboxylic acid t-butyl ester was dissolved in a solution of HCl in EtOH (1.25M, 8 mL) and stirred at room temperature for 18 hours, and then evaporated to dryness. The residue was purified by reverse phase preparative HPLC to afford the TFA salt of the RS/SR mixture of enantiomers of the title compound as a TFA salt (90 mg, 95% purity). MS m/z: [M+H]$^+$ calcd for C$_{18}$H$_{21}$NO$_2$, 284.16. Found 284.4. $^1$H NMR (CD$_3$OD, 400 MHz) δ (ppm): 7.40-7.35 (m, 4H), 7.32-7.28 (m, 1H), 7.00-6.98 (m, 1H), 6.92-6.88 (m, 1H), 6.71-6.65 (m, 2H), 5.32 (d, J=5.2, 1H), 3.90 (s, 3H), 3.62-3.55 (m, 1H), 3.36-3.30 (obscure, 3H, overlap with solvent), 2.97-2.92 (m, 1H), 2.28-2.21 (m, 1H), 2.13-2.07 (m, 1H).

Example 3

3-[(3,5-Dichlorophenoxy)phenylmethyl]pyrrolidine

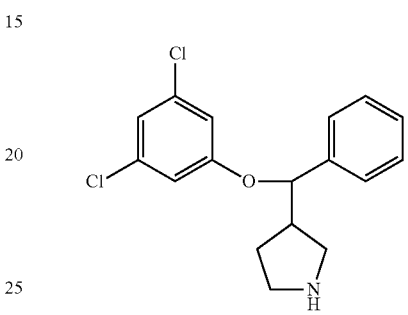

Using a method similar to that of Example 2, and, in Preparation 3, substituting 2-iodoanisole with 1,3-dichloro-5-iodobenzene, the TFA salt of the RS/SR mixture of enantiomers of the title compound was prepared (437 mg, 99% purity). MS m/z: [M+H]$^+$ calcd for C$_{17}$H$_{17}$Cl$_2$NO, 322.07. Found, 322.2. $^1$H NMR (CD$_3$OD, 400 MHz) δ (ppm): 7.41-7.39 (m, 4H), 7.35-7.33 (m, 1H), 6.96 (s, 1H), 6.88 (s, 2H), 5.40 (d, J=6.0, 1H), 3.48-3.43 (m, 1H), 3.31-3.25 (obscure, 2H, overlap with solvent), 3.17-3.14 (m, 1H), 2.98-2.92 (m, 1H), 2.17-2.11 (m, 2H).

Example 4

3-(Phenyl-o-tolyloxymethyl)pyrrolidine (4-1; R$^2$=—CH$_3$) and 3-[(2-Methoxyphenoxy)phenylmethyl] pyrrolidine (4-2; R$^2$=—OCH$_3$)

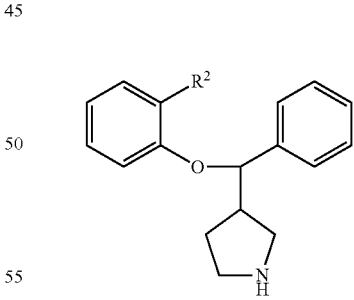

The title compounds were prepared as TFA salts using a method similar to that of Example 2, and, in Preparation 3, substituting the RS/SR mixture of enantiomers with the SS/RR mixture of enantiomers of 3-(hydroxyphenylmethyl)pyrrolidine-1-carboxylic acid t-butyl ester (47.5 mg, 0.2 mmol), and substituting 2-iodoanisole with the appropriate aryl iodide.

The SS/RR mixture of enantiomers of title compound 4-1 (13.8 mg): MS m/z: [M+H]$^+$ calcd for C$_{18}$H$_{21}$NO, 268.16. Found 268.2.

The SS/RR mixture of enantiomers of title compound 4-2 (11.2 mg): MS m/z: [M+H]$^+$ calcd for $C_{18}H_{21}NO_2$, 284.16. Found, 284.4. $^1$H NMR (CD$_3$OD, 400 MHz) δ (ppm): 7.41-7.30 (m, 5H), 6.98-6.96 (m, 1H), 6.91-6.86 (m, 1H), 6.70-6.63 (m, 2H), 5.20 (d, J=6.8, 1H), 3.89 (s, 3H), 3.53-3.46 (m, 3H), 3.31-3.30 (obscure, 1H, overlap with solvent), 2.98-2.96 (m, 1H), 2.02-1.95 (m, 2H).

Example 5

3-[(2-Ethoxyphenoxy)phenylmethyl]pyrrolidine

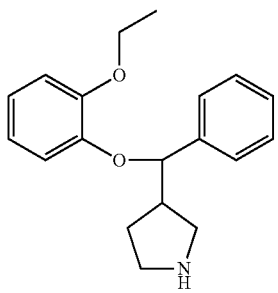

A mixture of the SS/RR mixture of enantiomers of 3-(hydroxyphenylmethyl)pyrrolidine-1-carboxylic acid t-butyl ester (30 mg, 0.11 mmol), 2-ethoxyphenol (16 µL, 0.13 mmol), and PPh$_3$ (29.8 mg, 114 µmol) in THF (0.09 mL) was sonicated for several minutes. While sonicating, DIAD (22.4 µL, 114 µmol) was added dropwise to the reaction mixture over a couple minutes and sonicated further for 15 minutes. The reaction was concentrated to yield the BOC-protected form of the title compound as an oily residue, which was used without further purification.

The BOC-protected compound was dissolved in a solution of HCl in EtOH (1.25M, 0.7 mL) and stirred at room temperature for 18 hours, and then evaporated to dryness. The residue was purified by reverse phase preparative HPLC to afford the TFA salt of the RS/SR mixture of enantiomers of the title compound (23.2 mg, 97% purity). MS m/z: [M+H]$^+$ calcd for $C_{19}H_{23}NO_2$, 298.17. Found, 298.6.

Example 6

Separation of the RS/SR mixture of enantiomers of 3-[(2-methoxyphenoxy)phenylmethyl]pyrrolidine into the RS (6-1) and SR (6-2) enantiomers The RS/SR mixture of enantiomers of 3-[(2-methoxyphenoxy)phenylmethyl]pyrrolidine was prepared as described in Example 2 and subsequently made into a 40 mg/mL solution in MeOH. The RS and SR enantiomers were separated by a chiral column. The column was a Chiralpak AD-H-SFC (10 mm×250 mm, 5 micron particle size) containing amylase tris-(3,5-dimethylphenylcarbamate). Solvent A was CO$_2$ and Solvent B was MeOH with 0.1% triethylamine. 8% Solvent B was run at 10 mL/min with 200 Barr back pressure. A 20 mL injection of the 40 mg/mL solution was used.

RS enantiomer compound 6-1: MS m/z: [M+H]$^+$ calcd for $C_{18}H_{21}NO_2$, 284.16. Found 284.4; SFC: 10.3 min.

SR enantiomer compound 6-2: MS m/z: [M+H]$^+$ calcd for $C_{18}H_{21}NO_2$, 284.16. Found 284.4; SFC: 12.4 min.

Preparation 4

(S)-3-Formylpyrrolidine-1-carboxylic Acid t-Butyl Ester

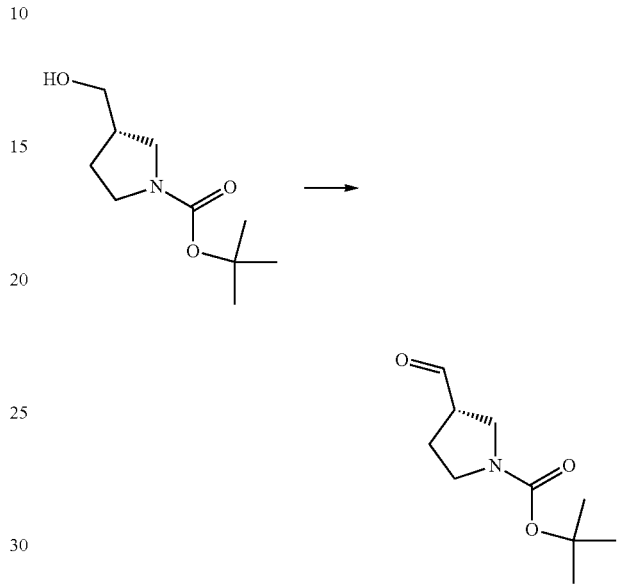

To a solution of (S)-3-hydroxymethylpyrrolidine-1-carboxylic acid t-butyl ester (7.4 g, 37 mmol) in DCM (74 mL, 1.2 mol) was added TEMPO (100 mg, 0.7 mmol) and potassium bromide (200 mg, 2 mmol). This mixture was cooled to 0° C. and vigorously stirred as a pre-chilled (at 0° C.) 1:1 mixture of 0.7 M of NaOCl in water (78 mL, 55 mmol) and a saturated, aqueous NaHCO$_3$ solution (75 mL) was added dropwise over a period of 10 minutes. The resultant mixture was extracted with DCM (3×100 mL). The combined organic layers were washed with water (2×100 mL), then saturated aqueous NaCl (1×100 mL). The organic layer was dried over anhydrous Na$_2$SO$_4$, filtered and concentrated in vacuo to yield the title compound, which was used without further purification (5.8 g).

Preparation 5

(S)-3-((R)-Hydroxyphenylmethyl)pyrrolidine-1-carboxylic Acid t-Butyl Ester and (S)-3-((S)-Hydroxyphenylmethyl)pyrrolidine-1-carboxylic Acid t-Butyl Ester

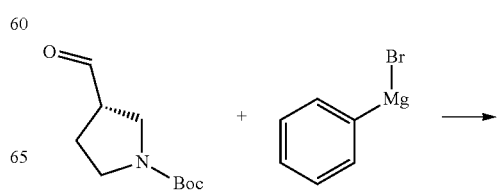

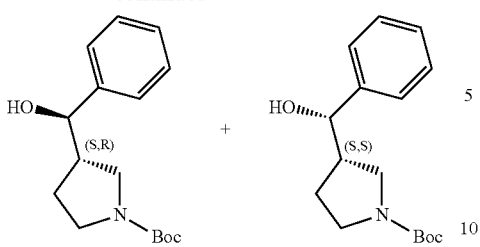

(S)-3-Formylpyrrolidine-1-carboxylic acid t-butyl ester (5.8 g, 29.1 mmol) in THF (140 mL, 1.7 mol) was placed in a flask under nitrogen, and the solution was cooled to −78° C. 1.0 M of phenylmagnesium bromide in THF (43.7 mL, 43.7 mmol) was added dropwise over 20 minutes. The solution was allowed to warm to room temperature overnight, then 250 mL saturated NH₄Cl was added dropwise to quench the reaction. The resulting mixture was extracted with EtOAc (3×150 mL), and the combined organic layers were washed with saturated aqueous NaHCO₃ (1×100 mL) and saturated aqueous NaCl (1×100 mL), then dried over anhydrous Na₂SO₄, filtered, and concentrated in vacuo. The product was combined with a separate lot of material, purified and separated by preparative HPLC to yield 3.2 g of the (S,R) and 3.1 g of the (S,S) title compounds as TFA salts. The absolute stereochemistry of the products was determined by comparison with a crystal structure of previously synthesized (S)-3-((S)-hydroxyphenylmethyl)pyrrolidine-1-carboxylic acid t-butyl ester.

Example 7

(S)-3-[(R)-(2,4-Difluorophenoxy)phenylmethyl]pyrrolidine

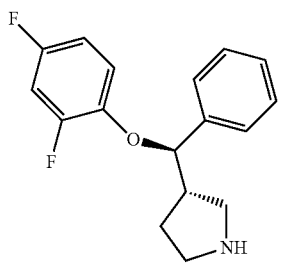

(S)-3-((R)-Hydroxyphenylmethyl)pyrrolidine-1-carboxylic acid t-butyl ester (250 mg, 0.9 mmol), copper(I) iodide (51 mg, 270 μmol), 1,10-phenanthroline (97 mg, 540 μmol) and 2,4-difluoro-1-iodobenzene (216 μL, 1.8 mmol) were combined. Toluene (1.4 mL, 14 mmol) was added, followed by the addition of cesium carbonate (587 mg, 1.8 mmol). Air was bubbled through the mixture, the vessel was sealed, and the mixture was heated at 105° C. for 48 hours. The mixture was filtered, rinsed with DCM, and concentrated. The remaining material was treated with 1.25 M of HCl in EtOH (5.8 mL, 7.2 mmol) and stirred overnight. The mixture was concentrated, redissolved in a 1:1 AcOH:H₂O solution and purified by preparative HPLC to yield 76 mg (97% purity) of the title compound as the TFA salt. MS m/z: [M+H]⁺ calcd for $C_{17}H_{17}F_2NO$, 290.13. Found 290.2.

Example 8

(S)-3-[(R)-(2-Chloro-3,5-difluorophenoxy)phenylmethyl]pyrrolidine (8-1) and (R)-3-[(S)-(2-Chloro-3,5-difluorophenoxy)phenylmethyl]pyrrolidine (8-2)

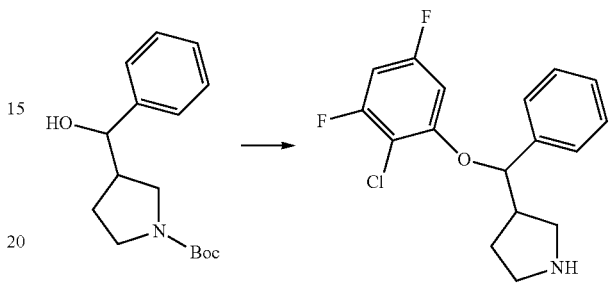

(S)-3-((S)-Hydroxyphenylmethyl)pyrrolidine-1-carboxylic acid t-butyl ester (250 mg, 0.9 mmol), PPh₃ (248 mg, 946 μmol) and 2-chloro-3,5-difluorophenol (222 mg, 1.4 mmol) were combined in THF (512 μL, 6.3 mmol). The mixture was sonicated for several minutes. While sonicating, DIAD (186 μL, 946 μmol) was added dropwise over a few minutes, then the mixture was sonicated for an additional 15 minutes. The mixture was concentrated, redissolved in 1.25M of HCl in EtOH (5 mL, 6 mmol) and stirred overnight. The mixture was concentrated, redissolved in 6 mL 1:1 AcOH:H₂O solution, and purified by preparative HPLC to yield compound (8-1) as the TFA salt. MS m/z: [M+H]⁺ calcd for $C_{17}H_{16}ClF_2NO$, 324.09. Found 324.4.

The TFA salt of compound (8-2) was prepared in a similar manner, and using (R)-3-((R)-hydroxyphenylmethyl)pyrrolidine-1-carboxylic acid t-butyl ester (250 mg, 0.9 mmol) as the starting material. MS m/z: [M+H]⁺ calcd for $C_{17}H_{16}ClF_2NO$, 324.09. Found 324.6.

Example 9

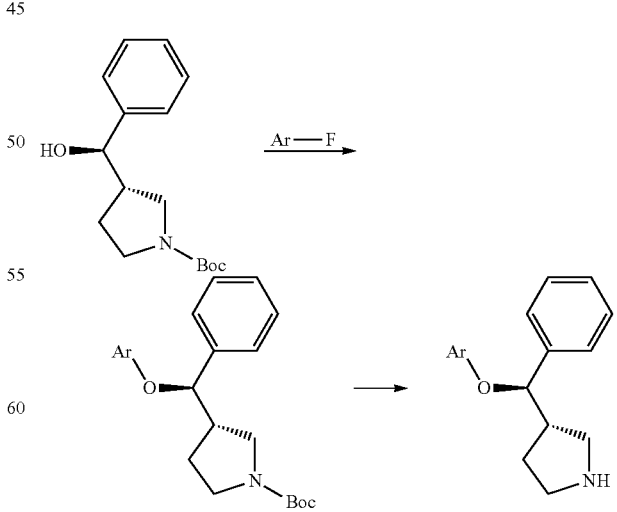

(S)-3-((R)-Hydroxyphenylmethyl)pyrrolidine-1-carboxylic acid t-butyl ester (50 mg, 0.2 mmol) was dissolved in DMF (660 μL, 8.5 mmol). Washed and dried sodium hydride (5.19 mg, 216 μmol) was slowly added. The mixture was stirred at room temperature for 15 minutes. The material was decanted and added directly into each of 5 vials containing the desired aryl fluoride. The mixtures were stirred at 70° C. for 3 hours. The crude mixtures were concentrated, dissolved in 1.20 M of HCl in EtOH (880 μL, 1.0 mmol), and stirred overnight. The mixtures were concentrated and purified by preparative HPLC to yield the following compounds as their TFA salts:

mmol), and PPh$_3$ (248 mg, 946 μmol) in THF (0.7 mL, 9 mmol) was sonicated for several minutes. While sonicating, DIAD (186 μL, 946 μmol) was added dropwise to the reaction mixture over a couple minutes and then sonicated further for 15 minutes. The reaction was concentrated, redissolved in 1.25 M HCl in EtOH (6 mL), and stirred overnight. The reaction mixture was concentrated and redissolved in 1:1 AcOH:H$_2$O solution, and purified by preparative HPLC to afford the TFA salt of the RS/SR mixture of enantiomers of

| Ex. | Ar—F (amt) | Product |
|---|---|---|
| 9-1 | 1-fluoro-2-methanesulfonyl-benzene (120 mg) | (S)-3-[(R)-(2-methanesulfonylphenoxy)-phenylmethyl]pyrrolidine. MS m/z: [M + H]$^+$ calcd for C$_{18}$H$_{21}$NO$_3$S, 332.12; found 332.0. (61.1 mg, 99% purity) |
| 9-2 | 1-fluoro-3-nitrobenzene (100 mg) | (S)-3-[(R)-(3-nitrophenoxy)phenylmethyl] pyrrolidine MS m/z: [M + H]$^+$ calcd for C$_{17}$H$_{18}$N$_2$O$_3$, 299.13; found 299.2. (45.4 mg, 99% purity) |
| 9-3 | 1-(2-fluorophenyl)ethanone (100 mg) | 1-[2-((R)-phenyl-(S)-pyrrolidin-3-yl-methoxy)phenyl]ethanone MS m/z: [M + H]$^+$ calcd for C$_{19}$H$_{21}$NO$_2$, 296.16; found 296.2. (9.3 mg, 97% purity) |
| 9-4 | 2-chloro-1,3-difluorobenzene (110 mg) | (S)-3-[((R)-(2-chloro-3-fluorophenoxy) phenylmethyl]pyrrolidine MS m/z: [M + H]$^|$ calcd for C$_{17}$H$_{17}$ClFNO, 306.10; found 306.0. (41.7 mg, 98% purity) |
| 9-5 | 2-fluorobenzoic acid methyl ester (110 mg) | 2-((R)-phenyl-(S)-pyrrolidin-3-yl-methoxy) benzoic acid methyl ester MS m/z: [M + H]$^+$ calcd for C$_{19}$H$_{21}$NO$_3$, 312.15; found 312.2. (37.8 mg, 90% purity) |

Example 10

RS/SR Mixture of Enantiomers of 3-[(2,6-Dichloro-3,5-difluorophenoxy)phenylmethyl]pyrrolidine (10-1) and RS/SR Mixture of Enantiomers of 3-[phenyl-(2,3,5,6-tetrachlorophenoxy)methyl] pyrrolidine (10-2)

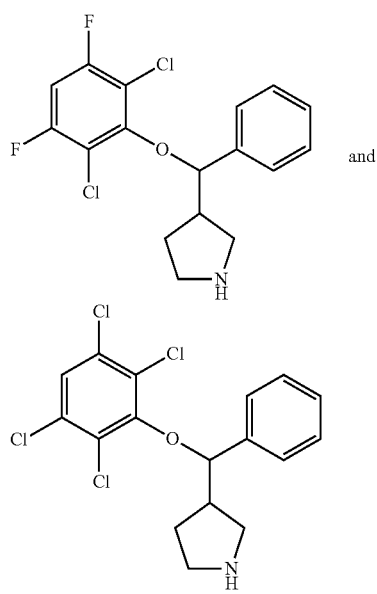

and

The SS/RR mixture of enantiomers of 3-(hydroxyphenyl-methyl)pyrrolidine-1-carboxylic acid t-butyl ester (250 mg, 0.90 mmol), 2,6-dichloro-3,5-difluorophenol (359 mg, 1.8 compound (10-1) (86 mg, 97% purity). MS m/z: [M+H]$^+$ calcd for C$_{17}$H$_{15}$Cl$_2$F$_2$NO, 358.05. Found 358.0.

The TFA salt of the RS/SR mixture of enantiomers of compound (10-2) was prepared in a similar manner using 2,3,5,6-tetrachlorophenol (9.5 g, 100% purity). MS m/z: [M+H]$^+$ calcd for C$_{17}$H$_{15}$Cl$_4$NO, 389.99. Found 390.0.

Example 11

(S)-3-[(R)-(2,6-dichloro-3,5-difluorophenoxy)phe-nylmethyl]pyrrolidine

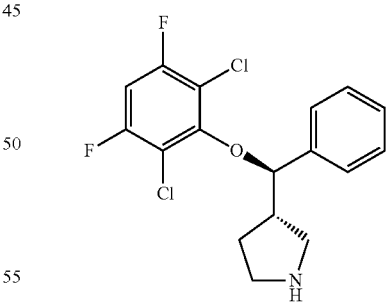

A mixture of (S)-3-((S)-hydroxyphenylmethyl)pyrrolidine-1-carboxylic acid t-butyl ester (600 mg, 2 mmol), 2,6-dichloro-3,5-difluorophenol (516 mg, 2.6 mmol), and PPh$_3$ (596 mg, 2.3 mmol) in THF (1.2 mL, 15.1 mmol) was sonicated for several minutes. While sonicating, DIAD (447 μL, 2.3 mmol) was added dropwise to the mixture over a couple minutes and sonicated further for 15 minutes. The mixture was concentrated to yield the BOC-protected form of the title compound as a yellow oil, which was used without further purification.

The BOC-protected compound was dissolved in 1.25 M HCl in EtOH (10 mL, 20 mmol) and stirred at room temperature for 18 hours, and then evaporated to dryness. The residue was purified by reverse phase preparative HPLC to afford the title compound as a TFA salt (449 mg, 96% purity). MS m/z: [M+H]$^+$ calcd for $C_{17}H_{15}Cl_2F_2NO$, 358.05. Found, 358.2. $^1$H NMR ($CD_3OD$, 400 MHz) δ (ppm): 7.45-7.42 (m, 2H), 7.36-7.33 (m, 3H), 7.09-7.04 (m, 1H), 5.75 (d, J=8.8, 1H), 3.51-3.48 (m, 1H), 3.41-3.36 (m, 1H), 3.21-3.16 (m, 2H), 2.93-2.87 (m, 1H), 2.55-2.52 (m, 1H), 2.41-2.36 (m, 1H).

Monohydrochloride Crystalline Salt

A mixture of (S)-3-((S)-hydroxyphenylmethyl)pyrrolidine-1-carboxylic acid t-butyl ester (7.9 g, 28.5 mmol), 2,6-dichloro-3,5-difluorophenol (6.8 g, 34.2 mmol) and $PPh_3$ (7.8 g, 29.9 mmol) in THF (16.2 mL, 199 mmol) was sonicated for several minutes. While sonicating, DIAD (5.9 mL, 29.9 mmol) was slowly added dropwise to the mixture over several minutes and sonicated further for 15 minutes. A second mixture of (S)-3-((S)-hydroxyphenylmethyl)pyrrolidine-1-carboxylic acid t-butyl ester (2.0 g, 7.21 mmol), 2,6-dichloro-3,5-difluorophenol (1.7 g, 8.7 mmol) and $PPh_3$ (2.0 g, 7.6 mmol) in THF (4.1 mL, 50.5 mmol) was sonicated for several minutes. While sonicating, DIAD (1.5 mL, 7.6 mmol) was slowly added dropwise to the reaction mixture over several minutes and sonicated further for 15 minutes. The mixtures were combined and concentrated. The crude material was triturated in hexanes for 12 hours. The $PPh_3$ oxide precipitate was filtered off, and the organic layer was concentrated to yield 20 g of a yellow oil. The crude mixture was diluted in EtOAc (300 mL) and washed with 1N NaOH (2×200 mL) to remove excess phenol. The organic layer was dried with anhydrous $MgSO_4$, filtered, and concentrated to yield 18.7 g of (S)-3-[(R)-(2,6-dichloro-3,5-difluorophenoxy)phenylmethyl]pyrrolidine-1-carboxylic acid t-butyl ester as a sticky yellow oil which was used in the next step without further purification.

The oily residue from the previous step was dissolved in 1.25M HCl in EtOH (200 mL, 0.2 mol) and stirred at room temperature for 18 hours, and then evaporated to dryness. EtOAc (200 mL) was added, and the resulting slurry was stirred for 2 hours. The solid material was rinsed with EtOAc and ether, and dried by lyophilization to yield 7.9 of an impure HCl salt. The material was dissolved in a 1:1 isopropyl alcohol:DCM mixture with minimal MeOH. The crude product was purified by flash column chromatography (40-70% IPA in DCM, 330 g column. The isolated material was diluted in EtOAc (200 mL) and freebased with saturated $NaHCO_3$ (2×200 mL), washed with saturated aqueous NaCl, dried with $MgSO_4$, filtered, and concentrated to yield 4.6 g of a pale white solid. The freebased material was then retreated with 1.0 eq of 1.25M HCl in EtOH (10.3 mL) and heated in order to dissolve all solids. The solution was then concentrated to yield (S)-3-[(R)-(2,6-dichloro-3,5-difluorophenoxy)phenylmethyl]pyrrolidine as a monohydrochloride crystalline salt (4.2 g, 30% yield, 98.4% purity). MS m/z: [M+H]$^+$ calcd for $C_{17}H_{15}Cl_2F_2NO$, 358.05. Found, 358.2. $^1$H NMR (DMSO-$d_6$, 400 MHz) δ (ppm): 7.56-7.50 (m, 1H), 7.41-7.32 (m, 5H), 5.70 (d, J=9.2 Hz, 1H), 3.38-3.29 (obscure, 1H, overlap with solvent), 3.27-3.19 (m, 2H), 3.01-2.96 (m, 1H), 2.71-2.66 (m, 1H), 2.37-2.28 (m, 1H), 2.23-2.18 (m, 1H).

Powder X-Ray Diffraction

The PXRD pattern for the monohydrochloride salt showed the material to be crystalline. A representative PXRD pattern for a sample of this crystalline salt is shown in FIG. 1, and the peak positions are listed in the table below:

| 2-Theta Angle (Degree) | d-spacing (Å) | Intensity (Counts) | Relative intensity, % |
|---|---|---|---|
| 5.84 | 15.126 | 882 | 5.7 |
| 12.53 | 7.058 | 5073 | 33.1 |
| 15.23 | 5.812 | 1500 | 9.8 |
| 17.00 | 5.213 | 4617 | 30.1 |
| 19.39 | 4.573 | 2846 | 18.6 |
| 22.79 | 3.899 | 15332 | 100.0 |
| 24.50 | 3.630 | 6810 | 44.4 |
| 27.35 | 3.258 | 6102 | 39.8 |
| 31.64 | 2.826 | 4582 | 29.9 |
| 34.04 | 2.632 | 2991 | 19.5 |

Thus, this crystalline salt can be characterized by a PXRD pattern having two or more diffraction peaks at 2θ values selected from 5.8±0.2, 12.5±0.2, 15.2±0.2, 17.0±0.2, 19.4±0.2, 22.8±0.2, 24.5±0.2, 27.4±0.2, 31.6±0.2, and 34.0±0.2. In particular, crystalline salt can be characterized by a powder x-ray diffraction pattern comprising diffraction peaks at 2θ values of 12.5±0.2, 22.8±0.2, 24.5±0.2, and 27.4±0.2.

Thermal Analysis

Figure 2:
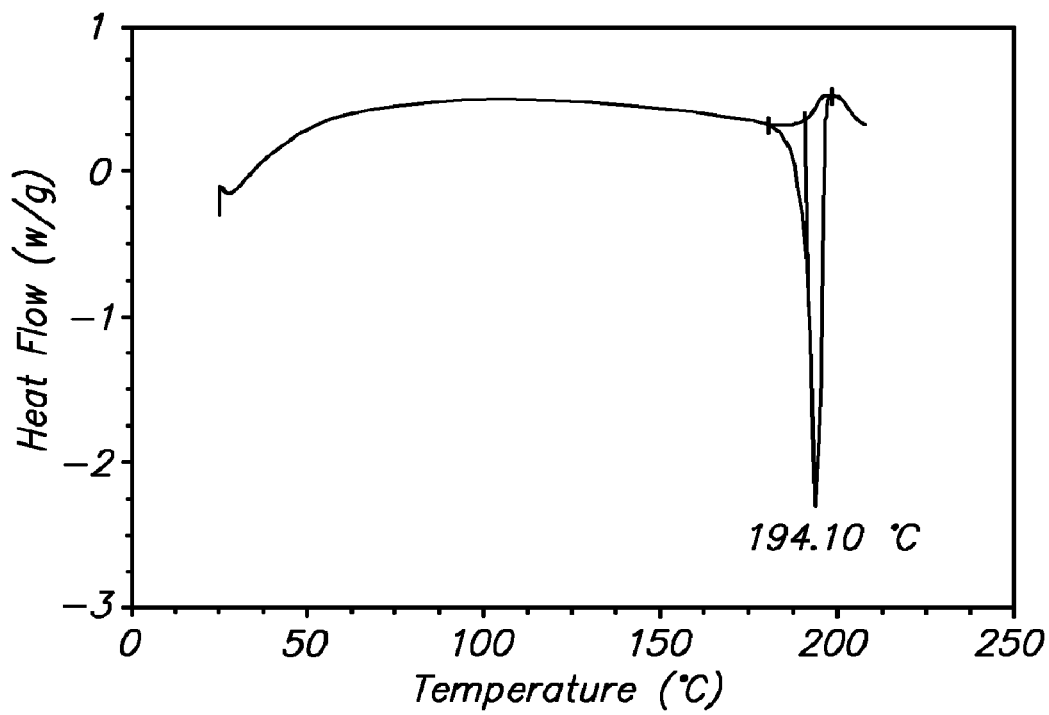
FIG. 2 shows a differential scanning calorimetry (DSC) trace and FIG. 3 shows a thermal gravimetric analysis (TGA) trace for this crystalline salt.

A representative DSC trace for a sample of this crystalline monohydrochloric acid salt (FIG. 2) showed that the crystalline salt has good thermal stability with the melting peak at about 194.1° C. and no thermal decomposition below 190.7° C.

Figure 3:
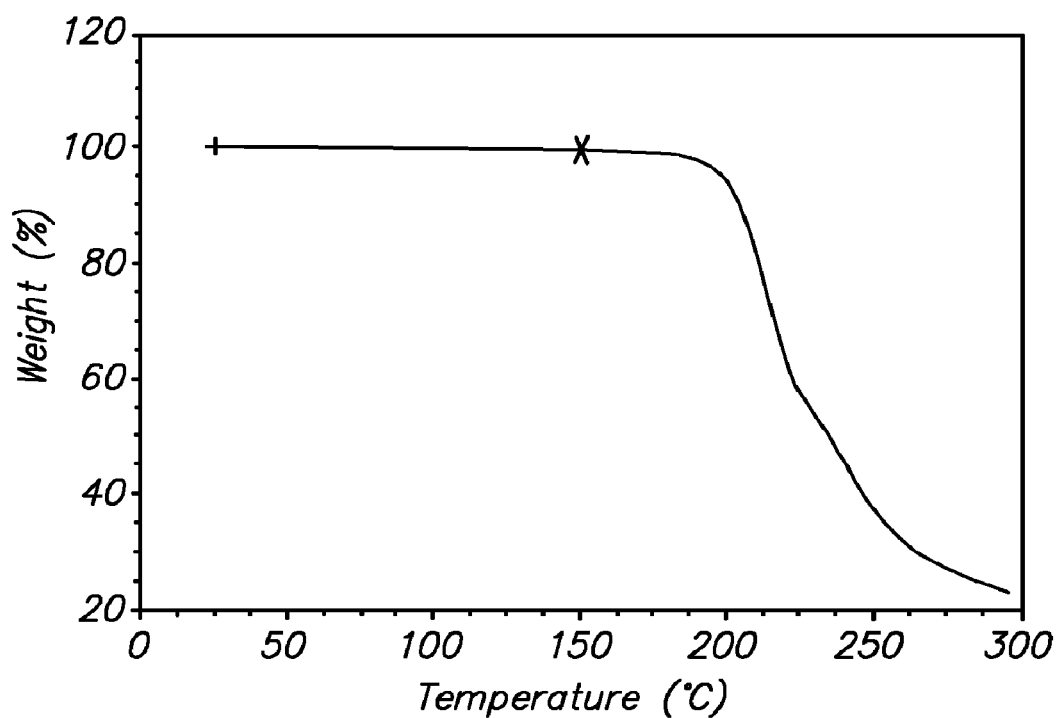

A representative TGA trace for a sample of this crystalline monohydrochloric acid salt showed a loss of solvents and/or water (<0.5%) at temperatures below 150° C., as seen in FIG. 3. This TGA trace indicate that the crystalline salt lost a small amount of weight from room temperature to moderately elevated temperatures, which is consistent with the loss of residual moisture or solvent.

Example 12

(S)-3-[(R)-phenyl-(2,4,6-trifluorophenoxy)methyl]pyrrolidine

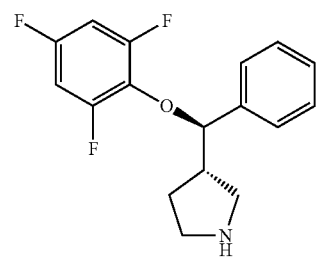

A mixture of (S)-3-((S)-hydroxyphenylmethyl)pyrrolidine-1-carboxylic acid t-butyl ester (250 mg, 0.9 mmol), 2,4,6-trifluorophenol (200 mg, 1.4 mmol) and $PPh_3$ (248 mg, 946 μmol) in THF (512 μL, 6.31 mmol) was sonicated for several minutes. While sonicating, DIAD (186 μL, 946 μmol) was added dropwise to the reaction mixture over a couple minutes and sonicated further for 15 minutes. The mixture was concentrated to yield the BOC-protected form of the title compound as a yellow oil, which was used without further purification.

The BOC-protected compound was dissolved in 1.25 M HCl in EtOH (5 mL, 6 mmol) and stirred at room temperature for 18 hours, and then evaporated to dryness. The residue was purified by reverse phase preparative HPLC to afford the title compound as a TFA salt (276 mg, 94% purity). MS m/z: [M+H]$^+$ calcd for $C_{17}H_{16}F_3NO$, 308.12. Found, 308.8. $^1$H NMR (400 MHz, DMSO-$d_6$) δ (ppm): 7.37-7.34 (m, 5H), 7.14 (t, J=8.8, 2H), 5.14 (d, J=8.4, 1H), 3.34-3.31 (m, 1H), 3.23-3.21 (m, 1H), 2.99-2.91 (m, 2H), 2.80-2.77 (m, 1H), 2.28-2.25 (m, 1H), 2.13-2.07 (m, 1H).

Example 13

(S)-3-[(R)-(2-chloro-6-fluoro-3-methylphenoxy)phenylmethyl]pyrrolidine

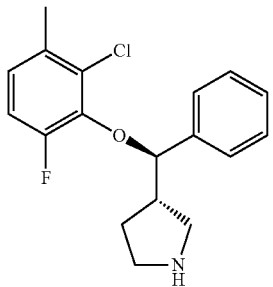

A mixture of (S)-3-((S)-hydroxyphenylmethyl)pyrrolidine-1-carboxylic acid t-butyl ester (600 mg, 2 mmol), 2-chloro-6-fluoro-3-methylphenol (521 mg, 3.2 mmol), and PPh$_3$ (596 mg, 2.3 mmol) in THF (1.2 mL, 15.1 mmol) was sonicated for several minutes. While sonicating, DIAD (447 μL, 2.3 mmol) was added dropwise to the mixture over a couple minutes and sonicated further for 15 minutes. The mixture was concentrated to yield the BOC-protected form of the title compound as a yellow oil, which was used without further purification.

The BOC-protected compound was dissolved in 1.25 M HCl in EtOH (5 mL, 6 mmol) and stirred at room temperature for 18 hours, and then evaporated to dryness. The residue was purified by reverse phase preparative HPLC to afford the title compound as a TFA salt (350 mg, 94% purity). MS m/z: [M+H]$^+$ calcd for $C_{18}H_{19}ClFNO$, 320.11. Found, 320.3. $^1$H NMR (400 MHz, DMSO-$d_6$) δ (ppm): 7.39-7.30 (m, 5H), 7.05-6.96 (m, 2H), 5.41 (d, J=8.0, 1H), 3.40-3.30 (m, 1H), 3.25-3.22 (m, 1H), 3.02-2.95 (m, 2H), 2.79-2.77 (m, 1H), 2.27-2.23 (m, 1H), 2.21 (s, 3H), 2.17-2.14-2.10 (m, 1H).

Preparation 6

(R)-3-Formylpyrrolidine-1-carboxylic Acid t-Butyl Ester

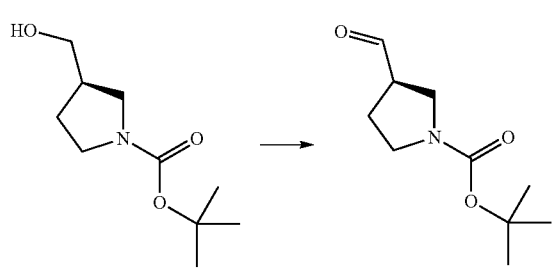

To a solution of (R)-Boc-3-pyrrolidinemethanol (5.0 g, 24.8 mmol) in DCM was added TEMPO (80 mg, 0.5 mmol) and potassium bromide (150 mg, 1.3 mmol). This mixture was cooled to 5° C. and vigorously stirred as a pre-chilled (at 0° C.) 1:1 mixture of NaOCl in water (53 mL) and a saturated, aqueous NaHCO$_3$ solution (53 mL) was added dropwise. The resultant mixture was extracted with DCM (3×50 mL). The combined organic layers were washed with water (50 mL) and saturated aqueous NaCl (50 mL). The organic layer was dried over anhydrous Na$_2$SO$_4$ to yield 4.3 g of the title compound, which was used without further purification.

Preparation 7

(R)-3-((S)-Hydroxyphenylmethyl)pyrrolidine-1-carboxylic Acid t-Butyl Ester and (R)-3-((R)-Hydroxyphenylmethyl)pyrrolidine-1-carboxylic Acid t-Butyl Ester

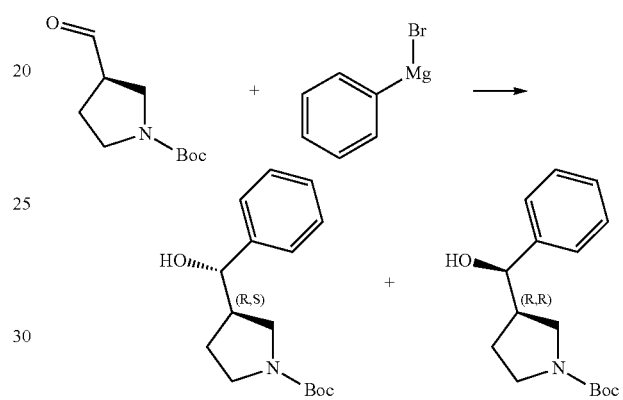

(R)-3-Formylpyrrolidine-1-carboxylic acid t-butyl ester (4.3 g, 22 mmol) in THF (100 mL) was placed in a flask under nitrogen, and the solution was cooled to −78° C. 1.0 M of phenylmagnesium bromide in THF (30 mL, 30 mmol) was added by syringe over 10 minutes. The solution was stirred at −78° C. for 15 minutes, then placed in an ice bath for 30 minutes. Saturated NH$_4$Cl (25 mL) was then added. The resulting mixture was extracted with EtOAc (3×50 mL), and the combined organic layers were washed with saturated aqueous NaHCO$_3$ (50 mL) and saturated aqueous NaCl (50 mL), then dried over anhydrous Na$_2$SO$_4$ and concentrated to yield 6.1 g of product. The mixture of products was purified and separated by preparative HPLC to yield the title compounds.

Example 14

(R)-3-[(S)-(2-chloro-3,6-difluorophenoxy)phenylmethyl]pyrrolidine

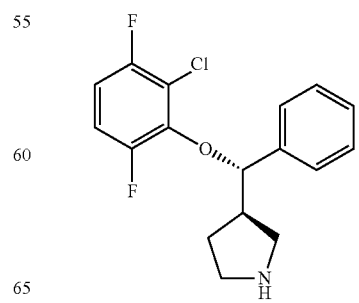

A mixture of (R)-3-((R)-hydroxyphenylmethyl)pyrrolidine-1-carboxylic acid t-butyl ester (10 g, 36.1 mmol), 2-chloro-3,6-difluorophenol (8.9 g, 54.1 mmol) and PPh₃ (9.93 g, 37.8 mmol) in THF (20.5 mL, 252 mmol) was sonicated for several minutes. While sonicating, DIAD (7.5 mL, 37.8 mmol) was slowly added dropwise to the mixture over several minutes and sonicated further for 15 minutes. The mixture was concentrated and then triturated in excess hexanes for 16 hours. The PPh₃ oxide precipitate was filtered off and the organic layer was concentrated to yield a yellow oil. The crude mixture was diluted in EtOAc (300 mL), washed with 1N NaOH (2×200 mL) and saturated aqueous NaCl (100 mL). The organic layer was dried with anhydrous MgSO₄, filtered, and concentrated. The organic material was purified by silica gel chromatography (330 g column, 20-50% EtOAc in hexanes) to yield 14 g of (R)-3-[(S)-(2-chloro-3,6-difluorophenoxy)phenylmethyl]pyrrolidine-1-carboxylic acid t-butyl ester as a yellow oil which was used in the next step without further purification.

The oily residue from the previous step was dissolved in 1.25M HCl in EtOH (200 mL, 0.2 mol) and stirred at room temperature for 18 hours, and then evaporated to dryness to yield a pink solid. The material was triturated with excess ether for 16 hours with impurities still remaining The material was triturated again in excess EtOAc for 2 hours and filtered to yield 8.43 g of the title compound as a monohydrochloride crystalline salt (8.43 g, 65% yield, 98.6% purity). MS m/z: [M+H]⁺ calcd for $C_{17}H_{16}ClF_2NO$, 324.09. Found, 324.2. ¹H NMR (DMSO-d₆, 400 MHz) δ (ppm): 7.40-7.32 (m, 5H), 7.26-7.19 (m, 1H), 7.13-7.07 (m, 1H), 5.49 (d, J=8.8 Hz, 1H), 3.38-3.34 (obscure, 1H, overlap with solvent), 3.26-3.19 (m, 1H), 3.07-3.02 (m, 1H), 2.99-2.92 (m, 1H), 2.81-2.74 (m, 1H), 2.32-2.23 (m, 1H), 2.18-2.08 (m, 1H).

Powder X-Ray Diffraction

Figure 4:
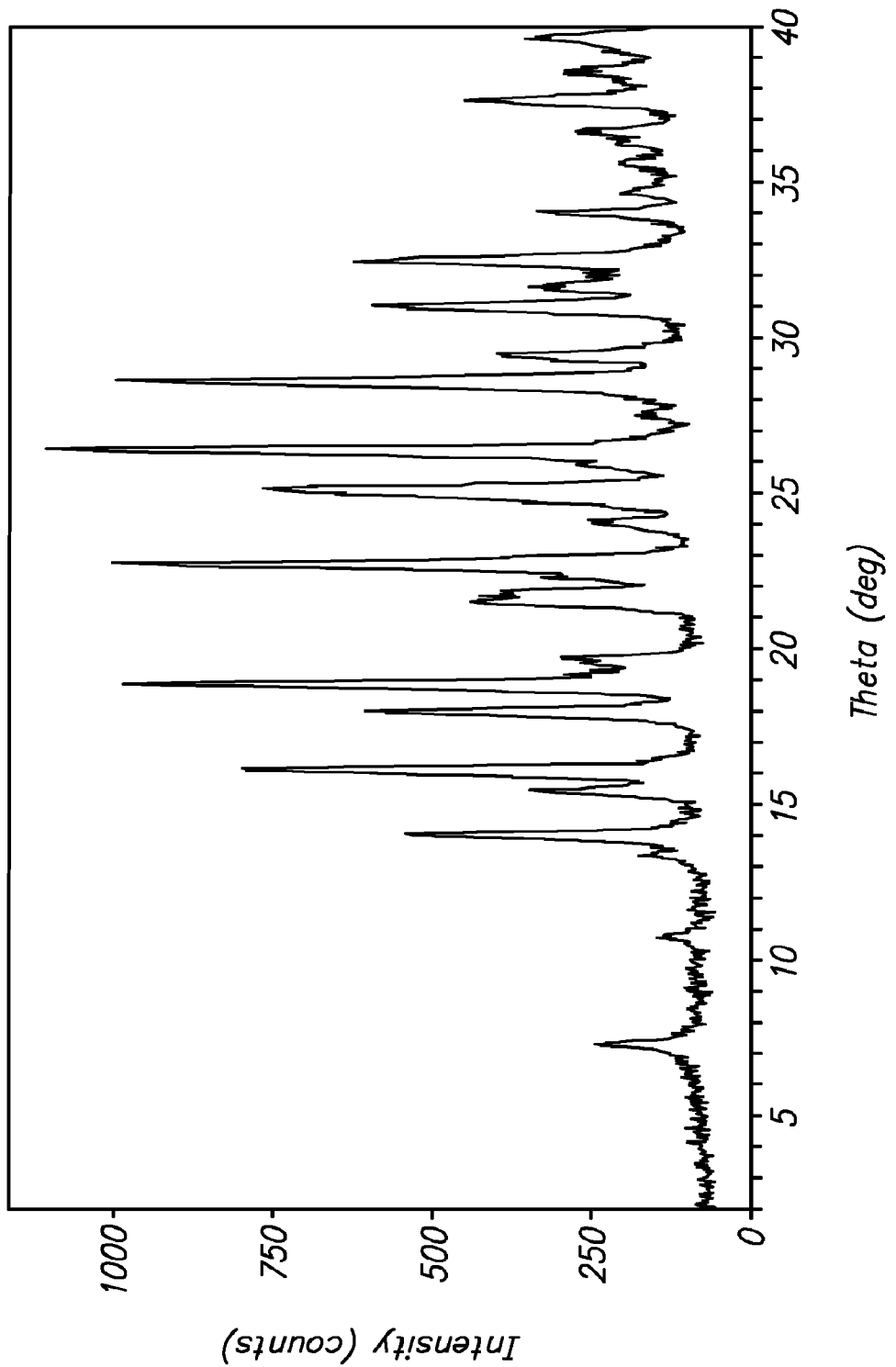
FIG. 4 shows a powder x-ray diffraction (PXRD) pattern of a crystalline monohydrochloride salt of the compound of Example 14, (R)-3-[(S)-(2-chloro-3,6-difluorophenoxy)phenyl-methyl]pyrrolidine.

A representative PXRD pattern for a sample of this crystalline salt is shown in FIG. 4, and the peak positions are listed in the table below:

| 2-Theta Angle (Degree) | d-spacing (Å) | Intensity (Counts) | Relative intensity, % |
|---|---|---|---|
| 7.28 | 12.135 | 1867 | 15.7 |
| 10.70 | 8.262 | 512 | 4.3 |
| 14.03 | 6.309 | 5213 | 43.9 |
| 16.10 | 5.501 | 8464 | 71.2 |
| 17.99 | 4.928 | 4705 | 39.6 |
| 18.80 | 4.716 | 9500 | 79.9 |
| 22.67 | 3.920 | 9784 | 82.3 |
| 25.07 | 3.549 | 9699 | 81.6 |
| 26.33 | 3.382 | 11884 | 100.0 |
| 28.55 | 3.124 | 10098 | 85.0 |

Thus, this crystalline salt can be characterized by a PXRD pattern having two or more diffraction peaks at 2θ values selected from 7.3±0.2, 10.7±0.2, 14.0±0.2, 16.1±0.2, 18.0±0.2, 18.8±0.2, 22.7±0.2, 25.1±0.2, 26.3±0.2, and 28.6±0.2. In particular, crystalline salt can be characterized by a powder x-ray diffraction pattern comprising diffraction peaks at 2θ values of 7.3±0.2, 16.1±0.2, 18.8±0.2, and 26.3±0.2.

Thermal Analysis

Figure 5:
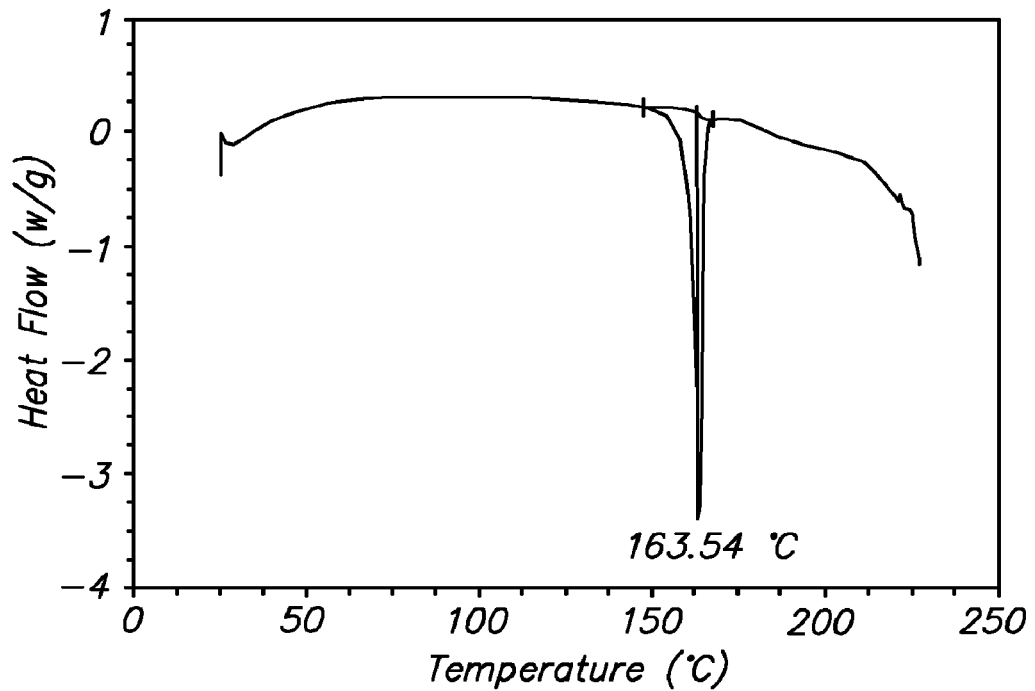
FIG. 5 shows a differential scanning calorimetry (DSC) trace and FIG. 6 shows a thermal gravimetric analysis (TGA) trace for this crystalline salt.

A representative DSC trace for a sample of this crystalline monohydrochloric acid salt (FIG. 5) showed that the crystalline salt has good thermal stability with the melting peak at about 163.5° C. and no thermal decomposition below 160° C.

Figure 6:
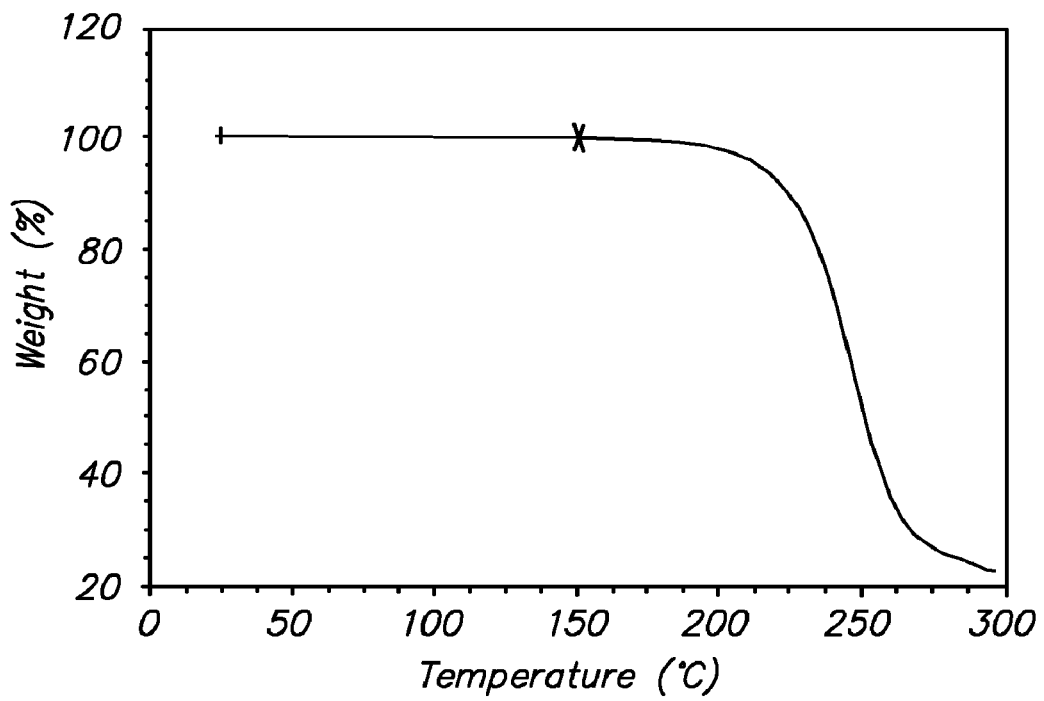

A representative TGA trace for a sample of this crystalline monohydrochloric acid salt showed a loss of solvents and/or water (<0.2%) at temperatures below 150° C., as seen in FIG. 6. This TGA trace indicate that the crystalline salt lost a small amount of weight from room temperature to moderately elevated temperatures, which is consistent with the loss of residual moisture or solvent.

Example 15

(S)-3-[(R)-(4-chloro-2-fluorophenoxy)phenylmethyl]pyrrolidine

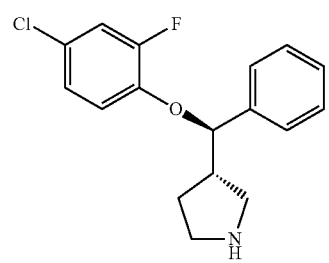

Under air, (S)-3-((R)-hydroxyphenylmethyl)pyrrolidine-1-carboxylic acid t-butyl ester (400 mg, 1.4 mmol) and 4-chloro-2-fluoro-1-iodobenzene (374 μL, 2.88 mmol) were dissolved in dry toluene (2.3 mL, 22 mmol). To this was added copper(I) iodide (82 mg, 430 μmol), 1,10-phenanthroline (160 mg, 860 μmol), and cesium carbonate (940 mg, 2.9 mmol). Air was bubbled through the mixture, the vessel was sealed, and the mixture was heated at 105° C. for 48 hours. The mixture was cooled to room temperature, rinsed with DCM, filtered, and concentrated to yield the BOC-protected form of the title compound as an oily residue, which was used without further purification.

The BOC-protected compound was dissolved in 1.25 M HCl in EtOH (9.2 mL, 11.5 mmol) and stirred at room temperature for 18 hours, and then evaporated to dryness. The residue was purified by reverse phase preparative HPLC to afford the title compound as a TFA salt (214 mg, 97% purity). MS m/z: [M+H]⁺ calcd for $C_{17}H_{17}ClFNO$, 306.10. Found, 306.4. ¹H NMR (400 MHz, DMSO-d₆) δ (ppm): 7.43-7.39 (m, 5H), 7.34-7.31 (m, 1H), 7.10-7.07 (m, 1H), 7.00-6.96 (m, 1H), 5.46 (d, J=6.8, 1H), 3.35-3.28 (m, 1H), 3.26-3.17 (m, 1H), 3.10-3.05 (m, 1H), 2.92-2.83 (m, 2H), 2.10-2.07 (m, 1H), 2.00-1.97 (m, 1H).

Example 16

(R)-3-[(S)-(3,5-Dichlorophenoxy)phenylmethyl]pyrrolidine

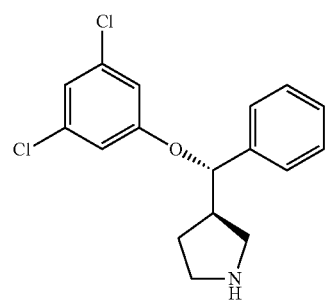

Under air, (R)-3-((S)-hydroxyphenylmethyl)pyrrolidine-1-carboxylic acid t-butyl ester (400 mg, 1 mmol) and 1,3-dichloro-5-iodobenzene (787 mg, 2.88 mmol) were dissolved in dry toluene (2.3 mL, 22 mmol). To this was added copper(I) iodide (82 mg, 430 μmol), 1,10-phenanthroline (160 mg, 0.86 mmol), and cesium carbonate (940 mg, 2.9 mmol). Air was bubbled through the mixture, the vessel was sealed, and the mixture was heated at 105° C. for 48 hours. The mixture was cooled to room temperature, rinsed with DCM, filtered, and concentrated to yield the BOC-protected form of the title compound ((R)-3-[(S)-(3,5-dichlorophenoxy)phenylmethyl]pyrrolidine-1-carboxylic acid t-butyl ester) as an oily residue, which was used without further purification.

The BOC-protected compound was dissolved in 1.25 M HCl in EtOH (9.2 mL, 11.5 mmol) and stirred at room temperature for 18 hours, and then evaporated to dryness. The residue was purified by reverse phase preparative HPLC to afford the title compound as a TFA salt (258 mg, 91% purity). MS m/z: $[M+H]^+$ calcd for $C_{17}H_{17}Cl_2NO$, 322.07. Found, 322.0.

Alternate Method (R)-3-((S)-hydroxyphenylmethyl)pyrrolidine-1-carboxylic acid t-butyl ester (10.0 g, 36.0 mmol) was dissolved in anhydrous DMF (65 mL, 840 mmol). Washed and dried sodium hydride (1.0 g, 43 mmol) was added, and the mixture stirred at room temperature for 15 minutes. 3,5-Dichlorofluorobenzene (10 mL, 80 mmol) was then added, and the mixture stirred at 70° C. for 3 hours. The mixture was cooled to room temperature. EtOAc (200 mL) and 1M HCl (200 mL) was added, mixed, and the phases separated. The organic layer was washed with 2×200 mL of diluted aqueous NaCl, dried over $Na_2SO_4$, and concentrated to dryness to yield 19 g of crude product. The crude product was purified on a 300 g SiG column to yield (R)-3-[(S)-(3,5-dichlorophenoxy)phenylmethyl]pyrrolidine-1-carboxylic acid t-butyl ester as a white sticky foam (14.1 g, 91.67% purity).

Monohydrochloride Crystalline Salt (R)-3-[(S)-(3,5-dichlorophenoxy)phenylmethyl]pyrrolidine-1-carboxylic acid t-butyl ester (14.0 g, 33.1 mmol) was dissolved in EtOH (100 mL, 2 mol). Into the mixture was added an HCl solution prepared by the slow addition of acetyl chloride (23.6 mL, 331 mmol) into EtOH (50 mL, 860 mmol) at 0° C. The mixture was stirred at room temperature overnight. The solvent was removed by rotary evaporation, EtOAc (200 mL) was added, followed by removal of most of the solvent. EtOAc (50 mL) was added, the solution was heated to 75° C. for 15 minutes, cooled to room temperature, filtered and dried to yield (R)-3-[(S)-(3,5-dichlorophenoxy)phenylmethyl]pyrrolidine as an HCl salt (10.5 g, >99% purity).

(R)-3-[(S)-(3,5-dichlorophenoxy)phenylmethyl]pyrrolidine-1-carboxylic acid t-butyl ester (14.0 g, 33.1 mmol) was dissolved in EtOH (100 mL, 2 mol). Into the mixture was added an HCl solution prepared by the slow addition of acetyl chloride (23.6 mL, 331 mmol) into EtOH (50 mL, 860 mmol) at 0° C. The mixture was stirred at room temperature overnight. The solvent was removed by rotary evaporation, EtOAc (200 mL) was added, followed by removal of most of the solvent. EtOAc (100 mL) was added, the solution was heated to 75° C. for 15 minutes, cooled to room temperature (seeded at 35° C.) and stirred for 2 hours. The solids were filtered off and dried to yield 5 g of product. The product was slurried twice in 65° C. EtOAc (5 vol) to yield (R)-3-[(S)-(3,5-dichlorophenoxy)phenylmethyl]pyrrolidine as an HCl salt (4.1 g, >99% purity).

(R)-3-(S)-hydroxyphenylmethyl)pyrrolidine-1-carboxylic acid t-butyl ester (2.0 g, 7.2 mmol) was dissolved in anhydrous DMF (10 mL, 100 mmol). Lithium hydride (86 mg, 11 mmol) was added in 3 separate portions. The mixture was stirred at room temperature for 15 minutes. Into the mixture was added 3,5-dichlorofluorobenzene (1.7 mL, 14 mmol), and the resultant mixture stirred at room temperature for 15 minutes. The mixture was then stirred at 70° C. overnight. The mixture was cooled to room temperature, and EtOAc (80 mL) and 1M HCl (50 mL) were added. After mixing, the phases were separated and the organic layer was washed with diluted aqueous NaCl (1×50 mL), dried over $Na_2SO_4$, and concentrated to dryness to yield 3.5 g of crude product. Into the crude product was added 25 mL cold HCl in an EtOH/EtOAc solution and stirred at room temperature for 3 hours. Most of the solvent was removed by rotary evaporation, EtOAc was added (50 mL) and most of the solvent was removed again. Recrystallization and reslurry from EtOAc (20 mL) gave (R)-3-[(S)-(3,5-dichlorophenoxy)phenylmethyl]pyrrolidine as an HCl salt (2 g, ~99% purity).

The three batches of (R)-3-[(S)-(3,5-dichlorophenoxy)phenylmethyl]pyrrolidine.HCl (16.5 g, 46.0 mmol) was suspended in EtOAc (100 mL, 1 mol) and then stirred at room temperature for 2 hours, filtered and dried in vacuum over 48 hours to yield (R)-3-[(S)-(3,5-dichlorophenoxy)phenylmethyl]pyrrolidine as a monohydrochloride crystalline salt (16.2 g).

Powder X-Ray Diffraction

Figure 7:
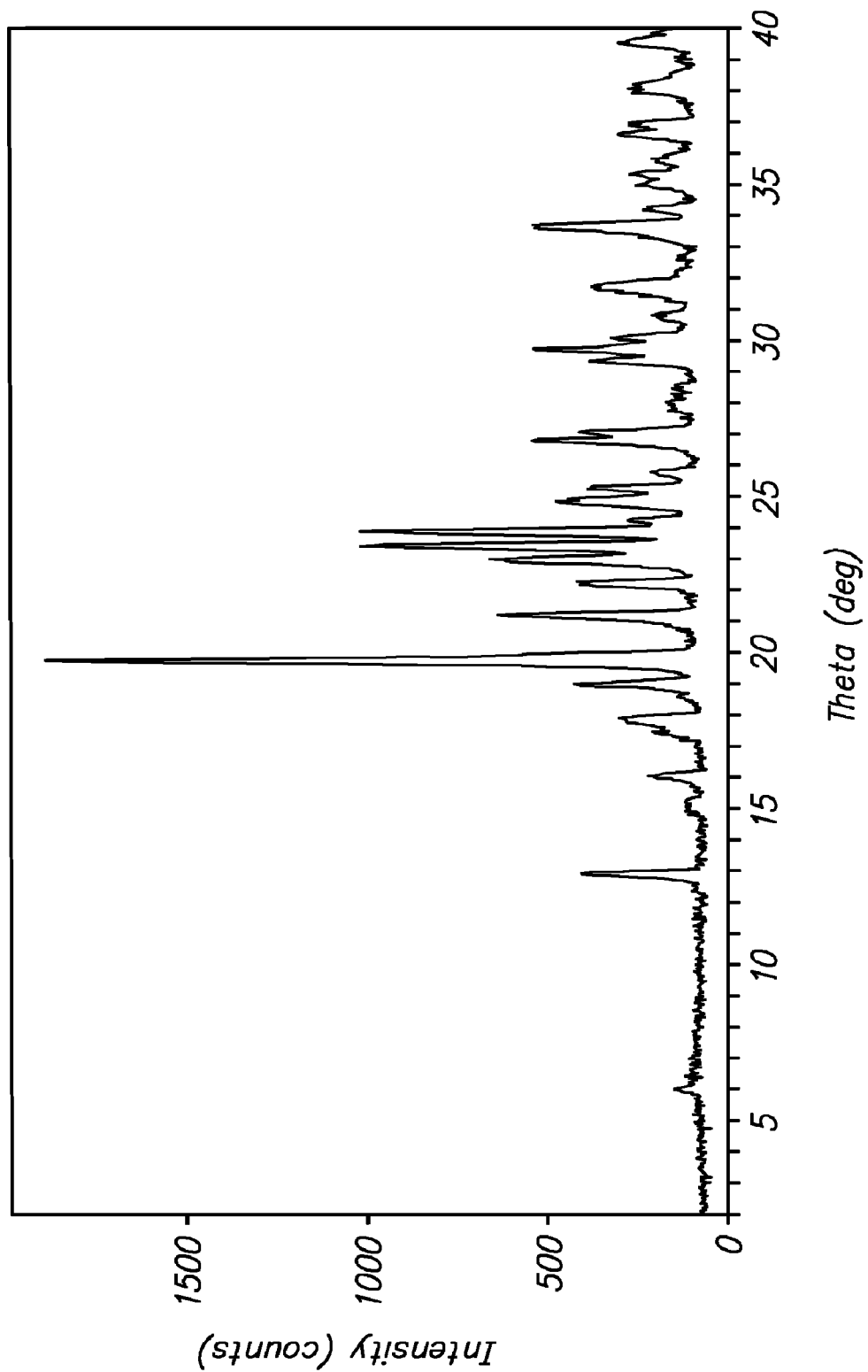
FIG. 7 shows a powder x-ray diffraction (PXRD) pattern of a crystalline monohydrochloride salt of the compound of Example 16, (R)-3-[(S)-(3,5-dichlorophenoxy)phenylmethyl]pyrrolidine.

The PXRD pattern for the monohydrochloride salt showed the material to be crystalline. A representative PXRD pattern for a sample of this crystalline salt is shown in FIG. 7, and the peak positions are listed in the table below:

| 2-Theta Angle (Degree) | d-spacing (Å) | Intensity (Counts) | Relative intensity, % |
| --- | --- | --- | --- |
| 5.99 | 14.740 | 331 | 2.2 |
| 12.92 | 6.847 | 2631 | 17.3 |
| 16.04 | 5.522 | 1030 | 6.8 |
| 18.97 | 4.673 | 2168 | 14.2 |
| 19.73 | 4.496 | 15244 | 100.0 |
| 21.20 | 4.188 | 4561 | 29.9 |
| 22.97 | 3.869 | 6526 | 42.8 |
| 23.39 | 3.799 | 7382 | 48.4 |
| 23.87 | 3.725 | 7756 | 50.9 |
| 33.68 | 2.659 | 6007 | 39.4 |

Thus, this crystalline salt can be characterized by a PXRD pattern having two or more diffraction peaks at 2θ values selected from 6.0±0.2, 12.9±0.2, 16.0±0.2, 19.0±0.2, 19.7±0.2, 21.2±0.2, 23.0±0.2, 23.4±0.2, 23.9±0.2, and 33.7±0.2. In particular, crystalline salt can be characterized by a powder x-ray diffraction pattern comprising diffraction peaks at 2θ values of 12.9±0.2, 19.7±0.2, 23.4±0.2, and 23.9±0.2.

Thermal Analysis

A representative DSC trace for a sample of this crystalline monohydrochloric acid salt (FIG. 8) showed that the crystalline salt has good thermal stability with the melting peak at about 223.0° C. and no thermal decomposition below 220° C.

Figure 8:
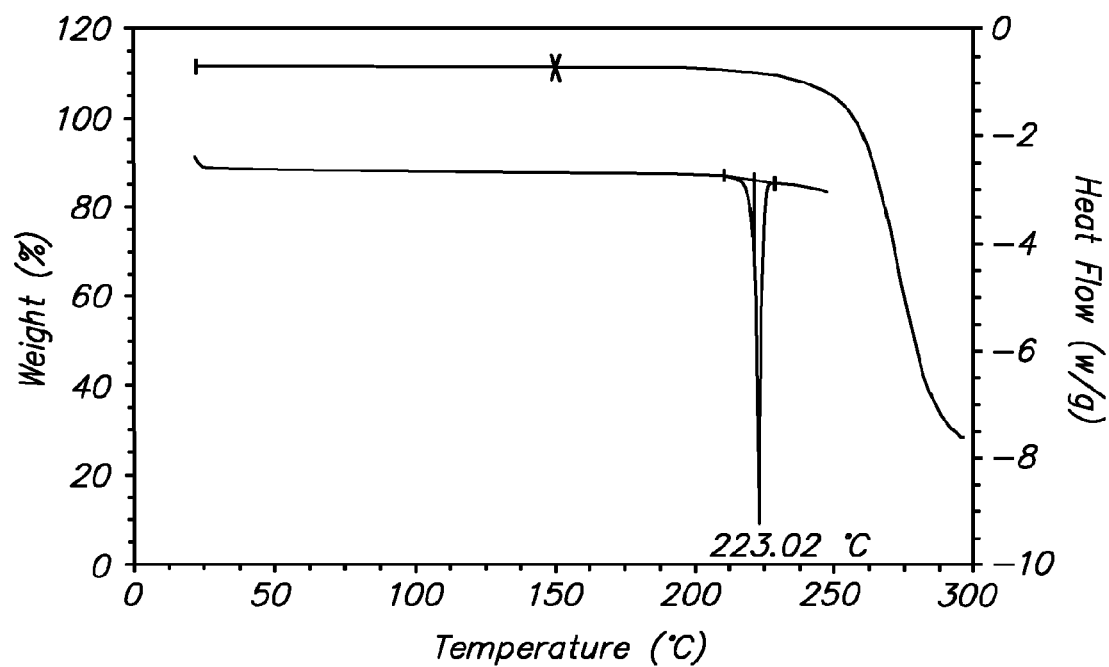
FIG. 8 shows a differential scanning calorimetry (DSC) trace and a thermal gravimetric analysis (TGA) trace for this crystalline salt.

A representative TGA trace for a sample of this crystalline monohydrochloric acid salt showed a loss of solvents and/or water (<0.1%) at temperatures below 150° C., as seen in FIG. 8. This TGA trace indicate that the crystalline salt lost a small amount of weight from room temperature to moderately elevated temperatures, which is consistent with the loss of residual moisture or solvent.

Preparation 8

3-(Methoxymethylcarbamoyl)pyrrolidine-1-carboxylic Acid t-Butyl Ester

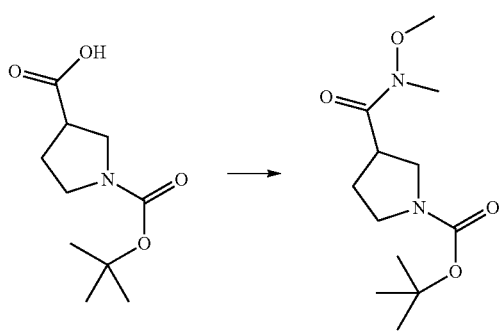

Pyrrolidine-1,3-dicarboxylic acid 1-t-butyl ester (0.7 g, 3.3 mmol), HCTU (2.0 g, 4.9 mmol), and HOBt (747 mg, 4.9 mmol), N,O-dimethylhydroxylamine HCl (1.6 g, 16.3 mmol) and DMF (10.0 mL, 129 mmol) were combined and cooled at 0° C. using an ice bath. DIPEA (5.7 mL, 32.5 mmol) was added slowly over 5 minutes. The mixture was allowed to warm to room temperature and stirred for 15 hours. The mixture was then diluted with sat. NaHCO₃ (75 mL) and extracted with EtOAc (2×100 mL). The combined organic layers were washed with sat. NaCl (50 mL), dried over Na₂SO₄, filtered, concentrated under high vacuum to yield 2.9 g of the crude title compound as a mixture of the (R) and (S) enantiomers.

Preparation 9

3-Benzoylpyrrolidine-1-carboxylic Acid t-Butyl Ester

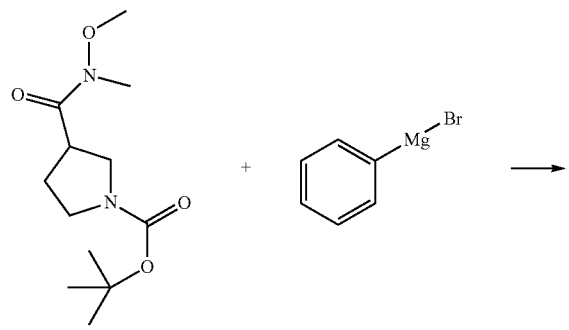

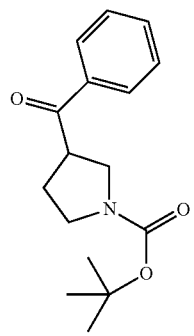

3-(Methoxymethylcarbamoyl)pyrrolidine-1-carboxylic acid t-butyl ester (400 mg, 1.6 mmol) and THF (10 mL, 0.1 mol) were combined under nitrogen. The solution was cooled at 0° C. using an ice bath. 1.0 M of Phenylmagnesium bromide in THF (2.0 mL, 2.0 mol) was added dropwise over 5 minutes. The mixture was slowly warmed to room temperature and stirred for 2 hours, at which point an additional amount of 1.0 M of phenylmagnesium bromide in THF (5.0 mL, 5.0 mol) was added over 10 minutes. After 5 minutes, the mixture was cooled in an ice bath and the reaction quenched by the slow addition of water (15 mL). The mixture was extracted with EtOAc (1×100 mL), and the organic layer was washed with saturated aqueous NaCl (50 mL), dried over Na₂SO₄, filtered, and concentrated to yield 850 mg of crude product, which was purified by flash chromatography (12 g column, 20-100% EtOAc in hexanes over 17 minutes) to yield a mixture of the (R) and (S) enantiomers of the title compound as a clear oil (412 mg).

Preparation 10

(S)-3-(Methoxymethylcarbamoyl)pyrrolidine-1-carboxylic Acid tert-Butyl Ester

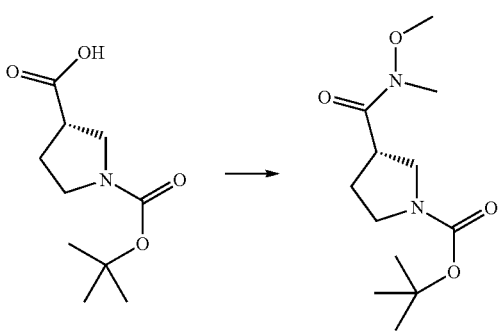

(3S)-Boc-β-Proline-OH (700 mg, 3.3 mmol; (S)-pyrrolidine-1,3-dicarboxylic acid 1-t-butyl ester), HCTU (1.7 g, 4.1 mmol), HOBt (622 mg, 4.1 mmol), N,O-dimethylhydroxylamine HCl (1.6 g, 16.3 mmol), and DMF (10.0 mL, 129 mmol) were combined and cooled at 0° C. using an ice bath. DIPEA (5.7 mL, 32.5 mmol) was added slowly over 5 minutes. The mixture was allowed to warm to room temperature and stirred for 15 hours. The mixture was then diluted with saturated NaHCO₃ (75 mL) and extracted with EtOAc (2×100 mL). The combined organic layers were washed with saturated aqueous NaCl (50 mL) and water (50 mL), dried over

Preparation 11

(R)-3-(Methoxymethylcarbamoyl)pyrrolidine-1-carboxylic Acid t-Butyl Ester

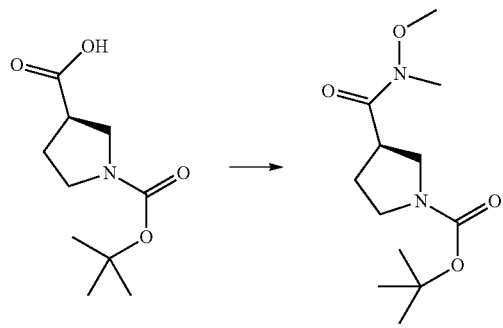

(R)-1-N-Boc-β-Proline (700 mg, 3.3 mmol; (R)-pyrrolidine-1,3-dicarboxylic acid 1-t-butyl ester), HCTU (1.7 g, 4.1 mmol), HOBt (622 mg, 4.1 mmol), N,O-dimethylhydroxylamine HCl (1.6 g, 16.3 mmol) and DMF (10.0 mL, 129 mmol) were combined and cooled at 0° C. using an ice bath. DIPEA (5.7 mL, 32.5 mmol) was added slowly over 5 minutes. The mixture was allowed to warm to room temperature and stirred for 15 hours. The mixture was then diluted with sat. NaHCO$_3$ (75 mL) and extracted with EtOAc (2×100 mL). The combined organic layers were washed with sat. NaCl (50 mL) and water (50 mL), dried over Na$_2$SO$_4$, filtered, and concentrated under high vacuum to yield 1.6 g of the crude product, which was purified by flash chromatography (12 g column, 10-100% EtOAc in hexanes over 16 minutes), and placed under high vacuum for 15 minutes to yield 723 mg of the title compound.

Preparation 12

(S)-3-Benzoylpyrrolidine-1-carboxylic Acid t-Butyl Ester

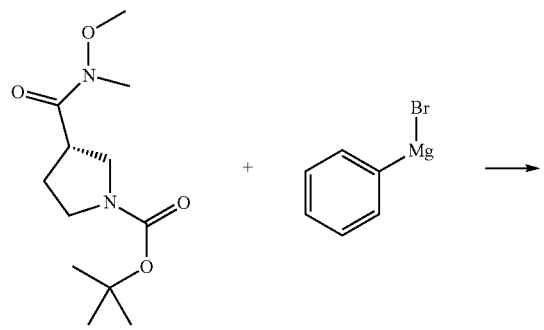

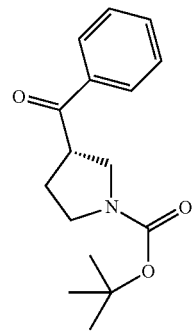

(S)-3-(Methoxymethylcarbamoyl)pyrrolidine-1-carboxylic acid t-butyl ester (400 mg, 1.6 mmol) and THF (10 mL, 0.1 mol) were combined under nitrogen. The solution was cooled at 0° C. using an ice bath. 1.0 M of Phenylmagnesium bromide in THF (7.0 mL, 7.0 mmol) was added dropwise over 5 minutes. The mixture was slowly warmed to room temperature and stirred for 30 minutes. The mixture was cooled in an ice bath and the reaction was quenched by the slow addition of water (15 mL). The mixture was extracted with EtOAc (1×100 mL), and the organic layer was washed with sat. NaCl (50 mL), dried over Na$_2$SO$_4$, filtered, and concentrated to yield 849 mg of crude product, which was purified by flash chromatography (12 g column, 20-100% EtOAc in hexanes over 17 minutes), and placed under high vacuum for 15 minutes to yield 372 mg of the title compound as a clear oil.

Example 17

RS/SR Mixture of Enantiomers (17-1) and SS/RR Mixture of Enantiomers (17-2) of 3-(Phenoxyphenylmethyl)pyrrolidine

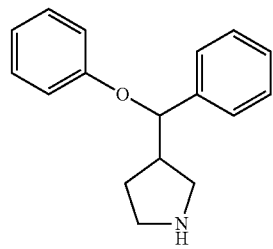

Following the procedure of Example 1 and using 3-(phenoxyphenylmethyl)pyrrolidine-1-carboxylic acid t-butyl ester in place of 3-(phenyl-o-tolyloxymethyl)pyrrolidine-1-carboxylic acid t-butyl ester, the RS/SR mixture of enantiomers (16-1) of the title compound was prepared as an HCl salt (56% yield; 98% purity). MS m/z: [M+H]$^+$ calcd for C$_{17}$H$_{19}$NO, 254.15. Found 254.1.

Following the procedure of Example 2, and, in Preparation 3, substituting the RS/SR mixture of enantiomers with the SS/RR mixture of enantiomers of 3-(hydroxyphenylmethyl)-pyrrolidine-1-carboxylic acid t-butyl ester (47.5 mg, 170 µmol), and substituting 2-iodoanisole with the appropriate aryl iodide, the SS/RR mixture of enantiomers (16-2) of the title compound was prepared (12.4 mg) as a TFA salt. MS m/z: [M+H]$^+$ calcd for C$_{17}$H$_{19}$NO, 254.15. Found 254.2.

While both of the aforementioned compounds exhibit affinity for SERT and NET, compound 17-1 exhibits a NET pK$_i$≧8 and a SERT K$_i$/NET K$_i$ in the range of 0.1-100.

| Cmpd. | NET p$K_i$ | SERT $K_i$/NET $K_i$ |
|---|---|---|
| Ex. 17-1 | 8.2 | 1.3 |

In the following figures, the two chiral centers are identified by the * and ** symbols. When describing the stereochemistry, the carbon atom indicated by the * symbol is designated first. Thus, an "SR" designation represents a compound having the (S) configuration at the carbon atom indicated by the * symbol and having the (R) configuration at the ** carbon atom. The same hold true for racemic mixtures. For example, an "RS/SR" designation represents a racemic mixture of (R,S) compounds and (S,R) compounds, i.e., a mixture of compounds having the (R) configuration at the * carbon atom and the (S) configuration at the ** carbon atom and compounds having the (S) configuration at the * carbon atom and the (R) configuration at the ** carbon atom.

Example 18

Following the procedures described in the examples above, and substituting the appropriate starting materials and reagents, compounds 18-1 to 18-7, having formula II', were also prepared:

(II')

where a = 1

| Cmpd. | Stereochemistry | $R^1$ | Formula | MS m/z: [M + H]$^+$ calcd | found |
|---|---|---|---|---|---|
| 18-1 | RS/SR | 2-F | $C_{17}H_{18}FNO$ | 272.14 | 272.2 |
| 18-2 | SR/RS | 3-Cl | $C_{17}H_{18}ClNO$ | 288.11 | 288.0 |
| 18-3 | SR/RS | 3-CH$_3$ | $C_{18}H_{21}NO$ | 268.16 | 268.2 |
| 18-4 | RS/SR | 3-OCH$_3$ | $C_{18}H_{21}NO_2$ | 284.16 | 284.2 |
| 18-5 | RS/SR | 3-OCF$_3$ | $C_{18}H_{18}F_3NO_2$ | 338.13 | 338.2 |
| 18-6 | SR/SS | 3-CH$_2$OH | $C_{18}H_{21}NO_2$ | 284.16 | 284.4 |
| 18-7 | SR/SS | 3-CHO | $C_{18}H_{19}NO_2$ | 282.14 | 282.8 |

While all the aforementioned compounds exhibit affinity for both SERT and NET, the compound listed in the table below exhibits a NET p$K_i \geq 8$ and a SERT $K_i$/NET $K_i$ in the range of 0.1-100.

| Cmpd. | NET p$K_i$ | SERT $K_i$/NET $K_i$ |
|---|---|---|
| 18-7 | 8 | 6.3 |

Example 19

Following the procedures described in the examples above, and substituting the appropriate starting materials and reagents, compounds 19-1 to 19-31 having the following formula, were also prepared:

(III)

| Cmpd. | Stereochemistry | $R^2$ | Formula | MS m/z: [M + H]$^+$ calcd | found |
|---|---|---|---|---|---|
| 19-1 | RS/SR | F | $C_{17}H_{18}FNO$ | 272.14 | 272.6 |
| 19-2 | SR | F | $C_{17}H_{18}FNO$ | 272.14 | 272.2 |
| 19-3 | RS | F | $C_{17}H_{18}FNO$ | 272.14 | 272.2 |
| 19-4 | RS/SR | Cl | $C_{17}H_{18}ClNO$ | 288.11 | 288.0 |
| 19-5 | SR | Cl | $C_{17}H_{18}ClNO$ | 288.11 | 288.0 |
| 19-6 | RS | Cl | $C_{17}H_{18}ClNO$ | 288.11 | 288.0 |
| 19-7 | RS/SR | Br | $C_{17}H_{18}BrNO$ | 332.06 | 332.0 |
| 19-8 | RS/SR | I | $C_{17}H_{18}INO$ | 380.04 | 380.4 |
| Ex. 1 | RS/SR | —CH$_3$ | $C_{18}H_{21}NO$ | 268.16 | 268.1 |
| Ex. 4-1 | SS/RR | —CH$_3$ | $C_{18}H_{21}NO$ | 268.16 | 268.2 |
| 19-9 | SR | —CH$_3$ | $C_{18}H_{21}NO$ | 268.16 | 268.2 |
| 19-10 | RS | —CH$_3$ | $C_{18}H_{21}NO$ | 268.16 | 268.2 |
| 19-11 | RS/SR | —CH$_2$CH$_3$ | $C_{19}H_{23}NO$ | 282.18 | 282.2 |
| 19-12 | RS/SR | —CH(CH$_3$)$_2$ | $C_{20}H_{25}NO$ | 296.19 | 296.2 |
| 19-13 | RS/SR | —CF$_3$ | $C_{18}H_{18}F_3NO$ | 322.13 | 322.2 |
| Ex. 2 | RS/SR | —OCH$_3$ | $C_{18}H_{21}NO_2$ | 284.16 | 284.4 |
| Ex. 6-1 | RS | —OCH$_3$ | $C_{18}H_{21}NO_2$ | 284.16 | 284.4 |
| Ex. 6-2 | SR | —OCH$_3$ | $C_{18}H_{21}NO_2$ | 284.16 | 284.4 |
| Ex. 4-2 | SS/RR | —OCH$_3$ | $C_{18}H_{21}NO_2$ | 284.16 | 284.4 |
| 19-14 | RR | —OCH$_3$ | $C_{18}H_{21}NO_2$ | 284.16 | 284.8 |
| 19-15 | SS | —OCH$_3$ | $C_{18}H_{21}NO_2$ | 284.16 | 284.8 |
| 19-16 | SS/RR | —OCH$_2$CH$_3$ | $C_{19}H_{23}NO_2$ | 298.17 | 298.6 |
| Ex. 5 | RS/SR | —OCH$_2$CH$_3$ | $C_{19}H_{23}NO_2$ | 298.17 | 298.6 |
| 19-17 | RS/SR | —OCH(CH$_3$)$_2$ | $C_{20}H_{25}NO_2$ | 312.19 | 312.4 |
| 19-18 | RS/SR | —OCF$_3$ | $C_{18}H_{18}F_3NO_2$ | 338.13 | 338.2 |
| 19-19 | RS/SR | -phenyl | $C_{23}H_{23}NO$ | 330.18 | 330.2 |
| 19-20 | RR/SS | —CH$_2$-phenyl | $C_{24}H_{25}NO$ | 344.19 | 344.2 |
| 19-21 | RS/SR | —CH$_2$-phenyl | $C_{24}H_{25}NO$ | 344.19 | 344.2 |
| 19-22 | RS/SR | —O-2,4-dichlorophenyl | $C_{23}H_{21}Cl_2NO_2$ | 414.10 | 414.0 |
| 19-23 | RS/SR | —O-benzyl | $C_{24}H_{25}NO_2$ | 360.19 | 360.2 |
| 19-24 | RS/SR | —CH$_2$OH | $C_{18}H_{21}NO_2$ | 284.16 | 284.2 |
| Ex. 9-3 | SR | —C(O)CH$_3$ | $C_{19}H_{21}NO_2$ | 296.16 | 296.2 |
| 19-25 | RS | —C(O)CH$_3$ | $C_{19}H_{21}NO_2$ | 296.16 | 296.2 |
| 19-26 | SR/RS | —C(O)CH$_2$CH$_3$ | $C_{20}H_{23}NO_2$ | 310.17 | 310.2 |
| 19-27 | SR | —C(O)CH$_2$CH$_3$ | $C_{20}H_{23}NO_2$ | 310.17 | 310.2 |
| Ex. 9-5 | SR | —C(O)OCH$_3$ | $C_{19}H_{21}NO_3$ | 312.15 | 312.2 |
| 19-28 | RS/SR | —NO$_2$ | $C_{17}H_{18}N_2O_3$ | 299.13 | 299.2 |
| 19-29 | RS/SR | —SCH$_3$ | $C_{18}H_{21}NOS$ | 300.13 | 300.2 |
| 19-30 | SR | —SCH$_3$ | $C_{18}H_{21}NOS$ | 300.13 | 300.4 |
| 19-31 | RS | —SCH$_3$ | $C_{18}H_{21}NOS$ | 300.13 | 300.4 |
| Ex. 9-1 | SR | —SO$_2$CH$_3$ | $C_{18}H_{21}NO_3S$ | 332.12 | 332.0 |

While all the aforementioned compounds exhibit affinity for both SERT and NET, the compounds listed in the table below exhibit a NET p$K_i \geq 8$ and a SERT $K_i$/NET $K_i$ in the range of 0.1-100.

| Cmpd. | NET p$K_i$ | SERT $K_i$/NET $K_i$ |
|---|---|---|
| 19-1 | 8.6 | 4 |
| 19-2 | 9 | 63 |
| 19-3 | 8 | 0.4 |
| 19-4 | 9.1 | 2 |
| 19-5 | 9.3 | 65 |
| 19-6 | 8.2 | 0.2 |
| 19-7 | 9 | 1 |

| Cmpd. | NET pK$_i$ | SERT K$_i$/NET K$_i$ |
|---|---|---|
| 19-8 | 9 | 0.6 |
| Ex. 1 | 8.5 | 1.3 |
| 19-9 | 9.1 | 13 |
| 19-11 | 8.5 | 4 |
| 19-12 | 8.7 | 16 |
| 19-13 | 8.6 | 7.9 |
| Ex. 2 | 9.1 | 13 |
| Ex. 6-2 | 9.4 | 50 |
| Ex. 5 | 8.9 | 32 |
| 19-17 | 8.5 | 40 |
| 19-18 | 8.9 | 20 |
| 19-19 | 8.7 | 32 |
| 19-20 | 8.1 | 1.6 |
| 19-21 | 8.3 | 5 |
| 19-23 | 8 | 3.2 |
| Ex. 9-3 | 8.5 | 50 |
| 19-26 | 8.4 | 50 |
| 19-27 | 8.7 | 100 |
| 19-28 | 8.4 | 13 |
| 19-29 | 9.2 | 25 |
| 19-30 | 9.4 | 63 |

Example 20

Following the procedures described in the examples above, and substituting the appropriate starting materials and reagents, compounds 20-1 to 20-39 having the following formula, were also prepared:

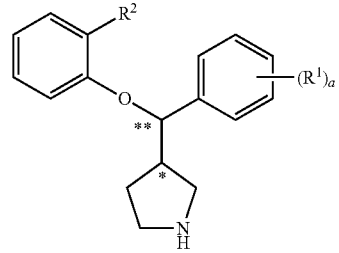

(III')

where a is 1 or 2

| Cmpd. | Stereo-chemistry | R$^1$ | R$^2$ | Formula | MS m/z: [M + H]$^+$ calcd | found |
|---|---|---|---|---|---|---|
| 20-1 | RS/SR | 2-Cl | Cl | C$_{17}$H$_{17}$Cl$_2$NO | 322.07 | 322.0 |
| 20-2 | RR/SS | 2-Cl | Cl | C$_{17}$H$_{17}$Cl$_2$NO | 322.07 | 322.0 |
| 20-3 | RS/SR | 2-F | Cl | C$_{17}$H$_{17}$ClFNO | 306.10 | 306.0 |
| 20-4 | RS/SR | 3-F | Cl | C$_{17}$H$_{17}$ClFNO | 306.10 | 306.0 |
| 20-5 | RS/SR | 3-Cl | Cl | C$_{17}$H$_{17}$Cl$_2$NO | 322.07 | 322.0 |
| 20-6 | RS/SR | 3-CH$_3$ | Cl | C$_{18}$H$_{20}$ClNO | 302.12 | 302.2 |
| 20-7 | RS/SR | 3-OCH$_3$ | Cl | C$_{18}$H$_{20}$ClNO$_2$ | 318.12 | 318.2 |
| 20-8 | RS/SR | 2-OCF$_3$ | Cl | C$_{18}$H$_{17}$ClF$_3$NO$_2$ | 372.09 | 372.0 |
| 20-9 | RS/SR | 3-OCF$_3$ | Cl | C$_{18}$H$_{17}$ClF$_3$NO$_2$ | 372.09 | 372.0 |
| 20-10 | RS/SR | 3-OCH$_3$ | —CH(CH$_3$)$_2$ | C$_{21}$H$_{27}$NO$_2$ | 326.20 | 326.2 |
| 20-11 | RS/SR | 3-OCF$_3$ | —CH(CH$_3$)$_2$ | C$_{21}$H$_{24}$F$_3$NO$_2$ | 380.18 | 380.2 |
| 20-12 | RS/SR | 3-Cl | —CH(CH$_3$)$_2$ | C$_{20}$H$_{24}$ClNO | 330.15 | 330.2 |
| 20-13 | RS/SR | 3-F | —CH(CH$_3$)$_2$ | C$_{20}$H$_{24}$FNO | 314.18 | 314.2 |
| 20-14 | RS/SR | 2-F | —OCH$_3$ | C$_{18}$H$_{20}$FNO$_2$ | 302.15 | 302.2 |
| 20-15 | RS/SR | 3-F | —OCH$_3$ | C$_{18}$H$_{20}$FNO$_2$ | 302.15 | 302.2 |
| 20-16 | RS/SR | 2-Cl | —OCH$_3$ | C$_{18}$H$_{20}$ClNO$_2$ | 318.12 | 318.2 |
| 20-17 | SR | 2-Cl | —OCH$_3$ | C$_{18}$H$_{20}$ClNO$_2$ | 318.12 | 318.0 |
| 20-18 | RS | 2-Cl | —OCH$_3$ | C$_{18}$H$_{20}$ClNO$_2$ | 318.12 | 318.0 |
| 20-19 | RR/SS | 2-Cl | —OCH$_3$ | C$_{18}$H$_{20}$ClNO$_2$ | 318.12 | 318.2 |
| 20-20 | RS/SR | 3-Cl | —OCH$_3$ | C$_{18}$H$_{20}$ClNO$_2$ | 318.12 | 318.2 |
| 20-21 | RS/SR | 4-Cl | —OCH$_3$ | C$_{18}$H$_{20}$ClNO$_2$ | 318.12 | 318.2 |
| 20-22 | SR/RS | 3-OCH$_3$ | —OCH$_3$ | C$_{19}$H$_{23}$NO$_3$ | 314.17 | 314.2 |
| 20-23 | RS/SR | 2-OCF$_3$ | —OCH$_3$ | C$_{19}$H$_{20}$F$_3$NO$_3$ | 368.14 | 368.2 |
| 20-24 | RR/SS | 2-OCF$_3$ | —OCH$_3$ | C$_{19}$H$_{20}$F$_3$NO$_3$ | 368.14 | 368.2 |
| 20-25 | RS/SR | 3-OCF$_3$ | —OCH$_3$ | C$_{19}$H$_{20}$F$_3$NO$_3$ | 368.14 | 368.2 |
| 20-26 | SR/SS | 3-CH$_2$OH | —OCH$_3$ | C$_{19}$H$_{23}$NO$_3$ | 314.17 | 314.0 |
| 20-27 | SR | 3-CN | —OCH$_3$ | C$_{19}$H$_{20}$N$_2$O$_2$ | 309.15 | 309.8 |
| 20-28 | SR | 4-CN | —OCH$_3$ | C$_{19}$H$_{20}$N$_2$O$_2$ | 309.15 | 309.8 |
| 20-29 | SR | 2-SO$_2$CH$_3$ | —OCH$_3$ | C$_{19}$H$_{23}$NO$_4$S | 362.13 | 362.0 |
| 20-30 | SR | 3-CONH$_2$ | —OCH$_3$ | C$_{19}$H$_{22}$N$_2$O$_3$ | 327.16 | 327.4 |
| 20-31 | RR/SS | 3,5-F | —OCH$_3$ | C$_{18}$H$_{19}$F$_2$NO$_2$ | 320.14 | 320.2 |
| 20-32 | RS/SR | 3,5-F | —OCH$_3$ | C$_{18}$H$_{19}$F$_2$NO$_2$ | 320.14 | 320.2 |
| 20-33 | SR | 3,5-F | —OCH$_3$ | C$_{18}$H$_{19}$F$_2$NO$_2$ | 320.14 | 320.0 |
| 20-34 | RS | 3,5-F | —OCH$_3$ | C$_{18}$H$_{19}$F$_2$NO$_2$ | 320.14 | 320.2 |
| 20-35 | RS/SR | 3-F, 5-Cl | —OCH$_3$ | C$_{18}$H$_{19}$ClFNO$_2$ | 336.11 | 336.0 |
| 20-36 | RS/SR | 3-F, 5-CH$_3$ | —OCH$_3$ | C$_{19}$H$_{22}$FNO$_2$ | 316.16 | 316.2 |
| 20-37 | RR/SS | 3-F, 5-CH$_3$ | —OCH$_3$ | C$_{19}$H$_{22}$FNO$_2$ | 316.16 | 316.2 |

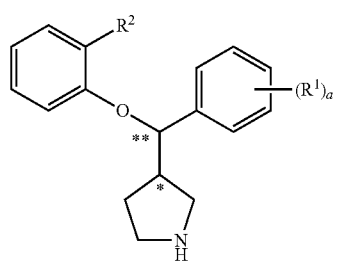

where a is 1 or 2

| Cmpd. | Stereo-chemistry | R¹ | R² | Formula | MS m/z: [M + H]⁺ calcd | found |
|---|---|---|---|---|---|---|
| 20-38 | RS/SR | 3-Cl, 5-$CF_3$ | —$OCH_3$ | $C_{19}H_{19}ClF_3NO_2$ | 386.11 | 386.0 |
| 20-39 | RS/SR | 3,5-diF | Ph | $C_{23}H_{21}F_2NO$ | 366.16 | 366.2 |

While all the aforementioned compounds exhibit affinity for both SERT and NET, the compounds listed in the table below exhibit a NET $pK_i \geq 8$ and a SERT $K_i$/NET $K_i$ in the range of 0.1-100.

| Cmpd. | NET $pK_i$ | SERT $K_i$/NET $K_i$ |
|---|---|---|
| 20-1 | 8.5 | 0.5 |
| 20-4 | 8.6 | 0.63 |
| 20-5 | 8.6 | 1.6 |
| 20-6 | 8.4 | 1.6 |
| 20-7 | 8.5 | 1.3 |
| 20-10 | 8.3 | 2.5 |
| 20-12 | 8.3 | 7.9 |
| 20-13 | 8.3 | 10 |
| 20-15 | 8.3 | 4 |
| 20-16 | 8.9 | 4 |
| 20-17 | 9 | 13 |
| 20-20 | 8.6 | 13 |
| 20-21 | 8.7 | 4 |
| 20-23 | 8.3 | 1.6 |
| 20-26 | 8.4 | 10 |
| 20-27 | 9.1 | 100 |
| 20-28 | 8.6 | 5 |
| 20-30 | 8.6 | 25 |
| 20-31 | 8.3 | 6.3 |
| 20-32 | 9.1 | 10 |
| 20-34 | 8.4 | 1 |
| 20-35 | 9.2 | 16 |
| 20-36 | 8.9 | 7.9 |
| 20-37 | 8.2 | 13 |

Example 21

Following the procedures described in the examples above, and substituting the appropriate starting materials and reagents, compounds 21-1 to 21-21, having the following formula, were also prepared:

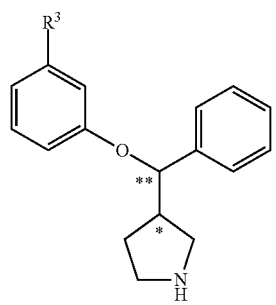

| Cmpd. | Stereo-chemistry | R³ | Formula | MS m/z: [M + H]⁺ calcd | found |
|---|---|---|---|---|---|
| 21-1 | RS/SR | F | $C_{17}H_{18}FNO$ | 272.14 | 272.2 |
| 21-2 | RS/SR | Cl | $C_{17}H_{18}ClNO$ | 288.11 | 288.2 |
| 21-3 | SR | Cl | $C_{17}H_{18}ClNO$ | 288.11 | 288.0 |
| 21-4 | RS | Cl | $C_{17}H_{18}ClNO$ | 288.11 | 288.0 |
| 21-5 | RS/SR | Br | $C_{17}H_{18}BrNO$ | 332.06 | 332.0 |
| 21-6 | RS/SR | I | $C_{17}H_{18}INO$ | 380.04 | 380.2 |
| 21-7 | RS/SR | —$CH_3$ | $C_{18}H_{21}NO$ | 268.16 | 268.2 |

-continued

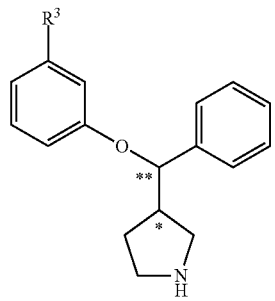

(IV)

| Cmpd. | Stereo-chemistry | R³ | Formula | MS m/z: [M + H]⁺ calcd | found |
|---|---|---|---|---|---|
| 21-8 | SR | —CH₃ | C₁₈H₂₁NO | 268.16 | 268.2 |
| 21-9 | RS | —CH₃ | C₁₈H₂₁NO | 268.16 | 268.2 |
| 21-10 | RS/SR | —CF₃ | C₁₈H₁₈F₃NO | 322.13 | 322.2 |
| 21-11 | RS/SR | —OCH₃ | C₁₈H₂₁NO₂ | 284.16 | 284.2 |
| 21-12 | RS/SR | —OCF₃ | C₁₈H₁₈F₃NO₂ | 338.13 | 338.2 |
| 21-13 | RS/SR | -O-phenyl | C₂₃H₂₃NO₂ | 346.17 | 346.2 |
| 21-14 | RS/SR | -O-(3-Cl-phenyl) | C₂₃H₂₂ClNO₂ | 380.13 | 380.2 |
| 21-15 | RS/SR | -O-(4-F-phenyl) | C₂₃H₂₂FNO₂ | 364.16 | 364.2 |
| 21-16 | RS/SR | -O-(4-Cl-phenyl) | C₂₃H₂₂ClNO₂ | 380.13 | 380.2 |
| 21-17 | RS/SR | -O-(3-Et-phenyl) | C₂₅H₂₇NO₂ | 374.20 | 374.2 |
| 21-18 | RS/SR | -O-(2-OEt-phenyl) | C₂₅H₂₇NO₃ | 390.20 | 390.2 |
| 21-19 | RS/SR | -O-(4-Et-phenyl) | C₂₅H₂₇NO₂ | 374.20 | 374.2 |

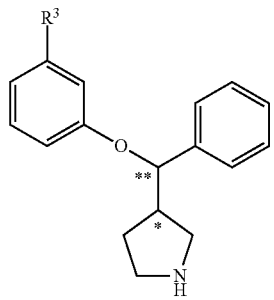

(IV)

| Cmpd. | Stereo-chemistry | $R^3$ | Formula | MS m/z: [M + H]$^+$ calcd | found |
|---|---|---|---|---|---|
| 21-20 | RS/SR | (4-OEt-phenoxy) | $C_{25}H_{27}NO_3$ | 390.20 | 390.2 |
| 21-21 | RS/SR | (benzyloxy-methyl) | $C_{24}H_{25}NO_2$ | 360.19 | 360.2 |
| Ex. 9-2 | SR | —NO$_2$ | $C_{17}H_{18}N_2O_3$ | 299.13 | 299.2 |

While all the aforementioned compounds exhibit affinity for both SERT and NET, the compounds listed in the table below exhibit a NET p$K_i \geqq 8$ and a SERT $K_i$/NET $K_i$ in the range of 0.1-100.

| Cmpd. | NET p$K_i$ | SERT $K_i$/NET $K_i$ |
|---|---|---|
| 21-1 | 8.4 | 1 |
| 21-2 | 8.6 | 0.3 |
| 21-3 | 8.6 | 2 |
| 21-4 | 8.3 | 0.1 |
| 21-5 | 8.5 | 0.2 |
| 21-6 | 8.4 | 0.2 |
| 21-7 | 8.4 | 0.5 |
| 21-8 | 8.2 | 2.5 |
| 21-13 | 8.9 | 1.3 |
| 21-14 | 8.3 | 0.8 |
| 21-15 | 8.7 | 1 |
| 21-16 | 8.2 | 0.3 |

Example 22

Following the procedures described in the examples above, and substituting the appropriate starting materials and reagents, compounds 22-1 to 22-8, having the following formula, were also prepared:

(IV')

where a is 1 or 2

| Cmpd. | Stereo-chemistry | $R^1$ | $R^3$ | Formula | MS m/z: [M + H]$^+$ calcd | found |
|---|---|---|---|---|---|---|
| 22-1 | SR | 3-SO$_2$CH$_3$, 5-F | F | $C_{18}H_{19}F_2NO_3S$ | 368.11 | 368.0 |
| 22-2 | RS/SR | 2-F | Cl | $C_{17}H_{17}ClFNO$ | 306.10 | 306.0 |
| 22-3 | RS/SR | 3-F | Cl | $C_{17}H_{17}ClFNO$ | 306.10 | 306.0 |
| 22-4 | RS/SR | 3-Cl | Cl | $C_{17}H_{17}Cl_2NO$ | 322.07 | 322.0 |
| 22-5 | RS/SR | 2-CH$_3$ | Cl | $C_{18}H_{20}ClNO$ | 302.12 | 302.2 |
| 22-6 | RS/SR | 3-CH$_3$ | Cl | $C_{18}H_{20}ClNO$ | 302.12 | 302.2 |
| 22-7 | RS/SR | 3-OCH$_3$ | Cl | $C_{18}H_{20}ClNO_2$ | 318.12 | 318.2 |
| 22-8 | RS/SR | 3-OCF$_3$ | Cl | $C_{18}H_{17}ClF_3NO_2$ | 372.09 | 372.0 |

While all the aforementioned compounds exhibit affinity for both SERT and NET, the compound listed in the table below exhibits a NET p$K_i \geqq 8$ and a SERT $K_i$/NET $K_i$ in the range of 0.1-100.

| Cmpd. | NET p$K_i$ | SERT $K_i$/NET $K_i$ |
|---|---|---|
| 22-3 | 8.1 | 0.1 |
| 22-4 | 8.1 | 0.2 |

Example 23

Following the procedures described in the examples above, and substituting the appropriate starting materials and reagents, compounds 23-1 to 23-17, having the following formula, were also prepared:

(V)

| Cmpd. | Stereo-chemistry | $R^4$ | Formula | MS m/z: $[M + H]^+$ calcd | found |
|---|---|---|---|---|---|
| 23-1 | RS/SR | F | $C_{17}H_{18}FNO$ | 272.14 | 272.2 |
| 23-2 | RS/SR | Cl | $C_{17}H_{18}ClNO$ | 288.11 | 288.2 |
| 23-3 | SR | Cl | $C_{17}H_{18}ClNO$ | 288.11 | 288.0 |
| 23-4 | RS | Cl | $C_{17}H_{18}ClNO$ | 288.11 | 288.0 |
| 23-5 | RS/SR | Br | $C_{17}H_{18}BrNO$ | 332.06 | 332.0 |
| 23-6 | RS/SR | —$CH_3$ | $C_{18}H_{21}NO$ | 268.16 | 268.2 |
| 23-7 | SR | —$CH_3$ | $C_{18}H_{21}NO$ | 268.16 | 268.2 |
| 23-8 | RS | —$CH_3$ | $C_{18}H_{21}NO$ | 268.16 | 268.2 |
| 23-9 | RS/SR | —$CF_3$ | $C_{18}H_{18}F_3NO$ | 322.13 | 322.2 |
| 23-10 | RS/SR | —$OCH_3$ | $C_{18}H_{21}NO_2$ | 284.16 | 284.2 |
| 23-11 | RS/SR | —$OCH_2CH_3$ | $C_{19}H_{23}NO_2$ | 298.17 | 298.2 |
| 23-12 | RS/SR | —$OCF_3$ | $C_{18}H_{18}F_3NO_2$ | 338.13 | 338.2 |
| 23-13 | RS/SR | Ph | $C_{23}H_{23}NO$ | 330.18 | 330.2 |
| 23-14 | RS/SR | —O—Ph | $C_{23}H_{23}NO_2$ | 346.17 | 346.2 |
| 23-15 | RS/SR | —$OCH_2$—Ph | $C_{24}H_{25}NO_2$ | 360.19 | 360.2 |
| 23-16 | SR | —$SO_2CH_3$ | $C_{18}H_{21}NO_3S$ | 332.12 | 332.2 |
| 23-17 | SR | —$CONH_2$ | $C_{18}H_{20}N_2O_2$ | 297.15 | 297.2 |

While all the aforementioned compounds exhibit affinity for both SERT and NET, the compounds listed in the table below exhibit a NET $pK_i \geq 8$ and a SERT $K_i$/NET $K_i$ in the range of 0.1-100.

| Cmpd. | NET $pK_i$ | SERT $K_i$/NET $K_i$ |
|---|---|---|
| 23-3 | 8.4 | 0.2 |
| 23-6 | 8.2 | 0.2 |
| 23-15 | 8.1 | 2 |

Example 24

Following the procedures described in the examples above, and substituting the appropriate starting materials and reagents, compounds 24-1 to 24-7, having the following formula, were also prepared:

(V')

where a = 1

| Cmpd. | Stereo-chemistry | $R^1$ | $R^4$ | Formula | MS m/z: $[M + H]^+$ calcd | found |
|---|---|---|---|---|---|---|
| 24-1 | RS/SR | 2-F | Cl | $C_{17}H_{17}ClFNO$ | 306.10 | 306.0 |
| 24-2 | RS/SR | 3-F | Cl | $C_{17}H_{17}ClFNO$ | 306.10 | 306.0 |
| 24-3 | RS/SR | 3-Cl | Cl | $C_{17}H_{17}Cl_2NO$ | 322.07 | 322.0 |
| 24-4 | RS/SR | 2-$CH_3$ | Cl | $C_{18}H_{20}ClNO$ | 302.12 | 302.2 |
| 24-5 | RS/SR | 3-$CH_3$ | Cl | $C_{18}H_{20}ClNO$ | 302.12 | 302.2 |
| 24-6 | RS/SR | 3-$OCH_3$ | Cl | $C_{18}H_{20}ClNO_2$ | 318.12 | 318.2 |
| 24-7 | RS/SR | 3-$OCF_3$ | Cl | $C_{18}H_{17}ClF_3NO_2$ | 372.09 | 372.0 |

The aforementioned compounds exhibit affinity for both SERT and NET.

Example 25

Following the procedures described in the examples above, and substituting the appropriate starting materials and reagents, compounds 25-1 to 25-34, having the following formula, were also prepared:

(VI)

| Cmpd. | Stereo-chemistry | $R^2$ | $R^3$ | Formula | MS m/z: $[M + H]^+$ calcd | found |
|---|---|---|---|---|---|---|
| 25-1 | SR | F | F | $C_{17}H_{17}F_2NO$ | 290.13 | 290.2 |
| 25-2 | RS | F | F | $C_{17}H_{17}F_2NO$ | 290.13 | 290.2 |

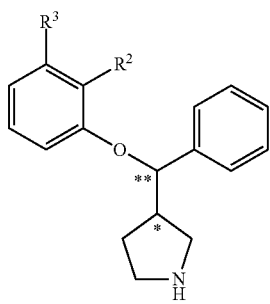

(VI)

| Cmpd. | Stereo-chemistry | R² | R³ | Formula | MS m/z: [M + H]⁺ calcd | found |
|---|---|---|---|---|---|---|
| 25-3 | RS/SR | F | Cl | C₁₇H₁₇ClFNO | 306.10 | 306.6 |
| 25-4 | SR | F | Cl | C₁₇H₁₇ClFNO | 306.10 | 306.0 |
| 25-5 | RS | F | Cl | C₁₇H₁₇ClFNO | 306.10 | 306.0 |
| 25-6 | SR | F | —CF₃ | C₁₈H₁₇F₄NO | 340.12 | 340.0 |
| 25-7 | RS | F | —CF₃ | C₁₈H₁₇F₄NO | 340.12 | 340.0 |
| 25-8 | RS/SR | F | —O—Ph | C₂₃H₂₂FNO₂ | 364.16 | 364.2 |
| 25-9 | RS/SR | Cl | Cl | C₁₇H₁₇Cl₂NO | 322.07 | 322.0 |
| 25-10 | RS | Cl | Cl | C₁₇H₁₇Cl₂NO | 322.07 | 322.0 |
| 25-11 | SR | Cl | Cl | C₁₇H₁₇Cl₂NO | 322.07 | 322.0 |
| 25-12 | SS | Cl | Cl | C₁₇H₁₇Cl₂NO | 322.07 | 322.0 |
| 25-13 | RR | Cl | Cl | C₁₇H₁₇Cl₂NO | 322.07 | 322.0 |
| Ex. 9-4 | SR | Cl | F | C₁₇H₁₇ClFNO | 306.10 | 306.0 |
| 25-14 | RS | Cl | F | C₁₇H₁₇ClFNO | 306.10 | 306.2 |
| 25-15 | RS/SR | Cl | —O—Ph | C₂₃H₂₂ClNO₂ | 380.13 | 380.0 |
| 25-16 | SR | Cl | —CF₃ | C₁₈H₁₇ClF₃NO | 356.10 | 356.0 |
| 25-17 | RS/SR | —CH₃ | F | C₁₈H₂₀FNO | 286.15 | 286.2 |
| 25-18 | RS | —CH₃ | F | C₁₈H₂₀FNO | 286.15 | 286.2 |
| 25-19 | SR | —CH₃ | F | C₁₈H₂₀FNO | 286.15 | 286.2 |
| 25-20 | RS/SR | —CH₃ | Cl | C₁₈H₂₀ClNO | 302.12 | 302.2 |
| 25-21 | SR | —CH₃ | Cl | C₁₈H₂₀ClNO | 302.12 | 302.0 |
| 25-22 | RS | —CH₃ | Cl | C₁₈H₂₀ClNO | 302.12 | 302.0 |
| 25-23 | RS/SR | —CH₃ | —CH₃ | C₁₉H₂₃NO | 282.18 | 282.2 |
| 25-24 | SR | —CH₃ | —CH₃ | C₁₉H₂₃NO | 282.18 | 282.2 |
| 25-25 | RS | —CH₃ | —CH₃ | C₁₉H₂₃NO | 282.18 | 282.2 |
| 25-26 | SR | —OCH₃ | F | C₁₈H₂₀FNO₂ | 302.15 | 302.2 |
| 25-27 | SR | —OCH₃ | Cl | C₁₈H₂₀ClNO₂ | 318.12 | 318.0 |
| 25-28 | RS/SR | —OCH₃ | —OCH₃ | C₁₉H₂₃NO₃ | 314.17 | 314.2 |
| 25-29 | RS/SR | —CN | F | C₁₈H₁₇FN₂O | 297.13 | 297.2 |
| 25-30 | SR/RS | —C(O)CH₃ | F | C₁₉H₂₀FNO₂ | 314.15 | 314.2 |
| 25-31 | SR | —C(O)CH₃ | Cl | C₁₉H₂₀ClNO₂ | 330.12 | 330.0 |
| 25-32 | SR/RS | —C(O)CH₃ | —CF₃ | C₂₀H₂₀F₃NO₂ | 364.14 | 364.2 |
| 25-33 | SR/RS | —C(O)CH₃ | —OCH₃ | C₂₀H₂₃NO₃ | 326.17 | 326.2 |
| 25-34 | SR | —C(O)OCH₃ | F | C₁₉H₂₀FNO₃ | 330.14 | 330.2 |

While all the aforementioned compounds exhibit affinity for both SERT and NET, the compounds listed in the table below exhibit a NET pK$_i$≧8 and a SERT K$_i$/NET K$_i$ in the range of 0.1-100.

| Cmpd. | NET pK$_i$ | SERT K$_i$/NET K$_i$ |
|---|---|---|
| 25-1 | 9.1 | 32 |
| 25-2 | 8.2 | 0.2 |
| 25-3 | 9.1 | 0.5 |
| 25-4 | 9.1 | 5 |
| 25-5 | 8.8 | 0.1 |
| 25-8 | 8.6 | 1.3 |
| 25-9 | 9.4 | 0.4 |
| 25-10 | 9.2 | 0.1 |
| 25-11 | 9.2 | 1.6 |
| Ex. 9-4 | 9.2 | 6.3 |
| 25-15 | 8.6 | 0.2 |
| 25-17 | 8.6 | 0.2 |
| 25-19 | 9.1 | 4 |
| 25-20 | 9.2 | 0.2 |
| 25-21 | 8.9 | 0.6 |
| 25-22 | 9.2 | 0.2 |
| 25-23 | 8.8 | 0.1 |
| 25-24 | 8.6 | 0.3 |
| 25-26 | 8.9 | 13 |
| 25-30 | 8.5 | 10 |
| 25-34 | 9 | 100 |

Example 26

Following the procedures described in the examples above, and substituting the appropriate starting materials and reagents, compounds 26-1 to 26-8, having the following formula, were also prepared:

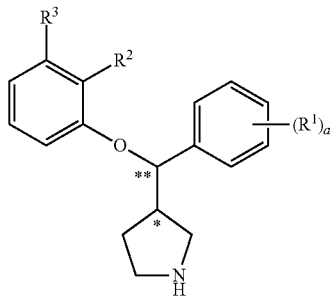

(VI')

where a = 1

| Cmpd. | Stereo-chemistry | $R^1$ | $R^2$ | $R^3$ | Formula | MS m/z: $[M + H]^+$ calcd | found |
|---|---|---|---|---|---|---|---|
| 26-1 | RS/SR | 2-F | —Cl | —Cl | $C_{17}H_{16}Cl_2FNO$ | 340.06 | 340.0 |
| 26-2 | RS/SR | 3-F | —Cl | —Cl | $C_{17}H_{16}Cl_2FNO$ | 340.06 | 340.0 |
| 26-3 | RS/SR | 3-Cl | —Cl | —Cl | $C_{17}H_{16}Cl_3NO$ | 356.03 | 356.0 |
| 26-4 | RS/SR | 2-$CH_3$ | —Cl | —Cl | $C_{18}H_{19}Cl_2NO$ | 336.08 | 336.0 |
| 26-5 | RS/SR | 3-$CH_3$ | —Cl | —Cl | $C_{18}H_{19}Cl_2NO$ | 336.08 | 336.0 |
| 26-6 | RS/SR | 3-$OCH_3$ | —Cl | —Cl | $C_{18}H_{19}Cl_2NO_2$ | 352.08 | 352.0 |
| 26-7 | RS/SR | 3-$OCF_3$ | —Cl | —Cl | $C_{18}H_{16}Cl_2F_3NO_2$ | 406.05 | 406.0 |
| 26-8 | SR | 3-$SO_2CH_3$, 5-F | —Cl | F | $C_{18}H_{18}ClF_2NO_3S$ | 402.07 | 402.0 |

While all the aforementioned compounds exhibit affinity for both SERT and NET, the compounds listed in the table below exhibit a NET $pK_i \geq 8$ and a SERT $K_i$/NET $K_i$ in the range of 0.1-100.

| Cmpd. | NET $pK_i$ | SERT $K_i$/NET $K_i$ |
|---|---|---|
| 26-1 | 8.8 | 0.1 |
| 26-3 | 8.3 | 0.1 |
| 26-6 | 8.4 | 0.1 |

Example 27

Following the procedures described in the examples above, and substituting the appropriate starting materials and reagents, compounds 27-1 to 27-39, having the following formula, were also prepared:

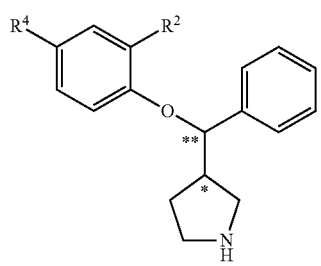

(VII)

| Cmpd. | Stereo-chemistry | $R^2$ | $R^4$ | Formula | MS m/z: $[M + H]^+$ calcd | found |
|---|---|---|---|---|---|---|
| 27-1 | RS/SR | F | F | $C_{17}H_{17}F_2NO$ | 290.13 | 290.2 |
| Ex. 7 | SR | F | F | $C_{17}H_{17}F_2NO$ | 290.13 | 290.2 |
| 27-2 | RS | F | F | $C_{17}H_{17}F_2NO$ | 290.13 | 290.0 |
| 27-3 | RS/SR | F | Cl | $C_{17}H_{17}ClFNO$ | 306.10 | 306.2 |
| 27-4 | SS | F | Cl | $C_{17}H_{17}ClFNO$ | 306.10 | 306.6 |

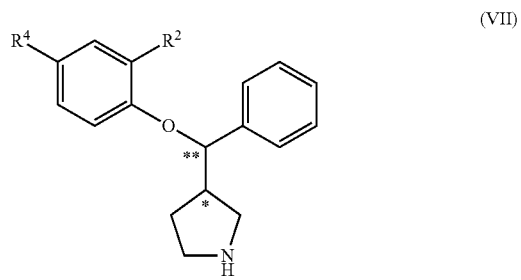

(VII)

| Cmpd. | Stereo-chemistry | $R^2$ | $R^4$ | Formula | MS m/z: $[M + H]^+$ calcd | found |
|---|---|---|---|---|---|---|
| Ex. 15 | SR | F | Cl | $C_{17}H_{17}ClFNO$ | 306.10 | 306.4 |
| 27-5 | RS/SR | Cl | Cl | $C_{17}H_{17}Cl_2NO$ | 322.07 | 322.0 |
| 27-6 | SR | Cl | Cl | $C_{17}H_{17}Cl_2NO$ | 322.07 | 322.0 |
| 27-7 | RS | Cl | Cl | $C_{17}H_{17}Cl_2NO$ | 322.07 | 322.0 |
| 27-8 | SR | Cl | F | $C_{17}H_{17}ClFNO$ | 306.10 | 306.0 |
| 27-9 | RS | Cl | F | $C_{17}H_{17}ClFNO$ | 306.10 | 306.0 |
| 27-10 | SR | Cl | —$CH_3$ | $C_{18}H_{20}ClNO$ | 302.12 | 302.0 |
| 27-11 | RS | Cl | —$CH_3$ | $C_{18}H_{20}ClNO$ | 302.12 | 302.0 |
| 27-12 | RS/SR | Cl | —$NO_2$ | $C_{17}H_{17}ClN_2O_3$ | 333.09 | 330.0 |
| 27-13 | RS/SR | —$CH_3$ | F | $C_{18}H_{20}FNO$ | 286.15 | 286.2 |
| 27-14 | SR | —$CH_3$ | F | $C_{18}H_{20}FNO$ | 286.15 | 286.2 |
| 27-15 | RS | —$CH_3$ | F | $C_{18}H_{20}FNO$ | 286.15 | 286.2 |
| 27-16 | RS/SR | —$CH_3$ | Cl | $C_{18}H_{20}ClNO$ | 302.12 | 302.2 |
| 27-17 | SR | —$CH_3$ | Cl | $C_{18}H_{20}ClNO$ | 302.12 | 302.0 |
| 27-18 | RS | —$CH_3$ | Cl | $C_{18}H_{20}ClNO$ | 302.12 | 302.0 |
| 27-19 | SS | —$CH_3$ | Cl | $C_{18}H_{20}ClNO$ | 302.12 | 302.0 |
| 27-20 | RR | —$CH_3$ | Cl | $C_{18}H_{20}ClNO$ | 302.12 | 302.0 |
| 27-21 | RS/SR | —$CF_3$ | Cl | $C_{18}H_{17}ClF_3NO$ | 356.10 | 356.0 |
| 27-22 | RS/SR | —$CH_3$ | —$NO_2$ | $C_{18}H_{20}N_2O_3$ | 313.15 | 313.2 |
| 27-23 | SR | —$CH_2CH_3$ | F | $C_{19}H_{22}FNO$ | 300.17 | 300.4 |
| 27-24 | RS | —$CH_2CH_3$ | F | $C_{19}H_{22}FNO$ | 300.17 | 300.2 |
| 27-25 | SR | —$OCH_3$ | F | $C_{18}H_{20}FNO_2$ | 302.15 | 302.2 |
| 27-26 | RS | —$OCH_3$ | F | $C_{18}H_{20}FNO_2$ | 302.15 | 302.2 |
| 27-27 | SR | —$OCH_3$ | Cl | $C_{18}H_{20}ClNO_2$ | 318.12 | 318.4 |
| 27-28 | RS | —$OCH_3$ | Cl | $C_{18}H_{20}ClNO_2$ | 318.12 | 318.4 |
| 27-29 | RS/SR | —$OCH_3$ | —$NO_2$ | $C_{18}H_{20}N_2O_4$ | 329.14 | 329.4 |
| 27-30 | RS | —$OCH_3$ | —$NO_2$ | $C_{18}H_{20}N_2O_4$ | 329.14 | 329.4 |
| 27-31 | SR | —$OCH_3$ | —$NO_2$ | $C_{18}H_{20}N_2O_4$ | 329.14 | 329.4 |
| 27-32 | SR/RS | —$C(O)CH_3$ | F | $C_{19}H_{20}FNO_2$ | 314.15 | 314.2 |
| 27-33 | RS/SR | —$NO_2$ | —$CH_3$ | $C_{18}H_{20}N_2O_3$ | 313.15 | 313.2 |
| 27-34 | SR | —$C(O)OCH_3$ | Cl | $C_{19}H_{20}ClNO_3$ | 346.11 | 346.0 |
| 27-35 | RS | —$C(O)OCH_3$ | Cl | $C_{19}H_{20}ClNO_3$ | 346.11 | 346.0 |
| 27-36 | SR | —$C(O)OCH_2CH_3$ | Cl | $C_{20}H_{22}ClNO_3$ | 360.13 | 360.0 |
| 27-37 | RS | —$C(O)OCH_2CH_3$ | Cl | $C_{20}H_{22}ClNO_3$ | 360.13 | 360.0 |
| 27-38 | SR | —$C(O)OCH(CH_3)_2$ | Cl | $C_{21}H_{24}ClNO_3$ | 374.14 | 374.2 |
| 27-39 | RS | —$C(O)OCH(CH_3)_2$ | Cl | $C_{21}H_{24}ClNO_3$ | 374.14 | 374.2 |

While all the aforementioned compounds exhibit affinity for both SERT and NET, the compounds listed in the table below exhibit a NET $pK_i \geq 8$ and a SERT $K_i$/NET $K_i$ in the range of 0.1-100.

| Cmpd. | NET $pK_i$ | SERT $K_i$/NET $K_i$ |
|---|---|---|
| 27-1 | 8.1 | 0.6 |
| Ex. 7 | 8.5 | 3.2 |
| 27-3 | 8.3 | 0.1 |
| Ex. 15 | 8.6 | 0.3 |
| 27-5 | 8.5 | 0.1 |
| 27-6 | 8.9 | 0.2 |
| 27-8 | 8.6 | 1.6 |
| 27-10 | 9.2 | 0.8 |
| 27-13 | 8.5 | 0.3 |
| 27-14 | 8.7 | 0.3 |
| 27-17 | 8.6 | 0.1 |
| 27-21 | 8 | 0.6 |
| 27-23 | 9 | 0.8 |
| 27-25 | 9.1 | 4.6 |
| 27-27 | 9.5 | 0.4 |
| 27-33 | 8 | 1.6 |
| 27-34 | 8.6 | 4 |
| 27-36 | 8.4 | 0.6 |

Example 28

Following the procedures described in the examples above, and substituting the appropriate starting materials and reagents, compounds 28-1 to 28-21, having the following formula, were also prepared:

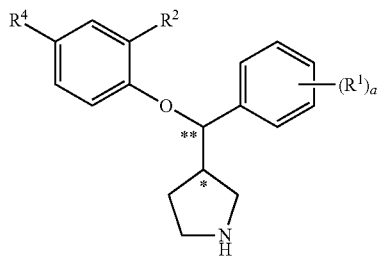

(VII')

where a is 1 or 2

| Cmpd | Stereo-chemistry | $R^1$ | $R^2$ | $R^4$ | Formula | MS m/z: $[M+H]^+$ calcd | found |
|---|---|---|---|---|---|---|---|
| 28-1 | SR | 2—$SO_2$—$CH_3$ | F | F | $C_{18}H_{19}F_2NO_3S$ | 368.11 | 368.0 |
| 28-2 | SR | 4—$SO_2$—$CH_3$ | F | F | $C_{18}H_{19}F_2NO_3S$ | 368.11 | 368.0 |
| 28-3 | SR | 3-CN | F | Cl | $C_{18}H_{16}ClFN_2O$ | 331.09 | 331.2 |
| 28-4 | SR | 4-CN | F | Cl | $C_{18}H_{16}ClFN_2O$ | 331.09 | 331.2 |
| 28-5 | RS/SR | 2-Cl | F | Cl | $C_{17}H_{16}Cl_2FNO$ | 340.06 | 340.0 |
| 28-6 | RS/SR | 4-F | F | Cl | $C_{17}H_{16}ClF_2NO$ | 324.09 | 324.0 |
| 28-7 | RS/SR | 4-Cl | F | Cl | $C_{17}H_{16}Cl_2FNO$ | 340.06 | 340.0 |
| 28-8 | SR | 4-$SO_2$—$CH_3$ | F | Cl | $C_{18}H_{19}ClFNO_3S$ | 384.08 | 384.0 |
| 28-9 | RS/SR | 3,5-diF | F | Cl | $C_{17}H_{15}ClF_3NO$ | 342.08 | 342.0 |
| 28-10 | RR/SS | 3,5-diF | F | Cl | $C_{17}H_{15}ClF_3NO$ | 342.08 | 342.0 |
| 28-11 | RS/SR | 3-F, 5-Cl | F | Cl | $C_{17}H_{15}Cl_2F_2NO$ | 358.05 | 358.0 |
| 28-12 | RS/SR | 3,5-di$CH_3$ | F | Cl | $C_{19}H_{21}ClFNO$ | 334.13 | 334.0 |
| 28-13 | RS/SR | 3-F, 5-$CH_3$ | F | Cl | $C_{18}H_{18}ClF_2NO$ | 338.10 | 338.0 |
| 28-14 | SR | 3,5-diF | —$CH_2CH_3$ | F | $C_{19}H_{20}F_3NO$ | 336.15 | 336.0 |
| 28-15 | RS | 3,5-diF | —$CH_2CH_3$ | F | $C_{19}H_{20}F_3NO$ | 336.15 | 336.0 |
| 28-16 | RR/SS | 2-Cl | —$OCH_3$ | F | $C_{18}H_{19}ClFNO_2$ | 336.11 | 336.0 |
| 28-17 | SR | 3,5-diF | —$OCH_3$ | F | $C_{18}H_{18}F_3NO_2$ | 338.13 | 338.0 |
| 28-18 | RS | 3,5-diF | —$OCH_3$ | F | $C_{18}H_{18}F_3NO_2$ | 338.13 | 338.0 |
| 28-19 | SR | 3,5-diF | —$OCH_3$ | Cl | $C_{18}H_{18}ClF_2NO_2$ | 354.10 | 354.0 |
| 28-20 | RS/SR | 3-Cl | —$OCH_3$ | —$NO_2$ | $C_{18}H_{19}ClN_2O_4$ | 363.10 | 363.0 |
| 28-21 | RS/SR | 3-$CH_3$ | $OCH_3$ | —$NO_2$ | $C_{19}H_{22}N_2O_4$ | 343.16 | 343.2 |

While all the aforementioned compounds exhibit affinity for both SERT and NET, the compounds listed in the table below exhibit a NET p$K_i \geq 8$ and a SERT $K_i$/NET $K_i$ in the range of 0.1-100.

| Cmpd. | NET p$K_i$ | SERT $K_i$/NET $K_i$ |
|---|---|---|
| 28-3 | 8.2 | 0.5 |
| 28-9 | 8.5 | 0.3 |
| 28-11 | 8.6 | 0.8 |
| 28-13 | 8.3 | 0.5 |

-continued

| Cmpd. | NET p$K_i$ | SERT $K_i$/NET $K_i$ |
|---|---|---|
| 28-14 | 8.8 | 3.2 |
| 28-17 | 9.4 | 25 |
| 28-19 | 9 | 0.8 |

Example 29

Following the procedures described in the examples above, and substituting the appropriate starting materials and reagents, compounds 29-1 to 29-32, having the following formula, were also prepared:

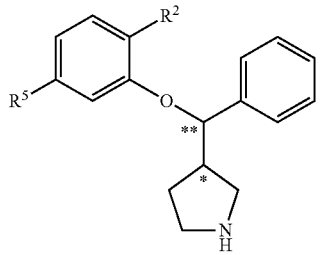

(VIII)

| Cmpd. | Stereo-chemistry | $R^2$ | $R^5$ | Formula | MS m/z: $[M + H]^+$ calcd | found |
|---|---|---|---|---|---|---|
| 29-1 | RS/SR | F | F | $C_{17}H_{17}F_2NO$ | 290.13 | 290.2 |
| 29-2 | SR | F | F | $C_{17}H_{17}F_2NO$ | 290.13 | 290.0 |
| 29-3 | RS | F | F | $C_{17}H_{17}F_2NO$ | 290.13 | 290.0 |
| 29-4 | RS/SR | F | Cl | $C_{17}H_{17}ClFNO$ | 306.10 | 306.6 |
| 29-5 | SR | F | Cl | $C_{17}H_{17}ClFNO$ | 306.10 | 306.0 |
| 29-6 | RS | F | Cl | $C_{17}H_{17}ClFNO$ | 306.10 | 306.0 |
| 29-7 | RS/SR | F | Br | $C_{17}H_{17}BrFNO$ | 350.05 | 350.0 |
| 29-8 | RS/SR | F | —$CH_3$ | $C_{18}H_{20}FNO$ | 286.15 | 286.2 |
| 29-9 | SR | F | —$CH_3$ | $C_{18}H_{20}FNO$ | 286.15 | 286.2 |
| 29-10 | RS | F | —$CH_3$ | $C_{18}H_{20}FNO$ | 286.15 | 286.2 |
| 29-11 | RS/SR | Cl | Cl | $C_{17}H_{17}Cl_2NO$ | 322.07 | 322.0 |
| 29-12 | RS/SR | Cl | F | $C_{17}H_{17}ClFNO$ | 306.10 | 306.2 |
| 29-13 | RS | Cl | F | $C_{17}H_{17}ClFNO$ | 306.10 | 306.0 |
| 29-14 | SR | Cl | F | $C_{17}H_{17}ClFNO$ | 306.10 | 306.0 |
| 29-15 | RS/SR | —$CH_3$ | F | $C_{18}H_{20}FNO$ | 286.15 | 286.2 |
| 29-16 | SR | —$CH_3$ | F | $C_{18}H_{20}FNO$ | 286.15 | 286.2 |
| 29-17 | RS | —$CH_3$ | F | $C_{18}H_{20}FNO$ | 286.15 | 286.2 |
| 29-18 | RS/SR | —$CH_3$ | Cl | $C_{18}H_{20}ClNO$ | 302.12 | 302.6 |
| 29-19 | SR | —$CH_3$ | Cl | $C_{18}H_{20}ClNO$ | 302.12 | 302.0 |
| 29-20 | RS | —$CH_3$ | Cl | $C_{18}H_{20}ClNO$ | 302.12 | 302.0 |
| 29-21 | RS/SR | —$OCH_3$ | Cl | $C_{18}H_{20}ClNO_2$ | 318.12 | 318.2 |
| 29-22 | SR | —$OCH_3$ | Cl | $C_{18}H_{20}ClNO_2$ | 318.12 | 318.0 |
| 29-23 | RS | —$OCH_3$ | Cl | $C_{18}H_{20}ClNO_2$ | 318.12 | 318.0 |
| 29-24 | SR | —$OCH_3$ | F | $C_{18}H_{20}FNO_2$ | 302.15 | 302.6 |
| 29-25 | RS | —$OCH_3$ | F | $C_{18}H_{20}FNO_2$ | 302.15 | 302.2 |
| 29-26 | RS/SR | —$OCH_3$ | —$CH_3$ | $C_{19}H_{23}NO_2$ | 298.17 | 298.2 |
| 29-27 | SR | —$OCH_3$ | —$CH_3$ | $C_{19}H_{23}NO_2$ | 298.17 | 298.6 |
| 29-28 | RS | —$OCH_3$ | —$CH_3$ | $C_{19}H_{23}NO_2$ | 298.17 | 298.6 |
| 29-29 | RS/SR | —CN | Cl | $C_{18}H_{17}ClN_2O$ | 313.10 | 313.0 |
| 29-30 | RS/SR | —$C(O)CH_3$ | Cl | $C_{19}H_{20}ClNO_2$ | 330.12 | 330.0 |
| 29-31 | SR | —$C(O)OCH_3$ | Cl | $C_{19}H_{20}ClNO_3$ | 346.11 | 346.0 |
| 29-32 | RS/SR | —$C(O)CH_3$ | —$OCH_3$ | $C_{20}H_{23}NO_3$ | 326.17 | 326.2 |

While all the aforementioned compounds exhibit affinity for both SERT and NET, the compounds listed in the table below exhibit a NET $pK_i \geq 8$ and a SERT $K_i$/NET $K_i$ in the range of 0.1-100.

| Cmpd. | NET $pK_i$ | SERT $K_i$/NET $K_i$ |
|---|---|---|
| 29-1 | 8.7 | 4 |
| 29-2 | 8.9 | 32 |
| 29-3 | 8.1 | 0.5 |
| 29-4 | 8.9 | 1.6 |
| 29-5 | 9.3 | 16 |
| 29-6 | 8.4 | 0.3 |
| 29-7 | 9.1 | 1.6 |
| 29-8 | 8.8 | 3.2 |
| 29-9 | 8.9 | 10 |
| 29-11 | 8.4 | 0.2 |
| 29-12 | 8.8 | 2 |
| 29-13 | 8 | 0.2 |
| 29-14 | 9 | 32 |
| 29-15 | 8.4 | 1.3 |

-continued

| Cmpd. | NET $pK_i$ | SERT $K_i$/NET $K_i$ |
|---|---|---|
| 29-16 | 8.8 | 7.9 |
| 29-18 | 8 | 0.1 |
| 29-19 | 8 | 0.3 |
| 29-21 | 8.5 | 1 |
| 29-22 | 8.6 | 2.5 |
| 29-24 | 9.0 | 34 |
| 29-25 | 8.1 | 0.3 |
| 29-27 | 8 | 2 |

Example 30

Following the procedures described in the examples above, and substituting the appropriate starting materials and reagents, compounds 30-1 to 30-12, having the following formula, were also prepared:

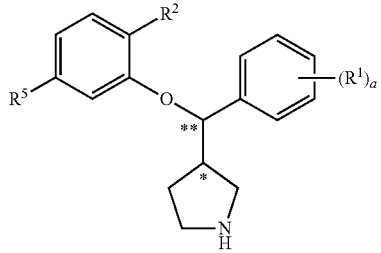

(VIII')

where a is 1 or 2

| Cmpd. | Stereo-chemistry | $R^1$ | $R^2$ | $R^5$ | Formula | MS m/z: $[M+H]^+$ calcd | found |
|---|---|---|---|---|---|---|---|
| 30-1 | RS/SR | 3,5-diF | F | Cl | $C_{17}H_{15}ClF_3NO$ | 342.08 | 342.0 |
| 30-2 | SR | 3,5-diF | F | Cl | $C_{17}H_{15}ClF_3NO$ | 342.08 | 342.0 |
| 30-3 | RS/SR | 3,5-diF | Cl | Cl | $C_{17}H_{15}Cl_2F_2NO$ | 358.05 | 358.0 |
| 30-4 | SR | 3,5-diF | Cl | Cl | $C_{17}H_{15}Cl_2F_2NO$ | 358.05 | 358.0 |
| 30-5 | SR | 3,5-diF | —$OCH_3$ | F | $C_{18}H_{18}F_3NO_2$ | 338.13 | 338.0 |
| 30-6 | RS | 3,5-diF | —$OCH_3$ | F | $C_{18}H_{18}F_3NO_2$ | 338.13 | 338.0 |
| 30-7 | RS/SR | 2-F | —$OCH_3$ | Cl | $C_{18}H_{19}ClFNO_2$ | 336.11 | 336.0 |
| 30-8 | RS/SR | 3-F | —$OCH_3$ | Cl | $C_{18}H_{19}ClFNO_2$ | 336.11 | 336.0 |
| 30-9 | RS/SR | 3-Cl | —$OCH_3$ | Cl | $C_{18}H_{19}Cl_2NO_2$ | 352.08 | 352.0 |
| 30-10 | RS/SR | 3-$CH_3$ | —$OCH_3$ | Cl | $C_{19}H_{22}ClNO_2$ | 332.13 | 332.2 |
| 30-11 | RS/SR | 3-$OCH_3$ | —$OCH_3$ | Cl | $C_{19}H_{22}ClNO_3$ | 348.13 | 348.2 |
| 30-12 | RS/SR | 3-$OCF_3$ | —$OCH_3$ | Cl | $C_{19}H_{19}ClF_3NO_3$ | 402.10 | 402.0 |

While all the aforementioned compounds exhibit affinity for both SERT and NET, the compounds listed in the table below exhibit a NET $pK_i \geq 8$ and a SERT $K_i$/NET $K_i$ in the range of 0.1-100.

| Cmpd. | NET $pK_i$ | SERT $K_i$/NET $K_i$ |
|---|---|---|
| 30-1 | 8.9 | 3.2 |
| 30-2 | 9.1 | 25 |
| 30-3 | 8.4 | 0.3 |
| 30-4 | 8.5 | 2.5 |
| 30-5 | 9.3 | 79 |

-continued

| Cmpd. | NET $pK_i$ | SERT $K_i$/NET $K_i$ |
|---|---|---|
| 30-6 | 8.3 | 0.4 |
| 30-9 | 8.1 | 0.6 |

Example 31

Following the procedures described in the examples above, and substituting the appropriate starting materials and reagents, compounds 31-1 to 31-17, having the following formula, were also prepared:

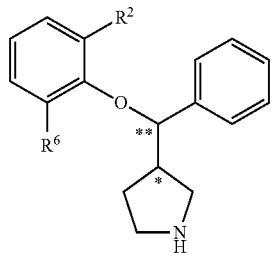

(IX)

| Cmpd. | Stereo-chemistry | $R^2$ | $R^6$ | Formula | MS m/z: $[M+H]^+$ calcd | found |
|---|---|---|---|---|---|---|
| 31-1 | RS/SR | F | F | $C_{17}H_{17}F_2NO$ | 290.13 | 290.0 |
| 31-2 | SR | F | F | $C_{17}H_{17}F_2NO$ | 290.13 | 290.0 |
| 31-3 | RS | F | F | $C_{17}H_{17}F_2NO$ | 290.13 | 290.0 |
| 31-4 | SR | F | Cl | $C_{17}H_{17}ClFNO$ | 306.10 | 306.0 |
| 31-5 | RS | F | Cl | $C_{17}H_{17}ClFNO$ | 306.10 | 306.0 |
| 31-6 | RS | F | —$CH_3$ | $C_{18}H_{20}FNO$ | 286.15 | 286.2 |
| 31-7 | SR | F | —$CH_3$ | $C_{18}H_{20}FNO$ | 286.15 | 286.4 |
| 31-8 | RS/SR | Cl | Cl | $C_{17}H_{17}Cl_2NO$ | 322.07 | 322.0 |

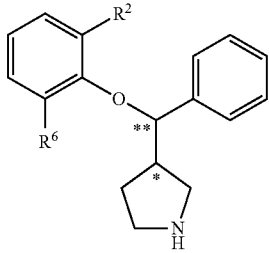

(IX)

| Cmpd. | Stereo-chemistry | R² | R⁶ | Formula | MS m/z: [M + H]⁺ calcd | found |
|---|---|---|---|---|---|---|
| 31-9 | RS | Cl | Cl | $C_{17}H_{17}Cl_2NO$ | 322.07 | 322.0 |
| 31-10 | SR | Cl | Cl | $C_{17}H_{17}Cl_2NO$ | 322.07 | 322.4 |
| 31-11 | RS/SR | —CH₃ | Cl | $C_{18}H_{20}ClNO$ | 302.12 | 302.2 |
| 31-12 | SR | —CH₃ | Cl | $C_{18}H_{20}ClNO$ | 302.12 | 302.0 |
| 31-13 | RS | —CH₃ | Cl | $C_{18}H_{20}ClNO$ | 302.12 | 302.0 |
| 31-14 | RS/SR | —CH₃ | —CH₂CH₃ | $C_{20}H_{25}NO$ | 296.19 | 296.2 |
| 31-15 | RS | —OCH₃ | F | $C_{18}H_{20}FNO_2$ | 302.15 | 302.2 |
| 31-16 | SR | —OCH₃ | F | $C_{18}H_{20}FNO_2$ | 302.15 | 302.2 |
| 31-17 | SR | —C(O)OCH₃ | Cl | $C_{19}H_{20}ClNO_3$ | 346.11 | 346.0 |

While all the aforementioned compounds exhibit affinity for both SERT and NET, the compounds listed in the table below exhibit a NET $pK_i \geqq 8$ and a SERT $K_i$/NET $K_i$ in the range of 0.1-100.

| Cmpd. | NET $pK_i$ | SERT $K_i$/NET $K_i$ |
|---|---|---|
| 31-1 | 9.1 | 20 |
| 31-2 | 9.4 | 79 |
| 31-3 | 8.3 | 1.6 |
| 31-4 | 9.9 | 40 |
| 31-5 | 9.2 | 1.3 |
| 31-6 | 8.8 | 2 |
| 31-7 | 9.7 | 5 |
| 31-8 | 9.3 | 7.9 |
| 31-9 | 8.9 | 2 |
| 31-10 | 9.5 | 16 |
| 31-11 | 8.7 | 1.3 |
| 31-12 | 9 | 1.6 |
| 31-13 | 8 | 0.6 |
| 31-15 | 8.7 | 2 |
| 31-16 | 9.7 | 79 |
| 31-17 | 8.5 | 25 |

Example 32

Following the procedures described in the examples above, and substituting the appropriate starting materials and reagents, compounds 32-1 to 32-27, having the following formula, were also prepared:

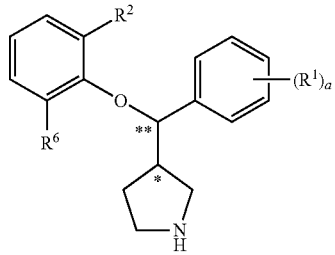

(IX')

where a is 1 or 2

| Cmpd. | Stereo-chemistry | R¹ | R² | R⁶ | Formula | MS m/z: [M + H]⁺ calcd | found |
|---|---|---|---|---|---|---|---|
| 32-1 | SR | 3,5-diF | F | Cl | $C_{17}H_{15}ClF_3NO$ | 342.08 | 342.0 |
| 32-2 | RS | 3,5-diF | F | Cl | $C_{17}H_{15}ClF_3NO$ | 342.08 | 342.2 |
| 32-3 | SR/RS | 2-Cl | F | —OCH₃ | $C_{18}H_{19}ClFNO_2$ | 336.11 | 336.0 |
| 32-4 | SS/RR | 2-Cl | F | —OCH₃ | $C_{18}H_{19}ClFNO_2$ | 336.11 | 336.0 |
| 32-5 | RS | 3,5-diF | F | —OCH₃ | $C_{18}H_{18}F_3NO_2$ | 338.13 | 338.0 |
| 32-6 | RS/SR | 2-F | Cl | Cl | $C_{17}H_{16}Cl_2FNO$ | 340.06 | 340.0 |

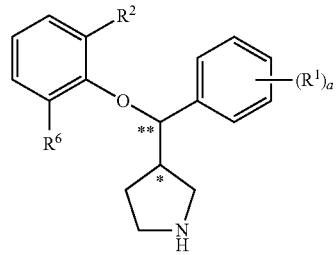

(IX')

where a is 1 or 2

| Cmpd. | Stereo-chemistry | $R^1$ | $R^2$ | $R^6$ | Formula | MS m/z: [M + H]+ calcd | found |
|---|---|---|---|---|---|---|---|
| 32-7 | RS/SR | 2-Cl | Cl | Cl | $C_{17}H_{16}Cl_3NO$ | 356.03 | 356.0 |
| 32-8 | RR/SS | 2-Cl | Cl | Cl | $C_{17}H_{16}Cl_3NO$ | 356.03 | 356.0 |
| 32-9 | RS/SR | 3-Cl | Cl | Cl | $C_{17}H_{16}Cl_3NO$ | 356.03 | 356.0 |
| 32-10 | RS/SR | 4-Cl | Cl | Cl | $C_{17}H_{16}Cl_3NO$ | 356.03 | 356.0 |
| 32-11 | RS/SR | 4-F | Cl | Cl | $C_{17}H_{16}Cl_2FNO$ | 340.06 | 340.0 |
| 32-12 | RS/SR | 3-$CH_3$ | Cl | Cl | $C_{18}H_{19}Cl_2NO$ | 336.08 | 336.0 |
| 32-13 | RS/SR | 3-$OCH_3$ | Cl | Cl | $C_{18}H_{19}Cl_2NO_2$ | 352.08 | 352.0 |
| 32-14 | RS/SR | 3-$OCF_3$ | Cl | Cl | $C_{18}H_{16}Cl_2F_3NO_2$ | 406.05 | 406.0 |
| 32-15 | SR | 3-CN | Cl | Cl | $C_{18}H_{16}Cl_2N_2O$ | 347.06 | 346.6 |
| 32-16 | SR | 4-CN | Cl | Cl | $C_{18}H_{16}Cl_2N_2O$ | 347.06 | 346.4 |
| 32-17 | SR | 3-C(O)$NH_2$ | Cl | Cl | $C_{18}H_{18}Cl_2N_2O_2$ | 365.07 | 365.4 |
| 32-18 | SR | 4-C(O)$NH_2$ | Cl | Cl | $C_{18}H_{18}Cl_2N_2O_2$ | 365.07 | 365.2 |
| 32-19 | SR | 2-$SO_2CH_3$ | Cl | Cl | $C_{18}H_{19}Cl_2NO_3S$ | 400.05 | 400.0 |
| 32-20 | SR | 4-$SO_2CH_3$ | Cl | Cl | $C_{18}H_{19}Cl_2NO_3S$ | 400.05 | 400.0 |
| 32-21 | RS/SR | 3-F, 5-$CH_3$ | Cl | Cl | $C_{18}H_{18}Cl_2FNO$ | 354.08 | 354.0 |
| 32-22 | RR/SS | 3-F, 5-$CH_3$ | Cl | Cl | $C_{18}H_{18}Cl_2FNO$ | 354.08 | 354.0 |
| 32-23 | RS/SR | 3-F, 5-Cl | Cl | Cl | $C_{17}H_{15}Cl_3FNO$ | 374.02 | 374.0 |
| 32-24 | RS/SR | 3,5-diF | Cl | Cl | $C_{17}H_{15}Cl_2F_2NO$ | 358.05 | 358.0 |
| 32-25 | SR | 3,5-diF | Cl | Cl | $C_{17}H_{15}Cl_2F_2NO$ | 358.05 | 358.0 |
| 32-26 | RR/SS | 3,5-diF | Cl | Cl | $C_{17}H_{15}Cl_2F_2NO$ | 358.05 | 358.0 |
| 32-27 | RS | 3,5-diF | Cl | Cl | $C_{17}H_{15}Cl_2F_2NO$ | 358.05 | 358.0 |

While all the aforementioned compounds exhibit affinity for both SERT and NET, the compounds listed in the table below exhibit a NET $pK_i \geq 8$ and a SERT $K_i$/NET $K_i$ in the range of 0.1-100.

| Cmpd. | NET $pK_i$ | SERT $K_i$/NET $K_i$ |
|---|---|---|
| 32-1 | 9.8 | 50 |
| 32-2 | 9.4 | 2.5 |
| 32-3 | 9.2 | 4 |
| 32-5 | 8.7 | 1.6 |
| 32-7 | 8.4 | 0.6 |
| 32-9 | 8.2 | 1.3 |
| 32-10 | 8.7 | 1.6 |
| 32-11 | 9.1 | 4 |
| 32-12 | 8.3 | 2 |
| 32-13 | 8 | 0.3 |
| 32-15 | 9 | 13 |
| 32-16 | 8.8 | 1 |
| 32-17 | 8.7 | 2 |
| 32-18 | 8.1 | 1.3 |
| 32-21 | 8.9 | 1 |
| 32-22 | 8 | 1.6 |
| 32-23 | 9.2 | 3.2 |
| 32-24 | 9.4 | 7.9 |
| 32-25 | 9.7 | 25 |
| 32-26 | 8.2 | 1 |
| 32-27 | 8.9 | 2.5 |

Example 33

Following the procedures described in the examples above, and substituting the appropriate starting materials and reagents, compounds 33-1 to 33-12, having the following formula, were also prepared:

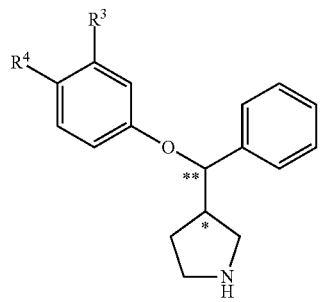

(X)

| Cmpd. | Stereo-chemistry | $R^3$ | $R^4$ | Formula | MS m/z: [M + H]+ calcd | found |
|---|---|---|---|---|---|---|
| 33-1 | RS/SR | F | F | $C_{17}H_{17}F_2NO$ | 290.13 | 290.2 |
| 33-2 | RS/SR | F | —$CH_3$ | $C_{18}H_{20}FNO$ | 286.15 | 286.2 |
| 33-3 | SR | F | —$CH_3$ | $C_{18}H_{20}FNO$ | 286.15 | 286.2 |
| 33-4 | RS | F | —$CH_3$ | $C_{18}H_{20}FNO$ | 286.15 | 286.2 |
| 33-5 | RS/SR | F | Cl | $C_{17}H_{17}ClFNO$ | 306.10 | 306.0 |
| 33-6 | SR | Cl | F | $C_{17}H_{17}ClFNO$ | 306.10 | 306.0 |

-continued

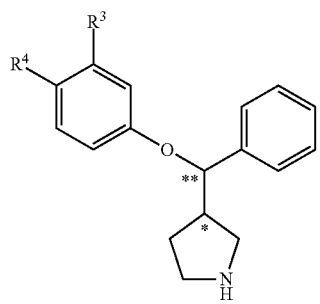
(X)

| Cmpd. | Stereo-chemistry | R³ | R⁴ | Formula | MS m/z: [M + H]⁺ calcd | found |
|---|---|---|---|---|---|---|
| 33-7 | RS | Cl | F | $C_{17}H_{17}ClFNO$ | 306.10 | 306.0 |
| 33-8 | RS/SR | Cl | Cl | $C_{17}H_{17}Cl_2NO$ | 322.07 | 322.0 |
| 33-9 | RS/SR | —CH₃ | Cl | $C_{18}H_{20}ClNO$ | 302.12 | 302.2 |
| 33-10 | SR | —CF₃ | F | $C_{18}H_{17}F_4NO$ | 340.12 | 340.0 |
| 33-11 | RS | —CF₃ | F | $C_{18}H_{17}F_4NO$ | 340.12 | 340.0 |
| 33-12 | RS/SR | —OCH₃ | —OCH₃ | $C_{19}H_{23}NO_3$ | 314.17 | 314.2 |

While all the aforementioned compounds exhibit affinity for both SERT and NET, the compounds listed in the table below exhibit a NET $pK_i \geqq 8$ and a SERT $K_i$/NET $K_i$ in the range of 0.1-100.

| Cmpd. | NET $pK_i$ | SERT $K_i$/NET $K_i$ |
|---|---|---|
| 33-2 | 8.3 | 0.1 |
| 33-3 | 8.3 | 0.3 |

Example 34

Following the procedures described in the examples above, and substituting the appropriate starting materials and reagents, compounds 34-1 to 34-12, having the following formula, were also prepared:

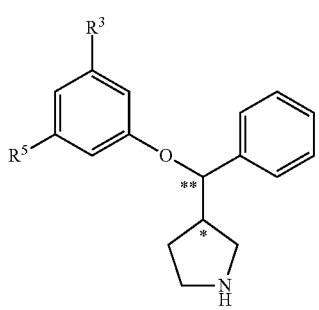
(XI)

| Cmpd. | Stereo-chemistry | R³ | R⁵ | Formula | MS m/z: [M + H]⁺ calcd | found |
|---|---|---|---|---|---|---|
| 34-1 | RS/SR | F | F | $C_{17}H_{17}F_2NO$ | 290.13 | 290.2 |
| 34-2 | SR | F | F | $C_{17}H_{17}F_2NO$ | 290.13 | 290.2 |
| 34-3 | RS | F | F | $C_{17}H_{17}F_2NO$ | 290.13 | 290.2 |
| 34-4 | SR | F | Cl | $C_{17}H_{17}ClFNO$ | 306.10 | 306.4 |
| 34-5 | RS | F | Cl | $C_{17}H_{17}ClFNO$ | 306.10 | 306.0 |
| 34-6 | SR | F | —CH₃ | $C_{18}H_{20}FNO$ | 286.15 | 286.4 |
| 34-7 | RS | F | —CH₃ | $C_{18}H_{20}FNO$ | 286.15 | 286.2 |
| Ex. 3 | RS/SR | Cl | Cl | $C_{17}H_{17}Cl_2NO$ | 322.07 | 322.2 |
| 34-8 | SR | Cl | Cl | $C_{17}H_{17}Cl_2NO$ | 322.07 | 322.4 |
| Ex. 16 | RS | Cl | Cl | $C_{17}H_{17}Cl_2NO$ | 322.07 | 322.0 |
| 34-9 | SS | Cl | Cl | $C_{17}H_{17}Cl_2NO$ | 322.07 | 322.0 |
| 34-10 | RR | Cl | Cl | $C_{17}H_{17}Cl_2NO$ | 322.07 | 322.0 |
| 34-11 | RS/SR | Cl | Br | $C_{17}H_{17}BrClNO$ | 366.02 | 366.0 |
| 34-12 | RS/SR | —CH₃ | —CH₃ | $C_{19}H_{23}NO$ | 282.18 | 282.2 |

While all the aforementioned compounds exhibit affinity for both SERT and NET, the compounds listed in the table below exhibit a NET $pK_i \geqq 8$ and a SERT $K_i$/NET $K_i$ in the range of 0.1-100.

| Cmpd. | NET $pK_i$ | SERT $K_i$/NET $K_i$ |
|---|---|---|
| 34-1 | 8.2 | 0.5 |
| 34-2 | 8.1 | 6.3 |
| 34-3 | 8.3 | 0.2 |
| 34-4 | 8 | 0.3 |
| 34-5 | 8.5 | 0.1 |
| Ex. 3 | 8.7 | 0.1 |
| 34-8 | 8.1 | 0.3 |
| Ex. 16 | 8.9 | 0.1 |
| 34-11 | 8.6 | 0.1 |

Example 35

Following the procedures described in the examples above, and substituting the appropriate starting materials and reagents, compounds 35-1 to 35-20, having the following formula, were also prepared:

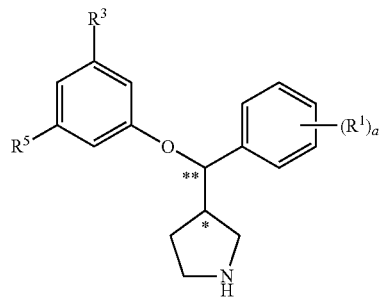

where a is 1 or 2

| Cmpd. | Stereo-chemistry | $R^1$ | $R^3$ | $R^4$ | Formula | MS m/z: $[M+H]^+$ calcd | found |
|---|---|---|---|---|---|---|---|
| 35-1 | RR/SS | 2-Cl | F | F | $C_{17}H_{16}ClF_2NO$ | 324.09 | 324.0 |
| 35-2 | SR/RS | 2-Cl | F | F | $C_{17}H_{16}ClF_2NO$ | 324.09 | 324.0 |
| 35-3 | RS/SR | 2-Cl | Cl | Cl | $C_{17}H_{16}Cl_3NO$ | 356.03 | 356.0 |
| 35-4 | RR/SS | 2-Cl | Cl | Cl | $C_{17}H_{16}Cl_3NO$ | 356.03 | 356.0 |
| 35-5 | RS/SR | 3-Cl | Cl | Cl | $C_{17}H_{16}Cl_3NO$ | 356.03 | 356.0 |
| 35-6 | RS/SR | 4-Cl | Cl | Cl | $C_{17}H_{16}Cl_3NO$ | 356.03 | 356.0 |
| 35-7 | RS/SR | 2-F | Cl | Cl | $C_{17}H_{16}Cl_2FNO$ | 340.06 | 340.0 |
| 35-8 | RS/SR | 3-F | Cl | Cl | $C_{17}H_{16}Cl_2FNO$ | 340.06 | 340.0 |
| 35-9 | RS/SR | 4-F | Cl | Cl | $C_{17}H_{16}Cl_2FNO$ | 340.06 | 340.0 |
| 35-10 | RS/SR | 2-$CH_3$ | Cl | Cl | $C_{18}H_{19}Cl_2NO$ | 336.08 | 336.0 |
| 35-11 | RS/SR | 3-$CH_3$ | Cl | Cl | $C_{18}H_{19}Cl_2NO$ | 336.08 | 336.0 |
| 35-12 | RS/SR | 4-$CH_3$ | Cl | Cl | $C_{18}H_{19}Cl_2NO$ | 336.08 | 336.0 |
| 35-13 | RS/SR | 3-$OCH_3$ | Cl | Cl | $C_{18}H_{19}Cl_2NO_2$ | 352.08 | 352.0 |
| 35-14 | RS/SR | 3,5-diF | Cl | Cl | $C_{17}H_{15}Cl_2F_2NO$ | 358.05 | 358.0 |
| 35-15 | RR/SS | 3,5-diF | Cl | Cl | $C_{17}H_{15}Cl_2F_2NO$ | 358.05 | 358.0 |
| 35-16 | SR | 3,5-diF | Cl | Cl | $C_{17}H_{15}Cl_2F_2NO$ | 358.05 | 358.0 |
| 35-17 | RS | 3,5-diF | Cl | Cl | $C_{17}H_{15}Cl_2F_2NO$ | 358.05 | 358.0 |
| 35-18 | RS/SR | 3-F, 5-Cl | Cl | Cl | $C_{17}H_{15}Cl_3FNO$ | 374.02 | 374.0 |
| 35-19 | RS/SR | 3-F, 5-$CH_3$ | Cl | Cl | $C_{18}H_{18}Cl_2FNO$ | 354.08 | 354.0 |

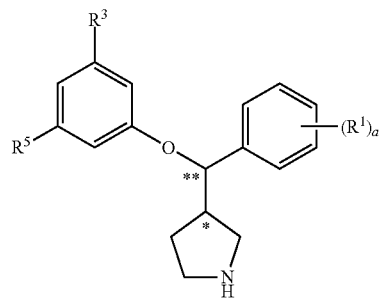

where a is 1 or 2

| Cmpd. | Stereo-chemistry | $R^1$ | $R^3$ | $R^4$ | Formula | MS m/z: $[M+H]^+$ calcd | found |
|---|---|---|---|---|---|---|---|
| 35-20 | RR/SS | 3-F, 5-$CH_3$ | Cl | Cl | $C_{18}H_{18}Cl_2FNO$ | 354.08 | 354.0 |

While all the aforementioned compounds exhibit affinity for both SERT and NET, the compounds listed in the table below exhibit a NET $pK_i \geqq 8$ and a SERT $K_i$/NET $K_i$ in the range of 0.1-100.

| Cmpd. | NET $pK_i$ | SERT $K_i$/NET $K_i$ |
|---|---|---|
| 35-3 | 8.5 | 0.1 |
| 35-9 | 8.1 | 0.1 |
| 35-12 | 8.1 | 0.1 |
| 35-14 | 8.7 | 0.3 |
| 35-16 | 8 | 0.5 |
| 35-17 | 8.8 | 0.2 |
| 35-18 | 8.3 | 0.5 |
| 35-19 | 8.2 | 0.4 |

Example 36

Following the procedures described in the examples above, and substituting the appropriate starting materials and reagents, compounds 36-1 to 36-11 having the following formula, were also prepared:

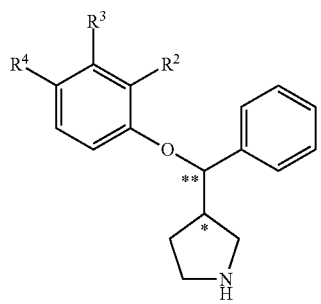

| Cmpd. | Stereo-chemistry | $R^2$ | $R^3$ | $R^4$ | Formula | MS m/z: $[M+H]^+$ calcd | found |
|---|---|---|---|---|---|---|---|
| 36-1 | SR | F | F | F | $C_{17}H_{16}F_3NO$ | 308.12 | 308.0 |
| 36-2 | RS | F | F | F | $C_{17}H_{16}F_3NO$ | 308.12 | 308.0 |
| 36-3 | SR | F | F | Cl | $C_{17}H_{16}ClF_2NO$ | 324.09 | 324.0 |

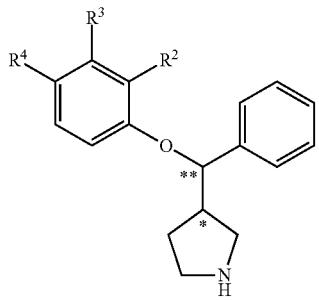

(XII)

| Cmpd. | Stereo-chemistry | R² | R³ | R⁴ | Formula | MS m/z: [M + H]⁺ calcd | found |
|---|---|---|---|---|---|---|---|
| 36-4 | SR | F | Cl | Cl | $C_{17}H_{16}Cl_2FNO$ | 340.06 | 340.0 |
| 36-5 | SR | F | F | —$CH_3$ | $C_{18}H_{19}F_2NO$ | 304.14 | 304.4 |
| 36-6 | RS | F | F | —$CH_3$ | $C_{18}H_{19}F_2NO$ | 304.14 | 304.4 |
| 36-7 | SR | F | —$CH_3$ | F | $C_{18}H_{19}F_2NO$ | 304.14 | 304.2 |
| 36-8 | RS | F | —$CH_3$ | F | $C_{18}H_{19}F_2NO$ | 304.14 | 304.2 |
| 36-9 | SR | F | —$OCH_3$ | F | $C_{18}H_{19}F_2NO_2$ | 320.14 | 320.2 |
| 36-10 | SR | Cl | F | Cl | $C_{17}H_{16}Cl_2FNO$ | 340.06 | 340.0 |
| 36-11 | SR | —$C(O)CH_3$ | Cl | Cl | $C_{19}H_{19}Cl_2NO_2$ | 364.08 | 364.0 |

While all the aforementioned compounds exhibit affinity for both SERT and NET, the compounds listed in the table below exhibit a NET p$K_i \geq 8$ and a SERT $K_i$/NET $K_i$ in the range of 0.1-100.

| Cmpd. | NET p$K_i$ | SERT $K_i$/NET $K_i$ |
|---|---|---|
| 36-1 | 8.2 | 0.8 |
| 36-3 | 8.2 | 0.1 |
| 36-5 | 8.9 | 0.5 |
| 36-10 | 8.5 | 0.1 |
| 36-7 | 8.3 | 0.3 |

Example 37

Following the procedures described in the examples above, and substituting the appropriate starting materials and reagents, compounds 37-1 and 37-4, having the following formula, were also prepared:

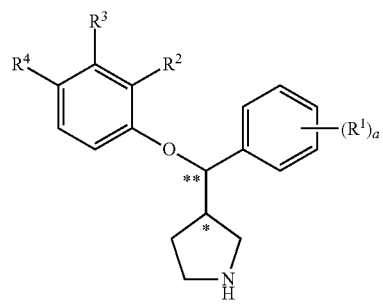

(XII')

where a is 1 or 2

| Cmpd. | Stereo-chemistry | R¹ | R² | R³ | R⁴ | Formula | MS m/z: [M + H]⁺ calcd | found |
|---|---|---|---|---|---|---|---|---|
| 37-1 | SR | 3,5-di-F | F | F | F | $C_{17}H_{14}F_5NO$ | 344.10 | 344.0 |
| 37-2 | RS | 3,5-di-F | F | F | F | $C_{17}H_{14}F_5NO$ | 344.10 | 344.0 |
| 37-3 | SR/RS | 2-Cl | F | F | F | $C_{17}H_{15}ClF_3NO$ | 342.08 | 342.0 |
| 37-4 | RR/SS | 2-Cl | F | F | F | $C_{17}H_{15}ClF_3NO$ | 342.08 | 342.0 |

While all the aforementioned compounds exhibit affinity for both SERT and NET, the compound listed in the table below exhibits a NET $pK_i \geq 8$ and a SERT $K_i$/NET $K_i$ in the range of 0.1-100.

| Cmpd. | NET $pK_i$ | SERT $K_i$/NET $K_i$ |
|---|---|---|
| 37-1 | 8.3 | 4 |

Example 38

Following the procedures described in the examples above, and substituting the appropriate starting materials and reagents, compounds 38-1 to 38-18, having the following formula, were also prepared:

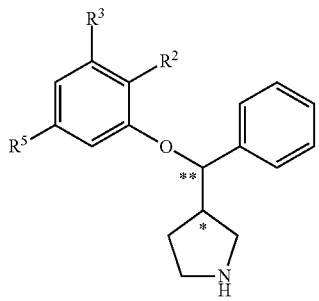

(XIII)

While all the aforementioned compounds exhibit affinity for both SERT and NET, the compounds listed in the table below exhibit a NET $pK_i \geq 8$ and a SERT $K_i$/NET $K_i$ in the range of 0.1-100.

| Cmpd. | NET $pK_i$ | SERT $K_i$/NET $K_i$ |
|---|---|---|
| 38-1 | 8.3 | 0.2 |
| 38-2 | 8.8 | 10 |
| 38-5 | 8.7 | 0.1 |
| 38-6 | 8.7 | 0.1 |
| 38-7 | 8.4 | 0.2 |
| 38-10 | 8.1 | 0.5 |
| Ex. 8-1 | 8.7 | 2.5 |
| 38-12 | 8.3 | 5 |

Example 39

Following the procedures described in the examples above, and substituting the appropriate starting materials and

| Cmpd. | Stereo-chemistry | $R^2$ | $R^3$ | $R^5$ | Formula | MS m/z: $[M+H]^+$ calcd | MS m/z: $[M+H]^+$ found |
|---|---|---|---|---|---|---|---|
| 38-1 | RS | F | F | F | $C_{17}H_{16}F_3NO$ | 308.12 | 308.0 |
| 38-2 | SR | F | F | F | $C_{17}H_{16}F_3NO$ | 308.12 | 308.0 |
| 38-3 | SR | F | Cl | —$CF_3$ | $C_{18}H_{16}ClF_4NO$ | 374.09 | 374.0 |
| 38-4 | RS | F | Cl | —$CF_3$ | $C_{18}H_{16}ClF_4NO$ | 374.09 | 374.0 |
| 38-5 | RS/SR | Cl | Cl | Cl | $C_{17}H_{16}Cl_3NO$ | 356.03 | 356.0 |
| 38-6 | RS | Cl | Cl | Cl | $C_{17}H_{16}Cl_3NO$ | 356.03 | 356.4 |
| 38-7 | SR | Cl | Cl | Cl | $C_{17}H_{16}Cl_3NO$ | 356.03 | 356.4 |
| 38-8 | SS | Cl | Cl | Cl | $C_{17}H_{16}Cl_3NO$ | 356.03 | 356.4 |
| 38-9 | RR | Cl | Cl | Cl | $C_{17}H_{16}Cl_3NO$ | 356.03 | 356.4 |
| 38-10 | SR | Cl | F | Cl | $C_{17}H_{16}Cl_2FNO$ | 340.06 | 340.2 |
| 38-11 | RS | Cl | F | Cl | $C_{17}H_{16}Cl_2FNO$ | 340.06 | 340.1 |
| Ex. 8-1 | SR | Cl | F | F | $C_{17}H_{16}ClF_2NO$ | 324.09 | 324.4 |
| Ex. 8-2 | RS | Cl | F | F | $C_{17}H_{16}ClF_2NO$ | 324.09 | 324.6 |
| 38-12 | SR | —$OCH_3$ | F | F | $C_{18}H_{19}F_2NO_2$ | 320.14 | 319.6 |
| 38-13 | RS | —$OCH_3$ | F | F | $C_{18}H_{19}F_2NO_2$ | 320.14 | 319.6 |
| 38-14 | SR | —$OCH_3$ | F | Cl | $C_{18}H_{19}ClFNO_2$ | 336.11 | 336.8 |
| 38-15 | RS | —$OCH_3$ | F | Cl | $C_{18}H_{19}ClFNO_2$ | 336.11 | 336.8 |
| 38-16 | SR | —$OCH_3$ | Cl | F | $C_{18}H_{19}ClFNO_2$ | 336.11 | 336.8 |
| 38-17 | RS | —$OCH_3$ | Cl | F | $C_{18}H_{19}ClFNO_2$ | 336.11 | 336.8 |
| 38-18 | SR | —$C(O)$—$CH_3$ | F | F | $C_{19}H_{19}F_2NO_2$ | 332.14 | 332.2 | reagents, compounds 39-1 to 39-7, having the following formula, were also prepared:

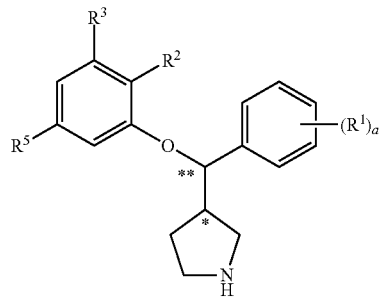

(XIII')

where a is 1 or 2

| Cmpd. | Stereo-chemistry | $R^1$ | $R^2$ | $R^3$ | $R^5$ | Formula | MS m/z: $[M+H]^+$ calcd | found |
|---|---|---|---|---|---|---|---|---|
| 39-1 | RR/SS | 2-Cl | F | F | F | $C_{17}H_{15}ClF_3NO$ | 342.08 | 342.0 |
| 39-2 | SR/RS | 2-Cl | F | F | F | $C_{17}H_{15}ClF_3NO$ | 342.08 | 342.0 |
| 39-3 | RS | 3,5-di-F | F | F | F | $C_{17}H_{14}F_5NO$ | 344.10 | 344.0 |
| 39-4 | RS/SR | 2-Cl | Cl | Cl | Cl | $C_{17}H_{15}Cl_4NO$ | 389.99 | 390.0 |
| 39-5 | RS/SR | 3,5-di-F | Cl | Cl | Cl | $C_{17}H_{14}Cl_3F_2NO$ | 392.01 | 392.4 |
| 39-6 | SR | 3,5-di-F | Cl | Cl | Cl | $C_{17}H_{14}Cl_3F_2NO$ | 392.01 | 392.0 |
| 39-7 | RS/SR | 4-Cl | Cl | Cl | Cl | $C_{17}H_{15}Cl_4NO$ | 389.99 | 390.6 |

While all the aforementioned compounds exhibit affinity for both SERT and NET, the compounds listed in the table below exhibit a NET $pK_i \geqq 8$ and a SERT $K_i$/NET $K_i$ in the range of 0.1-100.

| Cmpd. | NET $pK_i$ | SERT $K_i$/NET $K_i$ |
|---|---|---|
| 39-2 | 8.2 | 0.6 |
| 39-3 | 8.2 | 0.4 |
| 39-4 | 8.4 | 0.1 |
| 39-5 | 8.5 | 0.2 |

Example 40

Following the procedures described in the examples above, and substituting the appropriate starting materials and reagents, compounds 40-1 to 40-37, having the following formula, were also prepared:

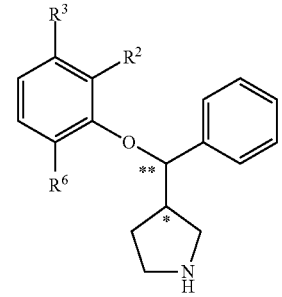

(XIV)

| Cmpd. | Stereo-chemistry | $R^2$ | $R^3$ | $R^6$ | Formula | MS m/z: $[M+H]^+$ calcd | found |
|---|---|---|---|---|---|---|---|
| 40-1 | RS | F | F | F | $C_{17}H_{16}F_3NO$ | 308.12 | 308.6 |
| 40-2 | RS/SR | F | F | F | $C_{17}H_{16}F_3NO$ | 308.12 | 308.6 |
| 40-3 | SR | F | F | F | $C_{17}H_{16}F_3NO$ | 308.12 | 308.6 |
| 40-4 | SR | F | —OCH$_3$ | F | $C_{18}H_{19}F_2NO_2$ | 320.14 | 320.2 |
| 40-5 | RS | F | —OCH$_3$ | F | $C_{18}H_{19}F_2NO_2$ | 320.14 | 320.2 |
| 40-6 | SR | F | —OCH$_3$ | Cl | $C_{18}H_{19}ClFNO_2$ | 336.11 | 336.0 |
| 40-7 | SR | F | F | —OCH$_3$ | $C_{18}H_{19}F_2NO_2$ | 320.14 | 320.0 |
| 40-8 | RS | F | F | —OCH$_3$ | $C_{18}H_{19}F_2NO_2$ | 320.14 | 319.8 |
| 40-9 | RS | Cl | Cl | Cl | $C_{17}H_{16}Cl_3NO$ | 356.03 | 356.4 |
| 40-10 | RS/SR | Cl | Cl | Cl | $C_{17}H_{16}Cl_3NO$ | 356.03 | 356.4 |
| 40-11 | SR | Cl | Cl | Cl | $C_{17}H_{16}Cl_3NO$ | 356.03 | 356.4 |
| 40-12 | SR | Cl | Cl | F | $C_{17}H_{16}Cl_2FNO$ | 340.06 | 340.2 |
| 40-13 | RS | Cl | Cl | F | $C_{17}H_{16}Cl_2FNO$ | 340.06 | 340.2 |
| 40-14 | RS | F | Cl | F | $C_{17}H_{16}ClF_2NO$ | 324.09 | 324.6 |
| 40-15 | RS/SR | F | Cl | F | $C_{17}H_{16}ClF_2NO$ | 324.09 | 324.0 |
| 40-16 | SR | F | Cl | F | $C_{17}H_{16}ClF_2NO$ | 324.09 | 324.6 |
| 40-17 | SR | Cl | F | Cl | $C_{17}H_{16}Cl_2FNO$ | 340.06 | 340.1 |
| 40-18 | RS | Cl | F | Cl | $C_{17}H_{16}Cl_2FNO$ | 340.06 | 340.1 |
| 40-19 | SR | Cl | F | F | $C_{17}H_{16}ClF_2NO$ | 324.09 | 324.0 |

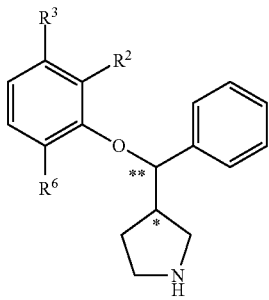

(XIV)

| Cmpd. | Stereo-chemistry | R² | R³ | R⁶ | Formula | MS m/z: [M + H]⁺ calcd | found |
|---|---|---|---|---|---|---|---|
| Ex. 14 | RS | Cl | F | F | $C_{17}H_{16}ClF_2NO$ | 324.09 | 324.0 |
| 40-20 | SS | Cl | F | F | $C_{17}H_{16}ClF_2NO$ | 324.09 | 324.0 |
| 40-21 | RR | Cl | F | F | $C_{17}H_{16}ClF_2NO$ | 324.09 | 324.0 |
| 40-22 | SR | Cl | F | —OCH₃ | $C_{18}H_{19}ClFNO_2$ | 336.11 | 336.8 |
| 40-23 | RS | Cl | F | —OCH₃ | $C_{18}H_{19}ClFNO_2$ | 336.11 | 336.8 |
| 40-24 | RS | F | —CH₃ | F | $C_{18}H_{19}F_2NO$ | 304.14 | 304.2 |
| 40-25 | RS/SR | F | —CH₃ | F | $C_{18}H_{19}F_2NO$ | 304.14 | 304.0 |
| 40-26 | SR | F | —CH₃ | F | $C_{18}H_{19}F_2NO$ | 304.14 | 304.2 |
| 40-27 | SR | F | —CH₃ | Cl | $C_{18}H_{19}ClFNO$ | 320.11 | 320.0 |
| 40-28 | RS | F | —CH₃ | Cl | $C_{18}H_{19}ClFNO$ | 320.11 | 320.0 |
| 40-29 | RS | Cl | —CH₃ | F | $C_{18}H_{19}ClFNO$ | 320.11 | 320.0 |
| Ex. 13 | SR | Cl | —CH₃ | F | $C_{18}H_{19}ClFNO$ | 320.11 | 319.8 |
| 40-30 | RR | Cl | —CH₃ | F | $C_{18}H_{19}ClFNO$ | 320.11 | 320.0 |
| 40-31 | RS | Cl | —CH₃ | Cl | $C_{18}H_{19}Cl_2NO$ | 336.08 | 337.2 |
| 40-32 | RS/SR | Cl | —CH₃ | Cl | $C_{18}H_{19}Cl_2NO$ | 336.08 | 336.0 |
| 40-33 | SR | Cl | —CH₃ | Cl | $C_{18}H_{19}Cl_2NO$ | 336.08 | 337.0 |
| 40-34 | SS | Cl | —CH₃ | Cl | $C_{18}H_{19}Cl_2NO$ | 336.08 | 337.0 |
| 40-35 | SR | Cl | —OCH₃ | F | $C_{18}H_{19}ClFNO_2$ | 336.11 | 336.0 |
| 40-36 | SR | —C(O)—CH₃ | Cl | —CH₃ | $C_{20}H_{22}ClNO_2$ | 344.13 | 344.2 |
| 40-37 | SR | —C(O)—OCH₃ | Cl | Cl | $C_{19}H_{19}Cl_2NO_3$ | 380.07 | 380.0 |

While all the aforementioned compounds exhibit affinity for both SERT and NET, the compounds listed in the table below exhibit a NET $pK_i \geqq 8$ and a SERT $K_i$/NET $K_i$ in the range of 0.1-100.

| Cmpd. | NET $pK_i$ | SERT $K_i$/NET $K_i$ |
|---|---|---|
| 40-1 | 8.7 | 0.8 |
| 40-2 | 9.3 | 5 |
| 40-3 | 9.6 | 63 |
| 40-4 | 9.2 | 6.3 |
| 40-6 | 9 | 5 |
| 40-8 | 9.0 | 1 |
| 40-9 | 9.4 | 0.4 |
| 40-10 | 9.5 | 0.5 |
| 40-11 | 9.5 | 1 |
| 40-12 | 9.6 | 1.3 |
| 40-13 | 9.7 | 0.3 |
| 40-14 | 9.3 | 0.4 |
| 40-15 | 9.6 | 1.3 |
| 40-16 | 9.8 | 10 |
| 40-17 | 9.5 | 3.2 |
| 40-18 | 9.3 | 0.5 |
| 40-19 | 9.7 | 6.3 |
| Ex. 14 | 9.5 | 0.4 |
| 40-20 | 8.5 | 0.1 |
| 40-21 | 8.4 | 0.2 |
| 40-22 | 9.2 | 13 |
| 40-23 | 8.5 | 0.1 |
| 40-24 | 8.8 | 0.4 |
| 40-25 | 9.3 | 2 |
| 40-26 | 9.6 | 20 |
| 40-27 | 9.6 | 5 |
| 40-28 | 9.1 | 0.4 |
| 40-29 | 9.7 | 0.4 |
| Ex. 13 | 9.6 | 1.3 |
| 40-30 | 8.3 | 0.1 |
| 40-31 | 9.1 | 0.6 |
| 40-32 | 9.3 | 1 |
| 40-33 | 9.5 | 3.2 |
| 40-34 | 8 | 0.1 |
| 40-35 | 9.4 | 0.3 |

Example 41

Following the procedures described in the examples above, and substituting the appropriate starting materials and reagents, compounds 41-1 to 41-39, having the following formula, were also prepared:

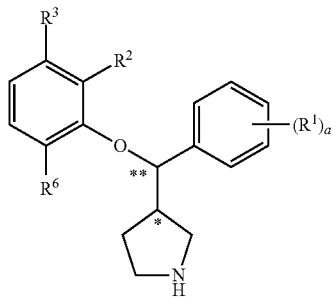

(XIV')

where a is 1 or 2

| Cmpd. | Stereo-chemistry | $R^1$ | $R^2$ | $R^3$ | $R^6$ | Formula | MS m/z: [M+H]+ calcd | found |
|---|---|---|---|---|---|---|---|---|
| 41-1 | SR | 3,5-diF | F | F | F | $C_{17}H_{14}F_5NO$ | 344.10 | 344.0 |
| 41-2 | RS | 3,5-diF | F | F | F | $C_{17}H_{14}F_5NO$ | 344.10 | 344.0 |
| 41-3 | SR | 3,5-diF | F | F | —$OCH_3$ | $C_{18}H_{17}F_4NO_2$ | 356.12 | 355.3 |
| 41-4 | RS | 3,5-diF | F | F | —$OCH_3$ | $C_{18}H_{17}F_4NO_2$ | 356.12 | 356.0 |
| 41-5 | SR | 3,5-diF | F | Cl | F | $C_{17}H_{14}ClF_4NO$ | 360.07 | 360.0 |
| 41-6 | RS | 3,5-diF | F | Cl | F | $C_{17}H_{14}ClF_4NO$ | 360.07 | 360.0 |
| 41-7 | RS | 3,5-diF | F | —$CH_3$ | F | $C_{18}H_{17}F_4NO$ | 340.12 | 340.2 |
| 41-8 | SR | 3,5-diF | F | —$CH_3$ | Cl | $C_{18}H_{17}ClF_3NO$ | 356.10 | 356.0 |
| 41-9 | RS | 3,5-diF | F | —$CH_3$ | Cl | $C_{18}H_{17}ClF_3NO$ | 356.10 | 356.0 |
| 41-10 | RS/SR | 2-Cl | Cl | Cl | Cl | $C_{17}H_{15}Cl_4NO$ | 389.99 | 390.8 |
| 41-11 | RS/SR | 3,5-diF | Cl | Cl | Cl | $C_{17}H_{14}Cl_3F_2NO$ | 392.01 | 392.4 |
| 41-12 | RS | 3,5-diF | Cl | Cl | Cl | $C_{17}H_{14}Cl_3F_2NO$ | 392.01 | 392.0 |
| 41-13 | SR | 3,5-diF | Cl | Cl | Cl | $C_{17}H_{14}Cl_3F_2NO$ | 392.01 | 392.0 |
| 41-14 | SR | 3-CN | Cl | —$CH_3$ | Cl | $C_{19}H_{18}Cl_2N_2O$ | 361.08 | 361.4 |
| 41-15 | SR | 4-CN | Cl | —$CH_3$ | Cl | $C_{19}H_{18}Cl_2N_2O$ | 361.08 | 361.4 |
| 41-16 | SR | 3-$CH_2OH$ | Cl | —$CH_3$ | Cl | $C_{19}H_{21}Cl_2NO_2$ | 366.10 | 366.2 |
| 41-17 | SS | 3-$CH_2OH$ | Cl | —$CH_3$ | Cl | $C_{19}H_{21}Cl_2NO_2$ | 366.10 | 366.2 |
| 41-18 | RS/SR | 2-Cl | Cl | —$CH_3$ | Cl | $C_{18}H_{18}Cl_3NO$ | 370.05 | 370.0 |
| 41-19 | RS/SR | 4-Cl | Cl | —$CH_3$ | Cl | $C_{18}H_{18}Cl_3NO$ | 370.05 | 370.0 |
| 41-20 | SR | 2-$SO_2CH_3$ | Cl | —$CH_3$ | Cl | $C_{19}H_{21}Cl_2NO_3S$ | 414.06 | 414.0 |
| 41-21 | SR | 4-$SO_2CH_3$ | Cl | —$CH_3$ | Cl | $C_{19}H_{21}Cl_2NO_3S$ | 414.06 | 414.0 |
| 41-22 | RR/SS | 3-F, 5-$CH_3$ | Cl | —$CH_3$ | Cl | $C_{19}H_{20}Cl_2FNO$ | 368.09 | 368.0 |
| 41-23 | RS/SS | 3-F, 5-$CH_3$ | Cl | —$CH_3$ | Cl | $C_{19}H_{20}Cl_2FNO$ | 368.09 | 368.0 |
| 41-24 | RS/SR | 3-F, 5-Cl | Cl | —$CH_3$ | Cl | $C_{18}H_{17}Cl_3FNO$ | 388.04 | 388.0 |
| 41-25 | RR/SS | 3,5-diF | Cl | —$CH_3$ | Cl | $C_{18}H_{17}Cl_2F_2NO$ | 372.07 | 372.0 |
| 41-26 | RS/SR | 3,5-diF | Cl | —$CH_3$ | Cl | $C_{18}H_{17}Cl_2F_2NO$ | 372.07 | 372.0 |
| 41-27 | SR | 3,5-diF | Cl | —$CH_3$ | Cl | $C_{18}H_{17}Cl_2F_2NO$ | 372.07 | 372.0 |
| 41-28 | SR | 3,5-diF | Cl | —$CH_3$ | F | $C_{18}H_{17}ClF_3NO$ | 356.10 | 356.0 |
| 41-29 | RS | 3,5-diF | Cl | —$CH_3$ | F | $C_{18}H_{17}ClF_3NO$ | 356.10 | 356.0 |
| 41-30 | SR | 3,5-diF | Cl | F | F | $C_{17}H_{14}ClF_4NO$ | 360.07 | 360.0 |
| 41-31 | RS | 3,5-diF | Cl | F | F | $C_{17}H_{14}ClF_4NO$ | 360.07 | 360.0 |
| 41-32 | SR | 3-CN | Cl | F | F | $C_{18}H_{15}ClF_2N_2O$ | 349.08 | 349.0 |
| 41-33 | RS | 3-CN | Cl | F | F | $C_{18}H_{15}ClF_2N_2O$ | 349.08 | 349.2 |
| 41-34 | RR | 3-CN | Cl | F | F | $C_{18}H_{15}ClF_2N_2O$ | 349.08 | 349.0 |
| 41-35 | SS | 3-CN | Cl | F | F | $C_{18}H_{15}ClF_2N_2O$ | 349.08 | 349.0 |
| 41-36 | SR | 3-C(O)—$NH_2$ | Cl | F | F | $C_{18}H_{17}ClF_2N_2O_2$ | 367.09 | 367.2 |
| 41-37 | SS | 3-C(O)$NH_2$ | Cl | F | F | $C_{18}H_{17}ClF_2N_2O_2$ | 367.09 | 367.2 |
| 41-38 | RS | 3-C(O)—$NH_2$ | Cl | F | F | $C_{18}H_{17}ClF_2N_2O_2$ | 367.09 | 367.2 |
| 41-39 | RR | 3-C(O)—$NH_2$ | Cl | F | F | $C_{18}H_{17}ClF_2N_2O_2$ | 367.09 | 367.2 |

While all the aforementioned compounds exhibit affinity for both SERT and NET, the compounds listed in the table below exhibit a NET $pK_i \geqq 8$ and a SERT $K_i$/NET $K_i$ in the range of 0.1-100.

| Cmpd. | NET $pK_i$ | SERT $K_i$/NET $K_i$ |
|---|---|---|
| 41-1 | 9.6 | 100 |
| 41-2 | 8.6 | 1 |
| 41-4 | 9 | 1 |
| 41-5 | 9.7 | 50 |
| 41-6 | 9.3 | 1 |
| 41-7 | 9 | 1.3 |
| 41-8 | 9.4 | 7.9 |
| 41-9 | 9.1 | 0.8 |
| 41-10 | 8.8 | 0.2 |
| 41-11 | 9.4 | 0.8 |
| 41-12 | 9.2 | 0.3 |
| 41-13 | 9.4 | 2 |
| 41-14 | 9.2 | 7.9 |
| 41-15 | 9 | 0.6 |
| 41-17 | 9 | 5 |
| 41-18 | 8.8 | 0.4 |

-continued

| Cmpd. | NET pK$_i$ | SERT K$_i$/NET K$_i$ |
|---|---|---|
| 41-19 | 8.9 | 0.6 |
| 41-22 | 8 | 0.3 |
| 41-23 | 8.8 | 0.5 |
| 41-24 | 9 | 1 |
| 41-25 | 8.2 | 0.2 |
| 41-26 | 9.3 | 1.3 |
| 41-27 | 9.1 | 0.8 |
| 41-28 | 9.5 | 6.3 |
| 41-29 | 9.6 | 0.5 |
| 41-30 | 9.7 | 32 |
| 41-31 | 9.6 | 0.6 |
| 41-32 | 9.4 | 40 |
| 41-33 | 9.1 | 0.4 |
| 41-34 | 8.1 | 0.8 |
| 41-36 | 9 | 7.9 |
| 41-38 | 8 | 0.1 |

Example 42

Following the procedures described in the examples above, and substituting the appropriate starting materials and reagents, compounds 42-1 to 42-10, having the following formula, were also prepared:

While all the aforementioned compounds exhibit affinity for both SERT and NET, the compounds listed in the table below exhibit a NET pK$_i \geq 8$ and a SERT K$_i$/NET K$_i$ in the range of 0.1-100.

| Cmpd. | NET pK$_i$ | SERT K$_i$/NET K$_i$ |
|---|---|---|
| 42-1 | 8.1 | 1.6 |
| 42-4 | 8.6 | 0.5 |
| 42-8 | 8.9 | 0.4 |

Example 43

Following the procedures described in the examples above, and substituting the appropriate starting materials and reagents, compounds 43-1 and 43-2, having the following formula, were also prepared:

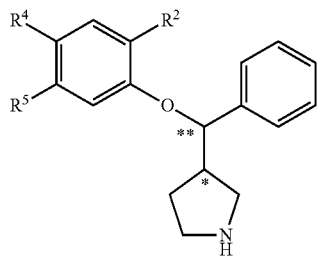

(XV)

| Cmpd. | Stereo-chemistry | R$^2$ | R$^4$ | R$^5$ | Formula | MS m/z: [M + H]$^+$ calcd | found |
|---|---|---|---|---|---|---|---|
| 42-1 | SR | F | F | F | C$_{17}$H$_{16}$F$_3$NO | 308.12 | 308.0 |
| 42-2 | RS | F | F | F | C$_{17}$H$_{16}$F$_3$NO | 308.12 | 308.0 |
| 42-3 | SR | Cl | Cl | Cl | C$_{17}$H$_{16}$Cl$_3$NO | 356.03 | 356.1 |
| 42-4 | SR | Cl | —CH$_3$ | F | C$_{18}$H$_{19}$ClFNO | 320.11 | 320.2 |
| 42-5 | RS | Cl | —CH$_3$ | F | C$_{18}$H$_{19}$ClFNO | 320.11 | 320.1 |
| 42-6 | SR | Cl | —CH$_3$ | —CH$_3$ | C$_{19}$H$_{22}$ClNO | 316.14 | 316.4 |
| 42-7 | RS | Cl | —CH$_3$ | —CH$_3$ | C$_{19}$H$_{22}$ClNO | 316.14 | 316.2 |
| 42-8 | SR | —OCH$_3$ | Cl | F | C$_{18}$H$_{19}$ClFNO$_2$ | 336.11 | 336.8 |
| 42-9 | RS | —OCH$_3$ | Cl | F | C$_{18}$H$_{19}$ClFNO$_2$ | 336.11 | 336.8 |
| 42-10 | SR | —C(O)CH$_3$ | —CH$_3$ | Cl | C$_{20}$H$_{22}$ClNO$_2$ | 344.13 | 344.2 |

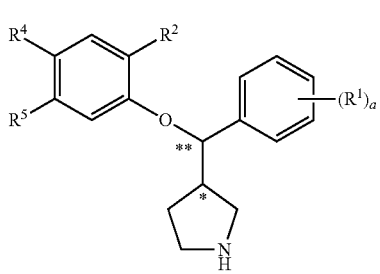

where a = 1

| Cmpd. | Stereo-chemistry | $R^1$ | $R^2$ | $R^4$ | $R^5$ | Formula | MS m/z: $[M+H]^+$ calcd | found |
|---|---|---|---|---|---|---|---|---|
| 43-1 | SR | 3,5-diF | F | F | F | $C_{17}H_{14}F_5NO$ | 344.10 | 344.0 |
| 43-2 | SR | 3,5-diF | —$OCH_3$ | Cl | F | $C_{18}H_{17}ClF_3NO_2$ | 372.09 | 372.0 |

While all the aforementioned compounds exhibit affinity for both SERT and NET, the compounds listed in the table below exhibit a NET $pK_i \geq 8$ and a SERT $K_i$/NET $K_i$ in the range of 0.1-100.

| Cmpd. | NET $pK_i$ | SERT $K_i$/NET $K_i$ |
|---|---|---|
| 43-1 | 8.7 | 32 |
| 43-2 | 8.7 | 1.3 |

Example 44

Following the procedures described in the examples above, and substituting the appropriate starting materials and reagents, compounds 44-1 to 44-29, having the following formula, were also prepared:

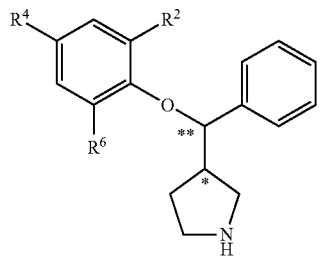

(XVI)

| Cmpd. | Stereo-chemistry | $R^2$ | $R^4$ | $R^6$ | Formula | MS m/z: $[M+H]^+$ calcd | found |
|---|---|---|---|---|---|---|---|
| 44-1 | RS | F | F | F | $C_{17}H_{16}F_3NO$ | 308.12 | 308.0 |
| Ex. 12 | SR | F | F | F | $C_{17}H_{16}F_3NO$ | 308.12 | 308.0 |
| 44-2 | SS | F | F | F | $C_{17}H_{16}F_3NO$ | 308.12 | 308.0 |
| 44-3 | RR | F | F | F | $C_{17}H_{16}F_3NO$ | 308.12 | 308.0 |
| 44-4 | SR | —$CH_2CH_3$ | F | F | $C_{19}H_{21}F_2NO$ | 318.16 | 318.0 |
| 44-5 | RS | —$CH_2CH_3$ | F | F | $C_{19}H_{21}F_2NO$ | 318.16 | 318.0 |
| 44-6 | SR | —$C(O)CH_3$ | F | F | $C_{19}H_{19}F_2NO_2$ | 332.14 | 332.4 |
| 44-7 | RS | —$C(O)CH_3$ | F | F | $C_{19}H_{19}F_2NO_2$ | 332.14 | 332.6 |
| 44-8 | RS/SR | F | Cl | F | $C_{17}H_{16}ClF_2NO$ | 324.09 | 324.4 |
| 44-9 | SR | F | Cl | F | $C_{17}H_{16}ClF_2NO$ | 324.09 | 324.0 |
| 44-10 | RS | F | Cl | F | $C_{17}H_{16}ClF_2NO$ | 324.09 | 324.0 |
| 44-11 | SR | F | —$OCH_3$ | F | $C_{18}H_{19}F_2NO_2$ | 320.14 | 320.2 |
| 44-12 | RS | F | —$OCH_3$ | F | $C_{18}H_{19}F_2NO_2$ | 320.14 | 320.2 |
| 44-13 | RS/SR | F | Cl | Br | $C_{17}H_{16}BrClFNO$ | 384.01 | 384.0 |
| 44-14 | RS/SR | Cl | Cl | Cl | $C_{17}H_{16}Cl_3NO$ | 356.03 | 356.0 |
| 44-15 | SR | F | Cl | Cl | $C_{17}H_{16}Cl_2FNO$ | 340.06 | 340.2 |
| 44-16 | RS | F | Cl | Cl | $C_{17}H_{16}Cl_2FNO$ | 340.06 | 340.3 |
| 44-17 | SR | Cl | Cl | —$CH_3$ | $C_{18}H_{19}Cl_2NO$ | 336.08 | 336.4 |
| 44-18 | RS | Cl | Cl | —$CH_3$ | $C_{18}H_{19}Cl_2NO$ | 336.08 | 336.4 |

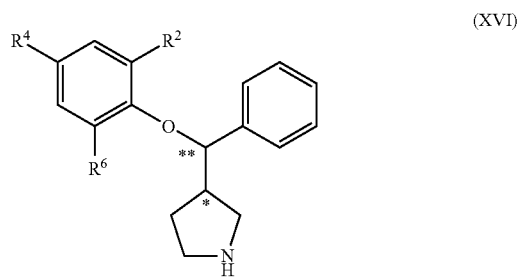

(XVI)

| Cmpd. | Stereo-chemistry | $R^2$ | $R^4$ | $R^6$ | Formula | MS m/z: $[M+H]^+$ calcd | found |
|---|---|---|---|---|---|---|---|
| 44-19 | RR/SS | Cl | F | Cl | $C_{17}H_{16}Cl_2FNO$ | 340.06 | 340.2 |
| 44-20 | RS/SR | Cl | F | Cl | $C_{17}H_{16}Cl_2FNO$ | 340.06 | 340.2 |
| 44-21 | SR | Cl | F | Cl | $C_{17}H_{16}Cl_2FNO$ | 340.06 | 340.0 |
| 44-22 | RS | Cl | F | Cl | $C_{17}H_{16}Cl_2FNO$ | 340.06 | 340.0 |
| 44-23 | SR | Cl | —$CH_3$ | Cl | $C_{18}H_{19}Cl_2NO$ | 336.08 | 336.4 |
| 44-24 | RS | Cl | —$CH_3$ | Cl | $C_{18}H_{19}Cl_2NO$ | 336.08 | 336.4 |
| 44-25 | RS/SR | Br | F | Br | $C_{17}H_{16}Br_2FNO$ | 427.96 | 428.0 |
| 44-26 | RS/SR | —$CH_3$ | Cl | Cl | $C_{18}H_{19}Cl_2NO$ | 336.08 | 336.0 |
| 44-27 | RS/SR | —$CH_3$ | —$CH_3$ | —$CH_3$ | $C_{20}H_{25}NO$ | 296.19 | 296.2 |
| 44-28 | SR | —C(O)—$OCH_3$ | F | F | $C_{19}H_{19}F_2NO_3$ | 348.13 | 348.2 |
| 44-29 | RS | —C(O)—$OCH_3$ | F | F | $C_{19}H_{19}F_2NO_3$ | 348.13 | 348.0 |

While all the aforementioned compounds exhibit affinity for both SERT and NET, the compounds listed in the table below exhibit a NET $pK_i \geqq 8$ and a SERT $K_i$/NET $K_i$ in the range of 0.1-100.

| Cmpd. | NET $pK_i$ | SERT $K_i$/NET $K_i$ |
|---|---|---|
| Ex. 14 | 8.7 | 4 |
| 44-4 | 9.2 | 0.3 |
| 44-6 | 8.8 | 13 |
| 44-8 | 8.4 | 0.1 |
| 44-9 | 8.6 | 0.1 |
| 44-15 | 9.1 | 0.2 |
| 44-21 | 8.2 | 0.5 |
| 44-28 | 9 | 2.5 |

Example 45

Following the procedures described in the examples above, and substituting the appropriate starting materials and reagents, compounds 45-1 to 45-11, having the following formula, were also prepared:

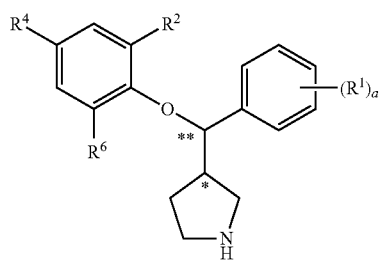

(XVI')

where a is 1 or 2

| Cmpd. | Stereo-chemistry | $R^1$ | $R^2$ | $R^4$ | $R^6$ | Formula | MS m/z: $[M+H]^+$ calcd | found |
|---|---|---|---|---|---|---|---|---|
| 45-1 | SR | 3,5-diF | F | F | F | $C_{17}H_{14}F_5NO$ | 344.10 | 344.0 |
| 45-2 | RS | 3,5-diF | F | F | F | $C_{17}H_{14}F_5NO$ | 344.10 | 344.0 |
| 45-3 | SR | 3-CN | F | F | F | $C_{18}H_{15}F_3N_2O$ | 333.11 | 333.2 |
| 45-4 | SR | 4-CN | F | F | F | $C_{18}H_{15}F_3N_2O$ | 333.11 | 333.2 |
| 45-5 | SR | 3-C(O)—$NH_2$ | F | F | F | $C_{18}H_{17}F_3N_2O_2$ | 351.12 | 351.6 |
| 45-6 | SR | 4-C(O)—$NH_2$ | F | F | F | $C_{18}H_{17}F_3N_2O_2$ | 351.12 | 351.6 |

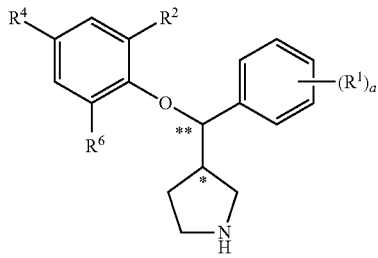

(XVI')

where a is 1 or 2

| Cmpd. | Stereo-chemistry | $R^1$ | $R^2$ | $R^4$ | $R^6$ | Formula | MS m/z: $[M+H]^+$ calcd | found |
|---|---|---|---|---|---|---|---|---|
| 45-7 | SR | 4-SO$_2$CH$_3$ | F | F | F | C$_{18}$H$_{18}$F$_3$NO$_3$S | 386.10 | 386.2 |
| 45-8 | RS/SR | 2-Cl | F | Cl | F | C$_{17}$H$_{15}$Cl$_2$F$_2$NO | 358.05 | 358.0 |
| 45-9 | RS/SR | 2-Cl | Cl | F | Cl | C$_{17}$H$_{15}$Cl$_3$FNO | 374.02 | 373.6 |
| 45-10 | SR | 3,5-diF | Cl | —CH$_3$ | Cl | C$_{18}$H$_{17}$Cl$_2$F$_2$NO | 372.07 | 372.0 |
| 45-11 | RS | 3,5-diF | Cl | —CH$_3$ | Cl | C$_{18}$H$_{17}$Cl$_2$F$_2$NO | 372.07 | 372.0 |

While all the aforementioned compounds exhibit affinity for both SERT and NET, the compounds listed in the table below exhibit a NET p$K_i$ ≧ 8 and a SERT $K_i$/NET $K_i$ in the range of 0.1-100.

| Cmpd. | NET p$K_i$ | SERT $K_i$/NET $K_i$ |
|---|---|---|
| 45-1 | 8.4 | 7.9 |
| 45-3 | 8 | 3.2 |
| 45-5 | 8.1 | 3.2 |

Example 46

Following the procedures described in the examples above, and substituting the appropriate starting materials and reagents, compounds 46-1 to 46-5, having the following formula, were also prepared:

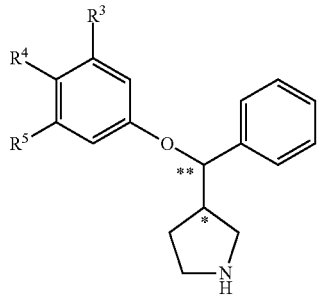

(XVII)

| Cmpd. | Stereo-chemistry | $R^3$ | $R^4$ | $R^5$ | Formula | MS m/z: $[M+H]^+$ calcd | found |
|---|---|---|---|---|---|---|---|
| 46-1 | SR | F | F | F | C$_{17}$H$_{16}$F$_3$NO | 308.12 | 308.0 |
| 46-2 | RS | F | F | F | C$_{17}$H$_{16}$F$_3$NO | 308.12 | 308.0 |
| 46-3 | SR | —CH$_3$ | Cl | —CH$_3$ | C$_{19}$H$_{22}$ClNO | 316.14 | 316.0 |
| 46-4 | RS | —CH$_3$ | Cl | —CH$_3$ | C$_{19}$H$_{22}$ClNO | 316.14 | 316.2 |
| 46-5 | RS | F | —OCH$_3$ | F | C$_{18}$H$_{19}$F$_2$NO$_2$ | 320.14 | 320.2 |

Example 47

The aforementioned compounds exhibit affinity for both SERT and NET.

Following the procedures described in the examples above, and substituting the appropriate starting materials and reagents, compounds 47-1 to 47-7, having the following formula, were also prepared:

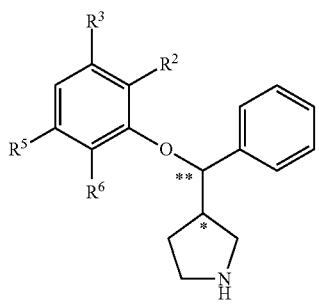

(XX)

| Cmpd. | Stereochemistry | $R^2$ | $R^3$ | $R^5$ | $R^6$ | Formula | MS m/z: $[M+H]^+$ calcd | found |
|---|---|---|---|---|---|---|---|---|
| 47-1 | RS/SR | F | F | F | F | $C_{17}H_{15}F_4NO$ | 326.11 | 326.0 |
| 47-2 | SR | F | F | F | F | $C_{17}H_{15}F_4NO$ | 326.11 | 326.0 |
| 47-3 | RS | F | F | F | F | $C_{17}H_{15}F_4NO$ | 326.11 | 326.0 |
| 47-4 | SS | F | F | F | F | $C_{17}H_{15}F_4NO$ | 326.11 | 326.0 |
| 47-5 | RR | F | F | F | F | $C_{17}H_{15}F_4NO$ | 326.11 | 326.0 |
| 47-6 | SR | Cl | F | F | F | $C_{17}H_{15}ClF_3NO$ | 342.08 | 342.4 |
| 47-7 | RS | Cl | F | F | F | $C_{17}H_{15}ClF_3NO$ | 342.08 | 342.2 |
| Ex. 10-1 | RS/SR | Cl | F | F | Cl | $C_{17}H_{15}Cl_2F_2NO$ | 358.05 | 358.0 |
| Ex. 11 | SR | Cl | F | F | Cl | $C_{17}H_{15}Cl_2F_2NO$ | 358.05 | 358.2 |
| 47-8 | SS | Cl | F | F | Cl | $C_{17}H_{15}Cl_2F_2NO$ | 358.05 | 358.0 |
| 47-9 | RR | Cl | F | F | Cl | $C_{17}H_{15}Cl_2F_2NO$ | 358.05 | 358.0 |
| 47-10 | RS | Cl | F | F | Cl | $C_{17}H_{15}Cl_2F_2NO$ | 358.05 | 358.2 |
| Ex. 10-2 | RS/SR | Cl | Cl | Cl | Cl | $C_{17}H_{15}Cl_4NO$ | 389.99 | 390.0 |
| 47-11 | RS/SR | —$CH_3$ | —$CH_3$ | —$CH_3$ | —$CH_3$ | $C_{21}H_{27}NO$ | 310.21 | 310.2 |

While all the aforementioned compounds exhibit affinity for both SERT and NET, the compounds listed in the table below exhibit a NET $pK_i \geq 8$ and a SERT $K_i$/NET $K_i$ in the range of 0.1-100.

| Cmpd. | NET $pK_i$ | SERT $K_i$/NET $K_i$ |
|---|---|---|
| 47-1 | 9.2 | 4 |
| 47-2 | 9.4 | 40 |
| 47-3 | 8.8 | 1 |
| 47-4 | 8.2 | 0.5 |
| 47-6 | 9.4 | 6.3 |
| 47-7 | 9.3 | 0.4 |
| Ex. 10-1 | 9.2 | 1.3 |
| Ex. 11 | 9.4 | 3.2 |
| 47-8 | 8.2 | 0.2 |
| 47-10 | 9.2 | 0.5 |
| Ex. 10-2 | 8.9 | 0.1 |

Example 48

Following the procedures described in the examples above, and substituting the appropriate starting materials and reagents, compounds 48-1 to 48-12, having the following formula, were also prepared:

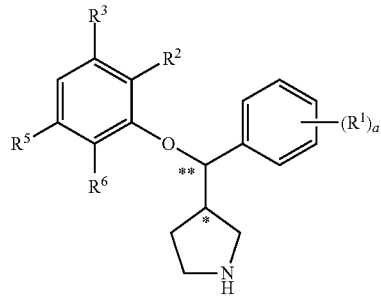

(XX')

where a is 1 or 2

| Cmpd. | Stereo-chemistry | R¹ | R² | R³ | R⁵ | R⁶ | Formula | MS m/z: [M + H]⁺ calcd | found |
|---|---|---|---|---|---|---|---|---|---|
| 48-1 | RS/SR | 3,5-diF | Cl | F | F | Cl | $C_{17}H_{13}Cl_2F_4NO$ | 394.03 | 394.0 |
| 48-2 | SR | 3,5-diF | Cl | F | F | Cl | $C_{17}H_{13}Cl_2F_4NO$ | 394.03 | 394.0 |
| 48-3 | RS | 3,5-diF | Cl | F | F | Cl | $C_{17}H_{13}Cl_2F_4NO$ | 394.03 | 394.0 |
| 48-4 | RS/SR | 2-Cl | Cl | F | F | Cl | $C_{17}H_{14}Cl_3F_2NO$ | 392.01 | 392.0 |
| 48-5 | SS | 3-COOH | Cl | F | F | Cl | $C_{18}H_{15}Cl_2F_2NO_3$ | 402.04 | 402.4 |
| 48-6 | SS | 3-CHO | Cl | F | F | Cl | $C_{18}H_{15}Cl_2F_2NO_2$ | 386.04 | 386.2 |
| 48-7 | SS | 3-C(O)—OCH₃ | Cl | F | F | Cl | $C_{19}H_{17}Cl_2F_2NO_3$ | 416.06 | 416.2 |
| 48-8 | SS | 3-C(O)—O—CH₂CH₃ | Cl | F | F | Cl | $C_{20}H_{19}Cl_2F_2NO_3$ | 430.07 | 430.1 |
| 48-9 | SS | 3-CH₂—NH(CH₂CH₃) | Cl | F | F | Cl | $C_{20}H_{22}Cl_2F_2N_2O$ | 415.11 | 415.0 |
| 48-10 | SS | 3-CH₂—N(CH₃)(CH₂—CH₃) | Cl | F | F | Cl | $C_{21}H_{24}Cl_2F_2N_2O$ | 429.12 | 429.0 |
| 48-11 | SS | 3-C(O)—NHCH₂CH₃ | Cl | F | F | Cl | $C_{20}H_{20}Cl_2F_2N_2O_2$ | 429.09 | 429.2 |
| 48-12 | SS | 3-C(O)—N(CH₃)CH₂CH₃ | Cl | F | F | Cl | $C_{21}H_{22}Cl_2F_2N_2O_2$ | 443.10 | 443.2 |

While all the aforementioned compounds exhibit affinity for both SERT and NET, the compounds listed in the table below exhibit a NET $pK_i \geq 8$ and a SERT $K_i$/NET $K_i$ in the range of 0.1-100.

| Cmpd. | NET $pK_i$ | SERT $K_i$/NET $K_i$ |
|---|---|---|
| 48-1 | 9.3 | 2 |
| 48-2 | 9.4 | 10 |

-continued

| Cmpd. | NET $pK_i$ | SERT $K_i$/NET $K_i$ |
|---|---|---|
| 48-3 | 9.6 | 2 |
| 48-4 | 8.1 | 0.2 |

Example 49

Following the procedures described in the examples above, and substituting the appropriate starting materials and reagents, compounds 49-1 and 49-8, having the following formula, were also prepared:

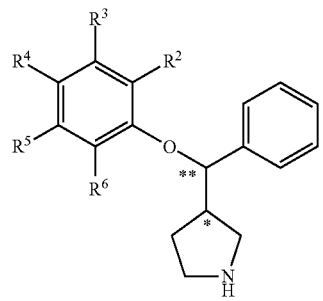

(XXI)

| Cmpd. | Stereo-chemistry | R² | R³ | R⁴ | R⁵ | R⁶ | Formula | MS m/z: [M + H]⁺ calcd | found |
|---|---|---|---|---|---|---|---|---|---|
| 49-1 | SR | F | F | F | F | F | $C_{17}H_{14}F_5NO$ | 344.10 | 344.0 |
| 49-2 | RS | F | F | F | F | F | $C_{17}H_{14}F_5NO$ | 344.10 | 344.0 |

-continued

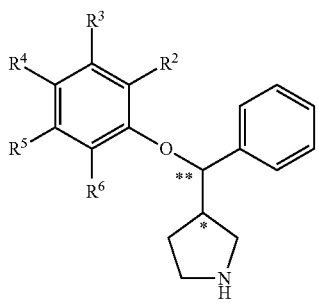

(XXI)

| Cmpd. | Stereo-chemistry | $R^2$ | $R^3$ | $R^4$ | $R^5$ | $R^6$ | Formula | MS m/z: $[M+H]^+$ calcd | found |
|---|---|---|---|---|---|---|---|---|---|
| 49-3 | SR | F | F | —$CF_3$ | F | F | $C_{18}H_{14}F_7NO$ | 394.10 | 394.0 |
| 49-4 | RS | F | F | —$CF_3$ | F | F | $C_{18}H_{14}F_7NO$ | 394.10 | 394.0 |
| 49-5 | RS | F | F | Cl | F | F | $C_{17}H_{14}ClF_4NO$ | 360.07 | 360.0 |
| 49-6 | SR | Cl | F | Cl | F | Cl | $C_{17}H_{14}Cl_3F_2NO$ | 392.01 | 392.0 |
| 49-7 | SR | —C(O)—$CH_3$ | F | F | F | F | $C_{19}H_{17}F_4NO_2$ | 368.12 | 368.0 |
| 49-8 | SR | —C(O)—$OCH_3$ | F | F | F | F | $C_{19}H_{17}F_4NO_3$ | 384.11 | 384.0 |

While all the aforementioned compounds exhibit affinity for both SERT and NET, the compounds listed in the table below exhibit a NET $pK_i \geq 8$ and a SERT $K_i$/NET $K_i$ in the range of 0.1-100.

| Cmpd. | NET $pK_i$ | SERT $K_i$/NET $K_i$ |
|---|---|---|
| 49-1 | 8.4 | 2.5 |
| 49-2 | 8 | 0.2 |
| 49-8 | 8.5 | 0.4 |

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statues and regulations, all publications, patents and patent applications cited herein are hereby incorporated by reference in their entirety to the same extent as if each document had been individually incorporated by reference herein.

What is claimed is:

1. A method of treating a patient that is suffering from inflammatory pain from osteoarthritis, comprising administering a therapeutically effective amount of a compound of formula I:

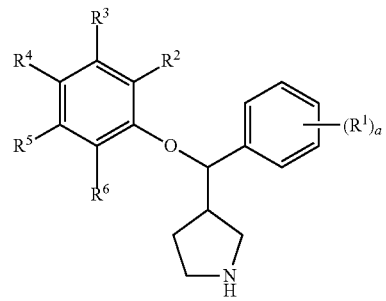

(I)

where:
a is 0 to 5;
each $R^1$ is independently selected from halo, —$C_{1-6}$alkyl, —$C_{2-6}$alkynyl, —O—$C_{1-6}$alkyl, —$C_{1-4}$alkylene-O—$C_{1-4}$alkyl, —$C_{0-1}$alkylene-phenyl, —O-$C_{0-3}$alkylene-phenyl, —$C_{0-6}$alkylene-OH, —CN, —$C_{0-2}$alkylene-COOH, —CHO, —C(O)—$C_{1-6}$alkyl, —C(O)O-$C_{1-4}$alkyl, —$CH_2SH$, —S—$C_{1-6}$alkyl, —$C_{1-4}$alkylene-S—$C_{1-4}$alkyl, —$SO_2$—$C_{1-6}$alkyl, —$SO_2NR^aR^b$, —$NHSO_2R^a$, —$C_{0-1}$alkylene-$NR^aR^b$, —NHC(O)—$C_{1-6}$alkyl, —$C(O)NR^aR^b$, and —$NO_2$;
$R^2$ through $R^6$ are independently selected from H, halo, —$C_{1-6}$alkyl, —$C_{2-6}$alkynyl, —O—$C_{1-6}$alkyl, —$C_{1-4}$alkylene-O—$C_{1-4}$alkyl, -$C_{0-1}$alkylene-phenyl, —O—$C_{0-3}$alkylene-phenyl, —$C_{0-6}$alkylene-OH, —CN, -$C_{0-2}$alkylene-COOH, —CHO, —C(O)—$C_{1-6}$alkyl, —C(O)O-$C_{1-4}$alkyl, —$CH_2SH$, —S—$C_{1-6}$alkyl, —$C_{1-4}$alkylene-S—$C_{1-4}$alkyl, —$SO_2$—$C_{1-6}$alkyl, —$SO_2NR^aR^b$, —$NHSO_2R^a$, —$C_{0-1}$alkylene-$NR^aR^b$, —NHC(O)—$C_{1-6}$alkyl, —$C(O)NR^aR^b$, and —$NO_2$;
$R^a$ and $R^b$ are independently H or —$C_{1-4}$alkyl;
each alkyl in $R^1$ through $R^6$ is optionally substituted with 1 to 5 fluoro atoms; and each phenyl in $R^1$ through $R^6$ is optionally substituted with 1 or 2 groups independently selected from halo, —$C_{1-6}$alkyl, and —O—$C_{1-6}$alkyl; or a pharmaceutically acceptable salt thereof.

2. The method of claim 1, where a is 0, 1 or 2.

3. The method of claim 1, where a is 1; and $R^1$ is halo, —$C_{1-6}$alkyl, —O—$C_{1-6}$alkyl optionally substituted with 1 to 5 fluoro atoms, -$C_{0-6}$alkylene-OH, —CN, —$C_{0-2}$alkylene-COOH, —CHO, —C(O)O—$C_{1-4}$alkyl or —C(O)NR$^a$R$^b$.

4. The method of claim 1, where a is 2; and each $R^1$ is independently halo, —$C_{1-6}$alkyl optionally substituted with 1 to 5 fluoro atoms, or —SO$_2$—$C_{1-6}$alkyl.

5. The method of claim 1, where $R^2$ is: H; halo; —$C_{1-6}$alkyl optionally substituted with 1 to 3 fluoro atoms; -O—$C_{1-6}$alkyl optionally substituted with 1 to 3 fluoro atoms; —$C_{0-1}$alkylene-phenyl optionally substituted with 1 to 2 halo atoms; —O—$C_{0-3}$alkylene-phenyl; —$C_{0-6}$alkylene-OH; —CN; —C(O)—$C_{1-6}$alkyl; —C(O)O—$C_{1-4}$alkyl; —S—$C_{1-6}$alkyl; —SO$_2$—$C_{1-6}$alkyl; or —NO$_2$.

6. The method of claim 1, where $R^3$ is: H; halo; —$C_{1-6}$alkyl optionally substituted with 1 to 3 fluoro atoms; —O—$C_{1-6}$alkyl optionally substituted with 1 to 3 fluoro atoms; —O—$C_{0-3}$alkylene-phenyl optionally substituted with 1 halo, —$C_{1-6}$alkyl, or —O—$C_{1-6}$alkyl group; or —NO$_2$.

7. The method of claim 1, where $R^4$ is: H; halo; —$C_{1-6}$alkyl optionally substituted with 1 to 5 fluoro atoms; —O—$C_{1-6}$alkyl optionally substituted with 1 to 5 fluoro atoms; —$C_{0-1}$alkylene-phenyl; —O—$C_{0-3}$alkylene-phenyl; —SO$_2$—$C_{1-6}$alkyl; —C(O)NH$_2$; or —NO$_2$.

8. The method of claim 1, where $R^5$ is H, halo, or —$C_{1-6}$alkyl.

9. The method of claim 1, where $R^6$ is H, halo, —$C_{1-6}$alkyl, or —O—$C_{1-6}$alkyl.

* * * * *